US008840878B2

(12) United States Patent
Brandl et al.

(10) Patent No.: US 8,840,878 B2
(45) Date of Patent: *Sep. 23, 2014

(54) PEPTIDOMIMETIC SULFAMIDE COMPOUNDS AND ANTIVIRAL USES THEREOF

(75) Inventors: Trixi Brandl, Basel (CH); Prakash Raman, Cambridge, MA (US); Pascal Rigollier, Basel (CH); Mohindra Seepersaud, Cambridge, MA (US); Oliver Simic, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/614,813

(22) Filed: Sep. 13, 2012

(65) Prior Publication Data

US 2013/0034519 A1 Feb. 7, 2013

Related U.S. Application Data

(63) Continuation of application No. 12/755,852, filed on Apr. 7, 2010, now Pat. No. 8,512,690.

(60) Provisional application No. 61/168,408, filed on Apr. 10, 2009, provisional application No. 61/181,038, filed on May 26, 2009.

(51) Int. Cl.
*A61K 45/00* (2006.01)
*C07D 417/14* (2006.01)
*C07D 401/12* (2006.01)
*C07D 209/96* (2006.01)
*C07D 401/14* (2006.01)
*C07K 5/087* (2006.01)
*C07K 5/078* (2006.01)
*C07K 5/107* (2006.01)
*C07D 403/12* (2006.01)
*C07D 403/14* (2006.01)
*C07D 405/14* (2006.01)
*C07K 5/103* (2006.01)
*C07K 5/083* (2006.01)

(52) U.S. Cl.
CPC ............ *C07D 401/14* (2013.01); *C07D 417/14* (2013.01); *C07D 401/12* (2013.01); *C07D 209/96* (2013.01); *C07K 5/0812* (2013.01); *C07K 5/06165* (2013.01); *C07K 5/1016* (2013.01); *C07D 403/12* (2013.01); *C07D 403/14* (2013.01); *C07D 405/14* (2013.01); *C07K 5/101* (2013.01); *C07K 5/0808* (2013.01)
USPC ........ 424/85.2; 424/85.4; 424/85.7; 514/21.9; 514/19.3; 514/3.8; 514/4.3; 530/4.3

(58) Field of Classification Search
USPC .............. 424/85.2, 85.7, 85.4; 530/330, 4.3; 514/4.3, 3.8, 19.3, 21.9
See application file for complete search history.

(56) References Cited

U.S. PATENT DOCUMENTS

| 6,894,072 | B2 | 5/2005 | Arasappan et al. |
| 7,244,721 | B2 | 7/2007 | Saksena et al. |
| 7,825,152 | B2 | 11/2010 | Brandl et al. |
| 8,008,263 | B2 | 8/2011 | Britt et al. |
| 2003/0036501 | A1 | 2/2003 | Saksena et al. |
| 2003/0216325 | A1 | 11/2003 | Saksena et al. |
| 2005/0107304 | A1 | 5/2005 | Britt et al. |
| 2005/0137140 | A1 | 6/2005 | Cottrell et al. |
| 2005/0197301 | A1 | 9/2005 | Njoroge et al. |
| 2005/0209164 | A1 | 9/2005 | Bogen et al. |
| 2005/0249702 | A1 | 11/2005 | Njoroge et al. |
| 2005/0267043 | A1 | 12/2005 | Bogen et al. |
| 2006/0046956 | A1 | 3/2006 | Sannigrahi et al. |
| 2006/0281689 | A1 | 12/2006 | Malcolm |
| 2007/0049536 | A1 | 3/2007 | Venkatraman et al. |
| 2007/0093430 | A1 | 4/2007 | Chen et al. |
| 2011/0182850 | A1 | 7/2011 | Brandl |

FOREIGN PATENT DOCUMENTS

| EP | 0 326 974 A1 | 8/1989 |
| WO | 0208244 A2 | 1/2002 |
| WO | 0218369 A2 | 3/2002 |
| WO | 03062265 A2 | 7/2003 |
| WO | 2004113295 A1 | 12/2004 |
| WO | 2005021584 A2 | 3/2005 |
| WO | 2005028502 A1 | 3/2005 |
| WO | 2005035525 A2 | 4/2005 |
| WO | 2005042020 A2 | 5/2005 |
| WO | 2005058821 A1 | 6/2005 |
| WO | 2005077969 A2 | 8/2005 |
| WO | 2005085242 A1 | 9/2005 |
| WO | 2005085275 A1 | 9/2005 |
| WO | 2005087731 A1 | 9/2005 |
| WO | 2005123076 A2 | 12/2005 |
| WO | 2006017295 A2 | 2/2006 |
| WO | 2006039488 A2 | 4/2006 |
| WO | 2006050250 A2 | 5/2006 |
| WO | 2006130553 A2 | 12/2006 |
| WO | 2006130666 A2 | 12/2006 |

(Continued)

OTHER PUBLICATIONS

Arasappan, A. et al. "Hepatitis C virus NS3-4A serine protease inhibitors: SAR of P'2 moiety with improved potency", Bioorganic & Medicinal Chemistry Letters, 2005, pp. 4180-4184, vol. 15(19).
Arasappan. A. et al. "Novel 2-oxoimidazolidine-4-carboxylic acid derivatives as hepatitis C virus NS3-4A serine protease inhibitors: synthesis, activity, and X-ray crystal structure of an enzyme inhibitor complex", Bioorganic & Medicinal Chemistry Letters, 2004, pp. 5751-5755, vol. 14(23).

(Continued)

*Primary Examiner* — Jason Sims
*Assistant Examiner* — Ibrahim D Bori
(74) *Attorney, Agent, or Firm* — Michael G. Smith

(57) ABSTRACT

The present application describes organic compounds that are useful for the treatment, prevention and/or amelioration of human diseases.

12 Claims, No Drawings

(56) References Cited

FOREIGN PATENT DOCUMENTS

| WO | 2006130686 A2 | 12/2006 |
|----|---------------|---------|
| WO | 2006130687 A2 | 12/2006 |
| WO | 2007005838 A2 | 1/2007 |
| WO | 2007016589 A2 | 2/2007 |
| WO | 2007025307 A2 | 3/2007 |
| WO | 2007120595 A2 | 10/2007 |
| WO | 2007121124 A2 | 10/2007 |
| WO | 2007121125 A2 | 10/2007 |
| WO | 2007133865 A2 | 11/2007 |
| WO | 2008064066 A1 | 5/2008 |

OTHER PUBLICATIONS

Arasappan, Ashok et al. "Practical and efficient method for amino acid derivatives containing beta-quaternary center: application toward synthesis of hepatitis C virus NS3 serine protease inhibitors". Tetrahedron Letters, 2007, pp. 6343-6347, vol. 48(36).

Arasappan, Ashok et al., "P2-P4 Macrocyclic inhibitors of hepatitis C virus NS3-4A serine protease", Biorganic & Medicinal Chemistry Letters, 2006, pp. 3960-3966, vol. 16(15).

Beaulieu, Pierrre L. et al., "Synthesis of (1R,2S)-1-Amino-2-vinylcyclopropanecarboxylic acid vinyl-ACCA) Derivatives: Key intermediates for the preparation of inhibitors of the hepatitis C virus NS3 protease", Journal of Organic Chemistry, 2005, pp. 5869-5879, vol. 70 (15).

Bogen, S. et al.; "Hepatitis C virus NS3-4A serine protease inhibitors: Use of a P2-P1 cyclopropyl alanine combination for improved potency": Bioorganic & Medicinal Chemistry Letters; 2005: pp. 4515-4519; vol. 15(20).

Bogen, Stephane L. et al., Discovery of SCH446211 (SCH6): A new ketoamide inhibitor of the HCV NS3 Serine Protease and HCV subgenomic RNA replication: Journal of Medicinal Chemistry, 2006, pp. 2750-2757, vol. 49(9).

Chen, Kevin X. et al. "Synthesis and biological activity of macrocyclic inhibitors of hepatitis C virus (HCV) NS3 protease" Bioorganic & Medicinal Chemistry Letters; May 13, 2005 (Pub. Aug. 19, 2005), pp. 4475-4478, vol. 15 (20).

Chen, Kevin X. et al.: "Novel Potent Hepatitis C Virus NS3 Serine Protease Inhibitors Derived from Proline-Based Macrocycles", J. Med. Chem., 2006, 995-1005; vol. 49 (3). Published on Web Jan. 7, 2006.

Chen, Kevin X. et al.; "Potent 7-hydroxy-1,2,3,4-tetrahydroisoquinoline-3-carboxylic acid-based macrocyclic inhibitors of hepatitis C virus NS3 protease", Journal of Medicinal Chemistry, Jun. 3, 2005 (Pub. 2006); pp. 567-574; vol. 49 (2).

Chen, Kevin X. et al.; "Proline-based macrocyclic inhibitors of the hepatitis C virus: Stereoselective synthesis and biological activity"; Angewandte Chemie, International Edition; 2005, pp. 7024-7028; vol. 44 (43).

Chen, Shu-Hui et al., "P1 and P1' optimization of [3,4]-bicycloproline P2 incorporated tetrapeptidyl alpha-ketoamide based HCV protease inhibitors", Letters in Drug Design & Discovery, 2005, pp. 118-123, vol. 2.

De Francesco et al: "Advances in the development of new therapeutic agents targeting the NS3-4A serine protease or the NS5B RNA-dependent RNA polymerase of the hepatitis C virus" Advanced Drug Delivery Reviews, vol. 59, No. 12, Aug. 11, 2007, pp. 1242-1262. Figure 2.

Farmer, Luc J. et al., "Inhibitors of hepatitis C virus NS3.bul.4A protease: P2 proline variants", Letters in Drug Design & Discovery, 2005, pp. 497-502, vol. 2(7).

Faucher, Anne-Marie et al., "Synthesis of BILN 2061, an HCV NS3 protease inhibitor with proven antiviral effect in humans", Organic Letters, 2004, pp. 2901-2904, vol. 6(17).

Frutos, Rogelio P. et al. "Practical synthesis of 2-[2-Isopropylaminothiazol-4-yl]-7-methoxy-1H-quinolin-4-one; key intermediate for the synthesis of potent HCV NS3 protease inhibitor BILN 2061", 2006, Synthesis, pp. 2563-2567, vol.

Goudreau, Nathalie et al. "Potent inhibitors of the hepatitis C virus NS3 protease: design and synthesis of macrocyclic substrate-based Beta-strand mimics", Journal of Organic Chemistry, 2004, pp. 6185-6201, vol. 69(19).

Lamarre, Daniel et al. "An NS3 protease inhibitor with antiviral effects in humans infected with hepatitis C virus", Nature Letters (London), 2003, pp. 186-189, vol. 426 (6963).

LaPlante, Steven R. et al., "Dynamics and structure-based design of drugs targeting the critical serine protease of the hepatitis C virus—from a peptidic substrate to BILN 2061", Current Medicinal Chemistry: Anti-Infective Agents, 2005, pp. 111-132, vol. 4(2).

Lin et al., "VX-950, a novel hepatitis C virus (HCV) NS3-4A protease inhibitor, exhibits potent antiviral activities in HCV replicon cells," Antimicrobial Agents and Chemotherapy 50(5):1813-1822 (2006).

Lin, C. et al., "Discovery and development of VX-950, a novel, covalent, and reversible inhibitor of hepatitis C virus NS3.bul.4A serine protease", Infectious Disorders: Drug Targets, 2006, pp. 3-16, vol. 6(1).

Lin, Kai et al., "Combination of Hepatitis C Virus NS3-NS4A protease inhibitor and alpha interferon synergistically inhibits viral RNA replication and facilities viral RNA clearance in replicon cells", Antimicrobial Agents and Chemotherapy, 2004, pp. 4784-4792, vol. 48(12).

Liu, Rang et al., "In vitro antiviral activity of SCH446211 (SCH6), a novel inhibitor of the hepatitis C virus NS3 serine protease", Journal of Antimicrobial Chemotherapy, 2007, pp. 51-58, vol. 59(1).

Llinas-Brunet, Montse et al. "A systematic approach to the optimization of substrate-based inhibitors of the hepatitis C virus NS3 protease: discovery of potent and specific tripeptide inhibitors", Journal of Medicinal Chemistry, 2004, pp. 6584-6594, vol. 47(26).

Llinas-Brunet, Montse et al.; "Structure-Activity Study on a Novel Series of Macrocyclic Inhibitors of the Hepatitis C Virus NS3 Protease Leading to the Discovery of BILN 2061", Journal of Medicinal Chemistry, 2004, pp. 1605-1608, vol. 47(7).

Malancona, Savina et al. "SAR and pharmacokinetic studies on penethylamide inhibitors of the hepatitis C virus NS3/NS4A serine protease", Bioorganic & Medicinal chemistry Letters, 2004, pp. 4575-4579, vol. 14(17).

Malcolm et al; "SCH 503034, a Mechanism-Based Inhibitor of Hepatitis C Virus NS3 Protease, Suppresses Polyprotein Maturation and Enhances the Antiviral Activity of Alpha Interferon in Replicon Cells"; Antimicrobial Agents and Chemotherapy 50(3):1013-1020 (2006).

Perni, Robert B. et al. "Inhibitors of hepatitis C virus NS3-4A protease 2. Warhead SAR and optimization" Biorganic & medicinal Chemistry Letters, 2004, pp. 1441-1446, vol. 14(6).

Perni, Robert B. et al., "Inhibitors of Hepatitis C virus NS3-4A protease. Effect of P4 capping groups on inhibitory potency and pharmacokinetics", Bioorganic and Medicinal Chemistry Letters, 2007, pp. 3406-3411, vol. 17(12).

Perni, Robert B. et al., "Inhibitors of hepatitis C virus NS3-4A protease 1. Non-charged tetrapeptide variants", Bioorganic & Medicinal Chemistry Letters, 2003, pp. 4059-4063, vol. 13(22).

Prongay, Andrew J. et al, "Discovery of the HCV NS3/4A Protease Inhibitor (1R,5S)-N[3-amino-1-(cyclobutylmethyl)-2,3-dioxopropyl]-3-[2(S)-[[[(1,1-dimethylethyl)amono]carbonyl]amino'-3,3-dimethyl-1-oxobutyl]--6,6-dimethyl-3-azahicyclo[3.1.0]hexan-2(s)-carboxamide (Sch503034). Key steps in structure-based optimization," Journal of Medicinal Chemistry, 2007, pp. 2310-2318, vol. 50(10).

Rönn, Robert et al. "Exploration of acyl sulfonamides as carboxylic acid replacements in protease inhibitors of the hepatitis C virus full-length NS3", Biorganic & Medicinal Chemistry, 2006. pp. 544-559, vol. 14(2).

Thomson, John A. et al., "Hepatitis C virus NS3.4A protease inhibitors: countering viral subversion in vitro and showing promise in the clinic", Current Opinion in Drug Discovery & Development,2006, pp. 606-617, vol. 9(5).

Tsantrizos, Youla et al. "Olefin ring-closing metathesis as a powerful tool in drug discovery and development-potent macrocyclic inhibitors of the hepatitis C virus NS3 protease" Journal of Organometallic Chemistry, 2006, pp. 5163-5171, vol. 691 (24-25).

(56) References Cited

OTHER PUBLICATIONS

Tsantrizos, Youla S. et al. "Macrocyclic inhibitors of the NS3 protease as potential therapeutic agents of hepatitis C virus infection", Angewandte chemie, International Edition, 2003, pp. 1356-1360, vol. 42(12).

Velazquez, Francisco et al., "Application of ring-closing metathesis for the synthesis of macrocyclic peptidomimetics as inhibitors of HCV NS3 protease", Organic Letters, 2007, pp. 3061-3064, vol. 9(16).

Venkatraman, Srikanth et al. "Design and synthesis of depeptidized macrocyclic inhibitors of hepatitis C NS3-4A Protease Using structure-based drug design" Journal Medicinal Chemistry, 2005, pp. 5088-5091, vol. 48(16).

Venkatraman, Srikanth et al., "Discovery of (1R,5S)-N-[3-Amino-1-(cyclobutylmethyl)-2,3-dioxopropyl]-3-[2(S)-[[[(1,1-dimethylethyl)amino]carbonyl]amino]-3,3-dimethyl-1-oxobutyl]-6,6-dimethyl-3-azabicyclo[3.1.0]hexan-2(S)-carboxamide(SCH 503034), a selective, potent, orally bioavailable hepatitis C virus NS3 Protease inhibitor: a potential therapeutic agent for the treatment of hepatitis C infection", Journal of Medicinal Chemistry, 2006, pp. 6074-6086, vol. 49(20).

Venkatraman, Srikanth et al., "Novel inhibitors of hepatitis C NS3-NS4A serine protease derived from 2-aza-bicyclo [2.2.1]heptane-3-carboxylic acid", Medicinal Chemistry Letters, 2006, pp. 1628-1632, vol. 16(6).

Yee, Nathan K. et al. "Efficient Large-Scale Synthesis of BILN 2061 a potent HCV protease inhibitor by a convergent approach based on ring-closing metathesis", 2006, Journal of Organic Chemistry, pp. 7133-7145, vol. 71(19).

PEPTIDOMIMETIC SULFAMIDE COMPOUNDS AND ANTIVIRAL USES THEREOF

This application is a Continuation Application of Ser. No. 12/755,852, filed Apr. 7, 2010, which claims benefit under 35 U.S.C. §119(e) of U.S. Provisional Application No. 61/168,408, filed Apr. 10, 2009, and U.S. Provisional Application No. 61/181,038, filed May 26, 2009, the contents of which are incorporated herein by reference in their entirety.

BACKGROUND

Chronic hepatitis C virus (HCV) infection is a major global health burden, with an estimated 170 million people infected worldwide and an additional 3 to 4 million infected each year (See e.g. World Health Organization Fact Sheet No. 164. October 2000). Although 25% of new infections are symptomatic, 60-80% of patients will develop chronic liver disease, of whom an estimated 20% will progress to cirrhosis with a 1-4% annual risk of developing hepatocellular carcinoma (See e.g. World Health Organization Guide on Hepatitis C. 2002; Pawlotsky, J-M. (2006) Therapy of Hepatitis C: From Empiricism to Eradication. Hepatology 43:S207-S220). Overall, HCV is responsible for 50-76% of all liver cancer cases and two thirds of all liver transplants in the developed world (See e.g. World Health Organization Guide on Viral Cancers. 2006). And ultimately, 5-7% of infected patients will die from the consequences of HCV infection (See e.g. World Health Organization Guide on Hepatitis C. 2002).

The current standard therapy for HCV infection is pegylated interferon alpha (IFN-α) in combination with ribavirin. However, only up to 50% of patients with genotype 1 virus can be successfully treated with this interferon-based therapy. Moreover, both interferon and ribavirin can induce significant adverse effects, ranging from flu-like symptoms (fever and fatigue), hematologic complications (leukopenia, thrombocytopenia), neuropsychiatric issues (depression, insomnia, irritability), weight loss, and autoimmune dysfunctions (hypothyroidism, diabetes) from treatment with interferon to significant hemolytic anemia from treatment with ribavirin. Therefore, more effective and better tolerated drugs are still greatly needed.

NS3, an approximately 70 kDa protein, has two distinct domains: a N-terminal serine protease domain of 180 amino acids (AA) and a C-terminal helicase/NTPase domain (AA 181 to 631). The NS3 protease is considered a member of the chymotrypsin family because of similarities in protein sequence, overall three-dimensional structure and mechanism of catalysis. The HCV NS3 serine protease is responsible for proteolytic cleavage of the polyprotein at the NS3/NS4A, NS4A/NS4B, NS4B/NS5A and NS5A/NS5B junctions (See e.g. Bartenschlager, R., L. et al. (1993) J. Virol. 67:3835-3844; Grakoui, A. et al. (1993) J. Virol. 67:2832-2843; Tomei, L. et al. (1993) J. Virol. 67:4017-4026). NS4A, an approximately 6 kDa protein of 54 AA, is a co-factor for the serine protease activity of NS3 (See e.g. Failla, C. et al. (1994) J. Virol. 68:3753-3760; Tanji, Y. et al. (1995) J. Virol. 69:1575-1581). Autocleavage of the NS3/NS4A junction by the NS3/NS4A serine protease occurs intramolecularly (i.e., cis) while the other cleavage sites are processed intermolecularly (i.e., trans). It has been demonstrated that HCV NS3 protease is essential for viral replication and thus represents an attractive target for antiviral chemotherapy.

There remains a need for new treatments and therapies for HCV infection, as well as HCV-associated disorders. There is also a need for compounds useful in the treatment or prevention or amelioration of one or more symptoms of HCV, as well as a need for methods of treatment or prevention or amelioration of one or more symptoms of HCV. Furthermore, there is a need for new compounds capable of modulating the activity of HCV-serine proteases, particularly the HCV NS3/NS4a serine protease and using said compounds to treat, prevent or ameliorate HCV infection.

SUMMARY OF THE INVENTION

In one aspect, the invention provides compounds of Formula I:

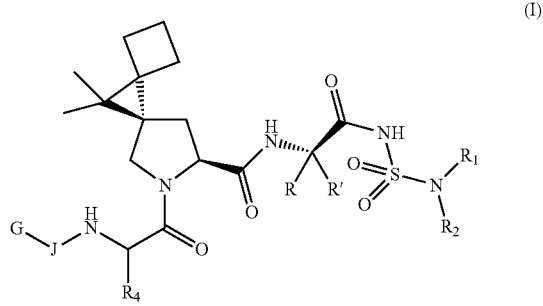

and isomers and pharmaceutically acceptable salts, hydrates, and solvates thereof.

In one embodiment, the invention provides a method of treating an HCV-associated disorder comprising administering to a subject in need thereof a pharmaceutically acceptable amount of a compound of the invention, such that the HCV-associated disorder is treated.

In another embodiment, the invention provides a method of treating an HIV infection comprising administering to a subject in need thereof a pharmaceutically acceptable amount of a compound of the invention.

In still another embodiment, the invention provides a method of treating, inhibiting or preventing the activity of HCV in a subject in need thereof, comprising administering to the subject a pharmaceutically acceptable amount of a compound of the invention. In one embodiment, the compounds of the invention inhibit the activity of the NS2 protease, the NS3 protease, the NS3 helicase, the NS5a protein, and/or the NS5b polymerase. In another embodiment, the interaction between the NS3 protease and NS4A cofactor is disrupted. In yet another embodiment, the compounds of the invention prevent or alter the severing of one or more of the NS4A-NS4B, NS4B-NS5A and NS5A-NS5B junctions of the HCV. In another embodiment, the invention provides a method of inhibiting the activity of a serine protease, comprising the step of contacting said serine protease with a compound of the invention. In another embodiment, the invention provides a method of treating, inhibiting or preventing the activity of HCV in a subject in need thereof, comprising administering to the subject a pharmaceutically acceptable amount of a compound of the invention, wherein the compound interacts with any target in the HCV life cycle. In one embodiment, the target of the HCV life cycle is selected from the group consisting of NS2 protease, NS3 protease, NS3 helicase, NS5a protein and NS5b polymerase.

In another embodiment, the invention provides a method of decreasing the HCV RNA load in a subject in need thereof comprising administering to the subject a pharmaceutically acceptable amount of a compound of the invention.

In another embodiment, the compounds of the invention exhibit HCV protease activity. In one embodiment, the compounds are an HCV NS3-4A protease inhibitor.

In another embodiment, the invention provides a method of treating an HCV-associated disorder in a subject, comprising administering to a subject in need thereof a pharmaceutically acceptable amount of a compound of the invention, and a pharmaceutically acceptable carrier, such that the HCV-associated disorder is treated.

In still another embodiment, the invention provides a method of treating an HCV-associated disorder comprising administering to a subject in need thereof a pharmaceutically effective amount of a compound of the invention, in combination with a pharmaceutically effective amount of an additional HCV-modulating compound, such as interferon or derivatized interferon, or a cytochrome P450 monooxygenase inhibitor, such that the HCV-associated disorder is treated. In one embodiment, the additional HCV-modulating compound is selected from the group consisting of NIM811, ITMN191, MK-7009, TMC 435350, Sch 503034 and VX-950.

In another embodiment, the invention provides a method of inhibiting hepatitis C virus replication in a cell, comprising contacting said cell with a compound of the invention.

In yet another embodiment, the invention provides a packaged HCV-associated disorder treatment, comprising an HCV-modulating compound of the invention, packaged with instructions for using an effective amount of the HCV-modulating compound to treat an HCV-associated disorder.

In certain embodiments, the HCV-associated disorder is selected from the group consisting of HCV infection, liver cirrhosis, chronic liver disease, hepatocellular carcinoma, cryoglobulinaemia, non-Hodgkin's lymphoma, liver fibrosis and a suppressed innate intracellular immune response.

In another embodiment, the invention provides a method of treating HCV infection, liver cirrhosis, chronic liver disease, hepatocellular carcinoma, cryoglobulinaemia, non-Hodgkin's lymphoma, liver fibrosis and/or a suppressed innate intracellular immune response in subject in need thereof comprising administering to the subject a pharmaceutically acceptable amount of a compound of the invention.

In one embodiment, the HCV to be treated is selected of any HCV genotype. In another embodiment, the HCV is selected from HCV genotype 1, 2 and/or 3.

Various embodiments of the invention are described herein. It will be recognized that features specified in each embodiment may be combined with other specified features to provide further embodiments.

Other aspects of the invention are discussed infra.

DETAILED DESCRIPTION OF THE INVENTION

This invention is directed to compounds, e.g., peptide compounds, and intermediates thereto, as well as pharmaceutical compositions containing the compounds for use in treatment of HCV infection. This invention is also directed to the compounds of the invention or compositions thereof as protease inhibitors, particularly as serine protease inhibitors, and more particularly as HCV NS3 protease inhibitors. The compounds are particularly useful in interfering with the life cycle of the hepatitis C virus and in treating or preventing an HCV infection or physiological conditions associated therewith. The present invention is also directed to methods of combination therapy for inhibiting HCV replication in cells, or for treating or preventing an HCV infection in patients using the compounds of the invention or pharmaceutical compositions, or kits thereof.

Certain compounds of the instant invention include those compounds of Formula (I):

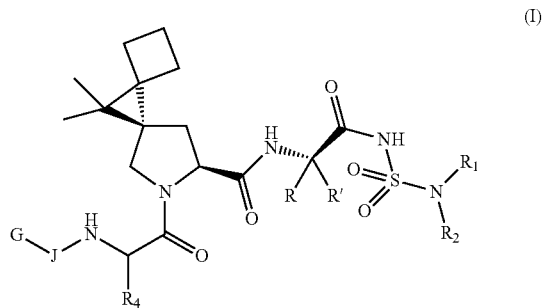

(I)

and pharmaceutically acceptable salts and stereoisomers thereof;

wherein

R is $C_1$-$C_6$alkyl, $C_2$-$C_6$alkenyl or $C_3$-$C_7$cycloalkyl$C_0$-$C_4$alkyl;

R' is hydrogen or $C_1$-$C_6$alkyl; or

R and R', together with the carbon atom to which they are attached, form a three to seven member carbocycle which is saturated or partially unsaturated, which carbocycle is substituted with 0, 1, 2, or 3 residues independently selected from the group consisting of $C_1$-$C_6$alkyl, $C_2$-$C_6$alkenyl, $C_1$-$C_4$alkylidenyl, and $C_3$-$C_7$cycloalkyl$C_0$-$C_4$alkyl;

$R_1$ and $R_2$ are independently hydrogen or are independently selected from the group consisting of $C_1$-$C_6$alkyl, $C_1$-$C_6$alkoxy and $C_3$-$C_7$cycloalkyl$C_0$-$C_2$alkyl, each of which is substituted with 0, 1, or 2 residues selected from halogen and $C_1$-$C_4$alkyl; or $R_1$ and $R_2$, taken in combination with the N to which they are attached, form a saturated, unsaturated or aromatic heterocyclic ring having 0, 1, or 2 additional ring heteroatoms independently selected from N, O, or S and which heterocyclic ring has from 4 to 7 total ring atoms, said heterocycle having 0, 1, 2, or 3 substituents which are independently selected from $C_1$-$C_4$alkyl, halo $C_1$-$C_4$alkyl, $C_2$-$C_4$alkenyl, $C_2$-$C_4$alkynyl, hydroxyl, $C_1$-$C_4$alkoxy, halo$C_1$-$C_4$alkoxy, amino, mono- and di-$C_{1-4}$alkylamino, $C_1$-$C_4$alkanoylamino$C_1$-$C_4$alkyl;

$R_4$ is $C_1$-$C_8$alkyl, $C_3$-$C_8$cycloalkyl, or saturated 5 or 6 membered heterocyclic ring having 1 or 2 ring heteroatoms independently selected from N, O or S, each of which is substituted with 0-2$C_1$-$C_4$alkyl groups;

J is a bond or a divalent residue of the formula:

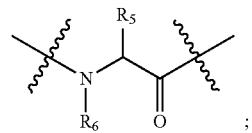

;

$R_5$ is $C_1$-$C_8$alkyl, $C_3$-$C_8$cycloalkyl, or saturated 5 or 6 membered heterocyclic ring having 1 or 2 ring heteroatoms independently selected from N, O or S, each of which is substituted with 0-2$C_1$-$C_4$alkyl groups;

$R_6$ is hydrogen or $C_1$-$C_4$alkyl;

G is a group of the formula -E-$R_7$;

E is a bond, $CH_2$, $C(O)$, $S(O)_2$, $C(R_9)_2C(O)$, or $C(O)C(R_9)_2$,

R$_7$ is selected from the group consisting of C$_1$-C$_6$alkyl, haloC$_1$-C$_6$alkyl, C$_3$-C$_7$cycloalkylC$_0$-C$_2$alkyl, C$_1$-C$_6$alkoxy, haloC$_1$-C$_6$alkoxy, C$_3$-C$_7$cycloalkylC$_0$-C$_2$alkoxy, mono- and di-C$_1$-C$_6$alkylamino, —S(O)$_2$R$_{10}$, —N(R$_9$)S(O)$_2$R$_{10}$, monocyclic or bicyclic heterocycle, and monocyclic or bicyclic aryl, wherein each residue is unsubstituted or substituted with 1, 2, or 3 R$_8$ groups each of which R$_8$ residues is independently selected from the group consisting of C$_1$-C$_6$alkyl, and C$_1$-C$_6$alkanoyl; or R$_6$ and R$_7$, taken in combination with the N atom to which they are attached, forms a 4 to 7 membered heterocyclic ring having 0, 1, or 2 additional ring heteroatoms selected from N, O or S and which ring is substituted by 0, 1, 2 or 3 substituents which are independently selected from the group consisting of oxo, C$_1$-C$_4$alkyl, halo C$_1$-C$_4$alkyl, C$_2$-C$_4$alkenyl, C$_2$-C$_4$alkynyl, hydroxyl, C$_1$-C$_4$alkoxy, haloC$_1$-C$_4$alkoxy, amino, mono- and di-C$_1$-$_4$alkylamino, aminoC$_1$-C$_4$alkyl, C$_1$-C$_4$alkanoylaminoC$_1$-C$_4$alkyl;

R$_9$ is independently selected at each occurrence from hydrogen and C$_1$-C$_4$alkyl;

R$_{10}$ is C$_1$-C$_6$alkyl, amino or mono- and di-C$_1$-C$_6$alkylamino; and pharmaceutically acceptable salts, hydrates, and solvates thereof.

Certain compounds of Formula I provided by the invention include compounds of Formula (II):

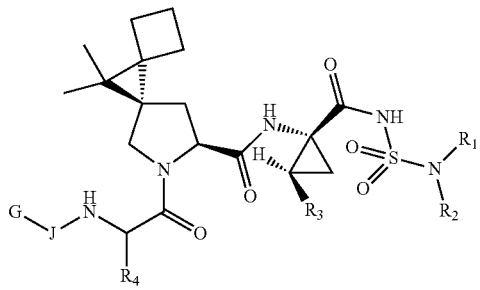

(II)

wherein R$_3$ is C$_1$-C$_6$alkyl or C$_2$-C$_6$alkenyl.

Certain other compounds of Formula I or Formula II provided by the invention include compounds of Formula (III):

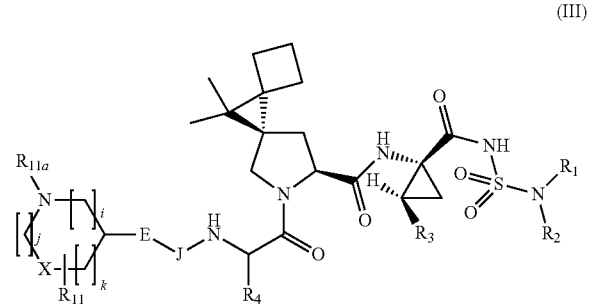

(III)

and pharmaceutically acceptable salts and stereoisomers thereof;
wherein
X is absent or selected from NR$^{11a}$ or oxygen;
i and k are independently selected integers selected from the group consisting of 0, 1, 2, 3 and 4;
j is an integer selected from the group consisting of 1, 2, 3 and 4, wherein the sum of i+j+k is less than or equal to 5 and greater than or equal to 2 when X is absent and the sum of i+j+k is less than or equal to 4 and greater than or equal to 1 when X is oxygen;

R$^{11}$ represents zero to three residues each independently selected at each occurrence from the group consisting of halogen, hydroxy, amino, C$_{1-4}$alkyl, C$_{3-6}$cycloalkyl, C$_{1-4}$alkoxy, mono- and di-C$_{1-4}$alkylamino, hydroxyC$_{1-4}$alkyl, and C$_{1-4}$alkoxyC$_{1-4}$alkyl; and R$^{11a}$ is independently selected at each occurrence from the group consisting of hydrogen, C$_{1-4}$alkyl, haloC$_{1-4}$alkyl, C$_{3-6}$cycloalkyl, hydroxyC$_{1-4}$alkyl, and C$_{1-4}$alkoxyC$_{1-4}$alkyl.

Certain compounds of Formula I, II or III provided by the invention include compounds of Formula (IV):

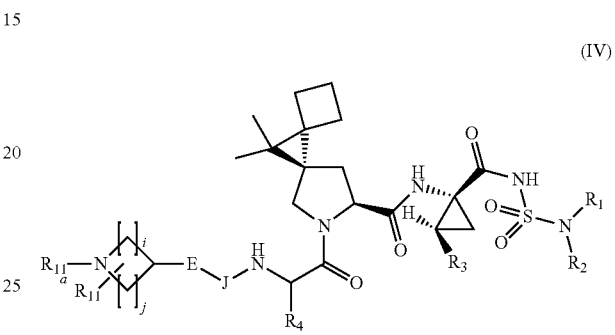

(IV)

and pharmaceutically acceptable salts and stereoisomers thereof;
wherein
i is an integer selected from the group consisting of 0, 1, 2, 3 and 4;
j is an integer selected from the group consisting of 1, 2, 3 and 4, wherein the sum of i+j is less than or equal to 5 and greater than or equal to 2;

represents zero to three residues each independently selected at each occurrence from the group consisting of halogen, hydroxy, amino, C$_{1-4}$alkyl, C$_{3-6}$cycloalkyl, C$_{1-4}$alkoxy, mono- and di-C$_{1-4}$alkylamino, hydroxyC$_{1-4}$alkyl, and C$_{1-4}$alkoxyC$_{1-4}$alkyl; and R$^{11a}$ is independently selected at each occurrence from the group consisting of hydrogen, C$_{1-4}$alkyl, haloC$_{1-4}$alkyl, C$_{3-6}$cycloalkyl, hydroxyC$_{1-4}$alkyl, and C$_{1-4}$alkoxyC$_{1-4}$alkyl.

Certain other compounds of Formula I, II, III, or IV provided by the invention include compounds of Formula (V):

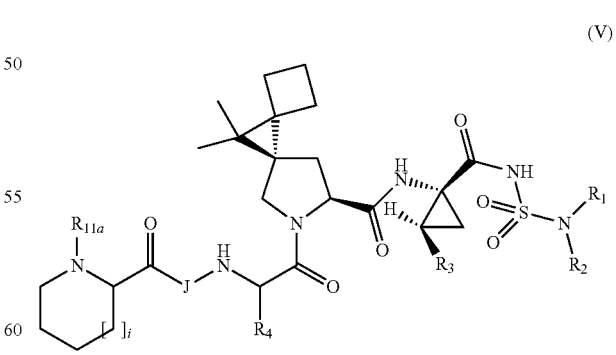

(V)

and pharmaceutically acceptable salts and stereoisomers thereof;
wherein
i is 0 or 1; and
R$^{11a}$ is hydrogen or C$_{1-4}$alkyl.

In certain compounds of Formula I, II, III, IV, or V provided by the invention, residue J is a divalent residue of the formula:

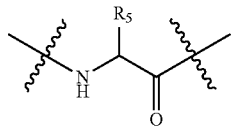

wherein $R_5$ is $C_1$-$C_6$alkyl, $C_4$-$C_7$cycloalkyl, or saturated 5 or 6 membered heterocyclic ring having 1 or 2 ring heteroatoms independently selected from N, O or S, each of which is substituted with 0-2$C_1$-$C_4$ alkyl groups.

Certain other compounds of Formula I, II, III, IV or V provided by the invention include compounds of Formula (VI):

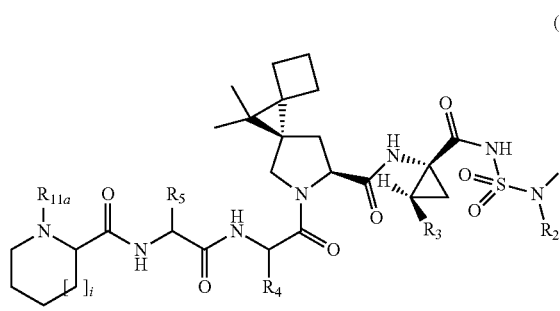

(VI)

wherein $R_1$ and $R_2$ are independently selected from $C_1C_4$alkyl, $C_3$-$C_6$cycloalkyl, cyclopropylmethyl, and halo$C_1$-$C_4$alkyl, or $R_1$, $R_2$ and the nitrogen atom to which they are attached form a pyrrolidinyl ring, a piperidinyl ring or a morpholinyl ring. In certain other compounds of Formula VI, $R_1$ and $R_2$ are ethyl-$d_5$, or $R_1$, $R_2$ and the nitrogen atom to which they are attached form pyrrolidinyl-$d_8$;

$R_3$ is ethyl or vinyl;

$R_4$ and $R_5$ are independently selected from the group consisting of tert-butyl, cyclohexyl, 1-methyl-cyclohexyl, tetrahydropyran-4-yl and 1-methyl-tetrahydropyran-4-yl;

$R_{11a}$ is selected from $C_1$-$C_4$ alkyl, or $R_{11a}$ is ethyl, isopropyl, ethyl-$d_5$, or isopropyl-$d_5$; and i is 0 or 1.

In certain compounds of Formula I, II, III, IV, or V provided by the invention, residues $R_4$ and $R_5$ are independently selected from the group consisting of tert-butyl, cyclohexyl, 1-methyl-cyclohexyl, tetrahydropyran-4-yl and 1-methyl-tetrahydropyran-4-yl.

Certain compounds of Formula I, II, III, IV, or V provided by the invention, include those compounds in which $R_1$ and $R_2$ are independently selected from the group consisting of hydrogen, $C_1$-$C_6$alkyl, and $C_3$-$C_7$cycloalkyl$C_0$-$C_2$alkyl, or $R_1$ and $R_2$, taken in combination with the N to which they are attached, form a saturated, unsaturated or aromatic heterocyclic ring having 0, 1, or 2 additional ring heteroatoms independently selected from N, O, or S and which heterocyclic ring has from 4 to 7 total ring atoms, said heterocycle having 0, 1, 2, or 3 substituents which are independently selected from $C_1$-$C_4$alkyl, halo $C_1$-$C_4$alkyl, $C_2$-$C_4$alkenyl, $C_2$-$C_4$alkynyl, hydroxyl, $C_1$-$C_4$alkoxy, halo$C_1$-$C_4$alkoxy, amino, mono- and di-$C_{1-4}$alkylamino, amino$C_1$-$C_4$alkyl, $C_1$-$C_4$alkanoylamino$C_1$-$C_4$alkyl.

Certain compounds of Formula I, II, III, IV, or V provided by the invention, include those compounds in which $R_1$ and $R_2$ are independently selected from the group consisting of $C_1$-$C_4$alkyl, $C_1$-$C_3$alkyl substituted with one or more fluorine atoms, $C_3$-$C_6$cycloalkyl and cyclopropylmethyl; or $R_1$, $R_2$ and the nitrogen atom to which they are attached form a pyrrolidinyl ring, a piperidinyl ring or a morpholinyl ring. In certain other compounds of Formula I, II, III, IV or V, $R_1$ and $R_2$ are independently selected from methyl, ethyl, ethyl-$d_5$, propyl, isopropyl, isopropyl-$d_7$, or tert-butyl; or $R_1$, $R_2$ and the nitrogen atom to which they are attached form a pyrrolidinyl ring or an octa-deutero-pyrrolidinyl ring, Certain compounds of Formula I provided by the invention, include those compounds in which R is $C_1$-$C_6$alkyl, $C_2$-$C_4$alkenyl or $C_3$-$C_6$cycloalkyl$C_0$-$C_2$alkyl;

R' is hydrogen or $C_1$-$C_4$alkyl; or

R and R', together with the carbon atom to which they are attached, form a cyclopropyl ring, which is substituted with 0 or 1 residues selected from the group consisting of $C_1$-$C_4$alkyl, $C_2$-$C_4$alkenyl, methylidene, and $C_3$-$C_6$cycloalkyl$C_0$-$C_2$alkyl.

In certain compounds of Formula III, IV, or V provided by the invention, residue $R_{11a}$ is selected from the group consisting of $C_1$-$C_4$alkyl and perdeutero$C_1$-$C_4$alkyl. Still other compounds of Formula III, IV or V include those compounds in which $R_{11a}$ is selected from the group consisting of ethyl, ethyl-$d_5$, isopropyl and isopropyl-$d_7$.

Preferred embodiments of the compounds of the invention (including pharmaceutically acceptable salts thereof, as well as enantiomers, stereoisomers, rotamers, tautomers, diastereomers, or racemates thereof) are provided in Examples 1-19 and in Tables A and Table B, and are also considered to be "compounds of the invention." Certain preferred compounds of the invention include but are not limited to:

(5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide;

(5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide;

(5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide;

(5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide;

(5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-10,10-dimethyl-N-{(1R,2S)-1-[(piperidin-1-ylsulfonyl)carbamoyl]-2-vinylcyclopropyl}-7-azadispiro[3.0.4.1]decane-8-carboxamide;

(5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide;

(5R,8S)-7-[(2S)-2-({cyclohexyl[(pyridin-4-ylacetyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide;

(5R)-7-[(2S)-2-[(N-{[(2S)-1-isopropylpiperidin-2-yl]carbonyl}-3-methyl-L-valyl)amino]-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide;
(5R,8S)-7-[(2S)-2-{[(2S)-2-cyclohexyl-2-({[(2S)-1-ethylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide; and
(5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide.

Using the HCV NS3-4A protease and Luciferase-HCV replicon assays described in the exemplification section below, the compounds of the invention are found to show $IC_{50}$ values for HCV inhibition in the range from 0.1 to more than 100 nM, or 0.5 to 30 nM, including, for example, the range from 0.5 to 10 nM or less.

In certain embodiments, a compound of the present invention is further characterized as a modulator of HCV, including a mammalian HCV, and especially including a human HCV. In a preferred embodiment, the compound of the invention is an HCV inhibitor.

The terms "HCV-associated state" or "HCV-associated disorder" include disorders and states (e.g., a disease state) that are associated with the activity of HCV, e.g., infection of HCV in a subject. HCV-associated states include HCV-infection, liver cirrhosis, chronic liver disease, hepatocellular carcinoma, cryoglobulinaemia, non-Hodgkin's lymphoma, liver fibrosis and a suppressed innate intracellular immune response.

HCV-associated states are often associated with the NS3 serine protease of HCV, which is responsible for several steps in the processing of the HCV polyprotein into smaller functional proteins. NS3 protease forms a heterodimeric complex with the NS4A protein, an essential cofactor that enhances enzymatic activity, and is believed to help anchor HCV to the endoplasmic reticulum. NS3 first autocatalyzes hydrolysis of the NS3-NS4A juncture, and then cleaves the HCV polyprotein intermolecularly at the NS4A-NS4B, NS4B-NS5A and NS5A-NS5B intersections. This process is associated with replication of HCV in a subject. Inhibiting or modulating the activity of one or more of the NS3, NS4A, NS4B, NS5A and NS5B proteins will inhibit or modulate replication of HCV in a subject, thereby preventing or treating the HCV-associated state. In a particular embodiment, the HCV-associated state is associated with the activity of the NS3 protease. In another particular embodiment, the HCV-associated state is associated with the activity of NS3-NS4A heterodimeric complex.

In one embodiment, the compounds of the invention are NS3/NS4A protease inhibitors. In another embodiment, the compounds of the invention are NS2/NS3 protease inhibitors.

Without being bound by theory, it is believed that the disruption of the above protein-protein interactions by the compounds of the invention will interfere with viral polyprotein processing by the NS3 protease and thus viral replication.

HCV-associated disorders also include HCV-dependent diseases. HCV-dependent diseases include, e.g., any disease or disorder that depend on or related to activity or misregulation of at least one strain of HCV.

The present invention includes treatment of HCV-associated disorders as described above, but the invention is not intended to be limited to the manner by which the compound performs its intended function of treatment of a disease. The present invention includes treatment of diseases described herein in any manner that allows treatment to occur, e.g., HCV infection.

In a related embodiment, the compounds of the invention can be useful for treating diseases related to HIV, as well as HIV infection and AIDS (Acquired Immune Deficiency Syndrome).

In certain embodiments, the invention provides a pharmaceutical composition of any of the compounds of the present invention. In a related embodiment, the invention provides a pharmaceutical composition of any of the compounds of the present invention and a pharmaceutically acceptable carrier or excipient of any of these compounds. In certain embodiments, the invention includes the compounds as novel chemical entities.

In one embodiment, the invention includes a packaged HCV-associated disorder treatment. The packaged treatment includes a compound of the invention packaged with instructions for using an effective amount of the compound of the invention for an intended use.

The compounds of the present invention are suitable as active agents in pharmaceutical compositions that are efficacious particularly for treating HCV-associated disorders. The pharmaceutical composition in various embodiments has a pharmaceutically effective amount of the present active agent along with other pharmaceutically acceptable excipients, carriers, fillers, diluents and the like. The phrase, "pharmaceutically effective amount" as used herein indicates an amount necessary to administer to a host, or to a cell, issue, or organ of a host, to achieve a therapeutic result, especially an anti-HCV effect, e.g., inhibition of proliferation of the HCV virus, or of any other HCV-associated disease.

In one embodiment, the diseases to be treated by compounds of the invention include, for example, HCV infection, liver cirrhosis, chronic liver disease, hepatocellular carcinoma, cryoglobulinaemia, non-Hodgkin's lymphoma, liver fibrosis and a suppressed innate intracellular immune response.

In other embodiments, the present invention provides a method for inhibiting the activity of HCV. The method includes contacting a cell with any of the compounds of the present invention. In a related embodiment, the method further provides that the compound is present in an amount effective to selectively inhibit the activity of one or more of the NS3, NS4A, NS4B, NS5A and NS5B proteins. In another related embodiment, the method provides that the compound is present in an amount effective to diminish the HCV RNA load in a subject.

In other embodiments, the present invention provides a use of any of the compounds of the invention for manufacture of a medicament to treat HCV infection in a subject.

In other embodiments, the invention provides a method of manufacture of a medicament, including formulating any of the compounds of the present invention for treatment of a subject.

DEFINITIONS

The term "treat," "treated," "treating" or "treatment" includes the diminishment or alleviation of at least one symptom associated or caused by the state, disorder or disease being treated. In certain embodiments, the treatment comprises the induction of an HCV-inhibited state, followed by the activation of the HCV-modulating compound, which would in turn diminish or alleviate at least one symptom associated or caused by the HCV-associated state, disorder or disease being treated. For example, treatment can be diminishment of one or several symptoms of a disorder or complete eradication of a disorder.

The term "subject" is intended to include organisms, e.g., prokaryotes and eukaryotes, which are capable of suffering from or afflicted with an HCV-associated disorder. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from an HCV-associated disorder, and for diseases or conditions described herein, e.g., HCV infection. In another embodiment, the subject is a cell.

The language "HCV-modulating compound," "modulator of HCV" or "HCV inhibitor" refers to compounds that modulate, e.g., inhibit, or otherwise alter, the activity of HCV. Similarly, an "NS3/NS4A protease inhibitor," or an "NS2/NS3 protease inhibitor" refers to a compound that modulates, e.g., inhibits, or otherwise alters, the interaction of these proteases with one another. Examples of HCV-modulating compounds include compounds of Formula I, subformulae thereof, as well as compounds of Examples 1-19 and Tables A and B (including pharmaceutically acceptable salts thereof, as well as enantiomers, stereoisomers, rotamers, tautomers, diastereomers, or racemates thereof).

Additionally, the method includes administering to a subject an effective amount of an HCV-modulating compound of the invention, e.g., HCV-modulating compounds of Formula I or Formula III, as well as Table A (including salts thereof, e.g., pharmaceutically acceptable salts thereof, as well as enantiomers, stereoisomers, rotamers, tautomers, diastereomers, or racemates thereof).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

It is understood that in all substituted groups defined above, polymers arrived at by defining substituents with further substituents to themselves are not intended for inclusion herein. In such cases, the maximum number of such substitutions is three. For example, serial substitutions of substituted aryl groups with two other substituted aryl groups are limited to—substituted aryl-(substituted aryl)-substituted aryl.

Similarly, it is understood that the above definitions are not intended to include impermissible substitution patterns (e.g., methyl substituted with 5 fluoro groups). Such impermissible substitution patterns are well known to the skilled artisan.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl, isobutyl and sec-butyl. Moreover, the term $C_{3-6}$-cycloalkyl includes, but is not limited to, cyclopropyl, cyclopentyl, and cyclohexyl. As discussed below, these alkyl groups, as well as cycloalkyl groups, may be further substituted. "$C_0$-$C_n$alkyl" refers to a single covalent bond (Co) or an alkyl group having from 1 to n carbon atoms; for example "$C_0$-$C_4$alkyl" refers to a single covalent bond or a $C_1$-$C_4$alkyl group; "$C_0$-$C_8$alkyl" refers to a single covalent bond or a $C_1$-$C_8$alkyl group. In some instances, a substituent of an alkyl group is specifically indicated. For example, "$C_1$-$C_4$ hydroxyalkyl" refers to a $C_1$-$C_4$alkyl group that has at least one hydroxy substituent.

"Alkylene" refers to a divalent alkyl group, as defined above. $C_0$-$C_4$alkylene is a single covalent bond or an alkylene group having from 1 to 4 carbon atoms; and $C_0$-$C_6$alkylene is a single covalent bond or an alkylene group having from 1 to 6 carbon atoms.

A "cycloalkyl" is a group that comprises one or more saturated and/or partially saturated rings in which all ring members are carbon, such as cyclopropyl, cyclobutyl, cyclopentyl, cyclohexyl, cycloheptyl, cyclooctyl, adamantyl, decahydro-naphthalenyl, octahydro-indenyl, and partially saturated variants of the foregoing, such as cyclohexenyl. Cycloalkyl groups do not comprise an aromatic ring or a heterocyclic ring. Certain cycloalkyl groups are $C_3$-$C_8$cycloalkyl, in which the group contains a single ring with from 3 to 8 ring members. A "($C_3$-$C_8$cycloalkyl)$C_0$-$C_4$alkyl" is a $C_3$-$C_8$cycloalkyl group linked via a single covalent bond or a $C_1$-$C_4$alkylene group.

Moreover, alkyl (e.g., methyl, ethyl, propyl, butyl, pentyl, hexyl, etc.) include both "unsubstituted alkyl" and "substituted alkyl", the latter of which refers to alkyl moieties having substituents replacing a hydrogen on one or more carbons of the hydrocarbon backbone, which allow the molecule to perform its intended function.

The term "substituted" is intended to describe moieties having substituents replacing a hydrogen on one or more atoms, e.g. C, O or N, of a molecule. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperazine, cyclopentane, cyclohexane, pyridine, 5H-tetrazole, triazole, piperidine, or an aromatic or heteroaromatic moiety.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, (CR'R")$_{0-3}$NR'R" (e.g., —NH$_2$), (CR'R")$_{0-3}$CN (e.g., —CN), —NO$_2$, halogen (e.g., —F, —Cl, —Br, or —I), (CR'R")$_{0-3}$C(halogen)$_3$ (e.g., —CF$_3$), (CR'R")$_{0-3}$CH(halogen)$_2$, (CR'R")$_{0-3}$CH$_2$(halogen), (CR'R")$_{0-3}$CONR'R", (CR'R")$_{0-3}$(CNH)NR'R", (CR'R")$_{0-3}$S(O)$_{1-2}$NR'R", (CR'R")$_{0-3}$CHO, (CR'R")$_{0-30}$(CR'R")$_{0-3}$H, (CR'R")$_{0-3}$S(O)$_{0-3}$R' (e.g., —SO$_3$H, —OSO$_3$H), (CR'R")$_{0-3}$O(CR'R")$_{0-3}$H (e.g., —CH$_2$OCH$_3$ and —OCH$_3$), (CR'R")$_{0-3}$S(CR'R")$_{0-3}$H (e.g., —SH and —SCH$_3$), (CR'R")$_{0-3}$OH (e.g., —OH), (CR'R")$_{0-3}$COR', (CR'R")$_{0-3}$ (substituted or unsubstituted phenyl), (CR'R")$_{0-3}$ ($C_3$-$C_8$cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety (C=O) may be further derivatized with an oxime moiety, e.g., an aldehyde moiety may be derivatized as its oxime (—C=N—OH) analog. It will be understood by those skilled in the art that the moieties substituted on the hydrocarbon chain can themselves be substituted, if appropriate. Cycloalkyls can be further substituted, e.g., with the substituents described above. An "aralkyl" moiety is an alkyl substituted with an aryl (e.g., phenylmethyl (i.e., benzyl)).

The term "alkenyl" includes unsaturated aliphatic groups analogous in length and possible substitution to the alkyls described above, but which contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes aromatic groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

Certain aryl groups recited herein are $C_6$-$C_{10}$aryl$C_0$-$C_8$alkyl groups (i.e., groups in which a 6- to 10-membered carbocyclic group comprising at least one aromatic ring is linked via a single covalent bond or a $C_1$-$C_8$alkylene group). Such groups include, for example, phenyl and indanyl, as well as groups in which either of the foregoing is linked via $C_1$-$C_8$alkylene, preferably via $C_1$-$C_4$alkylene. Phenyl groups linked via a single covalent bond or $C_1$-$C_6$alkylene group are designated phenyl$C_0$-$C_6$alkyl (e.g., benzyl, 1-phenyl-ethyl, 1-phenyl-propyl and 2-phenyl-ethyl).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrathydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

A "heterocycle$C_0$-$C_8$alkyl" is a heterocyclic group linked via a single covalent bond or $C_1$-$C_8$alkylene group. A (4- to 7-membered heterocycle)$C_0$-$C_8$alkyl is a heterocyclic group (e.g., monocyclic or bicyclic) having from 4 to 7 ring members linked via a single covalent bond or an alkylene group having from 1 to 8 carbon atoms. A "(6-membered heteroaryl)$C_0$-$C_8$alkyl" refers to a heteroaryl group linked via a direct bond or $C_1$-$C_6$alkyl group.

The term "acyl" includes compounds and moieties which contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids, amides, esters, anhydrides, etc. The term "carboxy moiety" or "carbonyl moiety" refers to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus.

It is to be understood that all of the compounds of the invention described above will further include bonds between adjacent atoms and/or hydrogens as required to satisfy the valence of each atom. That is, bonds and/or hydrogen atoms are added to provide the following number of total bonds to each of the following types of atoms: carbon: four bonds; nitrogen: three bonds; oxygen: two bonds; and sulfur: two bonds.

Groups that are "optionally substituted" are unsubstituted or are substituted by other than hydrogen at one or more available positions, typically 1, 2, 3, 4 or 5 positions, by one or more suitable groups (which may be the same or different). Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substitutents).

It will also be noted that the substituents of some of the compounds of this invention include isomeric cyclic structures. It is to be understood accordingly that constitutional isomers of particular substituents are included within the scope of this invention, unless indicated otherwise. For example, the term "tetrazole" includes tetrazole, 2H-tetrazole, 3H-tetrazole, 4H-tetrazole and 5H-tetrazole.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)- isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisufate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, sodium, potassium, ammonium, calcium, magnesium, iron, silver, zinc, copper and the like; particularly preferred are the ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like, specifically such as, isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

The present invention includes all pharmaceutically acceptable isotopically-labeled compounds of the invention, i.e. compounds of formula (I), wherein (1) one or more atoms are replaced by atoms having the same atomic number, but an atomic mass or mass number different from the atomic mass or mass number usually found in nature, and/or (2) the isotopic ratio of one or more atoms is different from the naturally occurring ratio.

Examples of isotopes suitable for inclusion in the compounds of the invention comprises isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviating, inhibiting, preventing and/or ameliorating a condition, or a disorder or a disease (i) mediated by NS3/NS4 serine protease activity; or (2) reducing or inhibiting the activity of NS3 serine protease; or (3) reducing or inhibiting replication of at least one virus which encodes a NS3 serine protease. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting viral load and/or viral replication. The meaning of the term "a therapeutically effective amount" as illustrated in the above embodiment for NS3 protease also applies by the same means to any other relevant proteins/peptides/enzymes, such as NS2 protease, the NS3 protease, the NS3 helicase, the NS5a protein, and/or the NS5b polymerase, and the like.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a primate. In another preferred embodiment, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the -(amino, mono- or di-lower alkylamino, carboxy, lower alkoxycarbonyl)-lower alkyl esters, the -(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

In another aspect, the present invention provides a pharmaceutical composition comprising a compound of the present invention and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin, eyes and mucas membranes, include aqueous solutions, suspensions, ointments, creams, gels or sprayable formulations, e.g., for delivery by aerosol or the like. Such topical delivery systems will in particular be appropriate for vaginal application, e.g., for the prevention of HCV infection. Such may contain solubilizers, stabilizers, tonicity enhancing agents, buffers and preservatives.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by in vitro & in vivo methods including but not limited to the methods provided infra.

In one embodiment, the invention provides a pharmaceutical composition comprising a compound of formula (I) and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by NS3 protease activity, including but not limited to viral infections selected from HCV, HIV and the like, wherein the medicament is prepared for administration with another therapeutic agent. The invention also provides the use of another therapeutic agent for treating a disease or condition mediated by NS3 protease activity], wherein the medicament is administered with a compound of formula (I).

The invention also provides a compound of formula (I) for use in a method of treating a disease or condition mediated by NS3 protease activity, wherein the compound of formula (I) is prepared for administration with another therapeutic agent. The invention also provides another therapeutic agent for use in a method of treating a disease or condition mediated by NS3 protease activity, wherein the other therapeutic agent is prepared for administration with a compound of formula (I). The invention also provides a compound of formula (I) for use in a method of treating a disease or condition mediated by NS3 protease activity, wherein the compound of formula (I) is administered with another therapeutic agent. The invention also provides another therapeutic agent for use in a method of treating a disease or condition mediated by NS3 protease activity, wherein the other therapeutic agent is administered with a compound of formula (I).

The invention also provides the use of a compound of formula (I) for treating a viral infection, wherein the patient has previously (e.g. within 24 hours) been treated with another therapeutic agent. The invention also provides the use of another therapeutic agent for treating a viral, wherein the patient has previously (e.g. within 24 hours) been treated with a compound of formula (I).

In one embodiment, the other therapeutic agent is selected from:

A compound of the present invention may also be used in combination with other agents, e.g., an additional HCV-modulating compound that is or is not of the formula I, for treatment of and HCV-associated disorder in a subject.

By the term "combination", is meant either a fixed combination in one dosage unit form, or a kit of parts for the combined administration where a compound of the present invention and a combination partner may be administered independently at the same time or separately within time intervals that especially allow that the combination partners show a cooperative, e.g., synergistic, effect, or any combination thereof.

For example, WO 2005/042020, incorporated herein by reference in its entirety, describes the combination of various HCV inhibitors with a cytochrome P450 ("CYP") inhibitor. Any CYP inhibitor that improves the pharmacokinetics of the relevant NS3/4A protease may be used in combination with the compounds of this invention. These CYP inhibitors include, but are not limited to, ritonavir (WO 94/14436, incorporated herein by reference in its entirety), ketoconazole, troleandomycin, 4-methylpyrazole, cyclosporin, NIM811, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497.

Preferred CYP inhibitors include ritonavir, ketoconazole, troleandomycin, 4-methylpyrazole, cyclosporin, NIM811, and clomethiazole.

Methods for measuring the ability of a compound to inhibit CYP activity are known (see, e.g., U.S. Pat. No. 6,037,157 and Yun, et al. Drug Metabolism & Disposition, vol. 21, pp. 403-407 (1993); incorporated herein by reference). For example, a compound to be evaluated may be incubated with 0.1, 0.5, and 1.0 mg protein/ml, or other appropriate concentration of human hepatic microsomes (e.g., commercially available, pooled characterized hepatic microsomes) for 0, 5, 10, 20, and 30 minutes, or other appropriate times, in the presence of an NADPH-generating system. Control incubations may be performed in the absence of hepatic microsomes for 0 and 30 minutes (triplicate). The samples may be analyzed for the presence of the compound. Incubation conditions that produce a linear rate of compound metabolism will be used a guide for further studies. Experiments known in the art can be used to determine the kinetics of the compound metabolism ($K_m$ and $V_{max}$). The rate of disappearance of compound may be determined and the data analyzed according to Michaelis-Menten kinetics by using Lineweaver-Burk, Eadie-Hofstee, or nonlinear regression analysis.

Inhibition of metabolism experiments may then be performed. For example, a compound (one concentration, <$K_m$) may be incubated with pooled human hepatic microsomes in the absence or presence of a CYP inhibitor (such as ritonavir) under the conditions determined above. As would be recognized, control incubations should contain the same concentration of organic solvent as the incubations with the CYP inhibitor. The concentrations of the compound in the samples may be quantitated, and the rate of disappearance of parent compound may be determined, with rates being expressed as a percentage of control activity.

Methods for evaluating the influence of co-administration of a compound of the invention and a CYP inhibitor in a subject are also known (see, e.g., US2004/0028755; incorporated herein by reference). Any such methods could be used in connection with this invention to determine the pharmacokinetic impact of a combination. Subjects that would benefit from treatment according to this invention could then be selected.

Accordingly, one embodiment of this invention provides a method for administering an inhibitor of CYP3A4 and a compound of the invention. Another embodiment of this invention provides a method for administering an inhibitor of isozyme 3A4 ("CYP3A4"), isozyme 2C19 ("CYP2C19"), isozyme 2D6 ("CYP2D6"), isozyme 1A2 ("CYP1A2"), isozyme 2C9 ("CYP2C9"), or isozyme 2E1 ("CYP2E1"). In embodiments where the protease inhibitor is VX-950 (or a sterereoisomer thereof), the CYP inhibitor preferably inhibits CYP3A4.

As would be appreciated, CYP3A4 activity is broadly observed in humans. Accordingly, embodiments of this invention involving inhibition of isozyme 3A4 would be expected to be applicable to a broad range of patients.

Accordingly, this invention provides methods wherein the CYP inhibitor is administered together with the compound of the invention in the same dosage form or in separate dosage forms.

The compounds of the invention (e.g., compound of Formula I or subformulae thereof) may be administered as the sole ingredient or in combination or alteration with other antiviral agents, especially agents active against HCV. In combination therapy, effective dosages of two or more agents are administered together, whereas in alternation or sequential-step therapy, an effective dosage of each agent is administered serially or sequentially. In general, combination therapy is typically preferred over alternation therapy because it induces multiple simultaneous stresses on the virus. The dosages given will depend on absorption, inactivation and excretion rate of the drug as well as other factors. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions. The efficacy of a drug against the viral infection can be prolonged, augmented, or restored by administering the compound in combination or alternation with a second, and perhaps third antiviral compound that induces a different gene mutation than that caused by the principle drug in a drug resistant virus. Alternatively, the pharmacokinetic, biodistribution or other parameters of the drug can be altered by such combination or alternation therapy.

Daily dosages required in practicing the method of the present invention will vary depending upon, for example, the compound of the invention employed, the host, the mode of administration, the severity of the condition to be treated. A preferred daily dosage range is about from 1 to 50 mg/kg per day as a single dose or in divided doses. Suitable daily dosages for patients are on the order of from e.g. 1 to 20 mg/kg p.o or i.v. Suitable unit dosage forms for oral administration comprise from ca. 0.25 to 10 mg/kg active ingredient, e.g. compound of Formula I or any subformulae thereof, together with one or more pharmaceutically acceptable diluents or carriers therefor. The amount of co-agent in the dosage form can vary greatly, e.g., 0.00001 to 1000 mg/kg active ingredient.

Daily dosages with respect to the co-agent used will vary depending upon, for example, the compound employed, the host, the mode of administration and the severity of the condition to be treated. For example, lamivudine may be administered at a daily dosage of 100 mg. The pegylated interferon may be administered parenterally one to three times per week, preferably once a week, at a total weekly dose ranging from 2 to 10 million IU, more preferable 5 to 10 million IU, most preferable 8 to 10 million IU. Because of the diverse types of co-agent that may be used, the amounts can vary greatly, e.g., 0.0001 to 5,000 mg/kg per day.

The current standard of care for treating hepatitis C is the combination of pegylated interferon alpha with ribavirin, of which the recommended doses are 1.5 µg/kg/wk peginterferon alfa-2b or 180 g/wk peginterferon alfa-2a, plus 1,000 to 1,200 mg daily of ribavirin for 48 weeks for genotype I patients, or 800 mg daily of ribavirin for 24 weeks for genotype 2/3 patients.

The compound of the invention (e.g., compound of Formula I or subformulae thereof) and co-agents of the invention may be administered by any conventional route, in particular enterally, e.g. orally, for example in the form of solutions for drinking, tablets or capsules or parenterally, for example in the form of injectable solutions or suspensions. Certain preferred pharmaceutical compositions may be e.g. those based on microemulsions as described in UK 2,222,770 A.

The compound of the invention (e.g., compound of Formula I or subformulae thereof) are administered together with other drugs (co-agents) e.g. a drug which has anti-viral activity, especially anti-Flaviviridae activity, most especially anti-HCV activity, e.g. an interferon, e.g. interferon-α-2a or interferon-α-2b, e.g. Intron$^R$ A, Roferon$^R$, Avonex$^R$, Rebif$^R$ or Betaferon$^R$, or an interferon conjugated to a water soluble polymer or to human albumin, e.g. albuferon, an anti-viral agent, e.g. ribavirin, lamivudine, the compounds disclosed in U.S. Pat. No. 6,812,219 and WO 2004/002422 A2 (the disclosures of which are incorporated herein by reference in their entireties), an inhibitor of the HCV or other Flaviviridae virus encoded factors like the NS3/4A protease, helicase or RNA polymerase or a prodrug of such an inhibitor, an anti-fibrotic agent, e.g. a N-phenyl-2-pyrimidine-amine derivative, e.g. imatinib, an immune modulating agent, e.g. mycophenolic acid, a salt or a prodrug thereof, e.g. sodium mycophenolate or mycophenolate mofetil, or a S1P receptor agonist, e.g. FTY720 or an analogue thereof optionally phosphorylated, e.g. as disclosed in EP627406A1, EP778263A1, EP1002792A1, WO02/18395, WO02/76995, WO 02/06268, JP2002316985, WO03/29184, WO03/29205, WO03/62252 and WO03/62248, the disclosures of which are incorporated herein by reference in their entireties.

Conjugates of interferon to a water-soluble polymer are meant to include especially conjugates to polyalkylene oxide homopolymers such as polyethylene glycol (PEG) or polypropylene glycols, polyoxyethylenated polyols, copolymers thereof and block copolymers thereof. As an alternative to polyalkylene oxide-based polymers, effectively non-antigenic materials such as dextran, polyvinyl pyrrolidones, polyacrylamides, polyvinyl alcohols, carbohydrate-based polymers and the like can be used. Such interferon-polymer conjugates are described in U.S. Pat. Nos. 4,766,106, 4,917,888, European Patent Application No. 0 236 987, European Patent Application No. 0 510 356 and International Application Publication No. WO 95/13090, the disclosures of which are incorporated herein by reference in their entireties. Since the polymeric modification sufficiently reduces antigenic responses, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

Especially preferred conjugates of interferon are pegylated alfa-interferons, for example pegylated interferon-α-2a, pegylated interferon-α-2b; pegylated consensus interferon or pegylated purified interferon-α product. Pegylated interferon-α-2a is described e.g. in European Patent 593,868 (incorporated herein by reference in its entirety) and commercially available e.g. under the tradename PEGASYS® (Hoffmann-La Roche). Pegylated interferon-α-2b is described, e.g. in European Patent 975,369 (incorporated herein by reference in its entirety) and commercially available e.g. under the tradename PEG-INTRON A® (Schering Plough). Pegylated consensus interferon is described in WO 96/11953 (incorporated herein by reference in its entirety). The preferred pegylated α-interferons are pegylated interferon-α-2a and pegylated interferon-α-2b. Also preferred is pegylated consensus interferon.

Other preferred co-agents are fusion proteins of an interferon, for example fusion proteins of interferon-α-2a, interferon-α-2b; consensus interferon or purified interferon-α product, each of which is fused with another protein. Certain preferred fusion proteins comprise an interferon (e.g., interferon-α-2b) and an albumin as described in U.S. Pat. No. 6,973,322 and international publications WO02/60071, WO05/003296 and WO05/077042 (Human Genome Sciences). A preferred interferon conjugated to a human albumin is Albuferon (Human Genome Sciences).

Cyclosporins which bind strongly to cyclophilin but are not immunosuppressive include those cyclosporins recited in U.S. Pat. Nos. 5,767,069 and 5,981,479 and are incorporated herein by reference. Melle⁴-Cyclosporin (i.e., NIM811) and Debio-025 (Debiopharm) are preferred non-immunosuppressive cyclosporins. Certain other cyclosporin derivatives are described in WO2006039668 (Scynexis) and WO2006038088 (Debiopharm SA) and are incorporated herein by reference. A cyclosporin is considered to be non-immunosuppressive when it has an activity in the Mixed Lymphocyte Reaction (MLR) of no more than 5%, preferably no more than 2%, that of cyclosporin A. The Mixed Lymphocyte Reaction is described by T. Meo in "Immunological Methods", L. Lefkovits and B. Peris, Eds., Academic Press, N.Y. pp. 227-239 (1979). Spleen cells ($0.5 \times 10^6$) from Balb/c mice (female, 8-10 weeks) are co-incubated for 5 days with $0.5 \times 10^6$ irradiated (2000 rads) or mitomycin C treated spleen cells from CBA mice (female, 8-10 weeks). The irradiated allogeneic cells induce a proliferative response in the Balb c spleen cells which can be measured by labeled precursor incorporation into the DNA. Since the stimulator cells are irradiated (or mitomycin C treated) they do not respond to the Balb/c cells with proliferation but do retain their antigenicity. The $IC_{50}$ found for the test compound in the MLR is compared with that found for cyclosporin A in a parallel experiment. In addition, non-immunosuppressive cyclosporins lack the capacity of inhibiting CN and the downstream NF-AT pathway. [Melle]⁴-ciclosporin is a preferred non-immunosuppressive cyclophilin-binding cyclosporin for use according to the invention.

Ribavirin (1-β-D-ribofuranosyl-1-1,2,4-triazole-3-caroxamide) is a synthetic, non-interferon-inducing, broad spectrum antiviral nucleoside analog sold under the trade name, Virazole (The Merck Index, 11th edition, Editor: Budavar, S, Merck & Co., Inc., Rahway, N.J., p 1304, 1989). U.S. Pat. No. 3,798,209 and RE29,835 (incorporated herein by reference in their entireties) disclose and claim ribavirin. Ribavirin is structurally similar to guanosine, and has in vitro activity against several DNA and RNA viruses including Flaviviridae (Gary L. Davis, Gastroenterology 118:S104-S114, 2000).

Ribavirin reduces serum amino transferase levels to normal in 40% of patients, but it does not lower serum levels of HCV-RNA (Gary L. Davis, Gastroenterology 118:S104-S114, 2000). Thus, ribavirin alone is not effective in reducing viral RNA levels. Additionally, ribavirin has significant toxicity and is known to induce anemia. Ribavirin is not approved for monotherapy against HCV; it is approved in combination with interferon alpha-2a or interferon alpha-2b for the treatment of HCV.

A further preferred combination is a combination of a compound of the invention (e.g., a compound of Formula I or any subformulae thereof) with a non-immunosuppressive cyclophilin-binding cyclosporine, with mycophenolic acid, a salt or a prodrug thereof, and/or with a S1P receptor agonist, e.g. FTY720.

Additional examples of compounds that can be used in combination or alternation treatments include:

(1) Interferons, including interferon alpha 2a or 2b and pegylated (PEG) interferon alpha 2a or 2b, for example:

(a) Intron-A®, interferon alfa-2b (Schering Corporation, Kenilworth, N.J.);

(b) PEG-Intron®, peginteferon alfa-2b (Schering Corporation, Kenilworth, N.J.);

(c) Roferon®, recombinant interferon alfa-2a (Hoffmann-La Roche, Nutley, N.J.);

(d) Pegasys®, peginterferon alfa-2a (Hoffmann-La Roche, Nutley, N.J.);

(e) Berefor®, interferon alfa 2 available (Boehringer Ingelheim Pharmaceutical, Inc., Ridgefield, Conn.);

(f) Sumiferon®, a purified blend of natural alpha interferons (Sumitomo, Japan)

(g) Wellferon®, lymphoblastoid interferon alpha n1 (GlaxoSmithKline);

(h) Infergen®, consensus alpha interferon (InterMune Pharmaceuticals, Inc., Brisbane, Calif.);

(i) Alferon®, a mixture of natural alpha interferons (Interferon Sciences, and Purdue Frederick Co., CT);

(j) Viraferon®;

(k) Consensus alpha interferon from Amgen, Inc., Newbury Park, Calif.,

Other forms of interferon include: interferon beta, gamma, tau and omega, such as Rebif (Interferon beta 1a) by Serono, Omniferon (natural interferon) by Viragen, REBIF (interferon beta-1a) by Ares-Serono, Omega Interferon by Bio-Medicines; oral Interferon Alpha by Amarillo Biosciences; an interferon conjugated to a water soluble polymer or to a human albumin, e.g., Albuferon (Human Genome Sciences), an antiviral agent, a consensus interferon, ovine or bovine interferon-tau Conjugates of interferon to a water-soluble polymer are meant to include especially conjugates to polyalkylene oxide homopolymers such as polyethylene glocol (PEG) or polypropylene glycols, polyoxyethylenated polyols, copolymers thereof and block copolymers thereof. As an alternative to polyalkylene oxid-based polymers, effectively non-antigenic materials such as dextran, polyvinyl pyrrolidones, polyacrylamides, polyvinyl alcohols, carbohydrate-based polymers and the like can be used. Since the polymeric modification sufficiently reduces antigenic response, the foreign interferon need not be completely autologous. Interferon used to prepare polymer conjugates may be prepared from a mammalian extract, such as human, ruminant or bovine interferon, or recombinantly produced. Preferred are conjugates of interferon to polyethylene glycol, also known as pegylated interferons.

(2) Ribavirin, such as ribavirin (1-beta-D-ribofuranosyl-1H-1,2,4-triazole-3-carboxamide) from Valeant Pharmaceuticals, Inc., Costa Mesa, Calif.); Rebetol® from Schering Corporation, Kenilworth, N.J., and Copegus® from Hoffmann-La Roche, Nutley, N.J.; and new ribavirin analogues in development such as Levovirin and Viramidine by Valeant, (3) Thiazolidine derivatives which show relevant inhibition in a reverse-phase HPLC assay with an NS3/4A fusion protein and NS5A/5B substrate (Sudo K. et al., *Antiviral Research*, 1996, 32, 9-18), especially compound RD-1-6250, possessing a fused cinnamoyl moiety substituted with a long alkyl chain, RD4 6205 and RD4 6193;

(4) Thiazolidines and benzanilides identified in Kakiuchi N. et al. *J. FEBS Letters* 421, 217-220; Takeshita N. et al. *Analytical Biochemistry*, 1997, 247, 242-246;

(5) A phenan-threnequinone possessing activity against protease in a SDS-PAGE and autoradiography assay isolated from the fermentation culture broth of *Streptomyces* sp., Sch 68631 (Chu M. et al., *Tetrahedron Letters*, 1996, 37, 7229-7232), and Sch 351633, isolated from the fungus *Penicillium griseofulvum*, which demonstrates activity in a scintillation proximity assay (Chu M. et al, *Bioorganic and Medicinal Chemistry Letters* 9, 1949-1952);

(6) Protease inhibitors.

Examples include substrate-based NS3 protease inhibitors (Attwood et al., Antiviral peptide derivatives, PCT WO 98/22496, 1998; Attwood et al., *Antiviral Chemistry and Chemotherapy* 1999, 10, 259-273; Attwood et al, Preparation and use of amino acid derivatives as anti-viral agents, German Patent Pub. DE 19914474; Tung et al. *Inhibitors of serine proteases, particularly hepatitis C virus NS3 protease*; PCT WO 98/17679), including alphaketoamides and hydrazinoureas, and inhibitors that terminate in an electrophile such as a boronic acid or phosphonate (Llinas-Brunet et al. Hepatitis C inhibitor peptide analogues, PCT WO 99/07734) are being investigated.

Non-substrate-based NS3 protease inhibitors such as 2,4,6-trihydroxy-3-nitro-benzamide derivatives (Sudo K. et al., *Biochemical and Biophysical Research Communications*, 1997, 238 643-647; Sudo K. et al. *Antiviral Chemistry and Chemotherapy*, 1998, 9, 186), including RD3-4082 and RD3-4078, the former substituted on the amide with a 14 carbon chain and the latter processing a para-phenoxyphenyl group are also being investigated.

Sch 68631, a phenanthrenequinone, is an HCV protease inhibitor (Chu M et al., *Tetrahedron Letters* 37:7229-7232, 1996). In another example by the same authors, Sch 351633, isolated from the fungus *Penicillium grieofulvum*, was identified as a protease inhibitor (Chu M. et al., *Bioorganic and Medicinal Chemistry Letters* 9:1949-1952). Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598-1607, 1997.

U.S. patents disclosing protease inhibitors for the treatment of HCV include, for example, U.S. Pat. No. 6,004,933 to Spruce et al (incorporated herein by reference in its entirety) which discloses a class of cysteine protease inhibitors for inhibiting HCV endopeptidase 2; U.S. Pat. No. 5,990,276 to Zhang et al. (incorporated herein by reference in its entirety) which discloses synthetic inhibitors of hepatitis C virus NS3 protease; U.S. Pat. No. 5,538,865 to Reyes et al. (incorporated herein by reference in its entirety). Peptides as NS3 serine protease inhibitors of HCV are disclosed in WO 02/008251 to Corvas International, Inc., and WO 02/08187 and WO 02/008256 to Schering Corporation (incorporated herein by reference in their entireties). HCV inhibitor tripeptides are disclosed in U.S. Pat. Nos. 6,534,523, 6,410,531 and 6,420,380 to Boehringer Ingelheim and WO 02/060926 to Bristol Myers Squibb (incorporated herein by reference in their entireties). Diaryl peptides as NS3 serine protease inhibitors of HCV are disclosed in WO 02/48172 to Schering Corporation (incorporated herein by reference). Imidazoleidinones as NS3 serine protease inhibitors of HCV are disclosed in WO 02/18198 to Schering Corporation and WO 02/48157 to Bristol Myers Squibb (incorporated herein by reference in their entireties). WO 98/17679 to Vertex Pharmaceuticals and WO 02/48116 to Bristol Myers Squibb also disclose HCV protease inhibitors (incorporated herein by reference in their entireties).

HCV NS3-4A serine protease inhibitors including BILN 2061 by Boehringer Ingelheim, VX-950 by Vertex, SCH 6/7 by Schering-Plough, TMC-435350 (Tibotec/Johnson&Johnson) and other compounds currently in preclinical development;

Substrate-based NS3 protease inhibitors, including alpha-ketoamides and hydrazinoureas, and inhibitors that terminate in an elecrophile such as a boronic acid or phosphonate; Non-substrate-based NS3 protease inhibitors such as 2,4,6-trihydroxy-3-nitro-benzamide derivatives including RD3-4082 and RD3-4078, the former substituted on the amide with a 14 carbon chain and the latter processing a para-phenoxyphenyl group; and Sch68631, a phenanthrene-quinone, an HCV protease inhibitor.

Sch 351633, isolated from the fungus *Penicillium griseofulvum* was identified as a protease inhibitor. Eglin c, isolated from leech is a potent inhibitor of several serine proteases such as *S. griseus* proteases A and B, α-chymotrypsin, chymase and subtilisin.

U.S. Pat. No. 6,004,933 (incorporated herein by reference in its entirety) discloses a class of cysteine protease inhibitors from inhibiting HCV endopeptidase 2; synthetic inhibitors of HCV NS3 protease (pat), HCV inhibitor tripeptides (pat), diaryl peptides such as NS3 serine protease inhibitors of HCV (pat), Imidazolidindiones as NS3 serine protease inhibitors of HCV (pat).

Thiazolidines and benzanilides (ref). Thiazolidine derivatives which show relevant inhibition in a reverse-phase HPLC assay with an NS3/4A fusion protein and NS5A/5B substrate especially compound RD-16250 possessing a fused cinnamoyl moiety substituted with a long alkyl chain, RD4 6205 and RD4 6193.

HCV NS5A inhibitors including BMS-790052 by Bristol-Myers Squibb and other compounds currently in preclinical development.

Phenan-threnequinone possessing activity against protease in a SDS-PAGE and autoradiography assay isolated from the fermentation culture broth of *Streptomyces* sp, Sch68631 and Sch351633, isolated from the fungus *Penicillium griseofulvum*, which demonstrates activity in a scintillation proximity assay.

(7) Nucleoside or non-nucleoside inhibitors of HCV NS5B RNA-dependent RNA polymerase, such as 2'-C-methyl-3'-O-L-valine ester ribofuranosyl cytidine (Idenix) as disclosed in WO 2004/002422 A2 (incorporated herein by reference in its entirety), R803 (Rigel), JTK-003 (Japan Tabacco), HCV-086 (ViroPharma/Wyeth) and other compounds currently in preclinical development;

gliotoxin (ref) and the natural product cerulenin;

2'-fluoronucleosides;

other nucleoside analogues as disclosed in WO 02/057287 A2, WO 02/057425 A2, WO 01/90121, WO 01/92282, and U.S. Pat. No. 6,812,219, the disclosures of which are incorporated herein by reference in their entirety.

Idenix Pharmaceuticals discloses the use of branched nucleosides in the treatment of flaviviruses (including HCV) and pestiviruses in International Publication Nos. WO 01/90121 and WO 01/92282 (incorporated herein by reference in their entireties). Specifically, a method for the treatment of hepatitis C infection (and flaviviruses and pestiviruses) in humans and other host animals is disclosed in the Idenix publications that includes administering an effective amount of a biologically active 1', 2', 3' or 4'-branched B-D or B-L nucleosides or a pharmaceutically acceptable salt or prodrug thereof, administered either alone or in combination with another antiviral agent, optionally in a pharmaceutically acceptable carrier. Certain preferred biologically active 1', 2', 3', or 4' branched B-D or B-L nucleosides, including Telbivudine, are described in U.S. Pat. Nos. 6,395,716 and 6,875,751, each of which are incorporated herein by reference.

Other patent applications disclosing the use of certain nucleoside analogs to treat hepatitis C virus include: PCTCA00/01316 (WO 01/32153; filed Nov. 3, 2000) and PCT/CA01/00197 (WO 01/60315; filed Feb. 19, 2001) filed by BioChem Pharma, Inc., (now Shire Biochem, Inc.); PCT/US02/01531 (WO 02/057425; filed Jan. 18, 2002) and PCT/US02/03086 (WO 02/057287; filed Jan. 18, 2002) filed by Merck & Co., Inc., PCT/EP01/09633 (WO 02/18404; published Aug. 21, 2001) filed by Roche, and PCT Publication Nos. WO 01/79246 (filed Apr. 13, 2001), WO 02/32920 (filed Oct. 18, 2001) and WO 02/48165 by Pharmasset, Ltd. (the disclosures of which are incorporated herein by reference in their entireties)

PCT Publication No. WO 99/43691 to Emory University (incorporated herein by reference in its entirety), entitled "2'-Fluoronucleosides" discloses the use of certain 2'-fluoronucleosides to treat HCV.

Eldrup et al. (Oral Session V, Hepatitis C Virus, Flaviviridae; $16^{th}$ International Conference on Antiviral Research (Apr. 27, 2003, Savannah, Ga.)) described the structure activity relationship of 2'-modified nucleosides for inhibition of HCV.

Bhat et al. (Oral Session V, Hepatitis C Virus, Flaviviridae, 2003 (Oral Session V, Hepatitis C Virus, Flaviviridae; $16^{th}$ International conference on Antiviral Research (Apr. 27, 2003, Savannah, Ga.); p A75) describes the synthesis and pharmacokinetic properties of nucleoside analogues as possible inhibitors of HCV RNA replication. The authors report that 2'-modified nucleosides demonstrate potent inhibitory activity in cell-based replicon assays.

Olsen et al. (Oral Session V, Hepatitis C Virus, Flaviviridae; $16^{th}$ International Conference on Antiviral Research (Apr. 27, 2003, Savannah, Ga.) p A76) also described the effects of the 2'-modified nucleosides on HCV RNA replication.

(8) Nucleotide polymerase inhibitors and gliotoxin (Ferrari R. et al. *Journal of Virology*, 1999, 73, 1649-1654), and the natural product cerulenin (Lohmann V. et al. *Virology*, 1998, 249, 108-118);

(9) HCV NS3 helicase inhibitors, such as VP_50406 by ViroPhama and compounds from Vertex. Other helicase inhibitors (Diana G. D. et al., Compounds, compositions and methods for treatment of hepatitis C, U.S. Pat. No. 5,633,358 (incorporated herein by reference in its entirety); Diana G. D. et al., Piperidine derivatives, pharmaceutical compositions thereof and their use in the treatment of hepatitis C, PCT WO 97/36554);

(10) Antisense phosphorothioate oligodeoxynucleotides (S-ODN) complementary to sequence stretches in the 5' non-coding region (NCR) of the virus (Alt M. et al., *Hepatology*, 1995, 22, 707-717), or nucleotides 326-348 comprising the 3' end of the NCR and nucleotides 371-388 located in the core coding region of the HCV RNA (Alt M. et al., *Archives of Virology*, 1997, 142, 589-599; Galderisi U. et al., *Journal of Cellular Physiology*, 199, 181, 251-257); such as ISIS 14803 by Isis Pharm/Elan, antisense by Hybridon, antisense by AVI bioPharma,

(11) Inhibitors of IRES-dependent translation (Ikeda N et al., Agent for the prevention and treatment of hepatitis C, Japanese Patent Pub. JP-08268890; Kai Y et al. Prevention and treatment of viral diseases, Japanese Patent Pub. JP-10101591); such as ISIS 14803 by Isis Pharm/Elan, IRES inhibitor by Anadys, IRES inhibitors by Immusol, targeted RNA chemistry by PTC Therapeutics

(12) Ribozymes, such as nuclease-resistant ribozymes (Maccjak, D. J. et al., *Hepatology* 1999, 30, abstract 995) and those directed in U.S. Pat. No. 6,043,077 to Barber et al., and U.S. Pat. Nos. 5,869,253 and 5,610,054 to Draper et al. (incorporated herein by reference in their entireties) for example, HEPTAZYME by RPI

(13) siRNA directed against HCV genome

(14) HCV replication inhibitor of any other mechanisms such as by VP50406ViroPharama/Wyeth, inhibitors from Achillion, Arrow

(15) An inhibitor of other targets in the HCV life cycle including viral entry, assembly and maturation

(16) An immune modulating agent such as an IMPDH inhibitor, mycophenolic acid, a salt or a prodrug thereof sodium mycophenolate or mycophenolate mofetil, or Merimebodib (VX-497); thymosin alpha-1 (Zadaxin, by Sci- Clone); or a S1P receptor agonist, e.g. FTY720 or analogue thereof optionally phosphorylated.

(17) An anti-fibrotic agent, such as a N-phenyl-2-pyrimidine-amine derivative, imatinib (Gleevac), IP-501 by Indevus, and Interferon gamma 1b from InterMune

(18) Therapeutic vaccine by Intercell, Epimmune/Genecor, Merix, Tripep (Chron-VacC), immunotherapy (Therapore) by Avant, T cell therapy by CellExSys, monoclonal antibody XTL-002 by STL, ANA 246 and ANA 246 BY Anadys,

(19) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other anti-oxidants (U.S. Pat. No. 5,922,757 to Chojkier et al.), amantadine, bile acids (U.S. Pat. No. 5,846, 964 to Ozeki et al.), N-(phosphonoacetyl)-L-aspartic acid) U.S. Pat. No. 5,830,905 to Diana et al.), benzenedicarboxamides (U.S. Pat. No. 5,633,388 to Diane et al.), polyadenylic acid derivatives (U.S. Pat. No. 5,496,546 to Wang et al.), 2'3'-dideoxyinosine (U.S. Pat. No. 5,026,687 to Yarchoan et al.), benzimidazoles (U.S. Pat. No. 5,891,874 to Colacino et al.), plant extracts (U.S. Pat. No. 5,837,257 to Tsai et al., U.S. Pat. No. 5,725,859 to Omer et al., and U.S. Pat. No. 6,056, 961) and piperidines (U.S. Pat. No. 5,830,905 to Diana et al.); the disclosures of which are incorporated herein by reference in their entireties. Also, squalene, telbivudine, N-(phosphonoacetyl)-L-aspartic acid, benzenedicarboxamides, polyadenylic acid derivatives, glycosylation inhibitors, and nonspecific cytoprotective agents that block cell injury caused by the virus infection.

(20) Any other compound currently in preclinical or clinical development for the treatment of HCV, including Interleukin-10 (Schering-Plough), AMANTADINE (Symmetrel) by Endo Labs Solvay, caspase inhibitor IDN-6556 by Idun Pharma, HCV/MF59 by Chiron, CIVACIR (Hepatitis C Immune Globulin) by NABI, CEPLENE (histamine dichloride) by Maxim, IDN-6556 by Idun PHARM, T67, a beta-tubulin inhibitor, by Tularik, a therapeutic vaccine directed to E2 by Innogenetics, FK788 by Fujisawa Helathcare, IdB1016 (Siliphos, oral silybin-phosphatidyl choline phytosome), fusion inhibitor by Trimeris, Dication by Immtech, hemopurifier by Aethlon Medical, UT 231B by United Therapeutics.

(21) Purine nucleoside analog antagonists of TlR7 (toll-like receptors) developed by Anadys, e.g., Isotorabine (ANA245) and its prodrug (ANA975), which are described in European applications EP348446 and EP636372, International Publications WO03/045968, WO05/121162 and WO05/25583, and U.S. Pat. No. 6,973,322, each of which is incorporated by reference.

(22) Non-nucleoside inhibitors developed by Genelabs and described in International Publications WO2004/108687, WO2005/12288, and WO2006/076529, each of which is incorporated by reference.

(23) Other co-agents (e.g., non-immunomodulatory or immunomodulatory compounds) that may be used in combination with a compound of this invention include, but are not limited to, those specified in WO 02/18369 and WO2008021927A2 (e.g., BMS-790052), the structures of said compounds are incorporated herein by reference.

Methods of this invention may also involve administration of another component comprising an additional agent selected from an immunomodulatory agent; an antiviral agent; an inhibitor of HCV protease; an inhibitor of another target in the HCV life cycle; a CYP inhibitor; or combinations thereof.

Accordingly, in another embodiment, this invention provides a method comprising administering a compound of the invention and another anti-viral agent, preferably an anti-HCV agent. Such anti-viral agents include, but are not limited to, immunomodulatory agents, such as α, β, and δ interferons, pegylated derivatized interferon-a compounds, and thymosin; other anti-viral agents, such as ribavirin, amantadine, and telbivudine; other inhibitors of hepatitis C proteases (NS2-NS3 inhibitors and NS3-NS4A inhibitors); inhibitors of other targets in the HCV life cycle, including helicase, polymerase, and metalloprotease inhibitors; inhibitors of internal ribosome entry; broad-spectrum viral inhibitors, such as IMPDH inhibitors (e.g., compounds of U.S. Pat. Nos. 5,807,876, 6,498,178, 6,344,465, 6,054,472, WO 97/40028, WO 98/40381, WO 00/56331, and mycophenolic acid and derivatives thereof, and including, but not limited to VX-497, VX-148, and/or VX-944); or combinations of any of the above.

In accordance with the foregoing the present invention provides in a yet further aspect(s):

A pharmaceutical combination comprising a) a first agent which is a compound of the invention, e.g. a compound of formula I or any subformulae thereof, and b) a co-agent, e.g. a second drug agent as defined above.

A method as defined above comprising co-administration, e.g. concomitantly or in sequence, of a therapeutically effective amount of a compound of the invention, e.g. a compound of formula I or any subformulae thereof, and a co-agent, e.g. a second drug agent as defined above.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time. Fixed combinations are also within the scope of the present invention. The administration of a pharmaceutical combination of the invention results in a beneficial effect, e.g. a synergistic therapeutic effect, compared to a monotherapy applying only one of its pharmaceutically active ingredients.

Each component of a combination according to this invention may be administered separately, together, or in any combination thereof. As recognized by skilled practitioners, dosages of interferon are typically measured in IU (e.g., about 4 million IU to about 12 million IU).

If an additional agent is selected from another CYP inhibitor, the method would, therefore, employ two or more CYP inhibitors. Each component may be administered in one or more dosage forms. Each dosage form may be administered to the patient in any order.

The compound of the invention and any additional agent may be formulated in separate dosage forms. Alternatively, to decrease the number of dosage forms administered to a patient, the compound of the invention and any additional agent may be formulated together in any combination. For example, the compound of the invention inhibitor may be formulated in one dosage form and the additional agent may be formulated together in another dosage form. Any separate dosage forms may be administered at the same time or different times.

Alternatively, a composition of this invention comprises an additional agent as described herein. Each component may be present in individual compositions, combination compositions, or in a single composition.

Use in HCV-Associated Disorders

The compounds of the present invention have valuable pharmacological properties and are useful in the treatment of diseases. In certain embodiments, compounds of the invention are useful in the treatment of HCV-associated disorders, e.g., as drugs to treat HCV infection.

The term "use" includes any one or more of the following embodiments of the invention, respectively: the use in the treatment of HCV-associated disorders; the use for the manufacture of pharmaceutical compositions for use in the treatment of these diseases, e.g., in the manufacture of a medicament; methods of use of compounds of the invention in the treatment of these diseases; pharmaceutical preparations having compounds of the invention for the treatment of these diseases; and compounds of the invention for use in the treatment of these diseases; as appropriate and expedient, if not stated otherwise. In particular, diseases to be treated and are thus preferred for use of a compound of the present invention are selected from HCV-associated disorders, including those corresponding to HCV-infection, as well as those diseases that depend on the activity of one or more of the NS3, NS4A, NS4B, NS5A and NS5B proteins, or a NS3-NS4A, NS4A-NS4B, NS4B-NS5A or NS5A-NS5B complex. The term "use" further includes embodiments of compositions herein which bind to an HCV protein sufficiently to serve as tracers or labels, so that when coupled to a fluor or tag, or made radioactive, can be used as a research reagent or as a diagnostic or an imaging agent.

In certain embodiments, a compound of the present invention is used for treating HCV-associated diseases, and use of the compound of the present invention as an inhibitor of any one or more HCVs. It is envisioned that a use can be a treatment of inhibiting one or more strains of HCV.

Assays

The inhibition of HCV activity may be measured as using a number of assays available in the art. An example of such an assay can be found in Anal Biochem. 1996 240(1): 60-7; which is incorporated by reference in its entirety. Assays for measurement of HCV activity are also described in the experimental section below.

Synthetic Procedure

Compounds of the present invention are prepared from commonly available compounds using procedures known to those skilled in the art, including any one or more of the following conditions without limitation:

Within the scope of this text, only a readily removable group that is not a constituent of the particular desired end product of the compounds of the present invention is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany. 2005. 41627 pp. (URL: http://www.science-of-synthesis.com (Electronic Version, 48 Volumes)); J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e., without the occurrence of undesired secondary reactions) for example by solvolysis, reduction, photolysis or alternatively under physiological conditions (e.g., by enzymatic cleavage).

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

General Process Conditions

The following applies in general to all processes mentioned throughout this disclosure.

The process steps to synthesize the compounds of the invention can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the $H^+$ form, depending on the nature of the reaction and/or of the reactants at reduced, normal or elevated temperature, for example in a temperature range of from about $-100°$ C. to about $190°$ C., including, for example, from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany. 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

EXEMPLIFICATION OF THE INVENTION

The invention is further illustrated by the following examples, which should not be construed to limit the scope of the invention. Demonstration of efficacy in these assays is predictive of efficacy in subjects.

General Synthesis Methods

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

| LIST OF ABBREVIATIONS | |
|---|---|
| Ac | acetyl |
| ACN | Acetonitrile |
| AcOEt/EtOAc | Ethyl acetate |
| AcOH | acetic acid |
| aq | aqueous |
| Ar | aryl |
| Bn | benzyl |
| Bu | butyl (nBu = n-butyl, tBu = tert-butyl) |
| CDI | Carbonyldiimidazole |
| $CH_3CN$ | Acetonitrile |
| DBU | 1,8-Diazabicyclo[5.4.0]-undec-7-ene |
| DCE | 1,2-Dichloroethane |
| DCM | Dichloromethane |
| DIPEA | N-Ethyldiisopropylamine |
| DMAP | Dimethylaminopyridine |
| DMF | N,N'-Dimethylformamide |
| DMSO | Dimethylsulfoxide |
| EI | Electrospray ionisation |
| $Et_2O$ | Diethylether |
| $Et_3N$ | Triethylamine |
| Ether | Diethylether |
| EtOH | Ethanol |
| FC | Flash Chromatography |
| h | hour(s) |
| HATU | O-(7-Azabenzotriazole-1-yl)-N,N,N'N'-tetramethyluronium hexafluorophosphate |
| HBTU | O-(Benzotriazol-1-yl)-N,N,N',N'-tetramethyluronium hexafluorophosphate |
| HCl | Hydrochloric acid |
| HOBt | 1-Hydroxybenzotriazole |
| HPLC | High Performance Liquid Chromatography |
| $H_2O$ | Water |
| L | liter(s) |
| LC-MS | Liquid Chromatography Mass Spectrometry |
| Me | methyl |
| MeI | Iodomethane |

| LIST OF ABBREVIATIONS -continued | |
|---|---|
| MeOH | Methanol |
| mg | milligram |
| min | minute(s) |
| mL | milliliter |
| MS | Mass Spectrometry |
| Pd/C | palladium on charcoal |
| PG | protecting group |
| Ph | phenyl |
| Prep | Preparative |
| Rf | ratio of fronts |
| RP | reverse phase |
| Rt | Retention time |
| rt | Room temperature |
| $SiO_2$ | Silica gel |
| TBAF | Tetrabutylammonium fluoride |
| TEA | Triethylamine |
| TFA | Trifluoroacetic acid |
| THF | Tetrahydrofurane |
| TLC | Thin Layer Chromatography |

HPLC Methods:
Method A:
HPLC
Instrument: Agilent system
Column: Zorbax eclipse XDB-C18, 1.8 microm., 2.1×50 mm, flow 1 mL/min
Solvent: CH3CN (0.1% CF3CO2H), H2O (0.1% CF3CO2H)
Gradient: 0-0.8 min: 10-95% CH3CN, 0.8-1.2 min: 95% CH3CN, 1.2-1.6 min 95% to 10% CH3CN
Method A2:
HPLC
Instrument: Agilent system
Column: MN Nucleosil C18HD CC70, 4 microm, 2.1×50 mm, flow 1 mL/min
Solvent: CH3CN (0.1% CF3CO2H), H2O (0.1% CF3CO2H)
Gradient: 0-6 min: 20-100% CH3CN, 6-7.5 min: 100% CH3CN, 7.5-8.0 min 100-20% CH3CN
Method A3:
HPLC
Instrument: Agilent system
Column: Agilent Eclipse, 1.8 microm., 4.6×50 mm, flow 1 mL/min
Solvent: CH3CN (0.1% CF3CO2H), H2O (0.1% CF3CO2H)
Gradient: 0-6 min: 20-100% CH3CN, 6-7.5 min: 100% CH3CN, 7.5-8.0 min 100-20% CH3CN
Method A4:
LCMS
Instrument: Agilent system
Column: Inertsil C8-3; 3.0×30 mm; 3 μm particle size, flow 2 mL/min
Solvent: CH3CN, H2O (5 mM ammonium formate)
Gradient: 0-1.7 min: 5-95% CH3CN, hold for 0.3 min, 2-2.1 min 95-5% CH3CN
Method A5:
LCMS
Instrument: Agilent system
Column: Inertsil ODS-3; 3.0×30 mm; 3 μm particle size, flow 2 mL/min
Solvent: CH3CN, H2O (5 mM ammonium formate)
Gradient: 0-1.7 min: 20-95% CH3CN, hold for 0.3 min, 2-2.1 min 95-20% CH3CN
Method A6:
LCMS
Instrument: Agilent system
Column: Waters Atlantis dC18; 4.6×150 mm; 5 μm particle size, flow 1.41 mL/min Solvent: CH3CN (0.07% TFA), H2O (0.1% TFA)
Gradient: 0-19 min: 5-95% CH3CN, hold for 0.8 min
Method B:
HPLC
Instrument: Agilent system
Column: Waters Symmetry C18, 3.5 microm., 2.1×50 mm, flow 0.6 mL/min
Solvent: CH3CN (0.1% CF3CO2H), H2O (0.1% CF3CO2H)
Gradient: 0-3.5 min: 20-95% CH3CN, 3.5-5 min: 95% CH3CN, 5.5-5.55 min 95% to 20% CH3CN
Method C:
HPLC
Instrument: Agilent system
Column: MN Nucleosil C18HD CC70, 4 microm., flow 0.6 mL/min
Solvent: CH3CN (0.1% CF3CO2H), H2O (0.1% CF3CO2H)
Gradient: 0-3.5 min: 20-95% CH3CN, 3.5-5 min: 95% CH3CN, 5.5-5.55 min 95% to 20% CH3CN, 5.55-6 min 20% CH3CN
Method D:
HPLC
Instrument: Agilent system
Column: Waters SunFire, 2.5 microm., 3×30 mm, flow 1.4 mL/min
Solvent: CH3CN (0.1% CF3CO2H), H2O (0.1% CF3CO2H)
Gradient: 0-2.5 min: 10-98% CH3CN, 2.5-3.2 min: 98% CH3CN, 3.2-3.21 min 98% to 10% CH3CN, 3.21-3.25 min 10% CH3CN
Method E:
LCMS
Instrument: Agilent system
Column: Waters SunFire, 2.5 microm., 3×30 mm, flow 1.4 mL/min
Solvent: CH3CN (0.1% HCO2H), H2O (0.1% HCO2H)
Gradient: 0-2.5 min: 10-98% CH3CN, 2.5-3.2 min: 98% CH3CN, 3.2-3.21 min 98% to 10% CH3CN, 3.21-3.25 min 10% CH3CN
Method F:
LCMS
Instrument: Agilent system
Column: Waters SunFire, 2.1×50 mm, flow 0.6 mL/min
Solvent: CH3CN (0.1% HCO2H), H2O (0.1% HCO2H)
Gradient: 0-2.5 min: 10-98% CH3CN, 2.5-3.2 min: 98% CH3CN, 3.2-3.21 min 98% to 10% CH3CN, 3.21-3.25 min 10% CH3CN
Method G:
LCMS
Instrument: Agilent system
Column: Halo C18, 2.7 microm., 2.1×30 mm, flow 1.1 mL/min
Solvent: CH3CN (0.1% HCO2H), H2O (0.1% HCO2H)
Gradient: 0-2 min: 5-95% CH3CN, 2-2.6 min: 95% CH3CN, 2.6-2.65 min 95% to 5% CH3CN, 2.65-3 min 5% CH3CN
Method H:
LCMS
Instrument: Agilent system
Column: YMC ODS, 2.5 microm., 2.1×50 mm, flow 0.6 mL/min
Solvent: CH3CN (0.1% HCO2H), H2O (0.1% HCO2H)
Gradient: 0-3.5 min: 20-95% CH3CN, 3.5-5.5 min: 95% CH3CN, 5.5-5.55 min 95% to 20% CH3CN, 5.55-6 min 20% CH3CN
Method I:
LCMS
Instrument: Agilent system
Column: Waters Atlantis, 2.1×30 mm, flow 0.6 mL/min
Solvent: CH3CN (0.1% HCO2H), H2O (0.1% HCO2H)
Gradient: 0-2.5 min: 20-95% CH3CN, 2.5-4.5 min: 95% CH3CN, 4.5-4.55 min 95% to 20% CH3CN, 4.55-5 min 20% CH3CN
Method I2:
LCMS
Instrument: Agilent system
Column: Waters Atlantis, 2.1×30 mm, flow 0.6 mL/min
Solvent: CH3CN (0.1% HCO2H), H2O (0.1% HCO2H)
Gradient: 0-2.5 min: 5-95% CH3CN, 2.5-4.5 min: 95% CH3CN, 4.5-4.55 min 95% to 5% CH3CN, 4.55-5 min 5% CH3CN
Method I3:
LCMS
Instrument: Agilent system
Column: Waters Atlantis, 3.0 microm., 2.1×30 mm, flow 0.6 mL/min
Solvent: CH3CN (0.1% HCO2H), H2O (0.1% HCO2H)
Gradient: 0-3.5 min: 20-95% CH3CN, 3.5-4.5 min: 95% CH3CN, 4.5-4.55 min 95% to 20% CH3CN, 4.55-5 min 20% CH3CN
Method J:
MS
Instrument: Agilent system
Method: Flow injection
Detection: API-ES, positive/negative
Method K:
Preparative HPLC
Instrument: Gilson system
column: waters C18 ODB, 5 microm, 50×19 mm
solvent: CH3CN (0.1% HCO2H); H2O (0.1% HCO2H)
Method L:
Preparative HPLC
Instrument: Gilson
Column: Sun-Fire prep C18 OBD 5 microm, Column 19×50 mm (flow 20 mL/min) or column 30×100 mm (flow 40 mL/min)
Solvent: CH3CN (0.1% CF3CO2H) and H2O (0.1% CF3CO2H)
Gradient: 0-20 min: 5-100% CH3CN
Method M:
HPLC-MS
Instrument: Waters
Column: Waters Atlantis, 2.1×30 mm, flow 0.6 mL/min
Solvent: CH3CN (0.1% HCO2H), H2O (0.1% HCO2H)
Gradient: 0-2.5 min: 20-95% CH3CN, 2.5-4.5 min: 95% CH3CN, 4.5-4.55 min 95% to 20% CH3CN, 4.55-5 min 20% CH3CN

Preparation of Intermediate I

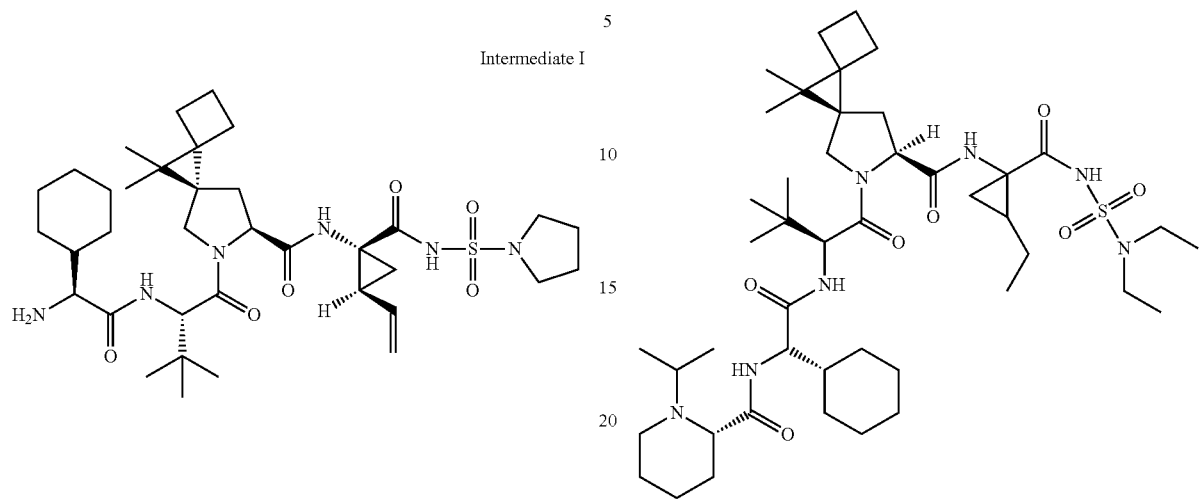

Intermediate I

Step 1a

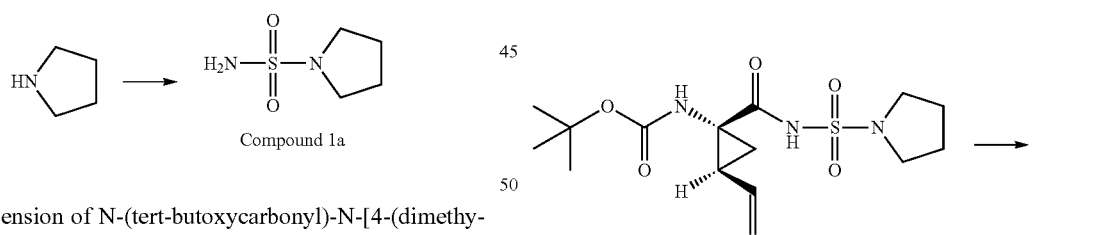

Compound 1a

A suspension of N-(tert-butoxycarbonyl)-N-[4-(dimethylazaniumylidene)-1,4-dihydropyridin-1-ylsulfonyl]azanide (3 g; 9.955 mmol) prepared according to the procedure from Winum et al (Organic Letters 2001, 3, 2241) in DCM (24 mL) was treated with pyrrolidine (0.864 mL; 10.453 mmol) and stirred at rt for 24 h. The reaction mixture was chromatographed by FC on silica gel (eluent: CH$_2$Cl$_2$/EtOAc 100:1) to give [N-(tert-butoxycarbonyl)]-pyrrolidine-1-sulfonic acid amide. TLC: Rf (DCM/EtOAc 100:1)=0.40. A solution of [N-(tert-butoxycarbonyl)]-pyrrolidine-1-sulfonic acid amide (57.09 g; 223 mmol) in DCM (450 mL) was treated with TFA (120 mL; 1.56 mol) and stirred at rt for 7 h. The reaction mixture was concentrated in vacuo and the residual oil was triturated with diisopropylether. The resulting powder was washed with diisopropylether and dried under high vacuum to provide Compound 1a. TLC: Rf (DCM/EtOAc 50:1)=0.10.

Step 1b

A solution of (1R,2S)-1-tert-butoxycarbonylamino-2-vinyl-cyclopropanecarboxylic acid prepared according to the procedure described in WO2000/09558 (8.24 g; 36.3 mmol) in THF (160 mL) was treated with CDI (9.09 g; 54.4 mmol) and heated to reflux for 1 h. The resulting reaction mixture was cooled to rt and treated with Compound 1a (7.62 g; 50.8 mmol) followed by DBU (8.28 g; 54.4 mmol). After 16 h at rt the reaction mixture was concentrated, the residue was taken up in DCM and washed with a saturated aq solution of KHSO$_4$ (3×). The aq phases were extracted with DCM, the organics were combined, dried over Na$_2$SO$_4$ and concentrated in vacuo. The residue was chromatographed on silica gel (eluent: hexane/EtOAc 4:1) to give Compound 1b. LCMS (method F) Rt=3.21 min; MS (method J): M/z=358 [M−1]

Step 1c

Compound 1c

Compound 1b (7.84 g; 21.81 mmol) was treated with 4N HCl in dioxane (84 mL) at rt. After 1.5 h the reaction mixture was concentrated under high vacuum to give Compound 1c as its hydrochloride salt. LCMS (method E) Rt=1.10 min; MS (method J): M/z=260 [M+1]

silica gel (eluent: DCM/MeOH 50:1) to give Compound 1d. TLC: Rf (DCM/MeOH 98:2)=0.28; MS (method J): M/z=549 [M−1]

Step 1d

Step 1e

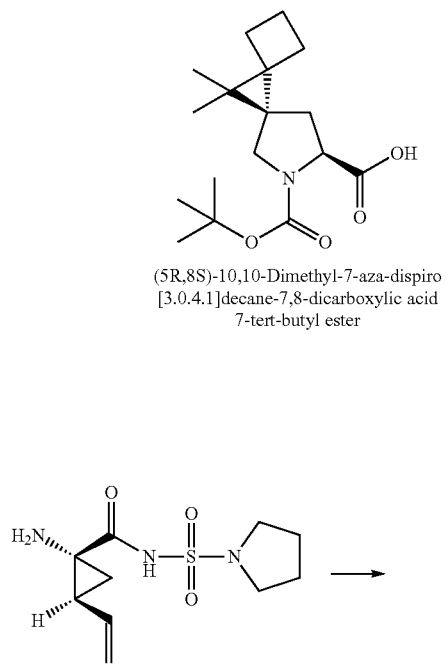

(5R,8S)-10,10-Dimethyl-7-aza-dispiro[3.0.4.1]decane-7,8-dicarboxylic acid 7-tert-butyl ester

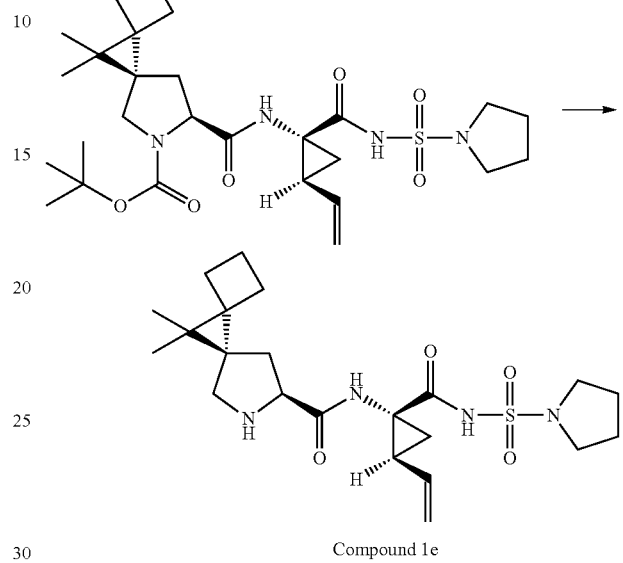

Compound 1e

Compound 1e hydrochloride was obtained from Compound 1d (0.296 g; 0.537 mmol) according to the method described at step 1c. TLC: Rf (DCM/MeOH 9:1)=0.48; MS (method J): M/z=451 [M+1]

Step 1f

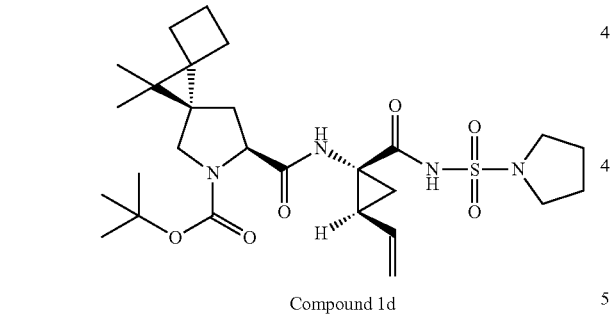

Compound 1d (5R,8S)-10,10-dimethyl-7-aza-dispiro[3.0.4.1]decane-7,8-dicarboxylic acid 7-tert-butyl ester is prepared by the procedure provided at page 113, line 12 to page 114, line 7 of copending international patent application PCT/EP08/063,460, which passage is expressly incorporated herein by reference. A solution of Compound 1c hydrochloride (1.363 g; 4.01 mmol) and (5R,8S)-10,10-dimethyl-7-aza-dispiro[3.0.4.1]decane-7,8-dicarboxylic acid 7-tert-butyl ester (1.24 g; 4.01 mmol) in DMF (20 mL) was treated with DIPEA (2.745 mL; 16.03 mmol), cooled to 0° C. and treated with HBTU (1.9 g; 5.01 mmol). The reaction mixture was stirred at 0° C. for 1 h and at rt for 19 h, partitioned between water and EtOAc: The organics were washed sequentially with saturated aq $KHSO_4$, $NaCO_3$ and water, dried over $Na_2SO_4$ and concentrated in vacuo. The residue was chromatographed on

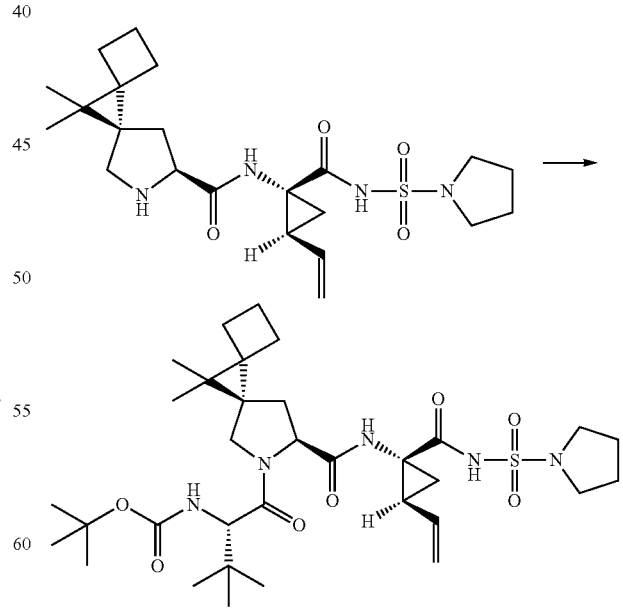

Compound 1f

A solution of Compound 1e (0.287 g; 0.536 mmol) and BOC-L-tert-leucine (0.248 g; 1.072 mmol) in DCM (15 mL)

was cooled to 0° C. and treated with DIPEA (0.46 mL; 2.68 mmol) and HATU (0.611 g; 1.608 mmol). The reaction mixture was stirred at rt for 20 h, concentrated in vacuo and the residue was purified by preparative HPLC (method K). After workup (Workup 2=fractions were treated with NaHCO$_3$ and concentrated; residue partitioned between water and EtOAc, extracted with EtOAc; organics combined, dried over Na$_2$SO$_4$ and concentrated) Compound 1f was obtained. TLC: Rf (DCM/MeOH 96:4)=0.70; MS (method J): M/z=662 [M−1]

Step 1g

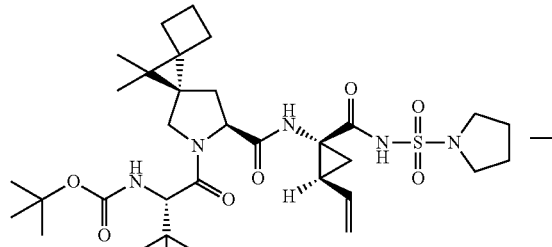

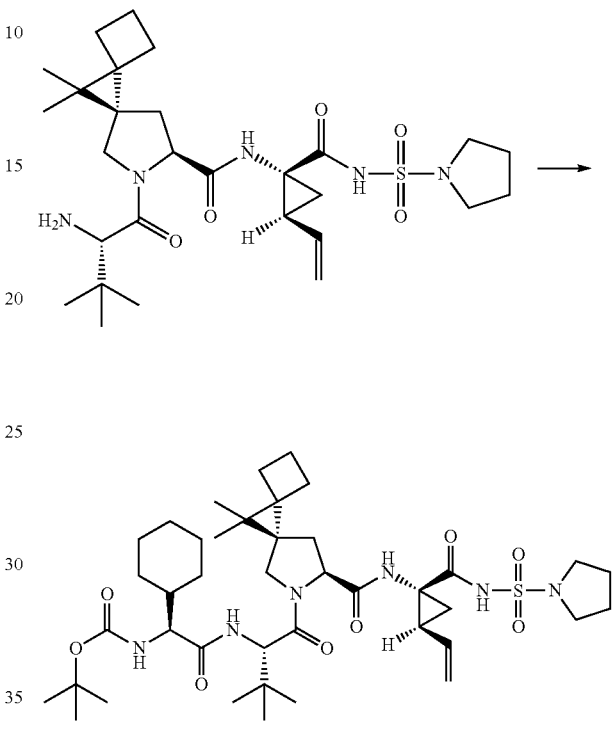

Compound 1g

Compound 1g hydrochloride was obtained from Compound 1f (0.204 g; 0.307 mmol) according to the method described at step 1c. TLC: Rf (DCM/MeOH 9:1)=0.39; MS (method J): M/z=564 [M+1]

Step 1h

Compound 1h

A solution of Compound 1g (1.845 g; 3.07 mmol) and BOC-L-cyclohexylglycine (1.582 g; 6.15 mmol) in DCM (65 mL) was cooled to 0° C. and treated with DIPEA (2.68 mL; 15.37 mmol) followed by HATU (3.51 g; 9.22 mmol). After 16 h at rt the reaction mixture was partitioned between DCM and 1N HCl, the organics were extracted with saturated aq NaHCO$_3$, dried over Na$_2$SO$_4$ and concentrated. Purification by preparative HPLC (method K) followed by workup (Workup 2) afforded Compound 1h. LC-MS (method E): Rt=3.18 min; M/z=826 [M+Na]

Step 1i

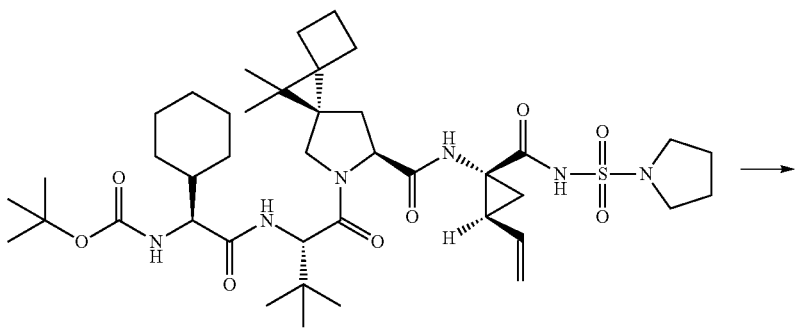

-continued

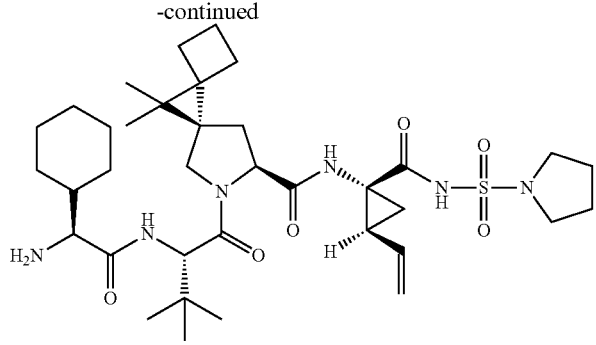

Intermediate I

Intermediate I hydrochloride was obtained from Compound 1h (1.64 g; 2.042 mmol) according to the method described at step 1c. LC-MS (method E): Rt=1.95 min; M/z=703 [M+1]

Preparation of Intermediate II

Intermediate II

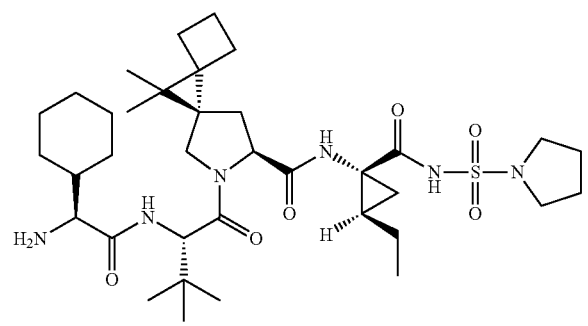

Step 2a

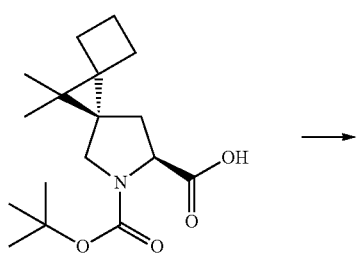

(5R,8S)-10,10-Dimethyl-7-aza-dispiro
[3.0.4.1]decane-7,8-dicarboxylic acid
7-tert-butyl ester -continued

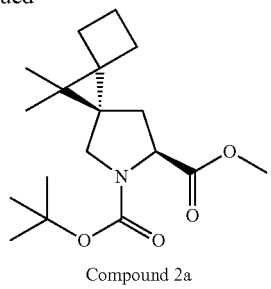

Compound 2a (5R,8S)-10,10-Dimethyl-7-aza-dispiro[3.0.4.1]decane-7,8-dicarboxylic acid 7-tert-butyl ester (32.84 g; 106 mmol) in DMF (1 L) was treated with $K_2CO_3$ (22.00 g; 159 mmol) followed by methyliodide (9.93 mL; 159 mmol). The reaction mixture was stirred at rt for 18 h, concentrated in vacuo. The resulting residue was partitioned between water and EtOAc and extracted with EtOAc. The organics were combined, washed with brine, dried over $Na_2SO_4$ and concentrated. The residue was chromatographed on silica gel (eluent DCM/Ethylether 120:1) to give Compound 2a. TLC: Rf (DCM/Ethylether 120:1)=0.22; MS (method J): M/z=346 [M+Na]

Step 2b

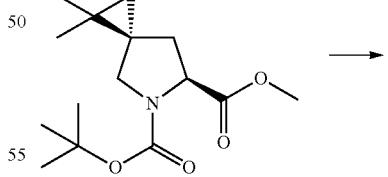

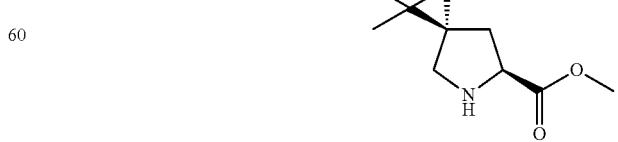

Compound 2b

Compound 2b hydrochloride was obtained from Compound 2a (6.3 g; 19.48 mmol) according to the method described at step 1c. MS (method J): M/z=224 [M+1]

Step 2c

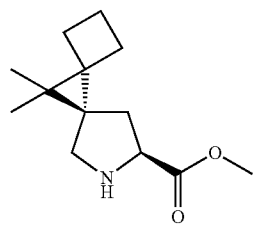

→

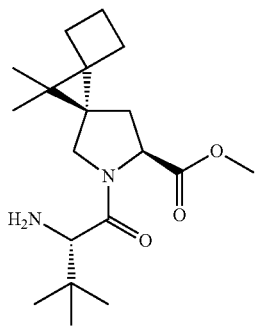

Compound 2d

Compound 2d hydrochloride was obtained from Compound 2c (10.55 g; 24.16 mmol) according to the method described at step 1c. TLC: Rf (DCM/MeOH 95:5)=0.39; MS (method J): M/z=337 [M+1]

Step 2e

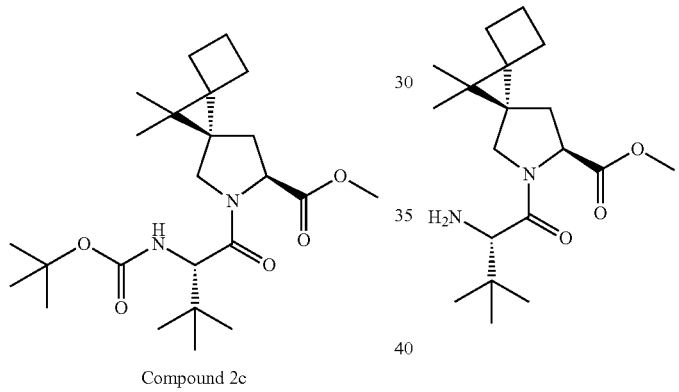

Compound 2c

Compound 2c was obtained from Compound 2b hydrochloride (7.33 g; 27.93 mmol) according to the method described at step 1f followed by chromatography on silica gel (eluent cyclohexane/EtOAc 1:1). TLC: Rf (hexane/EtOAc 4:1)=0.37; MS (method J): M/z=437 [M+1]

Step 2d

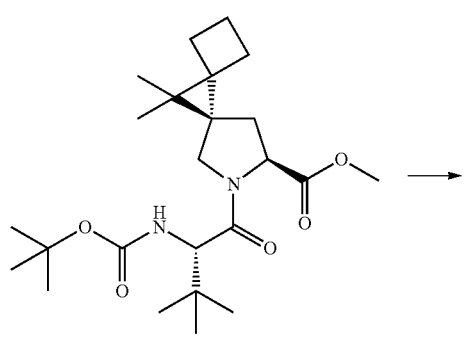

→

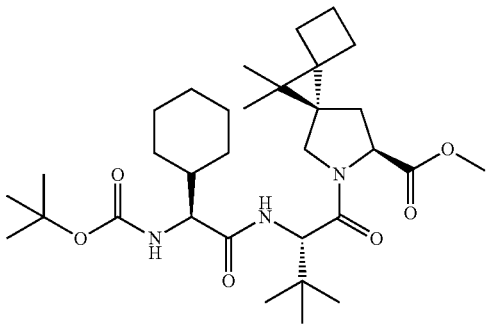

Compound 2e

Compound 2e was obtained from Compound 2d (0.2 g; 0.456 mmol) according to the method described at step 1h. LC-MS (method G): Rt=2.21 min; M/z=598 [M+Na]

Step 2f

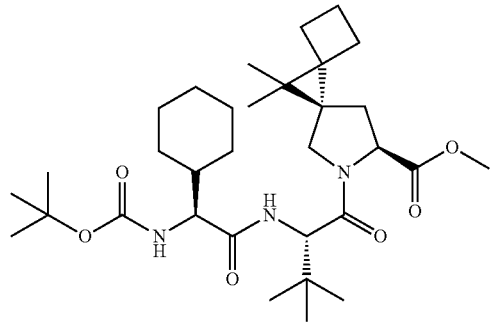

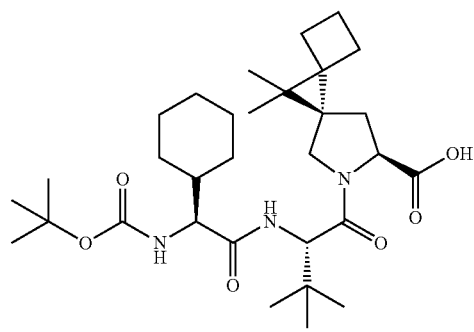

Compound 2f

A mixture of Compound 2e (1.136 g; 1.973 mmol) and LiOH.H₂O (0.09 g; 2.17 mmol) in THF/MeOH/water (6 mL; 2:1:1) was stirred at rt 16 h. The reaction mixture was partitioned between water and EtOAc. The aq phase was acidified with 1N HCl and extracted with EtOAC. Organics were combined, dried over Na₂SO₄ and concentrated to a residue that was chromatographed on silica gel (DCM/MeOH 100% to 9:1) to afford Compound 2f. LC-MS (method G): Rt=1.99 min; M/z=562 [M+1]

Step 2g

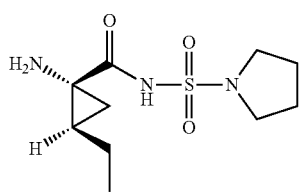

Pyrrolidine-1-sulfonic acid ((1R,2R)-1-amino-2-ethyl-cyclopropanecarbonyl)-amide

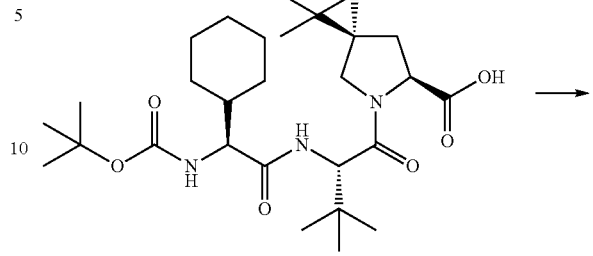

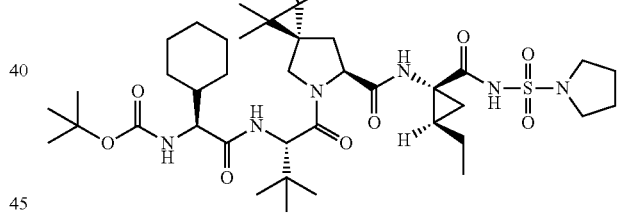

Compound 2g

A solution of Compound 2f (0.050 g; 0.089 mmol) and pyrrolidine-1-sulfonic acid ((1R,2R)-1-amino-2-ethyl-cyclopropanecarbonyl)-amide (0.030 g; 0.093 mmol) in DCM (2 mL) was cooled to 0° C. and treated with DIPEA (0.078 mL; 0.445 mmol) and HATU (0.102 g; 0.267 mmol). The reaction mixture was stirred at rt for 2 h, partitioned between DCM and 1N HCl. The organics were washed with a saturated aq NaHCO₃ solution, dried over Na₂SO₄ and concentrated in vacuo to a residue that was purified by preparative HPLC. After workup (Workup 2) Compound 2g was obtained. LC-MS (method G): Rt=2.25 min; M/z=828 [M+Na]

Step 2h

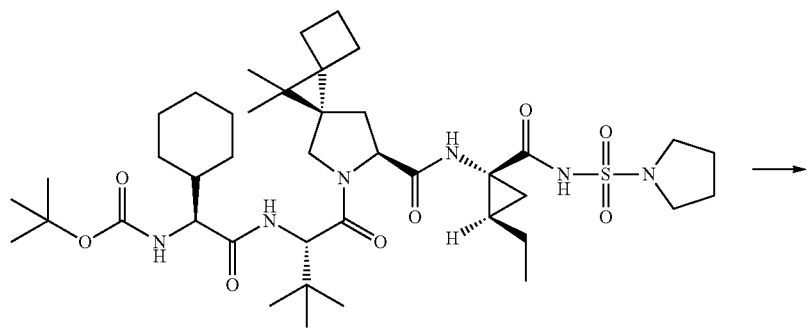

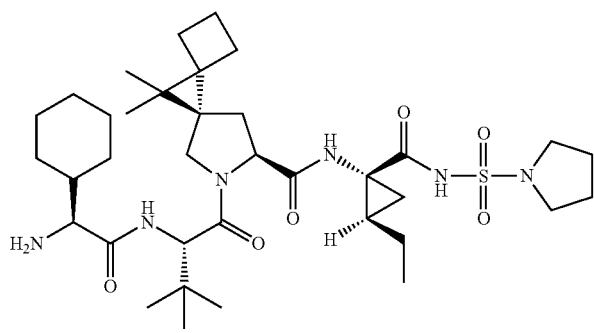

Intermediate II

Intermediate II hydrochloride was obtained from Compound 2g (0.02 g; 0.025 mmol) according to the method described at step 1c. LC-MS (method G): Rt=1.59 min; M/z=706 [M+1]

Preparation of Intermediate III pyrrolidine-1-sulfonic acid ((1R,2R)-1-amino-2-ethyl-cyclopropanecarbonyl)-amide

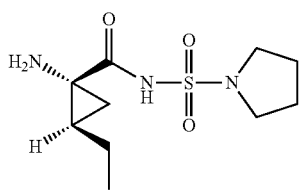

Intermediate III

Step 3a

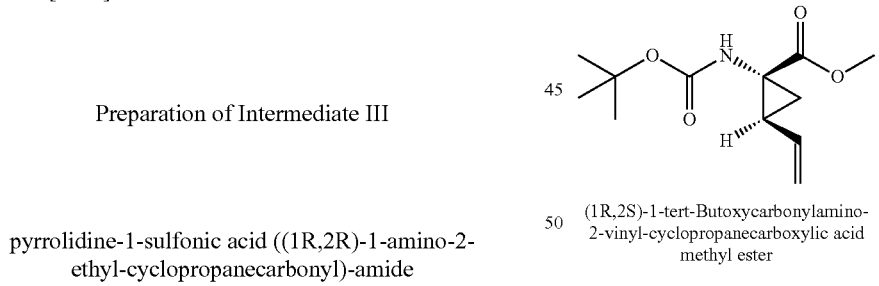

(1R,2S)-1-tert-Butoxycarbonylamino-2-vinyl-cyclopropanecarboxylic acid methyl ester

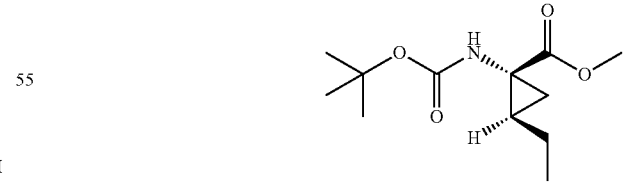

Compound 3a

A solution of (1R,2S)-1-tert-butoxycarbonylamino-2-vinyl-cyclopropanecarboxylic acid methyl ester prepared according to the procedure described in WO20009558 (60.16 g; 249 mmol) in 2 L EtOH was hydrogenated at RT under $H_2$, catalyzed by Rh—$Al_2O_3$ (5 g). Under completion, the catalyst was filtered off and the solution concentrated under high vacuum to afford Compound 3a. MS (method J): M/z=266 [M+Na]

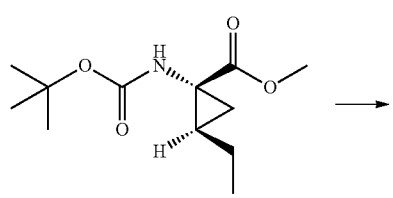

A mixture of Compound 3a (10 g; 41.1 mmol) and LiOH.H$_2$O (5.17 g; 123 mmol) in THF/MeOH/water (440 mL; 2:1:1) was stirred at rt for 20 h. The reaction mixture was concentrated. The resulting aq phase was washed with EtOAc, cooled to 5° C., acidified with 6N HCl and extracted with EtOAC. Organics were combined, dried over Na$_2$SO$_4$ and concentrated to a residue that was crystallized from cyclohexane to afford Compound 3b. LC-MS (method G): Rt=1.40 min; M/z=252 [M+Na]

Step 3c

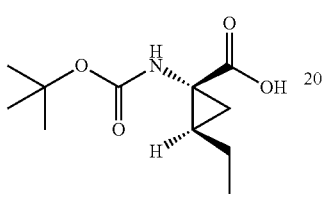

Compound 3c was obtained from Compound 3b (5 g; 21.81 mmol) according to the method described at step 1b. LC-MS (method D): Rt=1.91 min; M/z=360 [M-1]

Step 3d

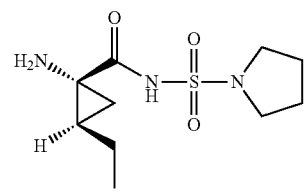

Pyrrolidine-1-sulfonic acid ((1R,2R)-1-amino-2-ethyl-cyclopropanecarbonyl)-amide Pyrrolidine-1-sulfonic acid ((1R,2R)-1-amino-2-ethyl-cyclopropanecarbonyl)-amide hydrochloride was obtained from Compound 3c (4.602 g; 12.73 mmol) according to the method described at step 1c. LC-MS (method E): Rt=1.06 min; M/z=262 [M+1]

Example 1

Compound 13

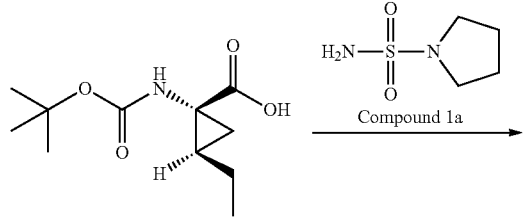

Compound 3b

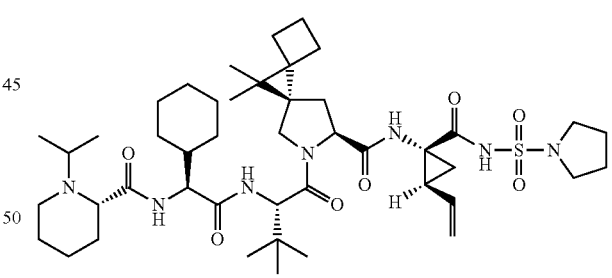

Compound 3c

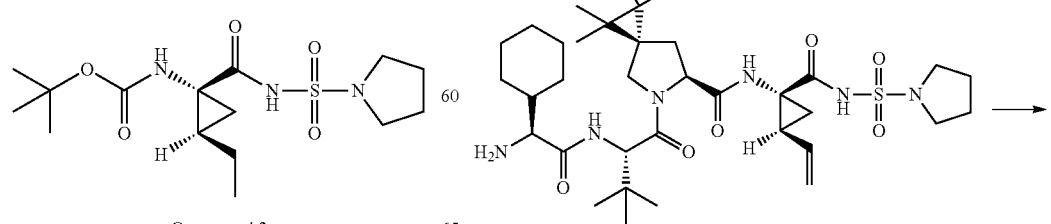

Intermediate I

-continued

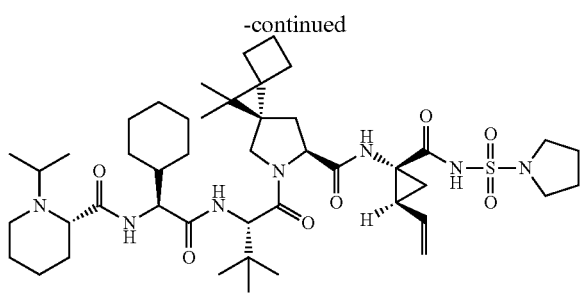

A suspension of (S)-1-isopropyl-piperidine-2-carboxylic acid (1.39 g; 8.11 mmol) in DMF (150 mL) was treated with HATU (3.86 g; 10.14 mmol) and DIPEA (3.54 mL; 20.29 mmol) and stirred at RT. The resulting solution was treated with Intermediate I hydrochloride (5 g; 6.76 mmol) and stirred at RT under Argon for 1 h. The reaction mixture was taken up in EtOAc, washed with water. The aqueous phase was extracted with EtOAc. The organics were combined, washed with saturated aq NaHCO$_3$, dried over Na$_2$SO$_4$ and concentrated to a brown oil. Purification by FC on silica gel (eluent: cyclohexane to cyclohexane/aceton 3:2) afforded Compound 1 as a foam. TLC: Rf (cyclohexane/aceton 3:2) =0.23; LC-MS (method E): M/z=856 [M+1]; HPLC (method D): Rt=2.13 min; 1H-NMR (500 MHz, DMSO-d6): δ (ppm) =10.2 (s, 1H), 9.6 (bs, 1H), 8.9 (d, 1H), 8.8 (s, 1H), 8.0 (d, 1H), 5.5 (dt, 1H), 5.2 (d, 1H), 5.1 (d, 1H), 4.55 (d, 1H), 4.35 (t, 1H), 4.15 (t, 1H), 4.05 (t, 1H), 3.4-3.65 (m, 5H), 3.3 (m, 4H), 3.1 (m, 2H), 2.85 (bs, 1H), 2.5 (t, 1H), 2.15 (m, 1H), 0.9-2.0 (m, 42H), 0.85 (s, 3H), 0.8 (s, 3H).

Example 2

Compound 34

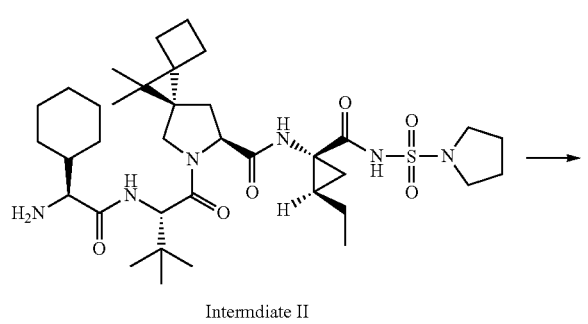

Interndiate II

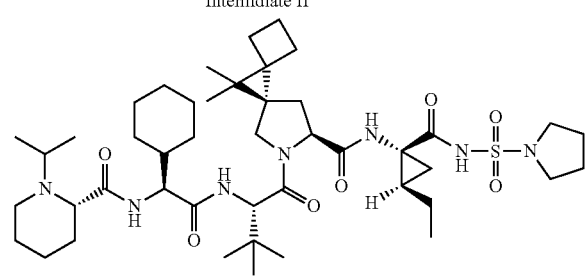

Compound 2 hydrochloride was obtained from Intermediate II (0.28 g; 0.378 mmol) according to the method described for the preparation of Compound 1. HPLC (method B): Rt=3.70 min; MS (method J) M/z=858 [M+1]

1H-NMR (400 MHz, methanol-d4): δ (ppm)=8.4 (d, 1H), 4.75 (d, 1H), 4.3 (d, 1H), 4.2 (t, 1H), 3.95 (bs, 1H), 3.4-3.7 (m, 9H), 3.0 (m, 1H), 2.15 (m, 1H), 1.05-2.1 (m, 43H), 1.05 (s, 9H), 0.9 (s, 3H), 0.95 (s, 3H).

The following compounds were prepared in an analogous manner:

Example 3

Compound 15

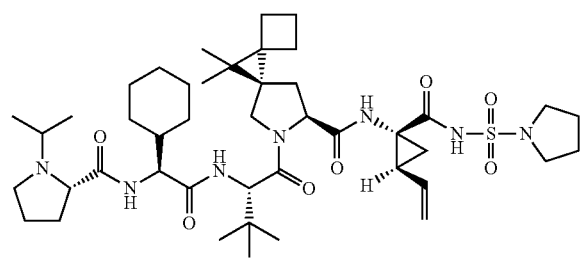 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N1CCCC1]

1H-NMR (500 MHz, DMSO-d6): δ (ppm)=10.1 (s, 1H), 9.15 (bs, 1H), 8.75 (s, 1H), 8.65 (d, 1H), 8.0 (d, 1H), 5.5 (m, 1H), 5.2 (d, 1H), 5.1 (d, 1H), 4.55 (d, 1H), 4.4 (t, 1H), 4.25 (m, 1H), 4.1 (t, 1H), 3.4-3.6 (m, 4H), 3.2 (m, 1H), 2.3 (m, 1H), 2.1 (m, 1H), 1.2 (d, 3H), 1.15 (d, 3H), 0.9-2.0 (m, 32H), 0.95 (s, 9H), 0.85 (s, 3H), 0.8 (s, 3H).

Example 4

Compound 37

1H-NMR (400 MHz, methanol-d4): δ (ppm)=8.4 (d, 1H), 5.75 (dt, 1H), 5.2 (d, 1H), 5.1 (d, 1H), 4.7 (d, 1H), 4.3 (d, 1H), 4.2 (t, 1H), 3.8 (bs, 1H), 3.35-3.7 (m, 7H), 2.9-3.3 (m, 3H), 2.2 (m, 1H), 1.1 (m, 35H), 1.05 (s, 9H), 0.9 (s, 3H), 0.95 (s, 3H).
Example 5
Compound 63
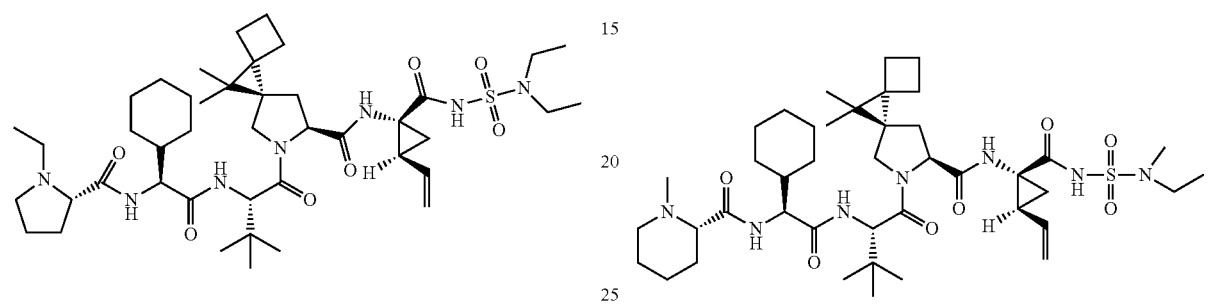
1H-NMR (500 MHz, DMSO-d6): δ (ppm)=10.2 (s, 1H), 8.8 (s, 1H), 8.05 (d, 1H), 7.75 (d, 1H), 5.55 (m, 1H), 5.2 (d, 1H), 5.1 (d, 1H), 4.5 (d, 1H), 4.4 (t, 1H), 4.1 (t, 1H), 3.5 (m, 2H), 3.2 (m, 4H), 3.1 (bs, 1H), 2.8 (m, 1H), 2.4 (m, 2H), 2.2 (m, 1H), 2.1 (m, 2H), 1.5-1.95 (m, 17H), 1.25 (t, 1H), 0.9-1.15 (m, 24H), 0.85 (s, 3H), 0.8 (s, 3H).
Example 6
Compound 65
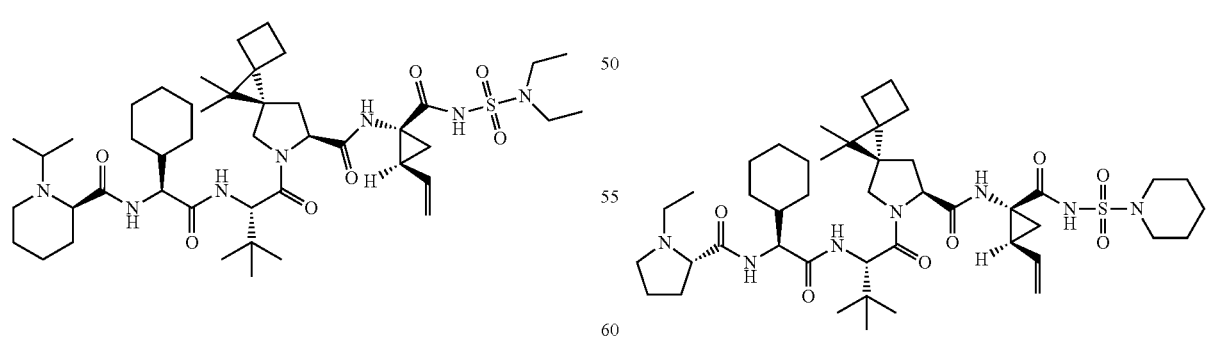
1H-NMR (500 MHz, DMSO-d6): δ (ppm)=10.15 (s, 1H), 9.5 (t, 1H), 8.8 (m, 2H), 8.0 (d, 1H), 5.55 (dt, 1H), 5.2 (d, 1H), 5.1 (d, 1H), 4.55 (d, 1H), 4.35 (t, 1H), 4.1 (t, 1H), 4.0 (m, 1H),
3.6 (d, 1H), 3.5 (d, 1H), 3.3 (m, 5H), 2.9 (bs, 1H), 2.1 (m, 1H), 1.0-2.0 (m, 34H), 1.1 (t, 6H), 1.0 (s, 9H), 0.9 (s, 3H), 0.85 (s, 3H).
Example 7
Compound 93
1H-NMR (500 MHz, DMSO-d6): δ (ppm)=10.2 (s, 1H), 9.5 (bs, 1H), 8.75 (s, 1H), 8.65 (d, 1H), 8.0 (d, 1H), 5.55 (m, 1H), 5.2 (d, 1H), 5.1 (d, 1H), 4.5 (d, 1H), 4.4 (t, 1H), 4.1 (t, 1H), 3.75 (t, 1H), 3.5 (m, 2H), 3.15 (m, 2H), 3.0 (m, 1H), 2.75 (m, 3H), 2.65 (m, 3H), 2.1 (m, 1H), 1.05-2.0 (m, 28H), 1.05 (t, 3H), 0.9 (s, 9H), 0.85 (s, 3H), 0.8 (s, 3H).
Example 8
Compound 95
1H-NMR (500 MHz, DMSO-d6): δ (ppm)=10.2 (s, 1H), 9.56 (bs, 1H), 8.7 (m, 2H), 8.05 (d, 1H), 5.55 (m, 1H), 5.25 (d, 1H), 5.1 (d, 1H), 4.55 (d, 1H), 4.4 (t, 1H), 4.15 (t, 1H), 3.5 (m, 2H), 3.0-3.5 (m, 8H), 0.75-2.5 (m, 28H), 0.95 (s, 9H), 0.85 (s, 3H), 0.8 (s, 3H).
Example 9
Compound 108
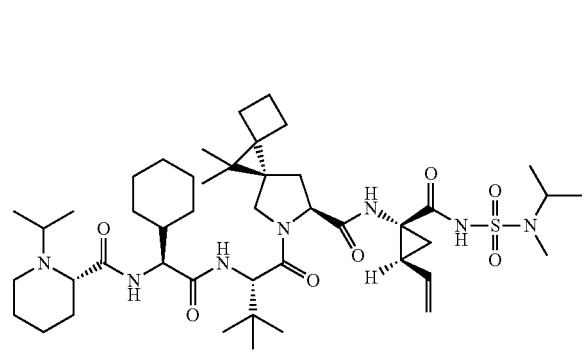 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)C(C)C]
1H-NMR (500 MHz, DMSO-d6): δ (ppm)=10.1 (s, 1H), 9.5 (bs, 1H), 8.8 (s, 1H), 8.75 (d, 1H), 8.05 (d, 1H), 6.0 (dt, 1H), 5.25 (d, 1H), 5.1 (d, 1H), 4.55 (m, 1H), 4.4 (m, 1H), 4.1 (t, 1H), 4.0 (m, 2H), 3.55 (m, 3H), 2.9 (m, 1H), 2.7 (s, 3H), 2.1 (m, 1H), 1.0-2.0 (m, 34H), 1.05 (t, 6H), 1.0 (s, 9H), 0.9 (s, 3H), 0.85 (s, 3H).
Example 10
Compound 120
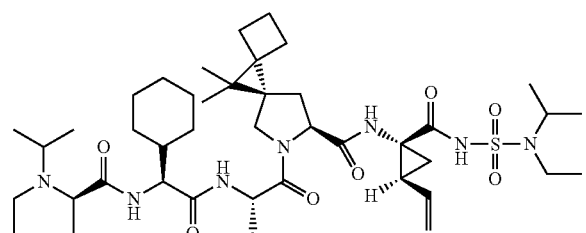
1H-NMR (500 MHz, DMSO-d6): δ (ppm)=10.1 (s, 1H), 9.4 (bs, 1H), 8.8 (s, 1H), 8.75 (d, 1H), 8.05 (d, 1H), 5.6 (dt, 1H), 5.2 (d, 1H), 5.05 (d, 1H), 4.55 (d, 1H), 4.35 (t, 1H), 4.1 (t, 1H), 3.95 (t, 1H), 3.5 (m, 2H), 3.35-3.4 (m, 4H), 3.2 (m, 2H), 2.85 (bs, 1H), 2.1 (m, 1H), 0.9-2.0 (m, 50H), 0.85 (s, 3H), 0.8 (s, 3H).
Example 11
Compound 142
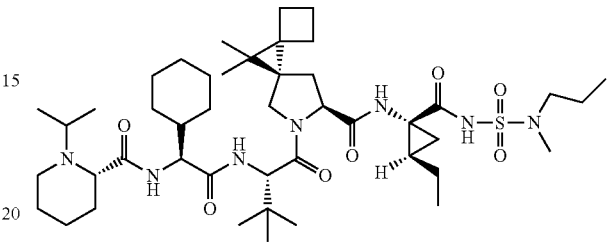
1H-NMR (500 MHz, DMSO-d6): δ (ppm)=10.15 (s, 1H), 9.5 (bs, 1H), 8.75 (d, 1H), 8.65 (s, 1H), 8.05 (d, 1H), 4.55 (d, 1H), 4.4 (t, 1H), 4.1 (t, 1H), 4.0 (t, 1H), 3.55 (m, 2H), 3.45 (m, 1H), 3.15 (m, 1H), 3.05 (m, 1H), 2.85 (m, 1H), 2.77 (s, 3H), 0.75-2.0 (m, 45H), 0.95 (s, 9H), 0.85 (s, 3H), 0.8 (s, 3H).
Example 12
Compound 99
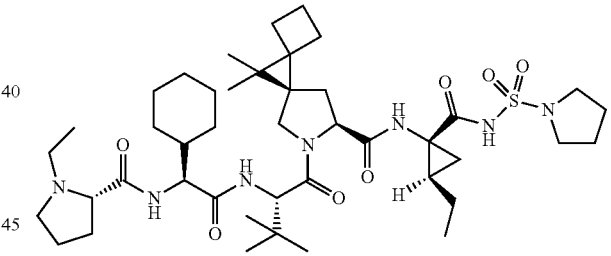
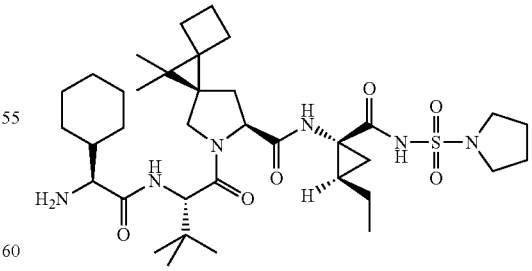
+
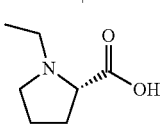
→

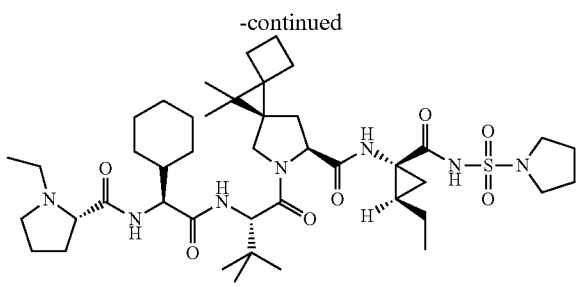
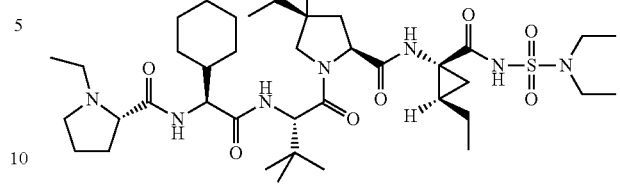

mixture of 100 mg (0.14 mmol) (5R,8S)-7-[(2S)-2-{[(2S)-2-amino-2-cyclohexylacetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide (hydrochloride salt), 20 mg (0.14 mmol) (S)-1-ethyl-pyrrolidine-2-carboxylic acid (lithium salt), 77 mg (0.20 mmol) HATU and 0.1 mL (0.61 mmol) DIPEA in 4 mL DMF was stirred at RT for 1 h. The reaction mixture was diluted with DCM and washed with 10% aq. KHSO$_4$ solution. The aq. layer was extracted with DCM (3×) and the combined organic layers were washed with sat. aq. NaHCO$_3$ solution, dried over Na$_2$SO$_4$ and concentrated in vacuo. The crude product was purified by prep. HPLC to yield the title compound. LC-MS (method E): Rt=1.862 min; M/z=830.5 [M+H]; HPLC (method D): Rt=2.093 min. 1H-NMR (500 MHz, DMSO-d6): d=0.83 (s, 3H), 0.86 (s, 3H), 0.88-0.91 (m, 5H), 0.93 (s, 9H), 1.28-1.44 (m, 6H), 1.52-1.80 (m, 22H), 1.83-1.90 (m, 5H), 2.04-2.07 (m, 1H), 2.23-2.26 (m, 1H), 2.40-2.47 (m, 2H), 2.84-2.85 (m, 1H), 3.11-3.13 (m, 1H), 3.31-3.34 (m, 4H), 3.49-3.54 (m, 2H), 4.11 (dd, 1H), 4.41 (dd, 1H), 4.53 (d, 1H), 7.78 (d, 1H), 8.04 (d, 1H), 8.55 (bs, 1H).

A mixture of 100 mg (0.14 mmol) (5R,8S)-7-[(2S)-2-{[(2S)-2-amino-2-cyclohexylacetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide (hydrochloride salt) (prepared in analogy as described for intermediate I starting with diethyl amine instead of pyrrolidine), 29 mg (0.20 mmol) (S)-1-ethyl-pyrrolidine-2-carboxylic acid (lithium salt), 102 mg (0.27 mmol) HATU and 0.1 mL (0.60 mmol) DIPEA in 3 mL DCM was stirred at RT overnight. The reaction mixture was concentrated in vacuo and the crude was purified by prep. HPLC to yield the title compound. LC-MS (method E): Rt=2.636 min; M/z=830.5 [M−H]; HPLC (method B): Rt=3.813 min. 1H-NMR (500 MHz, CDCl3): d=0.91 (s, 3H), 0.94 (s, 3H), 1.00 (t, 3H), 1.02 (s, 9H), 1.06-1.13 (m, 7H), 1.22 (t, 6H), 1.71-2.00 (m, 15H), 2.12-2.23 (m, 2H), 2.32-2.41 (m, 1H), 2.51-2.58 (m, 1H), 2.61-2.69 (m, 1H), 3.10-3.13 (m, 1H), 3.21-3.24 (m, 1H), 3.35-3.46 (m, 4H), 3.52-3.62 (m, 2H), 4.28-4.35 (m, 2H), 4.76 (d, 1H), 7.03 (bs, 1H), 8.08 (d, 1H), 9.90 (bs, 1H).

Example 13

Compound 100

Example 14

Compound 174

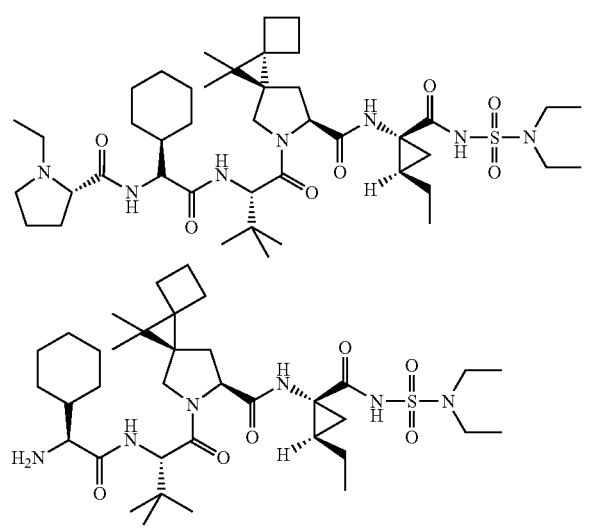
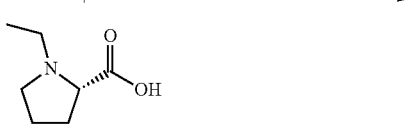
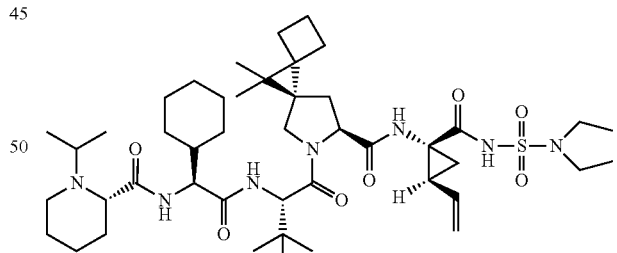

Prepared in analogy to example 100

1H NMR (400 MHz, CHLOROFORM-d) δ ppm 0.82 (d, 9H) 0.88-1.03 (m, 7H) 1.04-1.22 (m, 3H) 1.09 (t, 12H) 1.26 (br. s., 2H) 1.65 (br. s., 8H) 1.83 (br. s., 8H) 1.97 (br. s., 2H) 2.10 (br. s., 2H) 2.37 (br. s., 1H) 2.55 (br. s., 1H) 2.72 (br. s., 1H) 3.19-3.36 (m, 1H) 3.29 (ddd, 3H) 3.39 (br. s., 1H) 3.45 (br. s., 2H) 3.58 (s, 1H) 3.94 (br. s., 1H) 4.20 (br. s., 1H) 4.58

(br. s., 1H) 5.05 (s, 1H) 5.19 (s, 1H) 5.61 (s, 1H) 6.62 (br. s., 1H) 6.94 (d, 1H) 9.36 (br. s., 1H) 9.74 (br. s., 1H) 11.97 (br. s., 1H)

Example 15

Compound 203

Step a

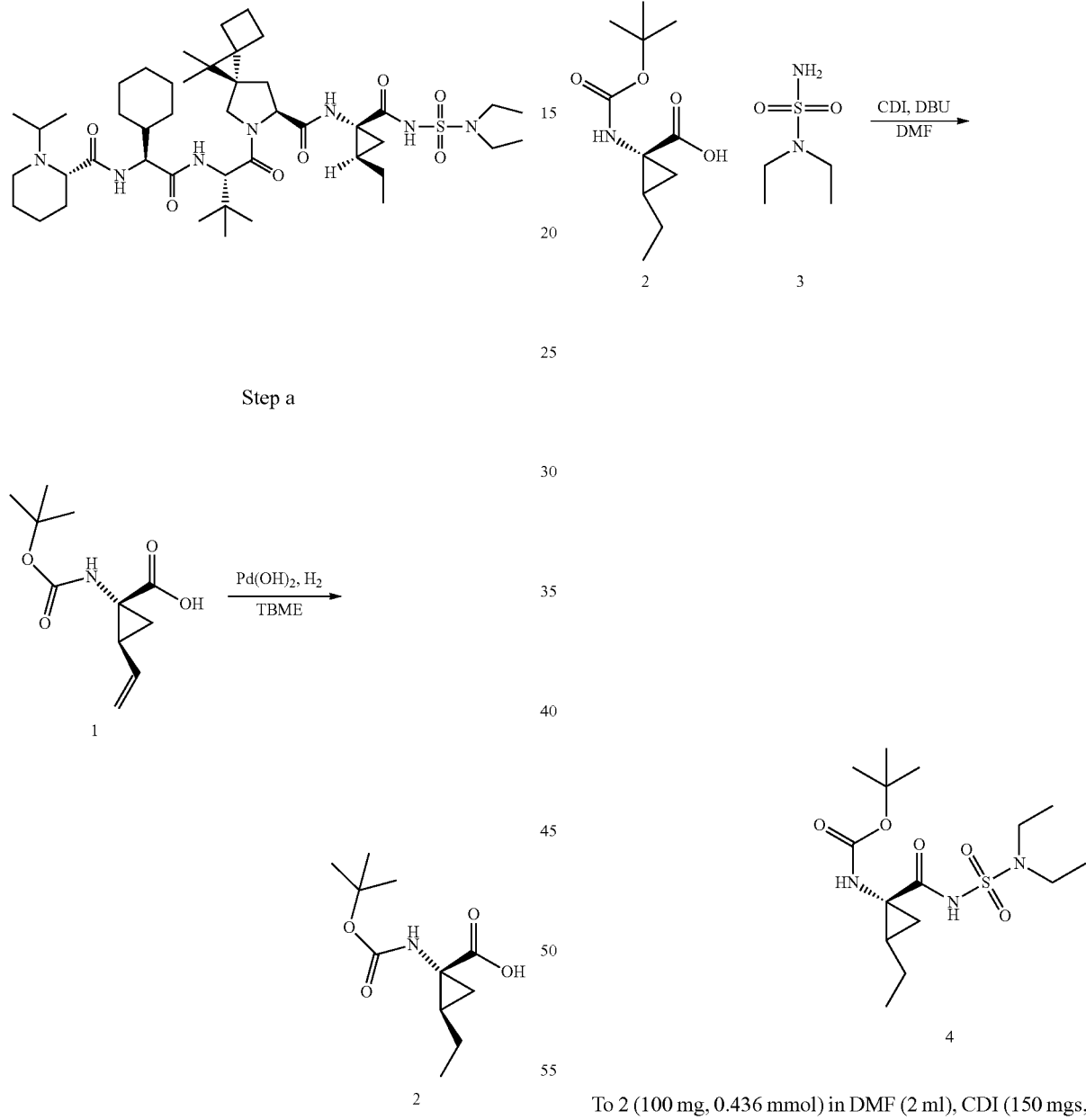

2 was prepared by a modification of the procedure published in the literature (*J. Org. Chem.*, 2005, 70, 5869). 1 (1.004 g, 4.40 mmol) was dissolved in TBME (25 ml) and hydrogenated (1 atm hydrogen gas) over 20% Pd(OH)$_2$/C (150 mgs) for 3 hours. The suspension was then filtered on celite and the crude concentrated under reduced pressure. The crude is crystallized from water-ethanol. The crude is taken in 100 ml water and heated to 70° C. and ethanol is added drop wise until the solution becomes clear. The solution is left overnight to cool and the solids are filtered to get the pure product 2 (494 mgs, 2.155 mmol, 49% yield). The pure product is dried under vacuum.

Step b

To 2 (100 mg, 0.436 mmol) in DMF (2 ml), CDI (150 mgs, 0.925 mmol) is added and stirred and heated to 100° C. for 1 hour. To the stirred solution 3 (100 mgs, 0.657 mmol) and DBU (0.5 ml, 3.32 mmol) are added and stirred to room temperature over night. The crude is diluted with ethyl acetate (25 ml) and washed successively with 1 M Sulfuric acid (3×100 ml) and saturated brine (. x̃. iml). The ethyl acetate layer containing the product is then concentrated under reduced pressure and purified on a silica column using 0-50% ethyl acetate in heptane as an eluent to get the pure product, 4 (64 mgs, 0.176 mmol, 40%).

1H NMR (400 MHz, CHLOROFORM-d) 1.00 (t, J=7.20 Hz, 3H) 1.05-1.13 (m, 1H) 1.22 (t, J=7.20 Hz, 6H) 1.36-1.43 (m, 1H) 1.48 (s, 9H) 1.56 (br. s., 4H) 3.42 (dd, 4H) 4.67-5.59 (m, 1H)

Step c

Step d

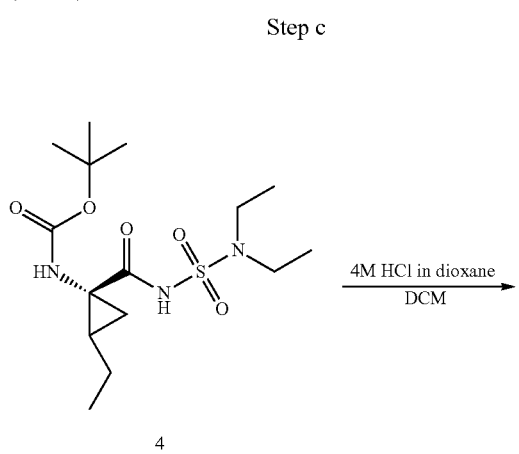

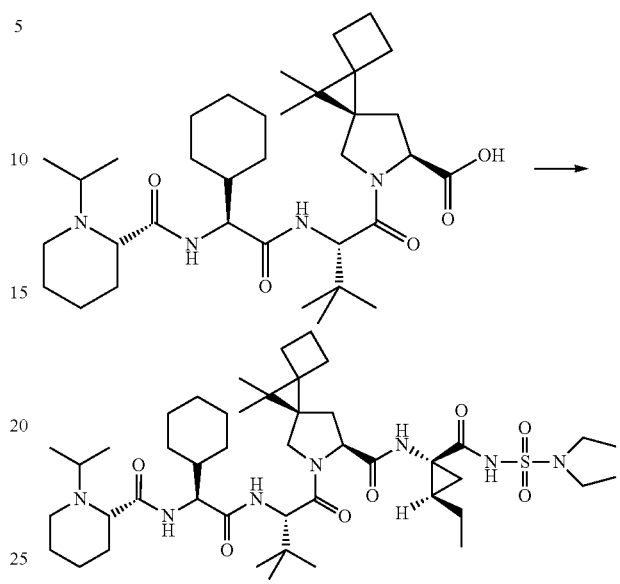

4 (64 mgs, 0.176 mmol) is dissolved in DCM (1 ml) and 4M HCl in dioxane (1 ml) was added and stirred at 32° C. for 1 hour until the deprotection is complete to yield the crude 5. The crude is concentrated under reduced pressure and is taken to the next step without further purification.

To (5R,8S)-7-((S)-2-{(S)-2-Cyclohexyl-2-[((S)-1-isopropyl-piperidine-2-carbonyl)-amino]-acetylamino}-3,3-dimethyl-butyryl)-10,10-dimethyl-7-aza-dispiro[3.0.4.1]decane-8-carboxylic acid (see example 150 step c) (90 mg, 0.146 mmol) and 5 (55 mg, 0.210 mmol) in DMF (1 ml), DIPEA (0.5 ml, 2.86 mmol) is added followed by HATU (80 mg, 0.210 mol) and the reaction is stirred to completion. The crude is diluted with ethyl acetate and washed with saturated brine to remove DMF. The crude ethyl acetate layer is concentrated under reduced pressure and taken for purification. A HPLC purification using ammonia (0.1%) in Acetonitrile-water yields the product (4 mg, 0.0046 mmol, 3% yield)

1H NMR (400 MHz, CHLOROFORM-d) δ ppm 0.83 (d, 8H) 0.98 (br. s., 1H) 1.00 (s, 9H) 1.09-1.26 (m, 11H) 1.54 (d, 10H) 1.63 (br. s., 2H) 1.68 (br. s., 4H) 1.87 (d, 8H) 2.09 (br. s., 1H) 2.26 (s, 1H) 2.40 (br. s., 1H) 2.61 (br. s., 1H) 3.22 (d, 1H) 3.24 (s, 1H) 3.33 (s, 1H) 3.31 (d, 2H) 3.44 (s, 2H) 3.53 (s, 2H) 3.95 (br. s., 1H) 4.23 (s, 2H) 4.58 (s, 1H) 6.64 (br. s., 1H) 6.93 (s, 1H) 9.42 (br. s., 1H) 9.69 (s, 1H) 12.00 (br. s., 1H)

Example 16

Compound 145

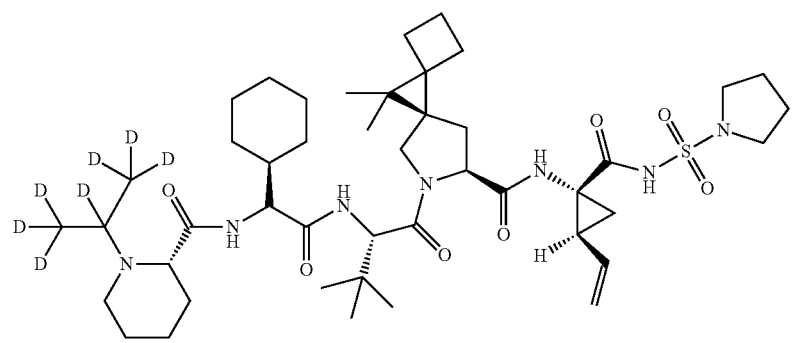

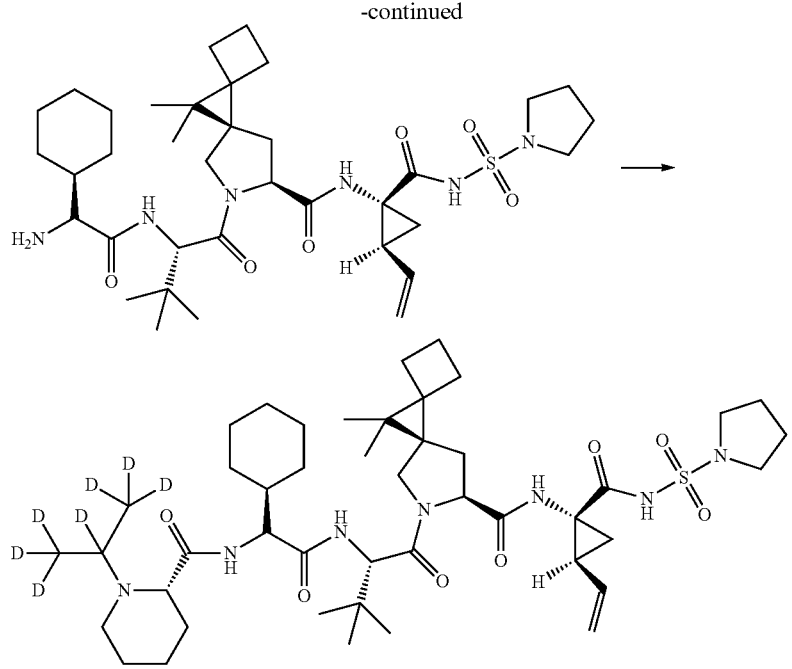

A solution of (S)-1-D₇-isopropyl-piperidine-2-carboxylic acid (0.039 g; 0.108 mmol), DIPEA (0.047 mL; 0.27 mmol) and HATU (0.041 g; 0.108 mmol) in DMF (2 mL) was stirred for 15 min at ambient temperature. After addition of (5R,8S)-7-[(S)-2-((S)-2-Amino-2-cyclohexyl-acetylamino)-3,3-dimethyl-butyryl]-10,10-dimethyl-7-aza-dispiro[3.0.4.1]decane-8-carboxylic acid [(1R,2S)-1-(pyrrolidine-1-sulfonylaminocarbonyl)-2-vinyl-cyclopropyl]-amide (0.040 g; 0.054 mmol) the reaction mixture was stirred overnight and purified without workup by preparative HPLC (method L) to yield the title compound. HPLC (method A3) Rt=5.69 min; MS (method E): M/z=863 [M+1]; 1H-NMR (500 MHz, DMSO-d6): 0.84 (s, 3H), 0.86 (s, 3H), 0.95 (s, 9H), 0.96-1.23 (m, 7H), 1.23-1.27 (m, 2H), 1.35-1.50 (m, 2H), 1.55-2.00 (m, 19H), 2.09-2.17 (m, 1H), 2.81-2.88 (m, 1H), 3.23-3.36 (m, 6H), 3.54 (dd, 2H), 3.99 (dd, 1H), 4.13 (dd, 1H), 4.41 (dd, 1H), 4.55 (d, 1H), 5.10 (dd, 2H), 5.51 (ddd, 1H), 8.04 (d, 1H), 8.72 (d, 1H), 9.49 (bs, 1H), 10.17 (bs, 1H).

Example 17

Compound 135

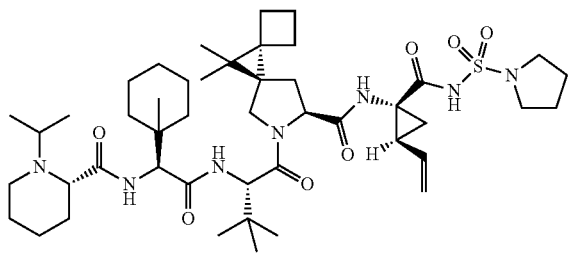

Step a

[(S)—((S)-1-{(5R,8S)-10,10-Dimethyl-8-[(1R,2S)-1-(pyrrolidine-1-sulfonylaminocarbonyl)-2-vinyl-cyclopropylcarbamoyl]-7-aza-dispiro[3.0.4.1]decane-7-carbonyl}-2,2-dimethyl-propylcarbamoyl)-(1-methyl-cyclohexyl)-methyl]-carbamic acid tert-butyl ester

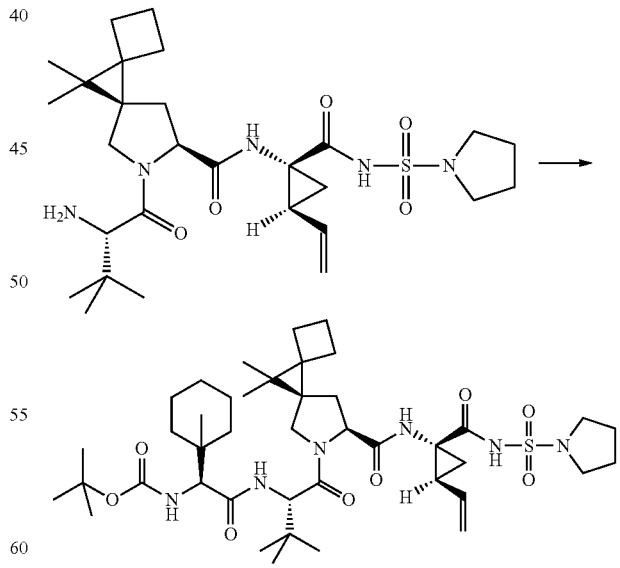

A solution of (S)-tert-Butoxycarbonylamino-(1-methyl-cyclohexyl)-acetic acid (0.217 g; 0.80 mmol) (prepared according to *Tetrahedron Let.* 2007, 48, 6343-6347) and HATU (0.38 g; 1.00 mmol) in DCM (10 mL) was stirred for 20 min at ambient temperature. After addition of DIPEA (0.698 mL; 4.00 mmol) and (5R,8S)-7-((S)-2-Amino-3,3-dimethyl-butyryl)-10,10-dimethyl-7-aza-dispiro[3.0.4.1]decane-8-carboxylic acid [(1R,2S)-1-(pyrrolidine-1-sulfonylaminocarbonyl)-2-vinyl-cyclopropyl]-amide (0.400 g; 0.67 mmol) in DCM (10 mL) the reaction mixture was stirred for 15 h, the solvent was removed in vacuo and the residue was purified by preparative HPLC (method L) to yield the title compound. LC-MS (method E): Rt=2.91 min; M/z=818 [M+H], HPLC (method A3) Rt=7.18 min Step b (5R,8S)-7-{(S)-2-[(S)-2-Amino-2-(1-methyl-cyclohexyl)-acetylamino]-3,3-dimethyl-butyryl}-10,10-dimethyl-7-aza-dispiro[3.0.4.1]decane-8-carboxylic acid [(1R,2S)-1-(pyrrolidine-1-sulfonylaminocarbonyl)-2-vinyl-cyclopropyl]-amide

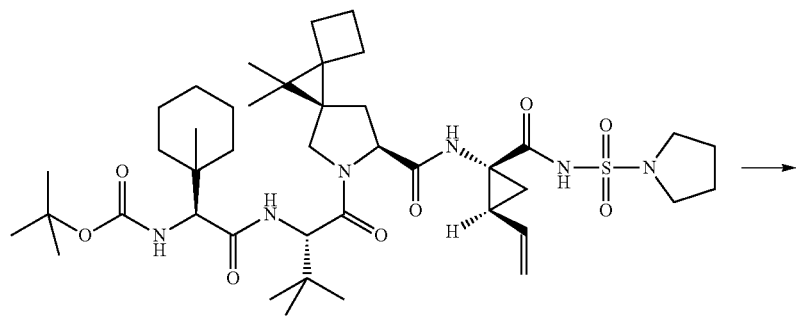

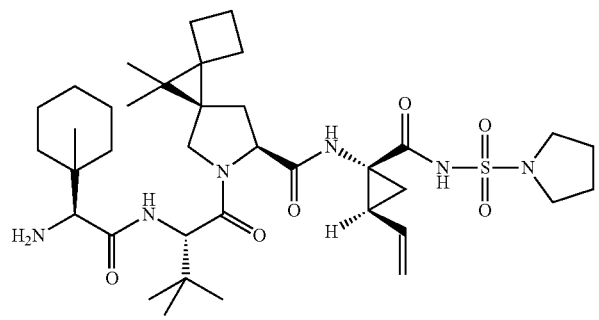

A mixture of [(S)—((S)-1-{(5R,8S)-10,10-Dimethyl-8-[(1R,2S)-1-(pyrrolidine-1-sulfonylaminocarbonyl)-2-vinyl-cyclopropylcarbamoyl]-7-aza-dispiro[3.0.4.1]decane-7-carbonyl}-2,2-dimethyl-propylcarbamoyl)-(1-methyl-cyclohexyl)-methyl]-carbamic acid tert-butyl ester (0.219 g; 0.27 mmol) and 2.0 mL HCl (4 M in dioxane) in 2 mL dioxane was stirred at ambient temperature for 2 h. The mixture was concentrated under reduced pressure and co-evaporated 2 times with DCM to yield the title compound which was used in the next step without further purification. LC-MS (method E): Rt=1.64 min; M/z=717 [M+]; HPLC (method A3): Rt=4.82 min

75
Step c

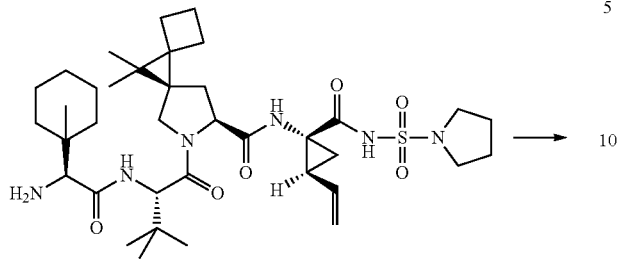

A solution of (S)-1-isopropyl-piperidine-2-carboxylic acid (0.014 g; 0.080 mmol) and HATU (0.038 g; 0.100 mmol) in DMF (2 mL) was stirred for 30 min at ambient temperature. After addition of DIPEA (0.070 mL; 0.398 mmol) and ((5R,8S)-7-{(S)-2-[(S)-2-Amino-2-(1-methyl-cyclohexyl)-acetylamino]-3,3-dimethyl-butyryl}-10,10-dimethyl-7-aza-dispiro[3.0.4.1]decane-8-carboxylic acid [(1R,2S)-1-(pyrrolidine-1-sulfonyl-aminocarbonyl)-2-vinyl-cyclopropyl]-amide (0.050 g; 0.066 mmol) the reaction mixture was stirred for 3 h and purified without workup by preparative HPLC (method L) to yield the title compound. HPLC (method A3) Rt=5.40 min; MS (method E): M/z=870 [M+]; 1H-NMR (500 MHz, DMSO-d6): 0.82 (s, 3H), 0.83 (s, 3H), 0.91 (s, 3H), 0.94 (s, 9H), 1.15-1.35 (m, 11H), 1.39-1.55 (m, 6H), 1.65-1.85 (m, 12H), 2.09-2.17 (m, 1H), 2.79-2.86 (m, 1H), 3.24-3.36 (m, 6H), 3.23-3.36 (m, 6H), 3.40-3.51 (m, 3H), 3.53-3.55 (m, 2H), 4.52-4.58 (m, 2H), 5.15 (dd, 2H), 5.50 (ddd, 1H), 8.00 (d, 1H), 8.62 (d, 1H), 9.50 (bs, 1H), 10.19 (bs, 1H).

Example 18

Compound 147

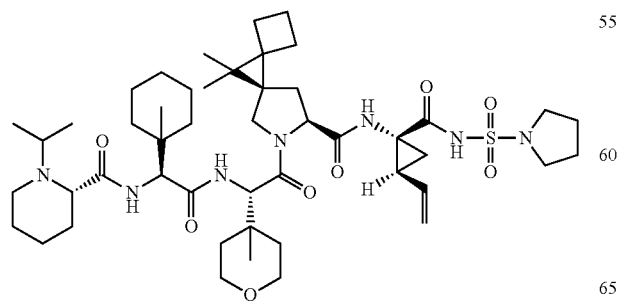

76
Step a (S)-2-{(5R,8S)-10,10-Dimethyl-8-[(1R,2S)-1-(pyrrolidine-1-sulfonylaminocarbonyl)-2-vinyl-cyclopropyl-carbamoyl]-7-aza-dispiro[3.0.4.1]dec-7-yl}-1-(4-methyl-tetrahydro-pyran-4-yl)-2-oxo-ethyl]-carbamic acid tert-butyl ester

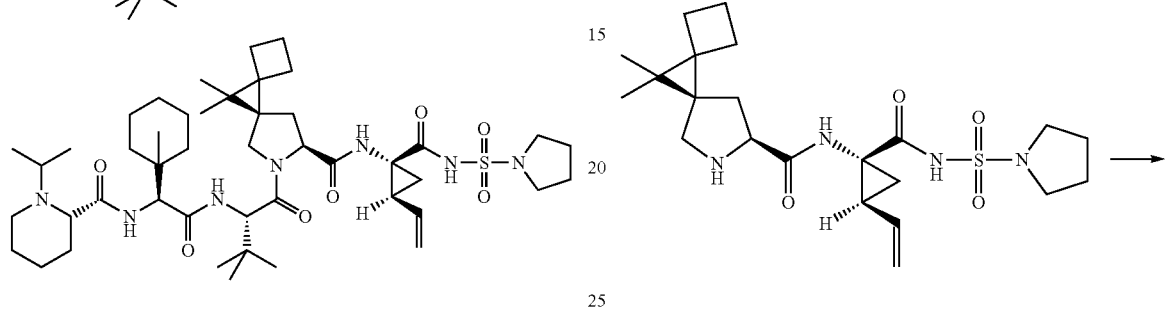

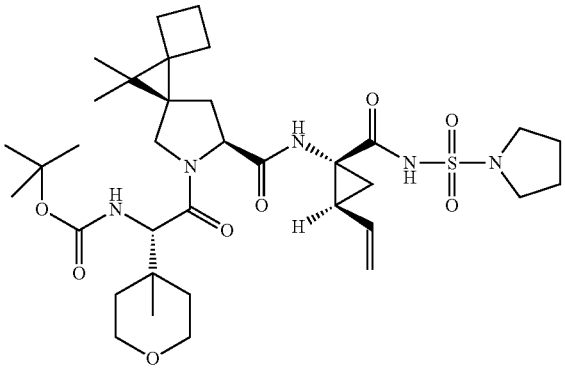

A solution of (S)-tert-Butoxycarbonylamino-(4-methyl-tetrahydro-pyran-4-yl)-acetic acid (0.306 g; 1.12 mmol) (prepared according to *Tetrahedron Let* 2007, 48, 6343-6347) and HATU (0.581 g; 1.53 mmol) in DCM (20 mL) was stirred for 10 min at ambient temperature. DIPEA (1.05 mL; 6.11 mmol) and (5R,8S)-10,10-Dimethyl-7-aza-dispiro[3.0.4.1]decane-8-carboxylic acid [(1R,2S)-1-(pyrrolidine-1-sufonylaminocarbonyl)-2-vinyl-cyclopropyl]-amide (0.57 g; 1.02 mmol) were added, the reaction mixture was stirred overnight and purified without workup by preparative HPLC (method L) to yield the title compound. LC-MS (method E): Rt=2.55 min; M/z=706 [M+]; HPLC (method A3): Rt=6.16 min

Step b (5R,8S)-7-[(S)-2-Amino-2-(4-methyl-tetrahydro-pyran-4-yl)-acetyl]-10,10-dimethyl-7-aza-dispiro-[3.0.4.1]decane-8-carboxylic acid [(1R,2S)-1-(pyrrolidine-1-sulfonylaminocarbonyl)-2-vinyl-cyclopropyl]-amide

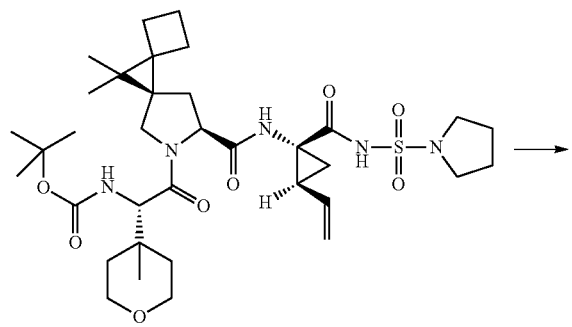

A mixture of [(S)-2-{(5R,8S)-10,10-Dimethyl-8-[(1R,2S)-1-(pyrrolidine-1-sulfonylaminocarbonyl)-2-vinyl-cyclopropyl-carbamoyl]-7-aza-dispiro[3.0.4.1]dec-7-yl}-1-(4-methyl-tetrahydro-pyran-4-yl)-2-oxo-ethyl]-carbamic acid tert-butyl ester (0.415 g; 0.588 mmol) and 13.0 mL HCl (4 M in dioxane) in 10 mL dioxane was stirred overnight at ambient temperature. The mixture was concentrated under reduced pressure to yield the title compound which was used in the next step without further purification. LC-MS (method E): Rt=1.45 min; M/z=606 [M+]; HPLC (method A3): Rt=4.01 min

Step c

[(S)-[(S)-2-{(5R,8S)-10,10-Dimethyl-8-[(1R,2S)-1-(pyrrolidine-1-sulfonylaminocarbonyl)-2-vinyl-cyclopropylcarbamoyl]-7-aza-dispiro[3.0.4.1]dec-7-yl}-2-oxo-1-(tetrahydro-pyran-4-yl)-ethylcarbamoyl]-(1-methyl-cyclohexyl)-methyl]-carbamic acid tert-butyl ester

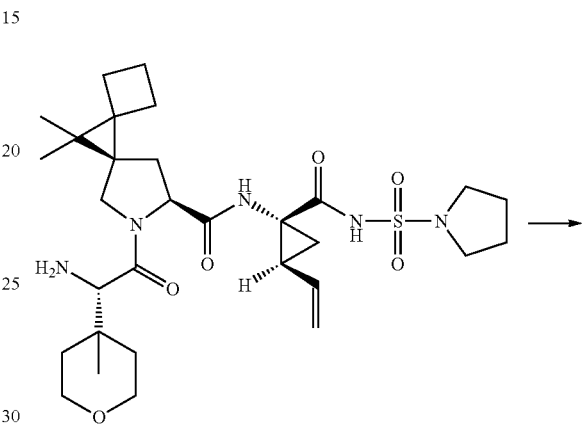

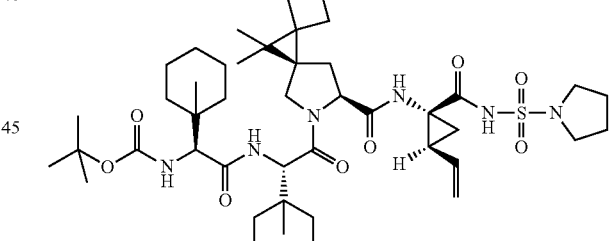

A solution of (S)-tert-Butoxycarbonylamino-(1-methyl-cyclohexyl)-acetic acid (0.15 g; 0.55 mmol) (prepared according to Tetrahedron Let. 2007, 48, 6343-6347) and HATU (0.31 g; 0.82 mmol) in DCM (15 mL) was stirred for 30 min at ambient temperature. After addition of DIPEA (0.56 mL; 3.27 mmol) and (5R,8S)-7-[(S)-2-Amino-2-(4-methyl-tetrahydro-pyran-4-yl)-acetyl]-10,10-dimethyl-7-aza-dispiro-[3.0.4.1]decane-8-carboxylic acid [(1R,2S)-1-(pyrrolidine-1-sulfonylaminocarbonyl)-2-vinyl-cyclopropyl]-amide (0.412 g; 0.55 mmol) in DCM (5 mL) the reaction mixture was stirred for 3 h, the solvent was removed in vacuo and the residue was purified by preparative HPLC (method L) to yield the title compound. LC-MS (method E): Rt=2.78 min; M/z=859 [M+], HPLC (method A3) Rt=6.81 min

Step d (5R,8S)-7-[(S)-2-[(S)-2-Amino-2-(1-methyl-cyclo-hexyl)-acetylamino]-2-(4-methyl-tetrahydro-pyran-4-yl)-acetyl]-10,10-dimethyl-7-aza-dispiro[3.0.4.1]decane-8-carboxylic acid [(1R,2S)-1-(pyrrolidine-1-sulfonylamin

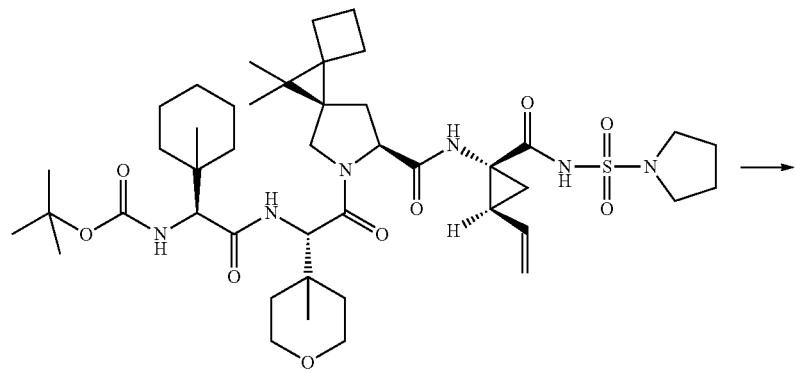

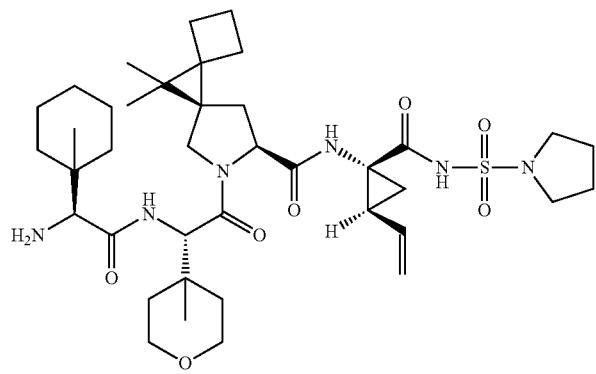

A mixture of [(S)-[(S)-2-{(5R,8S)-10,10-Dimethyl-8-[(1R,2S)-1-(pyrrolidine-1-sulfonylaminocarbonyl)-2-vinyl-cyclopropylcarbamoyl]-7-aza-dispiro[3.0.4.1]dec-7-yl}-2-oxo-1-(tetrahydro-pyran-4-yl)-ethylcarbamoyl]-(1-methyl-cyclohexyl)-methyl]-carbamic acid tert-butyl ester (0.227 g; 0.264 mmol) and 1.3 mL HCl (4 M in dioxane) in 2 mL dioxane was stirred overnight at ambient temperature. The mixture was concentrated under reduced pressure to yield the title compound which was used in the next step without further purification. LC-MS (method E): Rt=1.59 min; M/z=759 [M+]; HPLC (method A3): Rt=4.58 min

81

Step e

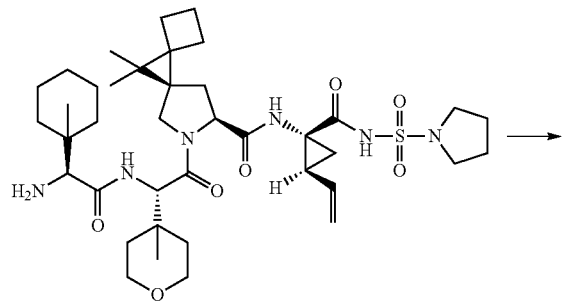

A solution of (S)-1-isopropyl-piperidine-2-carboxylic acid (0.011 g; 0.053 mmol) and HATU (0.031 g; 0.080 mmol) in DMF (2 mL) was stirred for 30 min at ambient temperature. DIPEA (0.055 mL; 0.32 mmol) and (5R,8S)-7-[(S)-2-[(S)-2-Amino-2-(1-methyl-cyclohexyl)-acetylamino]-2-(4-methyl-tetrahydro-pyran-4-yl)-acetyl]-10,10-dimethyl-7-aza-dispiro[3.0.4.1]decane-8-carboxylic acid [(1R,2S)-1-(pyrrolidine-1-sulfonylamino-carbonyl)-2-vinyl-cyclopropyl]-amide (0.050 g; 0.053 mmol) were added, the reaction mixture was stirred overnight and purified without workup by preparative HPLC (method L) to yield the title compound. LC-MS (method E): Rt=1.71 min; M/z=913 [M+H]; HPLC (method A3): Rt=5.11 min Example 19

Compound 149

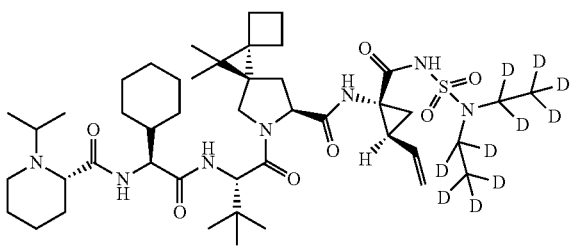

82

Step a (5R,8S)-7-[(S)-2-(S)-2-Amino-2-cyclohexyl-acetylamino)-3,3-dimethyl-butyryl]-10,10-dimethyl-7-aza-dispiro[3.0.4.1]decane-8-carboxylic acid methyl ester

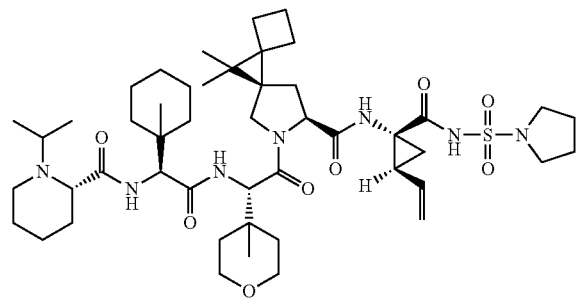

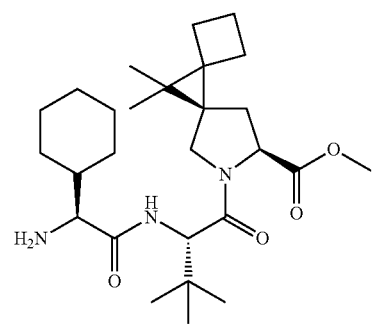

A mixture of (5R,8S)-7-[(S)-2-((S)-2-tert-Butoxycarbonylamino-2-cyclohexyl-acetylamino)-3,3-dimethyl-butyryl]-10,10-dimethyl-7-aza-dispiro[3.0.4.1]decane-8-carboxylic acid methyl ester (0.755 g; 1.31 mmol) and 4.9 mL HCl (4 M in dioxane) in 10 mL dioxane was stirred overnight at ambient temperature. The mixture was concentrated under reduced pressure to yield the title compound which was used in the next step without further purification. LC-MS (method E): Rt=1.47 min; M/z=476 [M+]; HPLC (method A3): Rt=4.27 min

Step b (5R,8S)-7-((S)-2-{(S)-2-Cyclohexyl-2-[((S)-1-isopropyl-piperidine-2-carbonyl)-amino]-acetylamino}-3,3-dimethyl-butyryl)-10,10-dimethyl-7-aza-dispiro[3.0.4.1]decane-8-carboxylic acid methyl ester

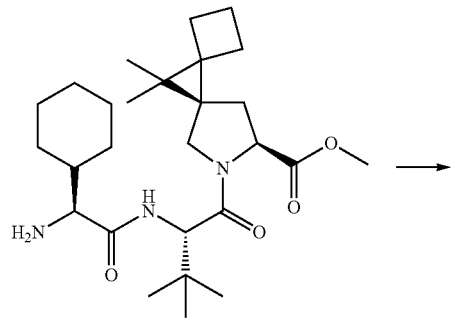

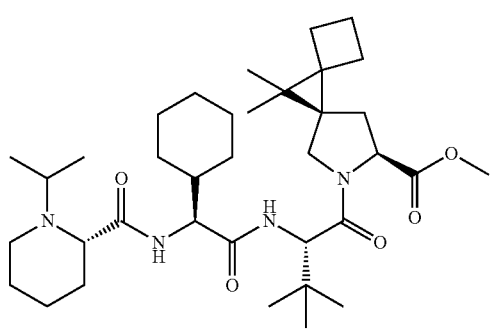

A solution of (S)-1-isopropyl-piperidine-2-carboxylic acid (0.497 g; 2.90 mmol) and HATU (1.65 g; 4.35 mmol) in DCM (100 mL) was cooled to 0° C. and (5R,8S)-7-[(S)-2-((S)-2-Amino-2-cyclohexyl-acetylamino)-3,3-dimethyl-butyryl]-10,10-dimethyl-7-aza-dispiro[3.0.4.1]decane-8-carboxylic acid methyl ester (1.65 g; 2.90 mmol) and DIPEA (2.98 mL; 17.4 mmol) were added. The reaction mixture was stirred for 3 h at room temperature quenched with saturated aqueous bicarbonate. The aq. phase was extracted twice with DCM, the combined organic phases dried with Na₂SO₄, filtered and the solvent was removed in vacuo. The product was purified by preparative HPLC (method L) to yield the title compound. LC-MS (method E): Rt=1.62 min; M/z=629 [M+]; HPLC (method A3): Rt=5.01 min

Step c (5R,8S)-7-((S)-2-{(S)-2-Cyclohexyl-2-[((S)-1-isopropyl-piperidine-2-carbonyl)-amino]-acetylamino}-3,3-dimethyl-butyryl)-10,10-dimethyl-7-aza-dispiro[3.0.4.1]decane-8-carboxylic acid

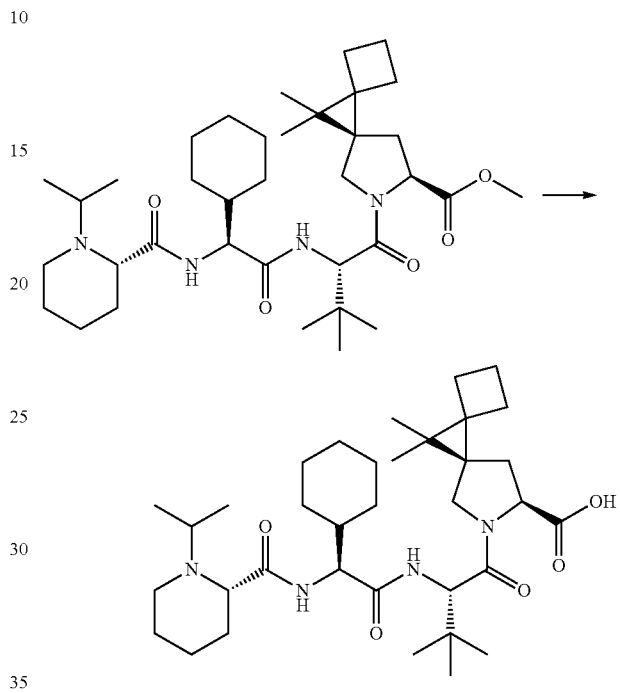

To a solution of (5R,8S)-7-((S)-2-{(S)-2-Cyclohexyl-2-[((S)-1-isopropyl-piperidine-2-carbonyl)-amino]-acetylamino}-3,3-dimethyl-butyryl)-10,10-dimethyl-7-aza-dispiro[3.0.4.1]decane-8-carboxylic acid methyl ester (0.69 g; 1.10 mmol) in THF/Methanol/water (2:1:1; 20 mL) was added LiOH monohydrate (0.138 g; 3.3 mmol) and the reaction was stirred overnight at room temperature. The solvent was removed in vacuo, water was added, the product was frozen in liquid nitrogen and lyophilized overnight to yield the title compound. LC-MS (method E): Rt=1.50 min; M/z=615 [M+]; HPLC (method A3): Rt=4.38 min

Step d

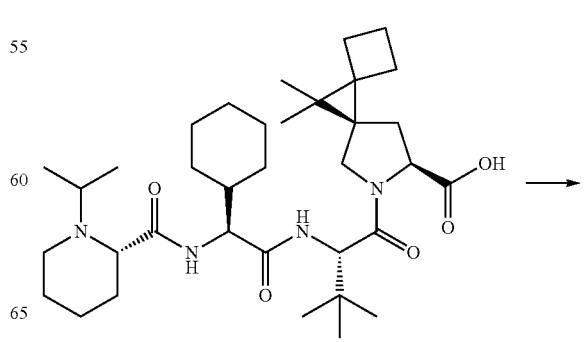

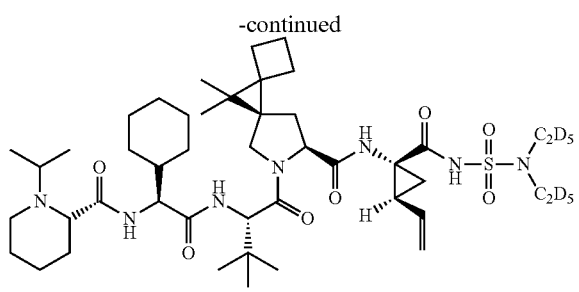

A solution of (5R,8S)-7-((S)-2-{(S)-2-Cyclohexyl-2-[((S)-1-isopropyl-piperidine-2-carbonyl)-amino]-acetylamino}-3,3-dimethyl-butyryl)-10,10-dimethyl-7-azadispiro[3.0.4.1]decane-8-carboxylic acid (0.040 g; 0.065 mmol) and HATU (0.050 g; 0.130 mmol) in DMF (2 mL) was stirred for 30 min at ambient temperature. After addition of DIPEA (0.057 mL; 0.325 mmol) and (D10)-Diethylamino-1-sulfonic acid ((1R,2S)-1-amino-2-vinyl-cyclopropanecarbonyl)-amide (0.040 g; 0.130 mmol) (prepared analogously as described for Intermediate III starting from commercially available deuterated d10-diethylamine) in DMF (2 mL) the reaction mixture was stirred overnight and purified without workup by preparative HPLC (method L) to yield the title compound. LC-MS (method E): Rt=1.76 min; M/z=869 [M+H], HPLC (method A3) Rt=5.78 min; 1H-NMR (500 MHz, DMSO-d6): 1H-NMR (500 MHz, DMSO-d6): 0.79-0.87 (m, 9H), 0.92-0.96 (m, 9H), 1.00-1.18 (m, 6H), 1.22-1.29 (m, 1H), 1.32-1.39 (m, 1H), 1.43-1.51 (m, 2H), 1.53-1.73 (m, 11H), 1.74-1.93 (m, 8H), 2.05-2.14 (m, 2H), 2.66-2.74 (m, 1H), 2.77 (dd, 1H), 2.66-1.74 (m, 1H), 2.89 (dd, 1H), 3.53 (dd, 2H), 4.11 (dd, 1H), 4.36 (dd, 1H), 4.50 (d, 1H), 5.15 (dd, 2H), 5.54 (ddd, 1H), 7.40 (d, 1H), 7.92 (d, 1H), 8.76 (s, 1H), 10.15 (s, 1H).

Additional compounds of the invention are provided in Table A. Compounds 1-203 have been prepared by methods of Examples 1 to 19 or by synthetic procedures which are analogous to the procedures used in Examples 1 to 19. Physical characterizing data and biological data for each compound of Table A is provided in Table C.

TABLE A

| Cmpd. # | Structure | Name |
|---|---|---|
| 1 | 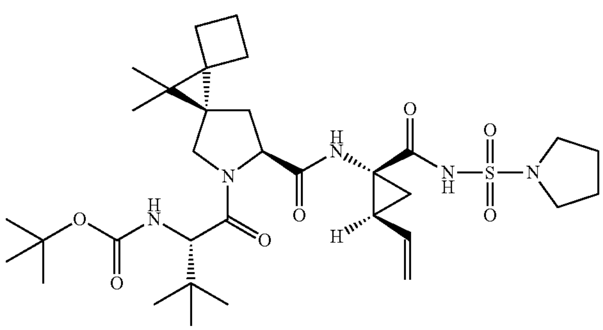 [SMILES: C=C[C@@H]1C[C@]1(NC(=O)[C@@H]1C[C@@]2(CN1C(=O)[C@@H](NC(=O)OC(C)(C)C)C(C)(C)C)C(C)(C)C21CCC1)C(=O)NS(=O)(=O)N1CCCC1] | tert-butyl [(1S)-1-{[(5R,8S)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]carbonyl}-2,2-dimethylpropyl]carbamate |
| 2 | 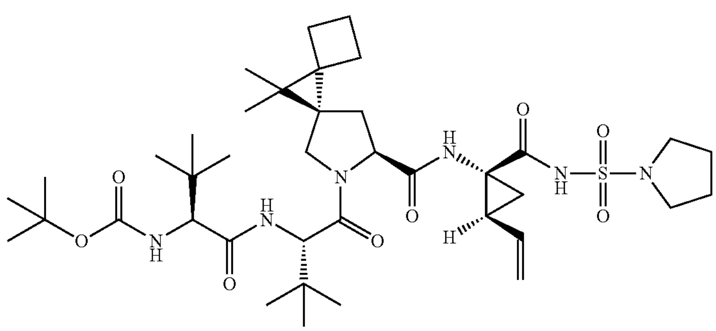 [SMILES: C=C[C@@H]1C[C@]1(NC(=O)[C@@H]1C[C@@]2(CN1C(=O)[C@@H](NC(=O)[C@@H](NC(=O)OC(C)(C)C)C(C)(C)C)C(C)(C)C)C(C)(C)C21CCC1)C(=O)NS(=O)(=O)N1CCCC1] | tert-butyl [(1S)-1-{[(1S)-1-{[(5R,8S)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]carbonyl}-2,2-dimethylpropyl]carbamoyl}-2,2-dimethylpropyl]carbamate |
| 3 | 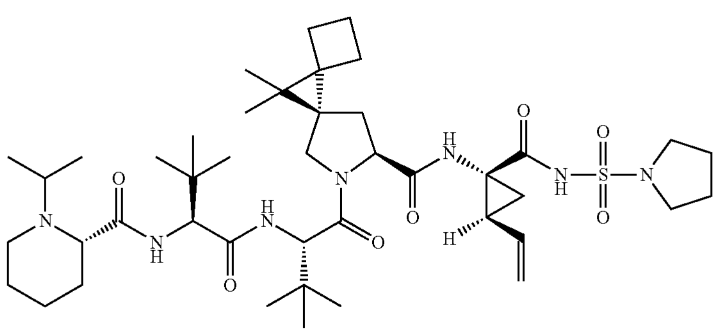 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-isopropylpiperidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 4 | 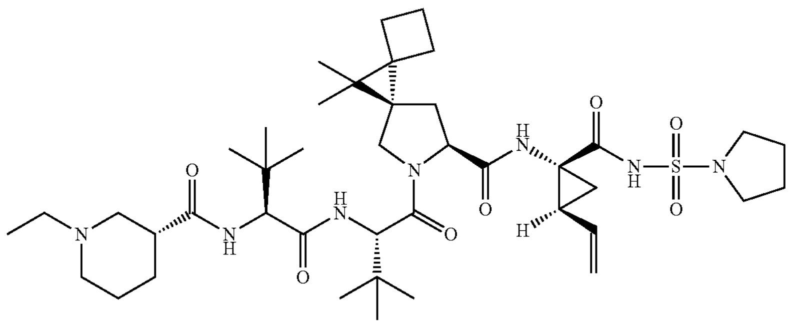 [SMILES: C=C[C@@H]1C[C@]1(NC(=O)[C@@H]1C[C@@]2(CN1C(=O)[C@@H](NC(=O)[C@@H](NC(=O)[C@@H]1CCCN(CC)C1)C(C)(C)C)C(C)(C)C)C(C)(C)C21CCC1)C(=O)NS(=O)(=O)N1CCCC1] | (5R,8S)-7-[(2S)-2-{[(2S)-2-({[(3R)-1-ethylpiperidin-3-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 5 | 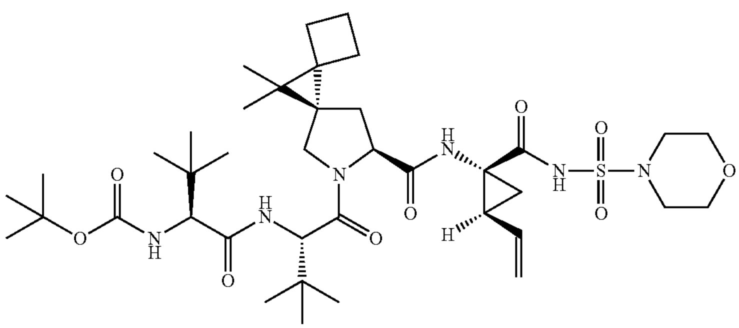 [SMILES: C=C[C@@H]1C[C@]1(NC(=O)[C@@H]1C[C@@]2(CN1C(=O)[C@@H](NC(=O)[C@@H](NC(=O)OC(C)(C)C)C(C)(C)C)C(C)(C)C)C(C)(C)C21CCC1)C(=O)NS(=O)(=O)N1CCOCC1] | tert-butyl [(1S)-1-{[(1S)-1-{[(5R,8S)-10,10-dimethyl-8-({(1R,2S)-1-[(morpholin-4-ylsulfonyl)carbamoyl]-2-vinylcyclopropyl}carbamoyl)-7-azadispiro[3.0.4.1]dec-7-yl]carbonyl}-2,2-dimethylpropyl]carbamoyl}-2,2-dimethylpropyl]carbamate |
| 6 | 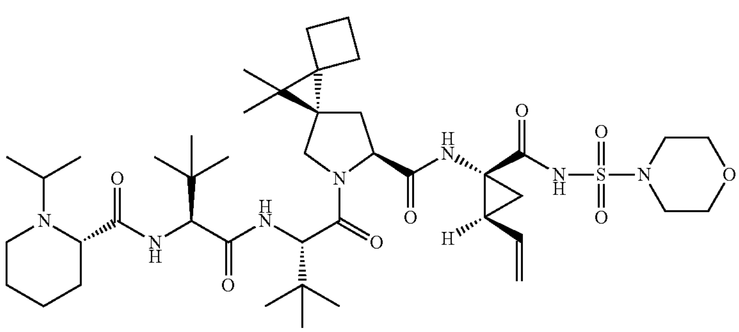 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C(C)(C)C)C(C)(C)C)C(C)(C)C21CCC1)C(=O)NS(=O)(=O)N1CCOCC1] | (5R,8S)-7-[(2S)-2-{[(2S)-2-({[(2S)-1-isopropylpiperidin-2-yl]carbonyl}amino)-3,3-dimethylbutanoyl]amino}-3,3-dimethylbutanoyl]-10,10-dimethyl-N-{(1R,2S)-1-[(morpholin-4-ylsulfonyl)carbamoyl]-2-vinylcyclopropyl}-7-azadispiro[3.0.4.1]decane-8-carboxamide |
| 7 | 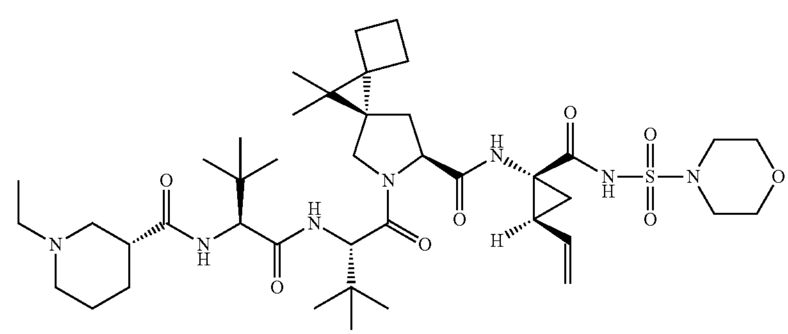 [SMILES: C=C[C@@H]1C[C@]1(NC(=O)[C@@H]1C[C@@]2(CN1C(=O)[C@@H](NC(=O)[C@@H](NC(=O)[C@@H]1CCCN(CC)C1)C(C)(C)C)C(C)(C)C)C(C)(C)C21CCC1)C(=O)NS(=O)(=O)N1CCOCC1] | (5R,8S)-7-[(2S)-2-{[(2S)-2-({[(3R)-1-ethylpiperidin-3-yl]carbonyl}amino)-3,3-dimethylbutanoyl]amino}-3,3-dimethylbutanoyl]-10,10-dimethyl-N-{(1R,2S)-1-[(morpholin-4-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 8 | 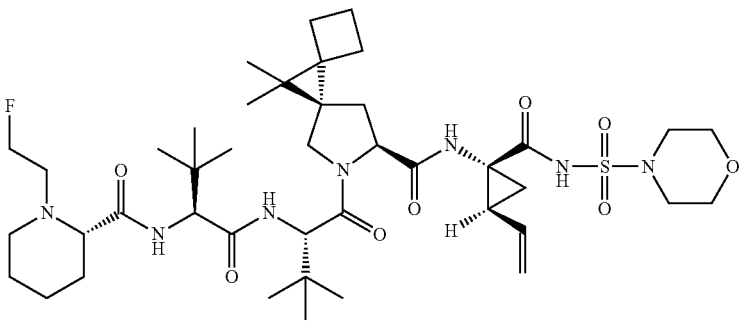 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CCF)C(C)(C)C)C(C)(C)C)C(C)(C)C21CCC1)C(=O)NS(=O)(=O)N1CCOCC1] | (5R,8S)-7-[(2S)-2-{[(2S)-2-({[(2S)-1-(2-fluoroethyl)piperidin-2-yl]carbonyl}amino)-3,3-dimethylbutanoyl]amino}-3,3-dimethylbutanoyl]-10,10-dimethyl-N-{(1R,2S)-1-[(morpholin-4-ylsulfonyl)carbamoyl]-2-vinylcyclopropyl}-7-azadispiro[3.0.4.1]decane-8-carboxamide |
| 9 | 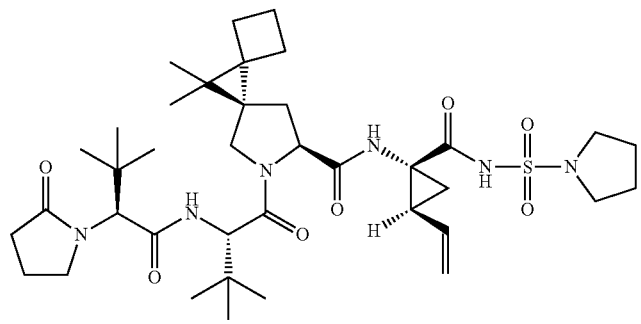 [SMILES: C=C[C@@H]1C[C@]1(NC(=O)[C@@H]1C[C@@]2(CN1C(=O)[C@@H](NC(=O)[C@@H](N1CCCC1=O)C(C)(C)C)C(C)(C)C)C(C)(C)C21CCC1)C(=O)NS(=O)(=O)N1CCCC1] | (5R,8S)-7-[(2S)-2-{[(2S)-3,3-dimethyl-2-(2-oxopyrrolidin-1-yl)butanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 10 | 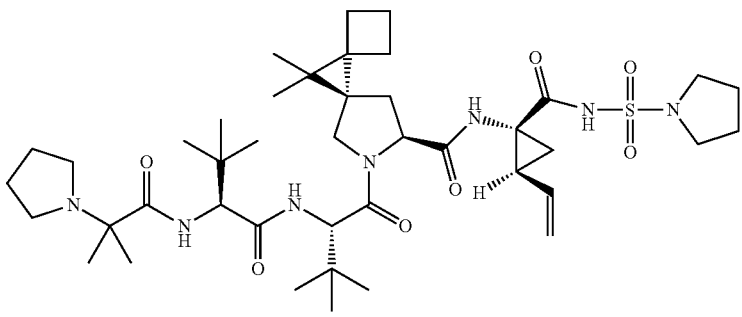 [SMILES: C=C[C@@H]1C[C@]1(NC(=O)[C@@H]1C[C@@]2(CN1C(=O)[C@@H](NC(=O)[C@@H](NC(=O)C(C)(C)N1CCCC1)C(C)(C)C)C(C)(C)C)C(C)(C)C21CCC1)C(=O)NS(=O)(=O)N1CCCC1] | (5R,8S)-7-[(2S)-2-({(2S)-3,3-dimethyl-2-[(2-methyl-2-pyrrolidin-1-ylpropanoyl)amino]butanoyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 11 | 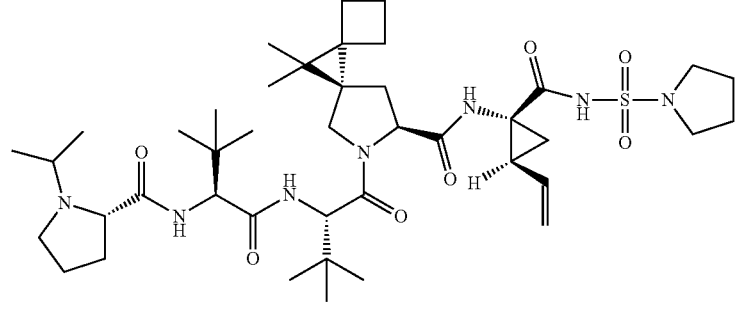 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-isopropylpyrrolidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 12 | 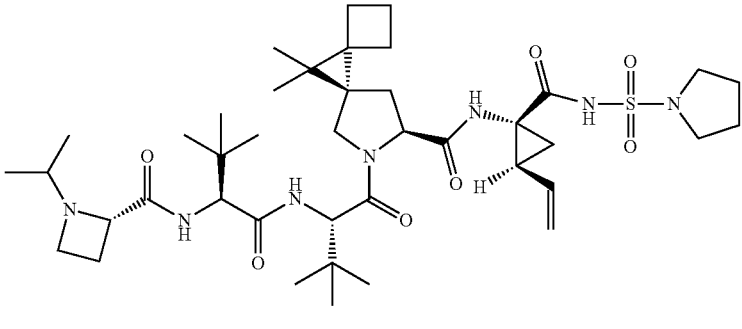 [SMILES: C=C[C@@H]1C[C@]1(NC(=O)[C@@H]1C[C@@]2(CN1C(=O)[C@@H](NC(=O)[C@@H](NC(=O)[C@@H]1CCN1C(C)C)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-isopropylazetidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 13 | 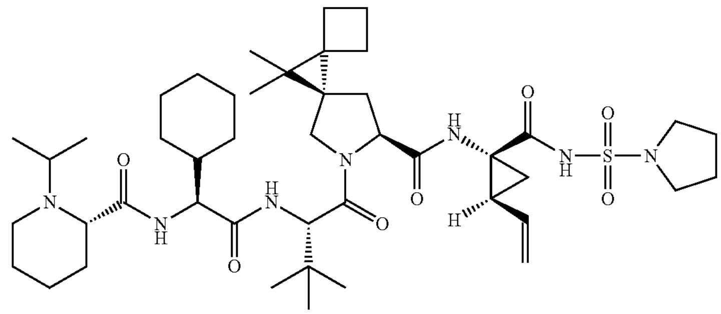 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 14 | 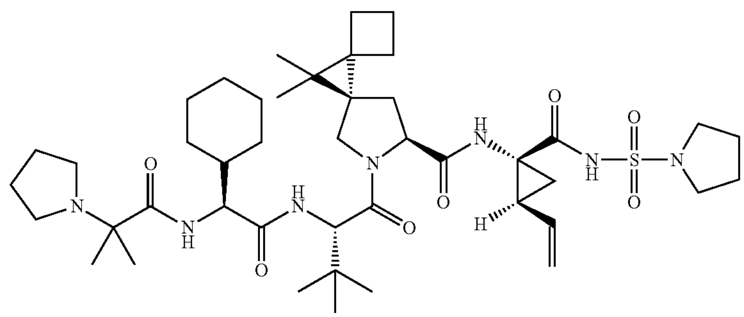 [SMILES: C=C[C@@H]1C[C@]1(NC(=O)[C@@H]1C[C@@]2(CN1C(=O)[C@@H](NC(=O)[C@@H](NC(=O)C(C)(C)N1CCCC1)C1CCCCC1)C(C)(C)C)C(C)(C)C21CCC1)C(=O)NS(=O)(=O)N1CCCC1] | (5R,8S)-7-[(2S)-2-({(2S)-2-cyclohexyl-2-[(2-methyl-2-pyrrolidin-1-ylpropanoyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 15 | 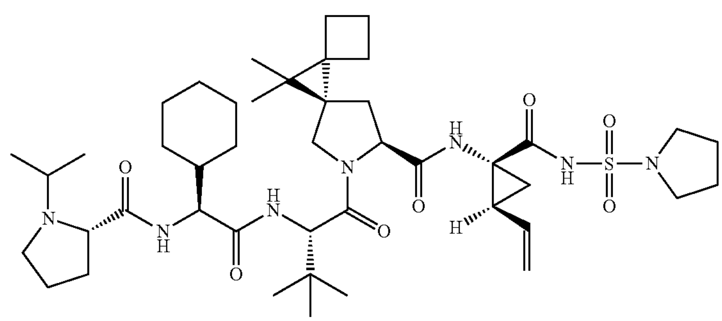 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 16 | 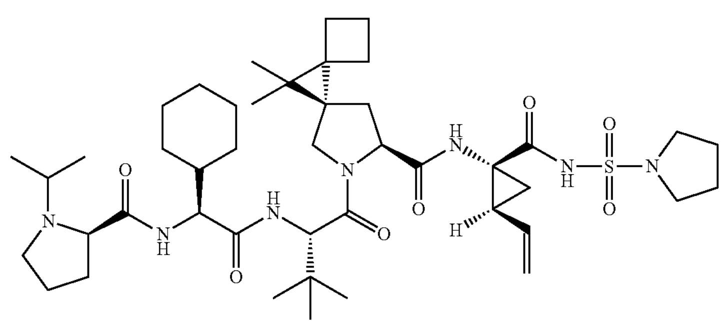 [SMILES: C=C[C@@H]1C[C@]1(NC(=O)[C@@H]1C[C@@]2(CN1C(=O)[C@@H](NC(=O)[C@@H](NC(=O)[C@H]1CCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 17 | 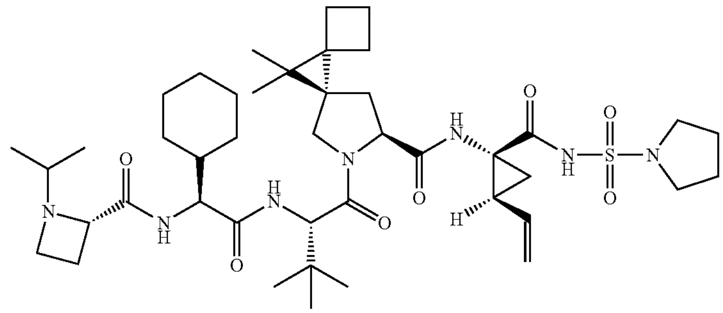 [SMILES: C=C[C@@H]1C[C@]1(NC(=O)[C@@H]1C[C@@]2(CN1C(=O)[C@@H](NC(=O)[C@@H](NC(=O)[C@@H]1CCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-isopropylazetidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 18 | 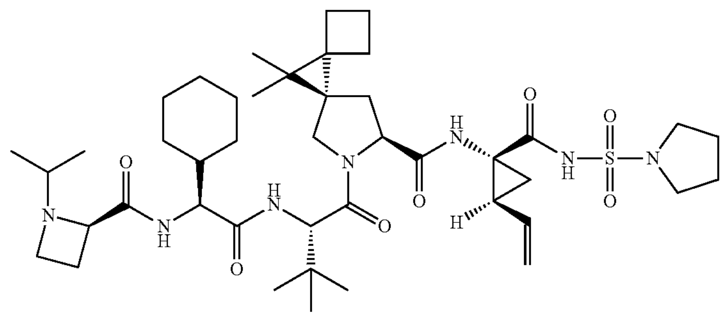 [SMILES: C=C[C@@H]1C[C@]1(NC(=O)[C@@H]1C[C@@]2(CN1C(=O)[C@@H](NC(=O)[C@@H](NC(=O)[C@H]1CCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-isopropylazetidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 19 | 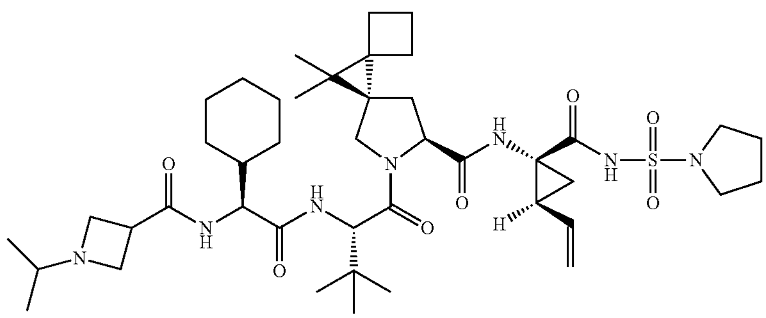 [SMILES: C=C[C@@H]1C[C@]1(NC(=O)[C@@H]1C[C@@]2(CN1C(=O)[C@@H](NC(=O)[C@@H](NC(=O)C1CN(C(C)C)C1)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-{[(1-isopropylazetidin-3-yl)carbonyl]amino}acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 20 | 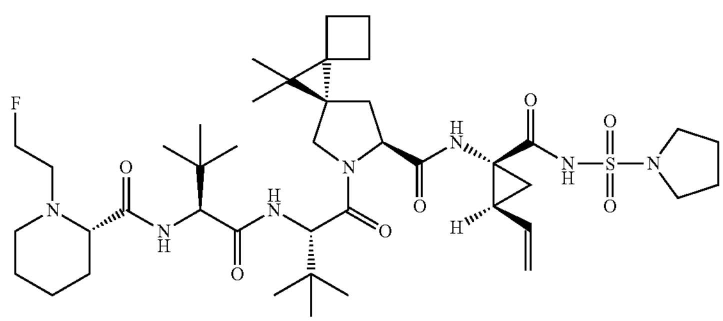 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CCF)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-(2-fluoroethyl)piperidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 21 | 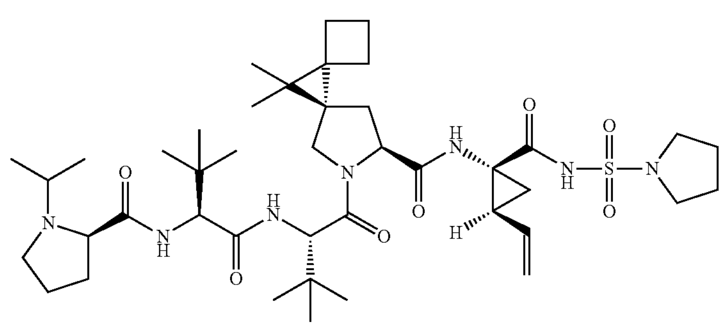 [SMILES: C=C[C@@H]1C[C@]1(NC(=O)[C@@H]1C[C@@]2(CN1C(=O)[C@@H](NC(=O)[C@@H](NC(=O)[C@H]1CCCN1C(C)C)C(C)(C)C)C(C)(C)C)C(C)(C)C21CCC1)C(=O)NS(=O)(=O)N1CCCC1] | (5R,8S)-7-[(2S)-2-{[(2S)-2-({[(2R)-1-isopropylpyrrolidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 22 | 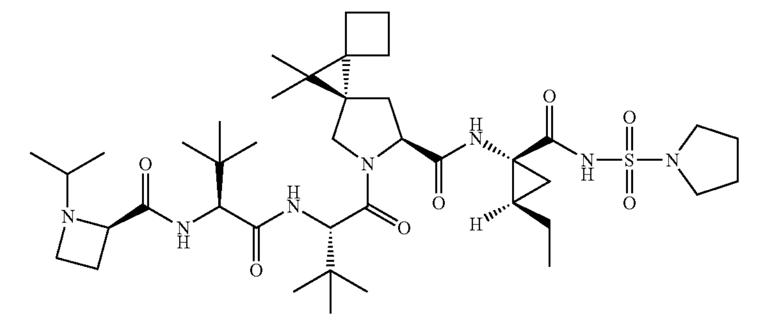 [SMILES: CC[C@@H]1C[C@]1(NC(=O)[C@@H]1C[C@@]2(CN1C(=O)[C@@H](NC(=O)[C@@H](NC(=O)[C@H]1CCN1C(C)C)C(C)(C)C)C(C)(C)C)C(C)(C)C21CCC1)C(=O)NS(=O)(=O)N1CCCC1] | (5R,8S)-7-[(2S)-2-{[(2S)-2-({[(2R)-1-isopropylazetidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 23 | 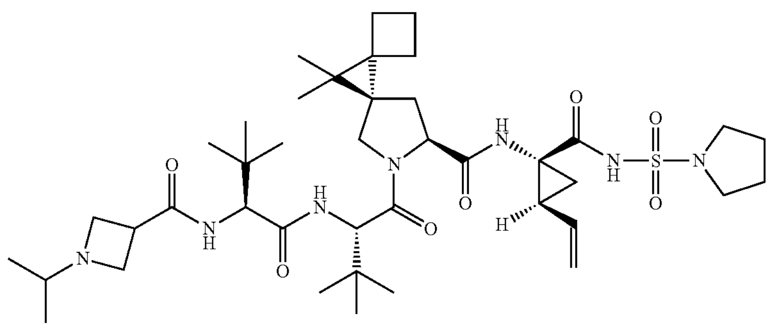 [SMILES: C=C[C@@H]1C[C@]1(NC(=O)[C@@H]1C[C@@]2(CN1C(=O)[C@@H](NC(=O)[C@@H](NC(=O)C1CN(C(C)C)C1)C(C)(C)C)C(C)(C)C)C(C)(C)C21CCC1)C(=O)NS(=O)(=O)N1CCCC1] | (5R,8S)-7-[(2S)-2-{[(2S)-2-{[(1-isopropylazetidin-3-yl)carbonyl]amino}-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 24 | 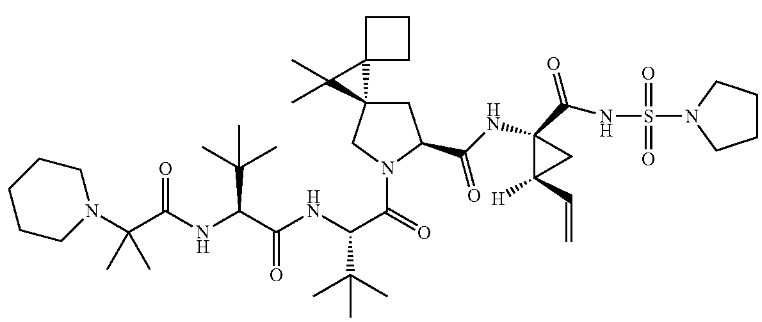 [SMILES: C=C[C@@H]1C[C@]1(NC(=O)[C@@H]1C[C@@]2(CN1C(=O)[C@@H](NC(=O)[C@@H](NC(=O)C(C)(C)N1CCCCC1)C(C)(C)C)C(C)(C)C)C(C)(C)C21CCC1)C(=O)NS(=O)(=O)N1CCCC1] | (5R,8S)-7-[(2S)-2-({(2S)-3,3-dimethyl-2-[(2-methyl-2-piperidin-1-ylpropanoyl)amino]butanoyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 25 | 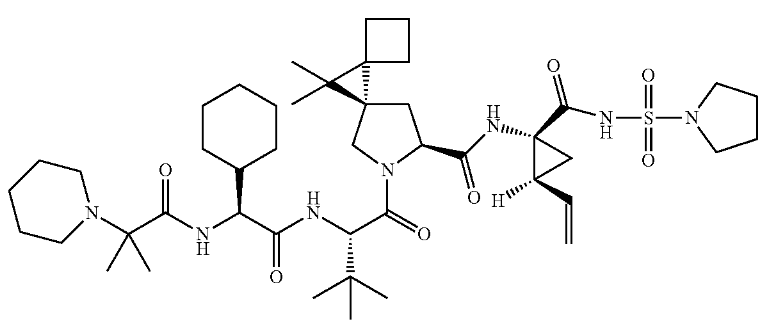 [SMILES: C=C[C@@H]1C[C@]1(NC(=O)[C@@H]1C[C@@]2(CN1C(=O)[C@@H](NC(=O)[C@@H](NC(=O)C(C)(C)N1CCCCC1)C1CCCCC1)C(C)(C)C)C(C)(C)C21CCC1)C(=O)NS(=O)(=O)N1CCCC1] | (5R,8S)-7-[(2S)-2-({(2S)-2-cyclohexyl-2-[(2-methyl-2-piperidin-1-ylpropanoyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 26 | 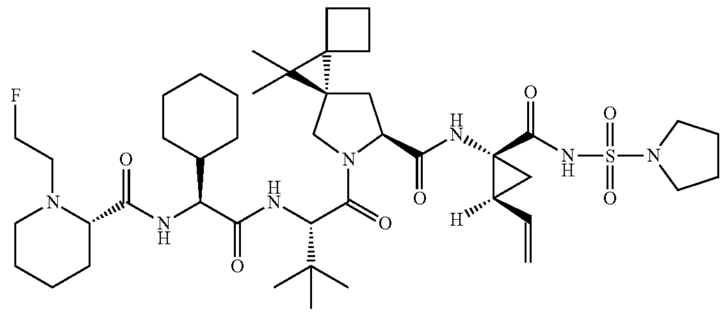 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CCF)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-(2-fluoroethyl)piperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 27 | 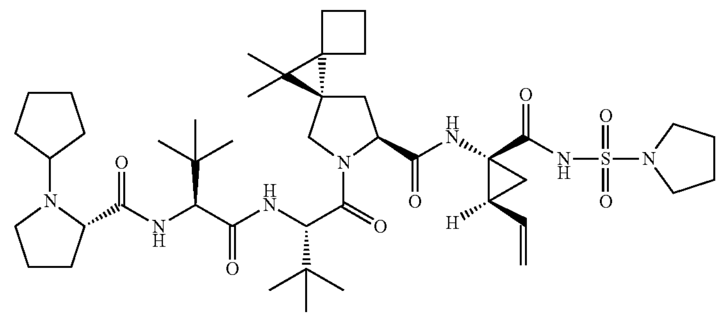 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C1CCCC1)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-cyclopentylpyrrolidin-2-yl]carbonyl}amino)-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 28 | 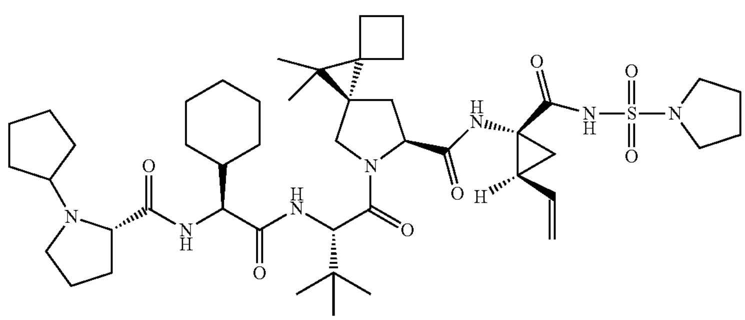 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C1CCCC1)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-cyclopentylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 29 | 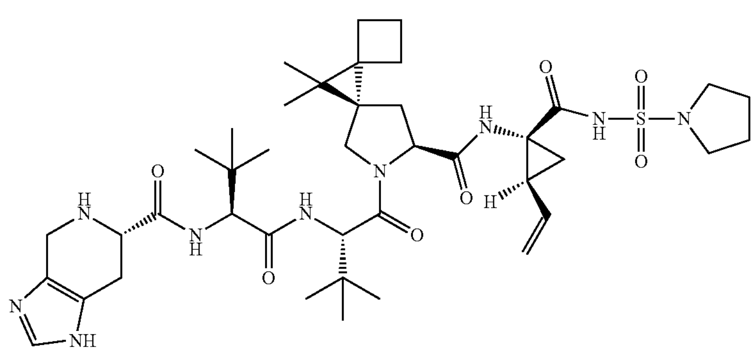 [SMILES: C=C[C@@H]1C[C@]1(NC(=O)[C@@H]1C[C@@]2(CN1C(=O)[C@@H](NC(=O)[C@@H](NC(=O)[C@@H]1Cc3[nH]cnc3CN1)C(C)(C)C)C(C)(C)C)C(C)(C)C21CCC1)C(=O)NS(=O)(=O)N1CCCC1] | (5R,8S)-7-[(2S)-2-{[(2S)-3,3-dimethyl-2-{[(6S)-4,5,6,7-tetrahydro-1H-imidazo[3,4-c]pyridin-6-ylcarbonyl]amino}butanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 30 | 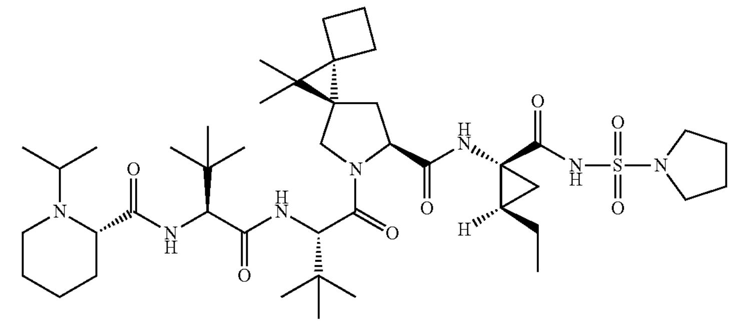 | (5R,8S)-N-{(1R,2R)-2-ethyl-1-[(pyrrolidin-1-ylsulfonyl)carbamoyl]cyclopropyl}-7-[(2S)-2-{[(2S)-2-({[(2S)-1-isopropylpiperidin-2-yl]carbonyl}amino)-3,3-dimethylbutanoyl]amino]-3,3-dimethylbutanoyl]-10,10-dimethyl-7-azadispiro[3.0.4.1]decane-8-carboxamide |
| 31 | 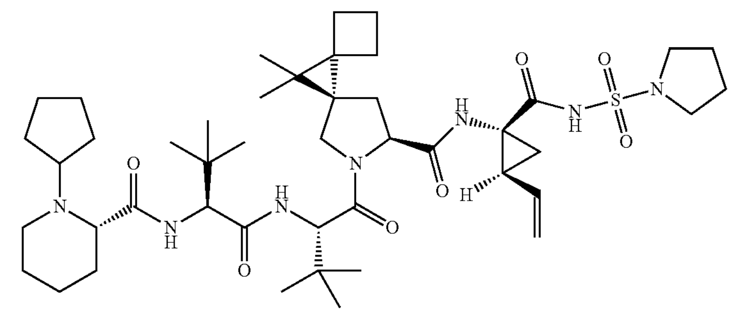 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C1CCCC1)C(C)(C)C)C(C)(C)C)C(C)(C)C21CCC1)C(=O)NS(=O)(=O)N1CCCC1] | (5R,8S)-7-[(2S)-2-{[(2S)-2-({[(2S)-1-cyclopentylpiperidin-2-yl]carbonyl}amino)-3,3-dimethylbutanoyl]amino]-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 32 | 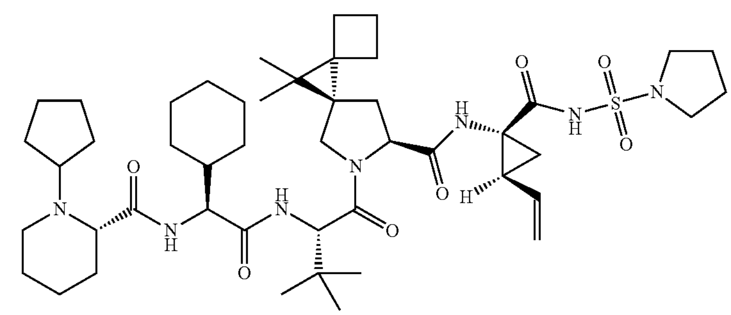 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C1CCCC1)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-cyclopentylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 33 | 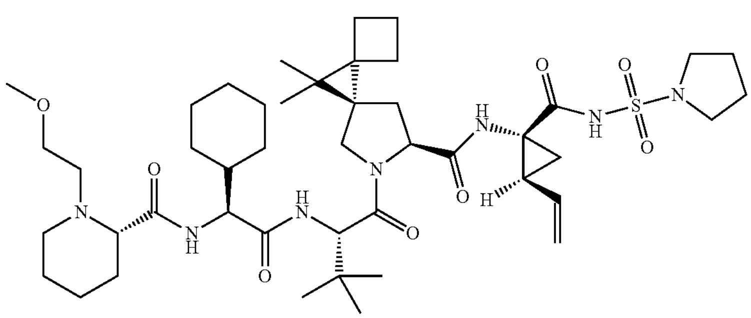 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CCOC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-(2-methoxyethyl)piperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 34 | 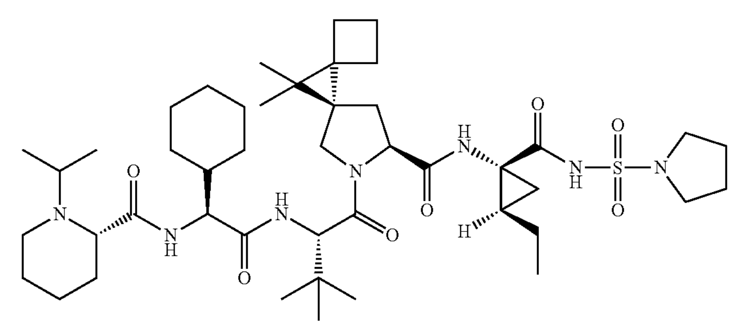 [SMILES: CC[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide |

TABLE A-continued

| Cmpd. # | Structure | Name |
|---|---|---|
| 35 | 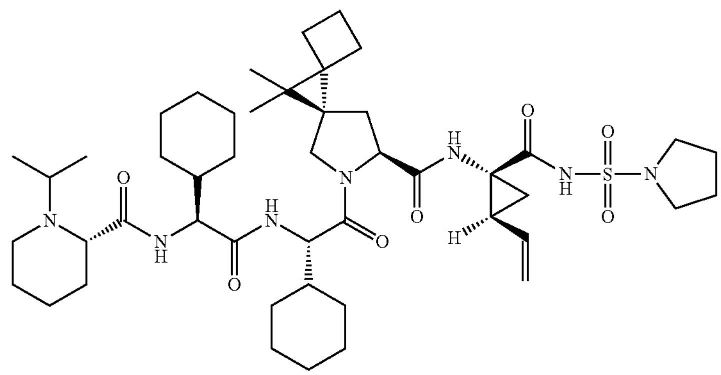 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C1CCCCC1)C(C)(C)C21CCC1)C(=O)NS(=O)(=O)N1CCCC1] | (5R,8S)-7-[(2S)-2-cyclohexyl-2-{[(2S)-2-cyclohexyl-2-({[(2S)-1-isopropylpiperidin-2-yl]carbonyl}amino)acetyl]amino}acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 36 | 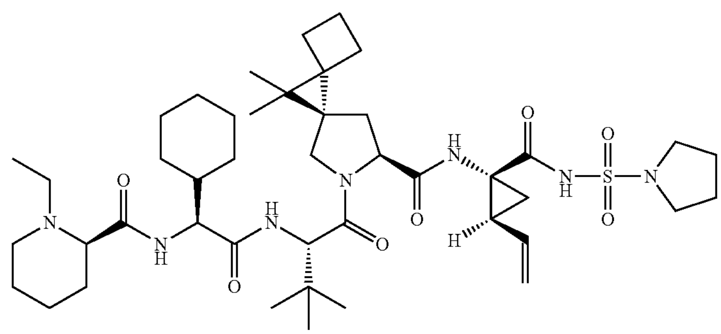 [SMILES: C=C[C@@H]1C[C@]1(NC(=O)[C@@H]1C[C@@]2(CN1C(=O)[C@@H](NC(=O)[C@@H](NC(=O)[C@H]1CCCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-ethylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 37 | 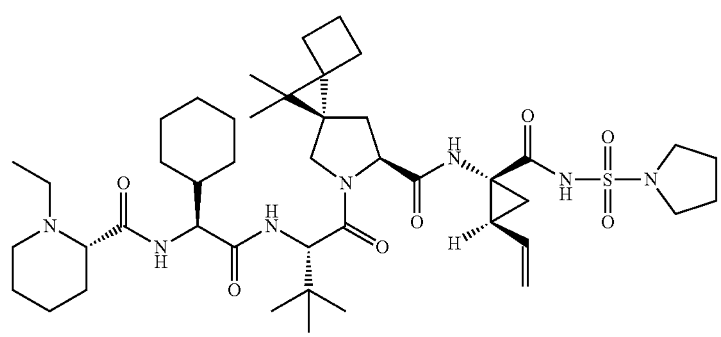 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-ethylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 38 | 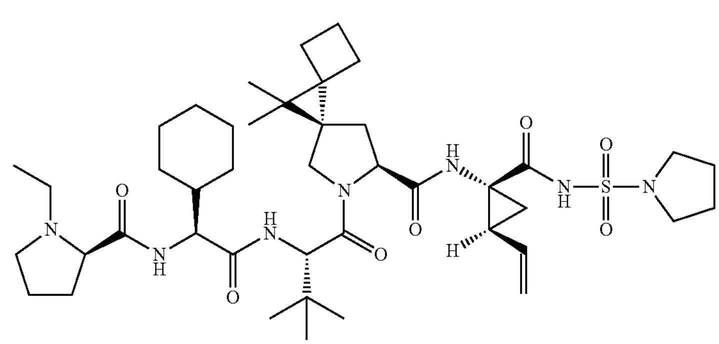 [SMILES: C=C[C@@H]1C[C@]1(NC(=O)[C@@H]1C[C@@]2(CN1C(=O)[C@@H](NC(=O)[C@@H](NC(=O)[C@H]1CCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-ethylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 39 | 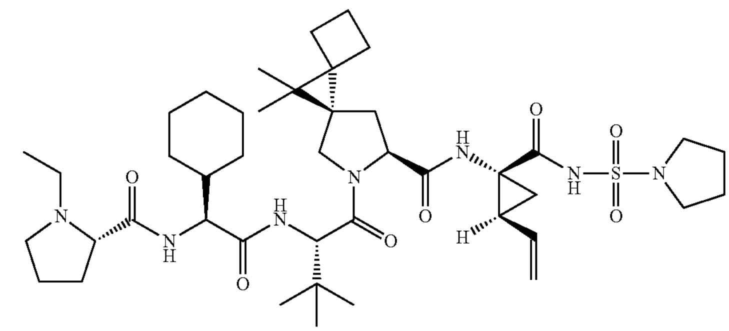 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 40 | 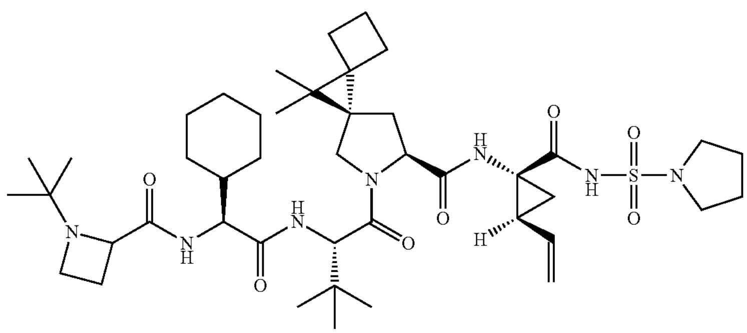 [SMILES: C=C[C@@H]1C[C@]1(NC(=O)[C@@H]1C[C@@]2(CN1C(=O)[C@@H](NC(=O)[C@@H](NC(=O)C1CCN1C(C)(C)C)C1CCCCC1)C(C)(C)C)C(C)(C)C21CCC1)C(=O)NS(=O)(=O)N1CCCC1] | (5R,8S)-7-[(2S)-2-{[(2S)-2-{[(1-tert-butylazetidin-2-yl)carbonyl]amino}-2-cyclohexylacetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 41 | 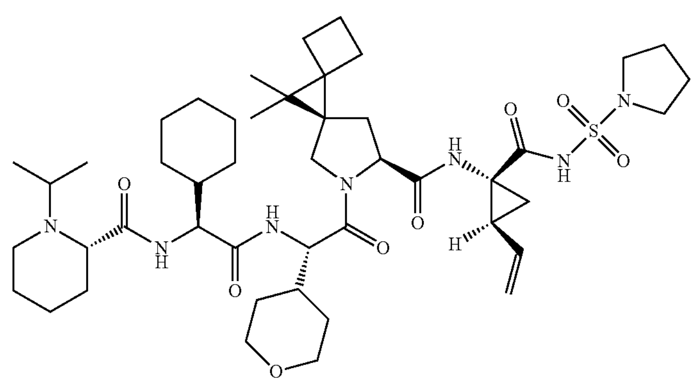 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C1CCOCC1)C(C)(C)C21CCC1)C(=O)NS(=O)(=O)N1CCCC1] | (5R,8S)-7-[(2S)-2-{[(2S)-2-cyclohexyl-2-({[(2S)-1-isopropylpiperidin-2-yl]carbonyl}amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 42 | 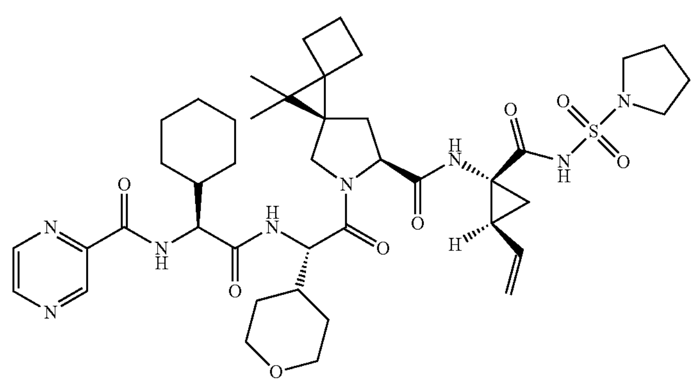 [SMILES: C=C[C@@H]1C[C@]1(NC(=O)[C@@H]1C[C@@]2(CN1C(=O)[C@@H](NC(=O)[C@@H](NC(=O)c1cnccn1)C1CCCCC1)C1CCOCC1)C(C)(C)C21CCC1)C(=O)NS(=O)(=O)N1CCCC1] | (5R,8S)-7-[(2S)-2-({(2S)-2-cyclohexyl-2-[(pyrazin-2-ylcarbonyl)amino]acetyl}amino)-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 43 | 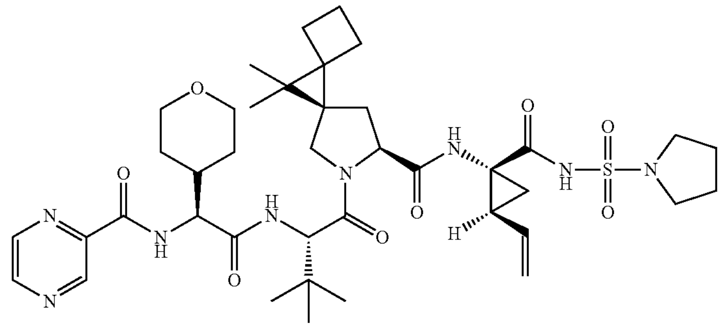 [SMILES: C=C[C@@H]1C[C@]1(NC(=O)[C@@H]1C[C@@]2(CN1C(=O)[C@@H](NC(=O)[C@@H](NC(=O)c1cnccn1)C1CCOCC1)C(C)(C)C)C(C)(C)C21CCC1)C(=O)NS(=O)(=O)N1CCCC1] | (5R,8S)-7-[(2S)-3,3-dimethyl-2-{[(2S)-2-[(pyrazin-2-ylcarbonyl)amino]-2-(tetrahydro-2H-pyran-4-yl)acetyl]amino}butanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 44 | 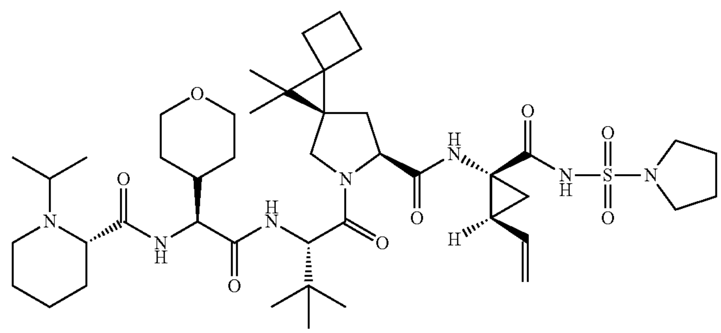 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCOCC1)C(C)(C)C)C(C)(C)C21CCC1)C(=O)NS(=O)(=O)N1CCCC1] | (5R,8S)-7-[(2S)-2-{[(2S)-2-({[(2S)-1-isopropylpiperidin-2-yl]carbonyl}amino)-2-(tetrahydro-2H-pyran-4-yl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 45 | 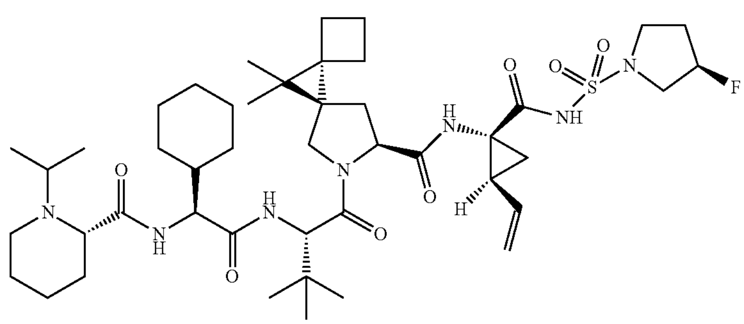 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[(3R)-3-fluoropyrrolidin-1-yl]sulfonyl}carbamoyl)-2-vinylcyclopropyl]-10,10-dimethyl-7-azadispiro[3.0.4.1]decane-8-carboxamide |
| 46 | 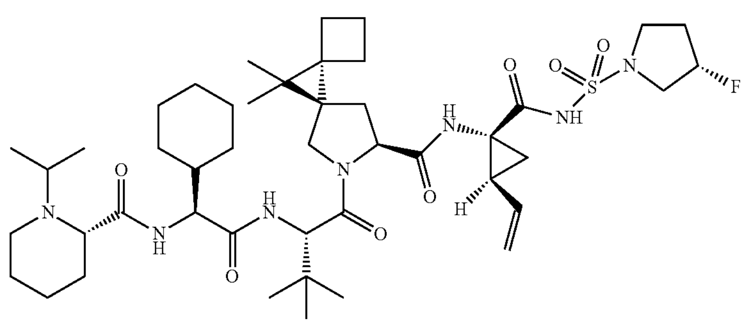 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[(3S)-3-fluoropyrrolidin-1-yl]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 47 | 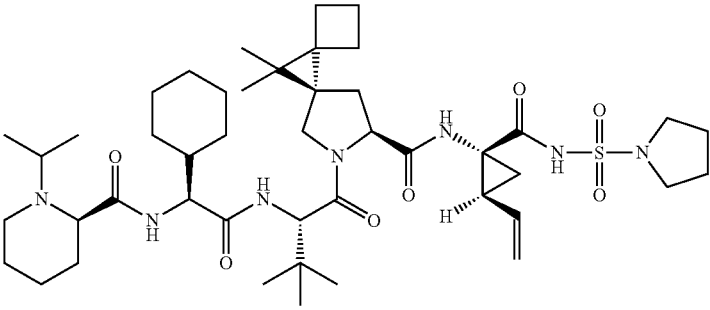 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 48 | 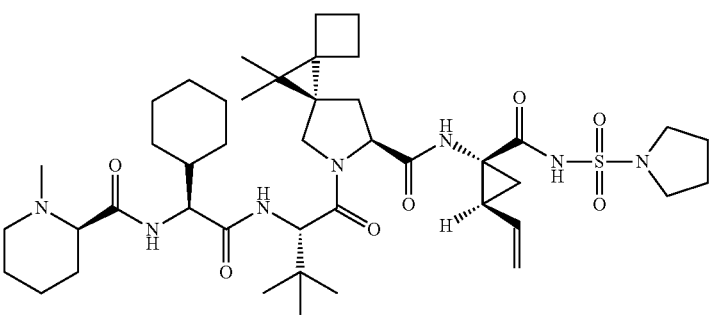 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-methylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 49 | 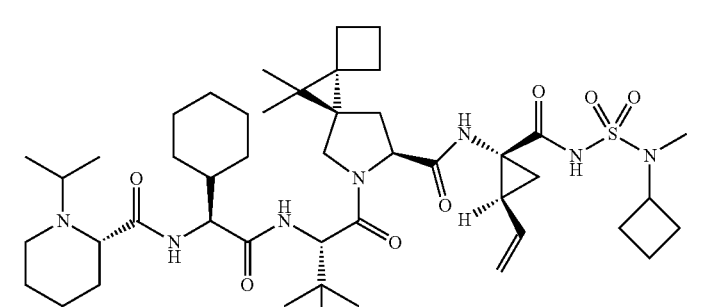 | (5R,8S)-N-[(1R,2S)-1-({[cyclobutyl(methyl)amino]sulfonyl}carbamoyl)-2-vinylcyclopropyl]-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-7-azadispiro[3.0.4.1]decane-8-carboxamide |
| 50 | 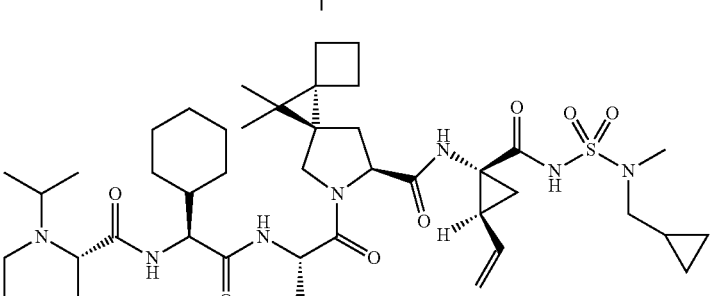 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[(cyclopropylmethyl)(methyl)amino]sulfonyl}carbamoyl)-2-vinylcyclopropyl]-10,10-dimethyl-7-azadispiro[3.0.4.1]decane-8-carboxamide |
| 51 | 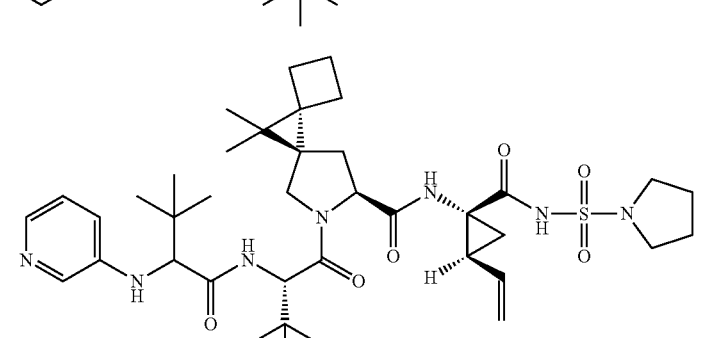 | (5R,8S)-7-[(2S)-2-{[3,3-dimethyl-2-(pyridin-3-ylamino)butanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 52 | 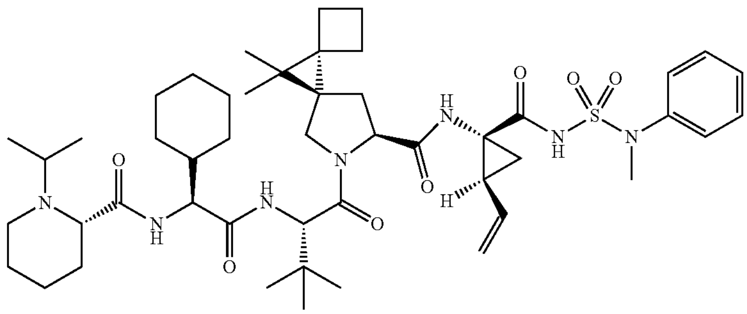 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-[(1R,2S)-1-({[methyl(phenyl)amino]sulfonyl}carbamoyl)-2-vinylcyclopropyl]-7-azadispiro[3.0.4.1]decane-8-carboxamide |
| 53 | 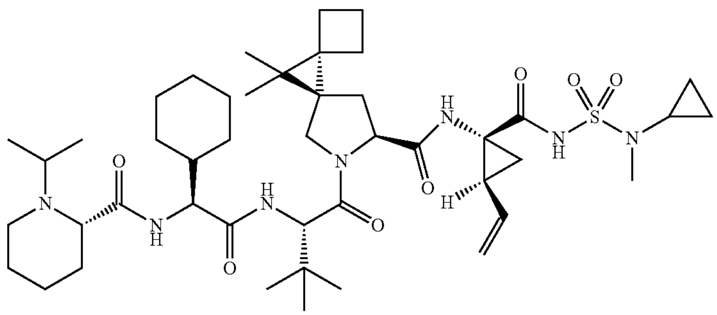 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[cyclopropyl(methyl)amino]sulfonyl}carbamoyl)-2-vinylcyclopropyl]-10,10-dimethyl-7-azadispiro[3.0.4.1]decane-8-carboxamide |
| 54 | 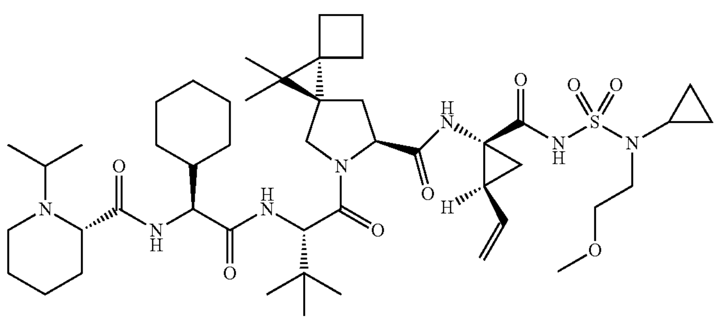 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[cyclopropyl(2-methoxyethyl)amino]sulfonyl}carbamoyl)-2-vinylcyclopropyl]-10,10-dimethyl-7-azadispiro[3.0.4.1]decane-8-carboxamide |
| 55 | 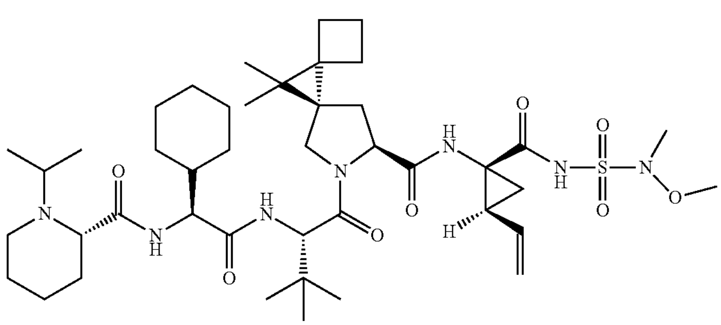 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)OC] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[methoxy(methyl)amino]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 56 | 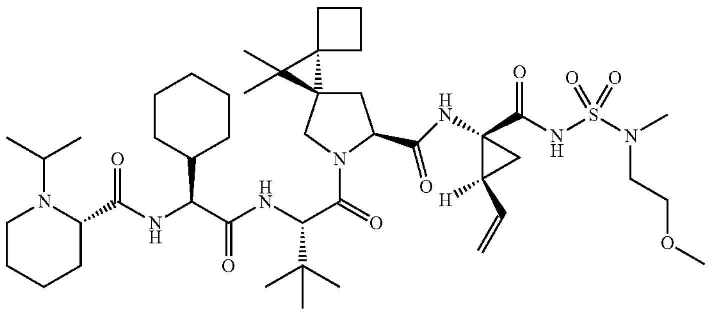 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[(2-methoxyethyl)(methyl)amino]sulfonyl}carbamoyl)-2-vinylcyclopropyl]-10,10-dimethyl-7-azadispiro[3.0.4.1]decane-8-carboxamide |
| 57 | 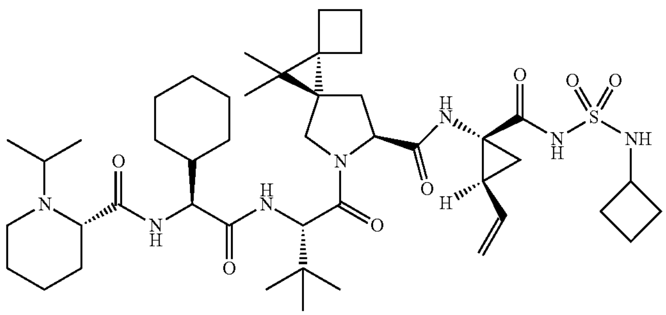 | (5R,8S)-N-[(1R,2S)-1-{[(cyclobutylamino)sulfonyl]carbamoyl}-2-vinylcyclopropyl]-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-7-azadispiro[3.0.4.1]decane-8-carboxamide |
| 58 | 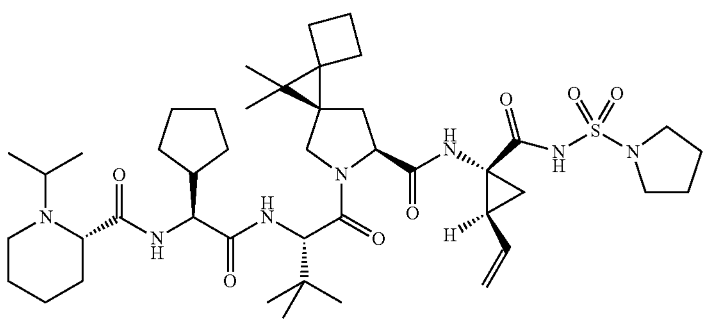 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCC1)C(C)(C)C)C(C)(C)C21CCC1)C(=O)NS(=O)(=O)N1CCCC1] | (5R,8S)-7-[(2S)-2-{[(2S)-2-cylcopentyl-2-({[(2S)-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 59 | 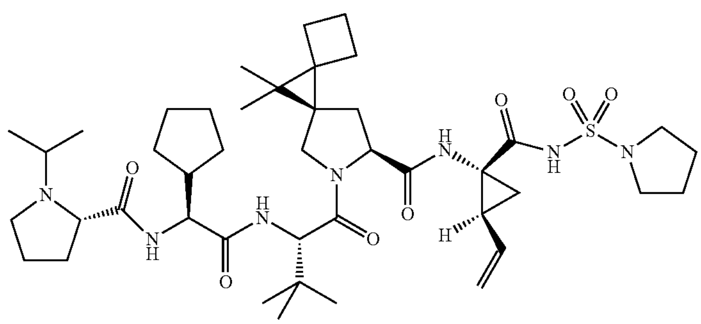 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCC1)C(C)(C)C)C(C)(C)C21CCC1)C(=O)NS(=O)(=O)N1CCCC1] | (5R,8S)-7-[(2S)-2-{[(2S)-2-cylcopentyl-2-({[(2S)-1-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 60 | 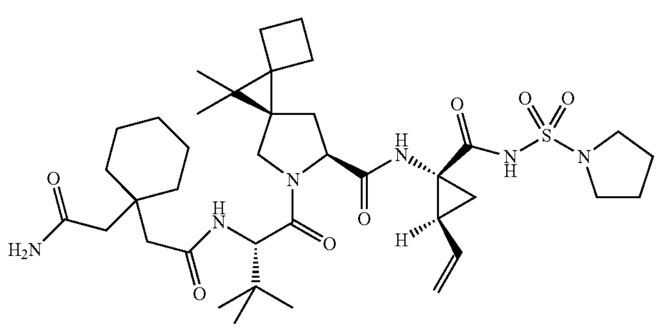 [SMILES: C=C[C@@H]1C[C@]1(NC(=O)[C@@H]1C[C@@]2(CN1C(=O)[C@@H](NC(=O)CC1(CC(N)=O)CCCCC1)C(C)(C)C)C(C)(C)C21CCC1)C(=O)NS(=O)(=O)N1CCCC1] | (5R,8S)-7-[(2S)-2-({[1-(2-amino-2-oxoethyl)cyclohexyl]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 61 | 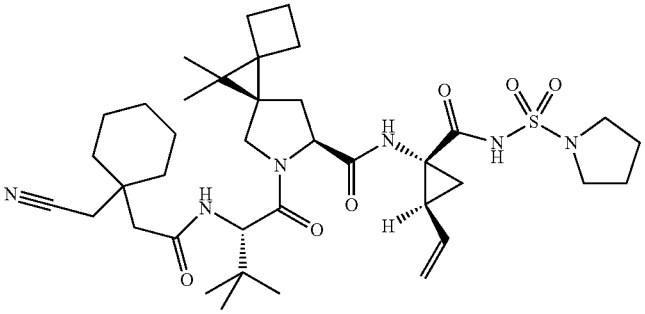 [SMILES: C=C[C@@H]1C[C@]1(NC(=O)[C@@H]1C[C@@]2(CN1C(=O)[C@@H](NC(=O)CC1(CC#N)CCCCC1)C(C)(C)C)C(C)(C)C21CCC1)C(=O)NS(=O)(=O)N1CCCC1] | (5R,8S)-7-[(2S)-2-({[1-(cyanomethyl)cyclohexyl]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 62 | 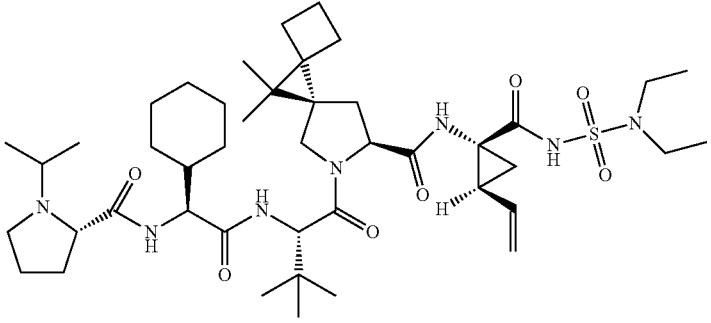 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 63 | 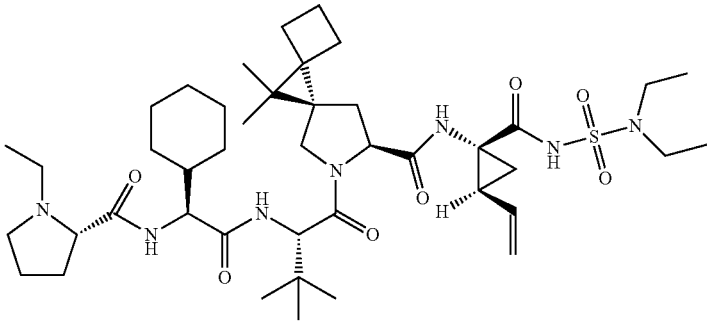 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 64 | 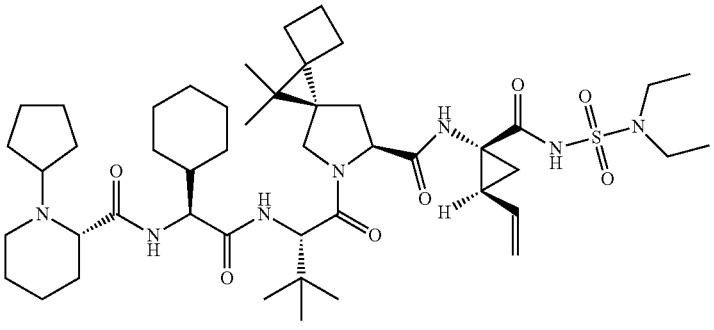 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C1CCCC1)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2S)-1-cyclopentylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azaidspiro[3.0.4.1]decane-8-carboxamide |

TABLE A-continued

| Cmpd. # | Structure | Name |
|---|---|---|
| 65 | 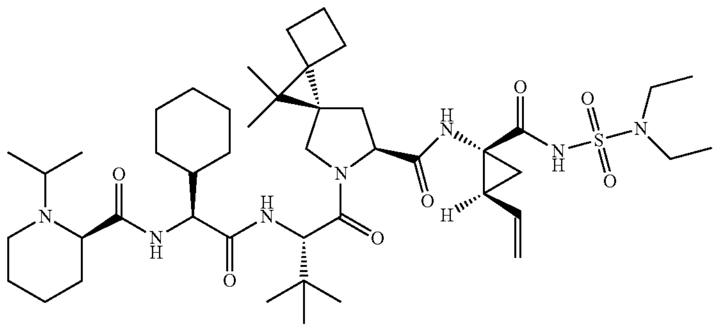 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 66 | 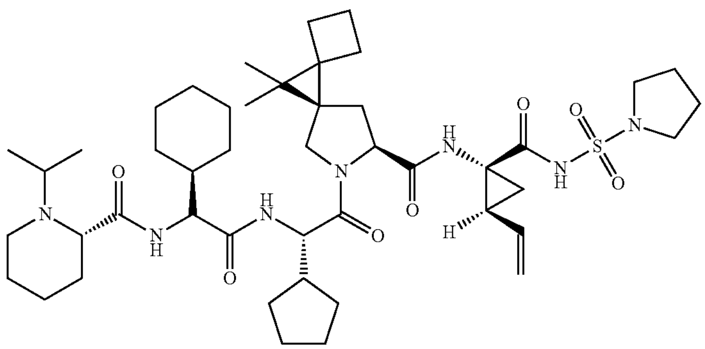 | (5R,8S)-7-[(2S)-2-{[(2S)-2-cylcohexyl-2-({[(2S)-1-isopropylpiperidin-2-yl]carbonyl}amino)acetyl]amino}-2-cyclopentylacetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 67 | 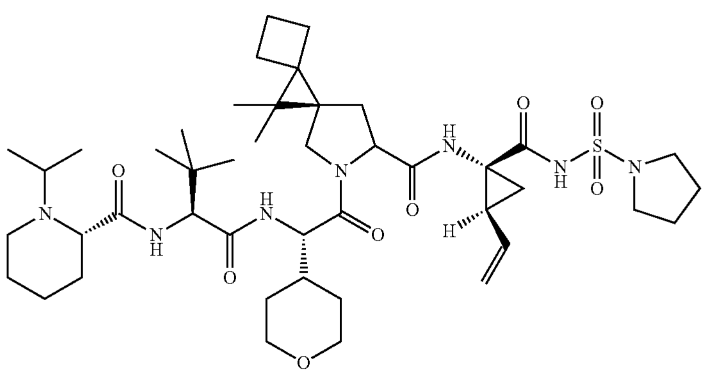 [SMILES: C=C[C@@H]1C[C@]1(NC(=O)C1C[C@@]2(CN1C(=O)[C@@H](NC(=O)[C@@H](NC(=O)[C@@H]1CCCCN1C(C)C)C(C)(C)C)C1CCOCC1)C(C)(C)C21CCC1)C(=O)NS(=O)(=O)N1CCCC1] | (5R)-7-[(2S)-2-[(N-{[(2S)-1-isopropylpiperidin-2-yl]carbonyl}-3-methyl-L-valyl)amino]-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 68 | 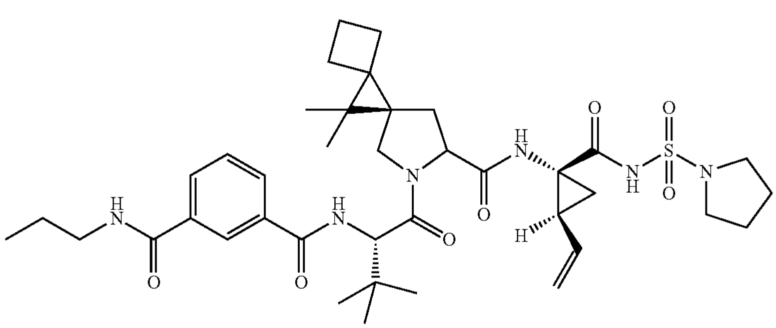 [SMILES: C=C[C@@H]1C[C@]1(NC(=O)C1C[C@@]2(CN1C(=O)[C@@H](NC(=O)c1cccc(C(=O)NCCC)c1)C(C)(C)C)C(C)(C)C21CCC1)C(=O)NS(=O)(=O)N1CCCC1] | N-[(1S)-1-{[(5R)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]carbonyl}-2,2-dimethylpropyl]-N'-propylisophthalamide |

TABLE A-continued

| Cmpd. # | Structure | Name |
|---|---|---|
| 69 | 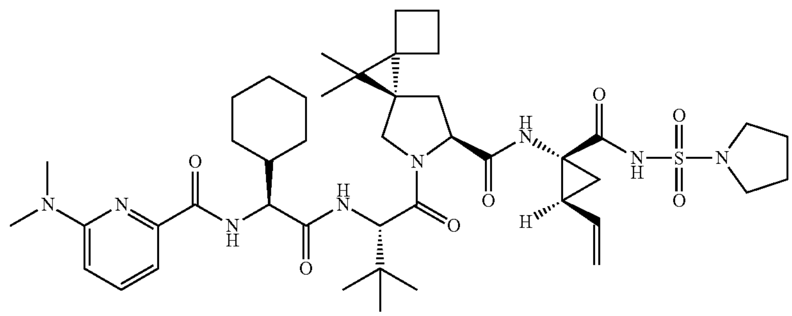 [SMILES: C=C[C@@H]1C[C@]1(NC(=O)[C@@H]1C[C@@]2(CN1C(=O)[C@@H](NC(=O)[C@@H](NC(=O)c1cccc(N(C)C)n1)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[6-(dimethylamino)pyridin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 70 | 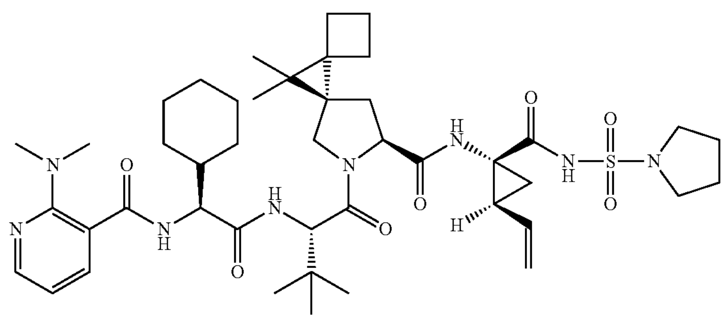 [SMILES: C=C[C@@H]1C[C@]1(NC(=O)[C@@H]1C[C@@]2(CN1C(=O)[C@@H](NC(=O)[C@@H](NC(=O)c1cccnc1N(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[2-(dimethylamino)pyridin-3-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 71 | 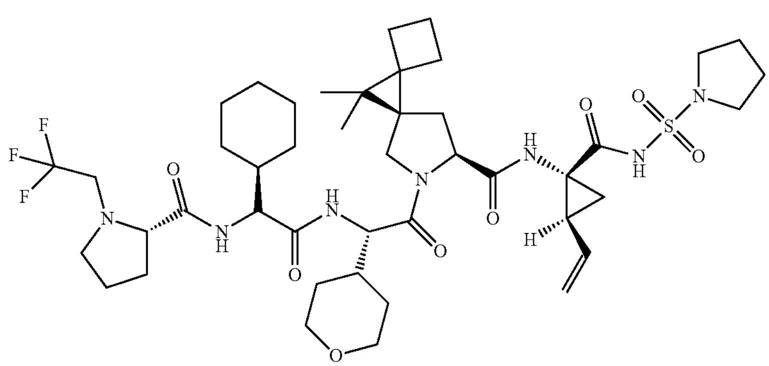 | (5R,8S)-7-[(2S)-2-{[(2S)-2-cyclohexyl-2-({[(2S)-1-(2,2,2-trifluoroethyl)pyrrolidin-2-yl]carbonyl}-amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 72 | 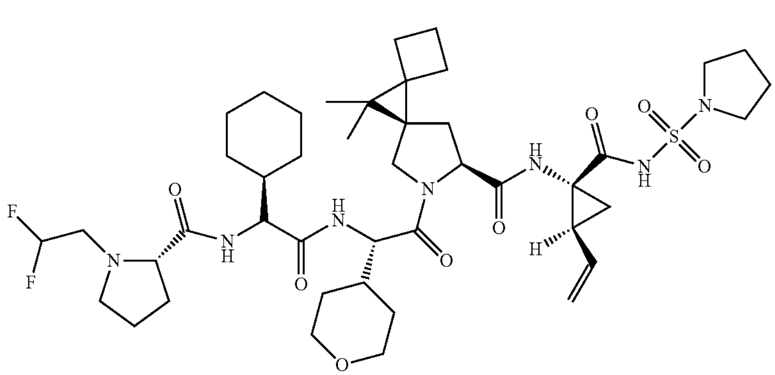 | (5R,8S)-7-[(2S)-2-{[(2S)-2-cyclohexyl-2-({[(2S)-1-(2,2-difluoroethyl)pyrrolidin-2-yl]carbonyl}amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 73 | 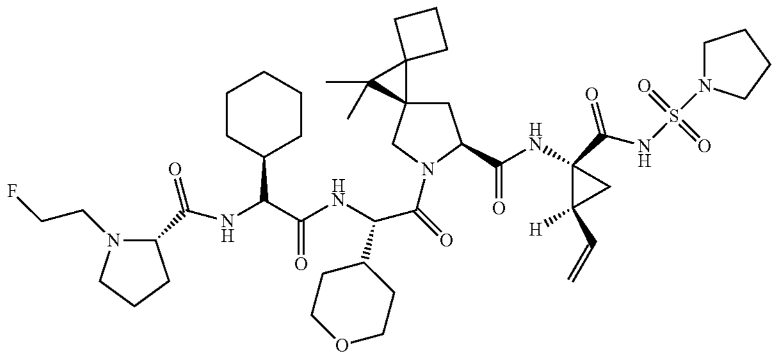 | (5R,8S)-7-[(2S)-2-{[(2S)-2-cyclohexyl-2-({[(2S)-1-(2-fluoroethyl)pyrrolidin-2-yl]carbonyl}amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 74 | 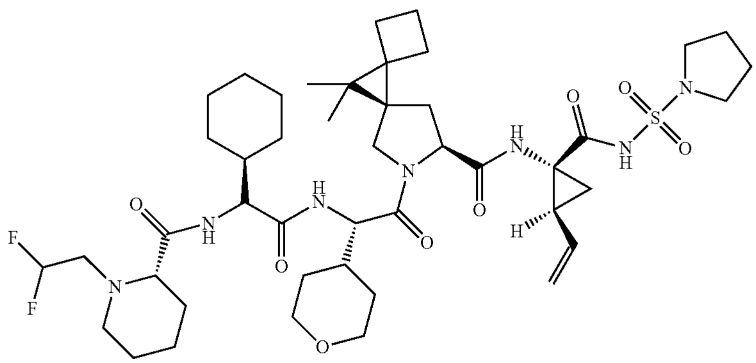 | (5R,8S)-7-[(2S)-2-{[(2S)-2-cyclohexyl-2-({[(2S)-1-(2,2-difluoroethyl)piperidin-2-yl]carbonyl}amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 75 | 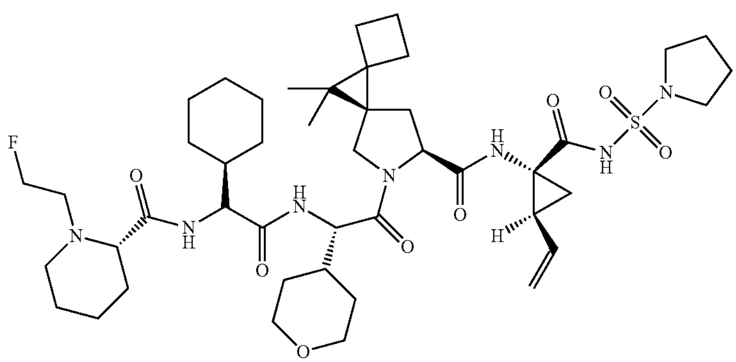 | (5R,8S)-7-[(2S)-2-{[(2S)-2-cylcohexyl-2-({[(2S)-1-(2-fluoroethyl)piperidin-2-yl]carbonyl}amino)acetyl]amino}-2-(tetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 76 | 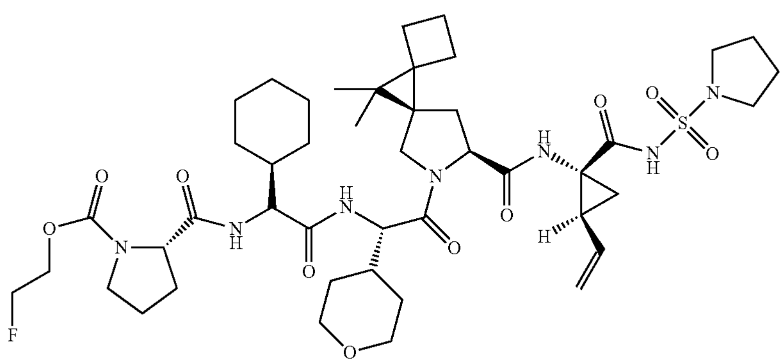 | 2-fluoroethyl (2S)-2-{[(1S)-1-cyclohexyl-2-{[(1S)-2-[(5R,8S)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]-2-oxo-1-(tetrahydro-2H-pyran-4-yl)ethyl]amino}-2-oxoethyl]carbamoyl}pyrrolidine-1-carboxylate |

TABLE A-continued

| Cmpd. # | Structure | Name |
|---|---|---|
| 77 | 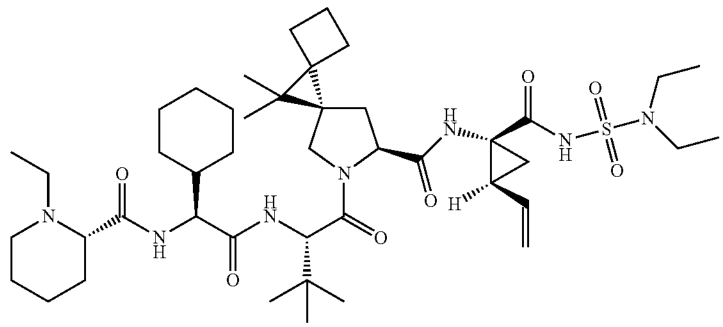 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CC)C1CCCCC1)C(C)(C)C)C(C)(C)C21CCC1)C(=O)NS(=O)(=O)N(CC)CC] | (5R,8S)-7-[(2S)-2-{[(2S)-2-cylcohexyl-2-({[(2S)-1-ethylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 78 | 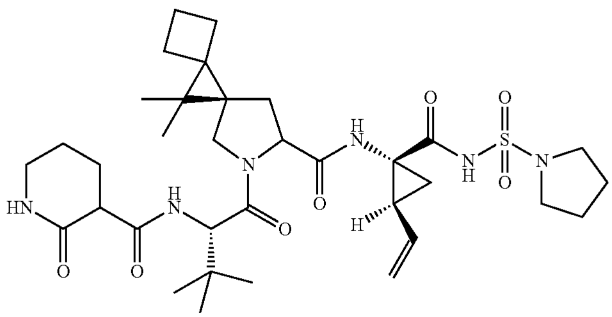 [SMILES: C=C[C@@H]1C[C@]1(NC(=O)C1C[C@@]2(CN1C(=O)[C@@H](NC(=O)C1CCCNC1=O)C(C)(C)C)C(C)(C)C21CCC1)C(=O)NS(=O)(=O)N1CCCC1] | (5R)-7-[(2S)-3,3-dimethyl-2-{[(2-oxopiperidin-3-yl)carbonyl]amino}butanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 79 | 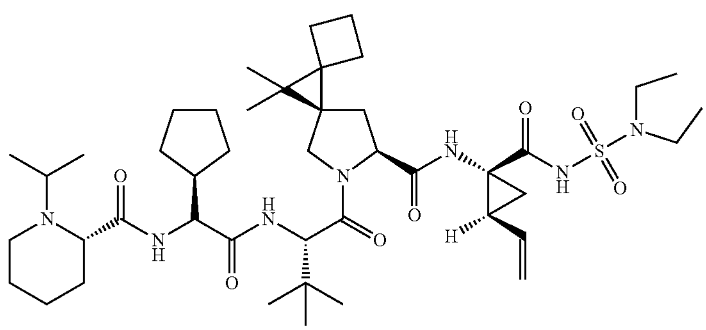 | (5R,8S)-7-[(2S)-2-{[(2S)-2-cyclopentyl-2-({[(2S)-1-isopropylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadiaspiro[3.0.4.1]decane-8-carboxamide |
| 80 | 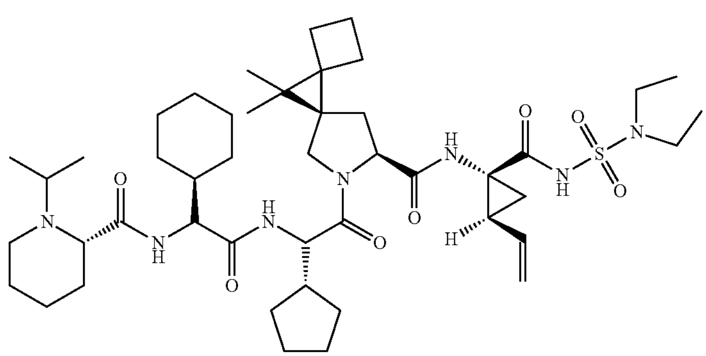 | (5R,8S)-7-[(2S)-2-{[(2S)-2-cyclohexyl-2-({[(2S)-1-isopropylpiperidin-2-yl]carbonyl}amino)acetyl]amino}-2-cyclopentylacetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 81 | 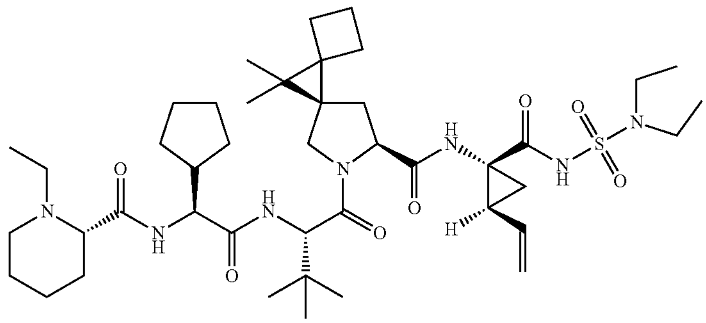 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CC)C1CCCC1)C(C)(C)C)C(C)(C)C21CCC1)C(=O)NS(=O)(=O)N(CC)CC] | (5R,8S)-7-[(2S)-2-{[(2S)-2-cyclopentyl-2-({[(2S)-1-ethylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 82 | 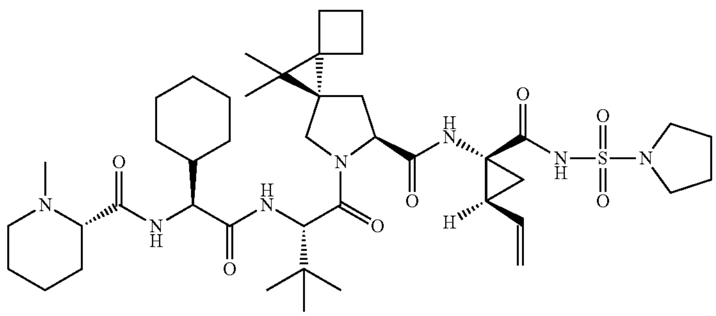 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C)C1CCCCC1)C(C)(C)C)C(C)(C)C21CCC1)C(=O)NS(=O)(=O)N1CCCC1] | (5R,8S)-7-[(2S)-2-{[(2S)-2-cylcohexyl-2-({[(2S)-1-methylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 83 | 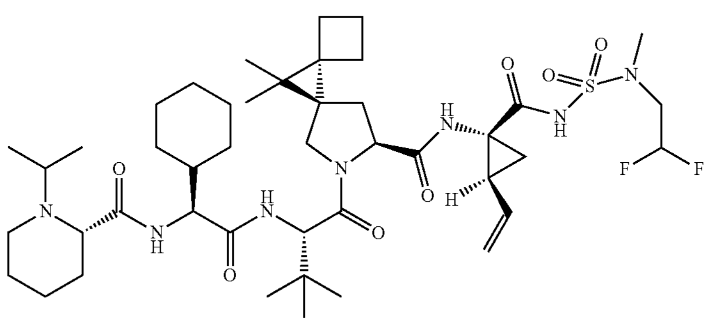 | (5R,8S)-7-[(2S)-2-{[(2S)-2-cyclohexyl-2-({[(2S)-1-isopropylpiperidin-2-yl]carbonyl}amino)acetyl]amino}-3,3-dimethybutanoyl]-N-[(1R,2S)-1-({[(2,2-difluoroethyl)(methyl)amino]sulfonyl}carbamoyl)-2-vinylcyclopropyl]-10,10-dimethyl-7-azadispiro[3.0.4.1]decane-8-carboxamide |
| 84 | 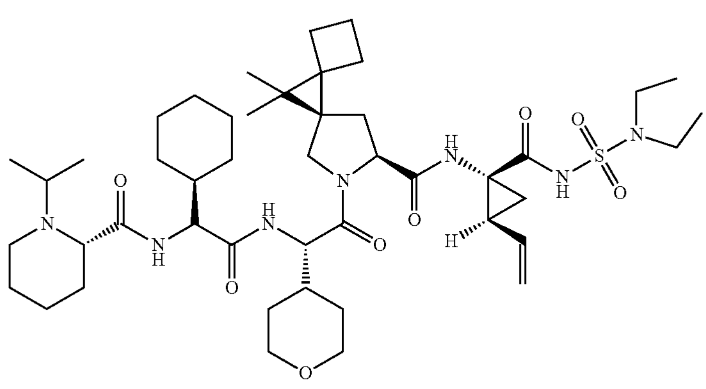 | (5R,8S)-7-[(2S)-2-{[(2S)-2-cyclohexyl-2-({[(2S)-1-isopropylpiperidin-2-yl]carbonyl}amino)acetyl]amino}-2-(tetrahydro-2H-pyran-4-yl)acetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |

| Cmpd. # | Structure | Name |
|---|---|---|
| 85 | 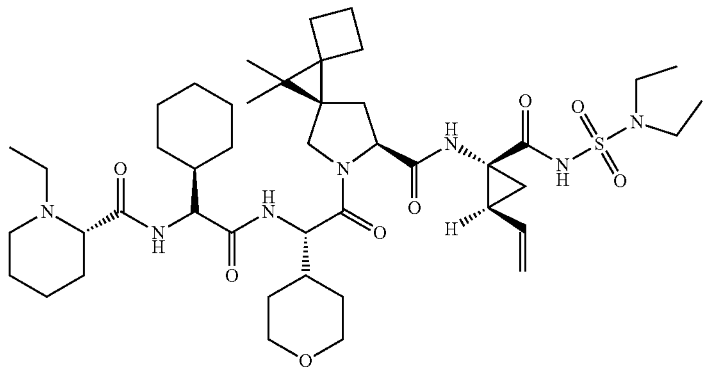 | (5R,8S)-7-[(2S)-2-{[(2S)-2-cyclohexyl-2-({[(2S)-1-ethylpiperidin-2-yl]carbonyl}amino)acetyl]amino}-2-(tetrahydro-2H-pyran-4-yl)acetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 86 | 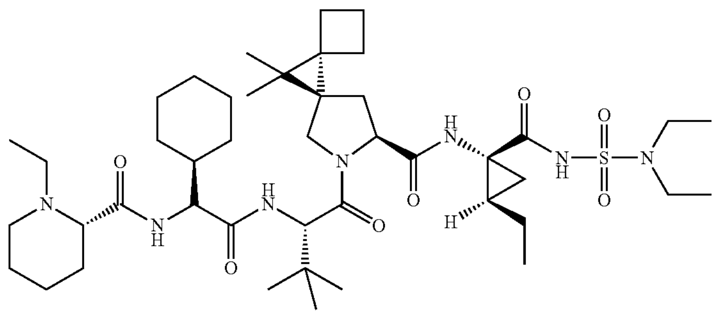 | (5R,8S)-7-[(2S)-2-{[(2S)-2-cyclohexyl-2-({[(2S)-1-ethylpiperidin-2-yl]carbonyl}amino)acetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide |
| 87 | 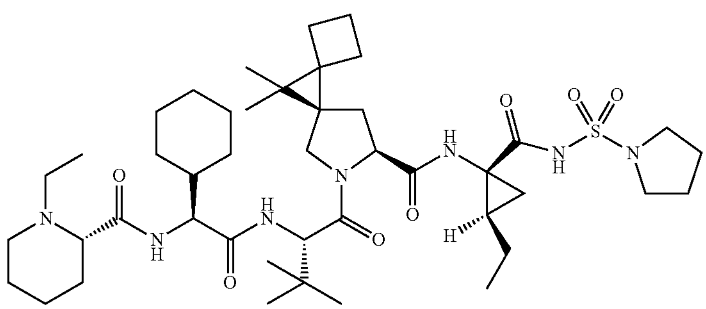 [SMILES: CC[C@@H]1C[C@]1(NC(=O)[C@@H]1C[C@@]2(CN1C(=O)[C@@H](NC(=O)[C@@H](NC(=O)[C@@H]1CCCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-ethylpiperidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide |
| 88 | 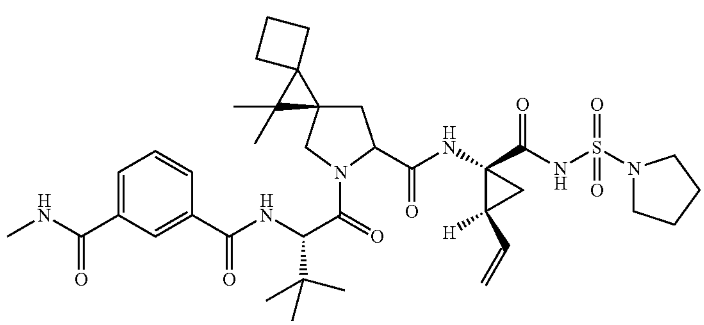 [SMILES: C=C[C@@H]1C[C@]1(NC(=O)C1C[C@@]2(CN1C(=O)[C@@H](NC(=O)c1cccc(C(=O)NC)c1)C(C)(C)C)C(C)(C)C21CCC1)C(=O)NS(=O)(=O)N1CCCC1] | N-[(1S)-1-{[(5R)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]carbonyl}-2,2-dimethylpropyl]-N'-methylisophthalamide |

TABLE A-continued

| Cmpd. # | Structure | Name |
|---|---|---|
| 89 | 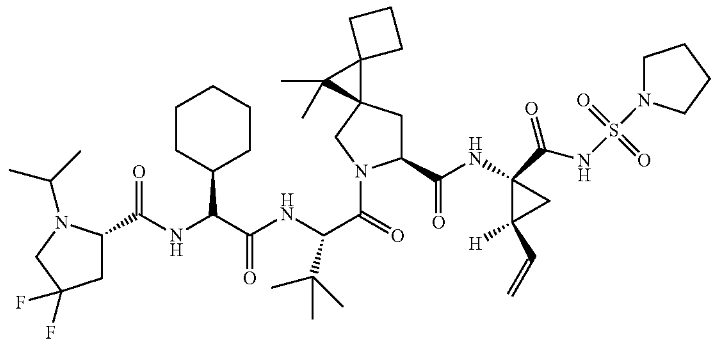 | (5R,8S)-7-[(2S)-2-{[(2S)-2-cyclohexyl-2-({[(2S)-4,4-difluoro-1-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 90 | 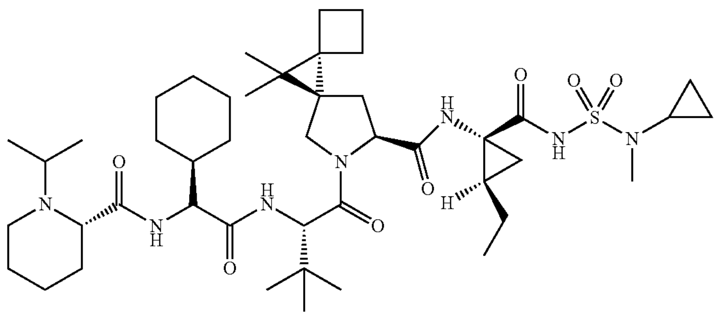 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2R)-1-({[cyclopropyl(methyl)amino]sulfonyl}carbamoyl)-2-ethylcyclopropyl]-10,10-dimethyl-7-azadispiro[3.0.4.1]decane-8-carboxamide |
| 91 | 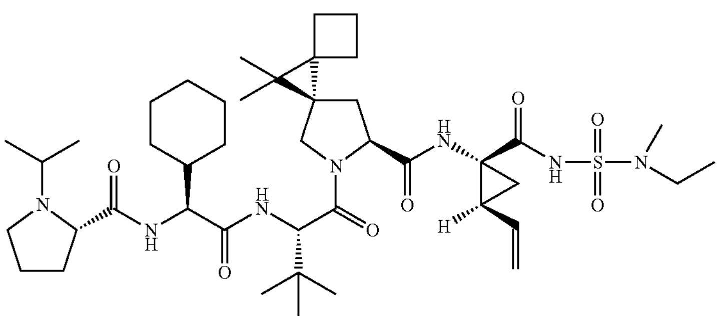 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N(C)CC] | (5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |
| 92 | 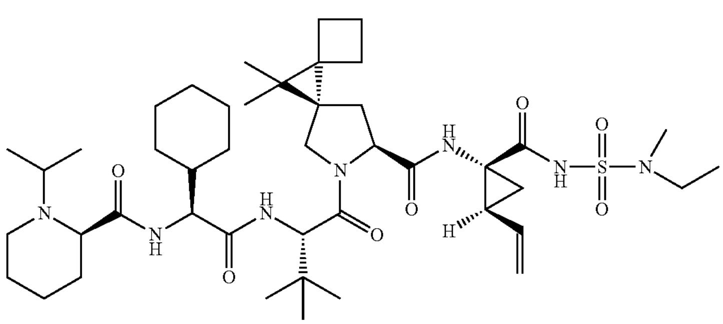 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(C)CC] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 93 | 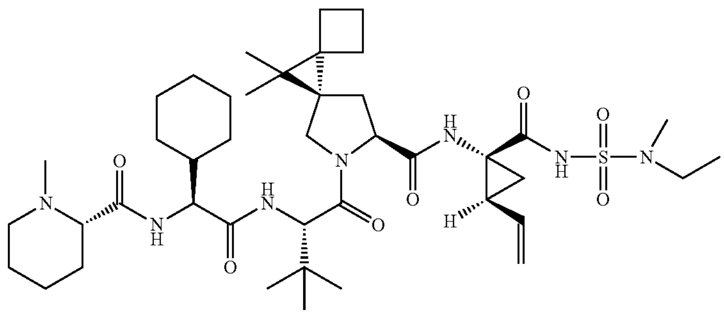 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C)C1CCCCC1)C(C)(C)C)C(C)(C)C21CCC1)C(=O)NS(=O)(=O)N(C)CC] | (5R,8S)-7-[(2S)-2-{[(2S)-2-cyclohexyl-2-({[(2S)-1-methylpiperidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |
| 94 | 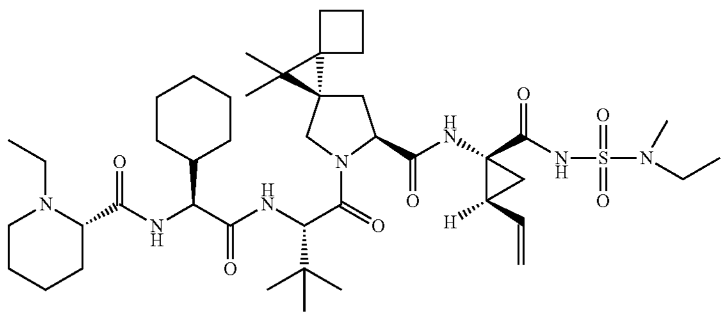 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CC)C1CCCCC1)C(C)(C)C)C(C)(C)C21CCC1)C(=O)NS(=O)(=O)N(C)CC] | (5R,8S)-7-[(2S)-2-{[(2S)-2-cylcohexyl-2-({[(2S)-1-ethylpiperidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |
| 95 | 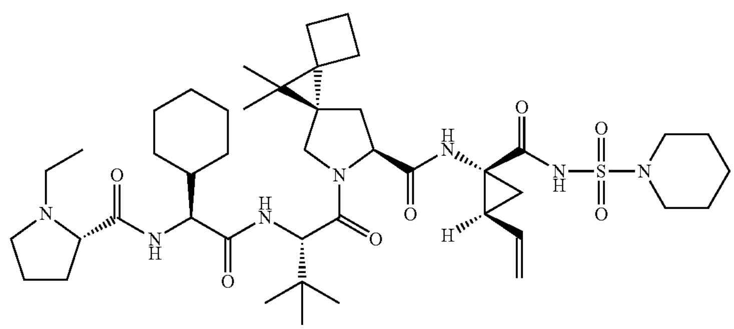 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N1CCCCC1] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-10,10-dimethyl-N-{(1R,2S)-1-[(piperidin-1-ylsulfonyl)carbamoyl]-2-vinylcyclopropyl}-7-azadispiro[3.0.4.1]decane-8-carboxamide |
| 96 | 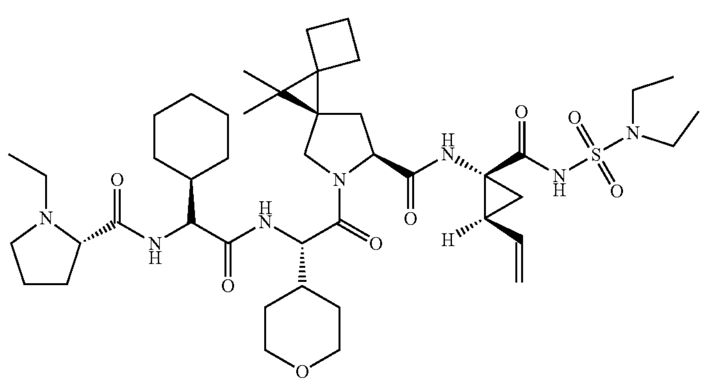 | (5R,8S)-7-[(2S)-2-{[(2S)-2-cyclohexyl-2-({[(2S)-1-ethylpyrrolidin-2-yl]carbonyl}amino)acetyl]amino}-2-(tetrahydro-2H-pyran-4-yl)acetyl]-N-[(1R,2S)-1-{[(diethylamino)sulfonyl)carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 97 | 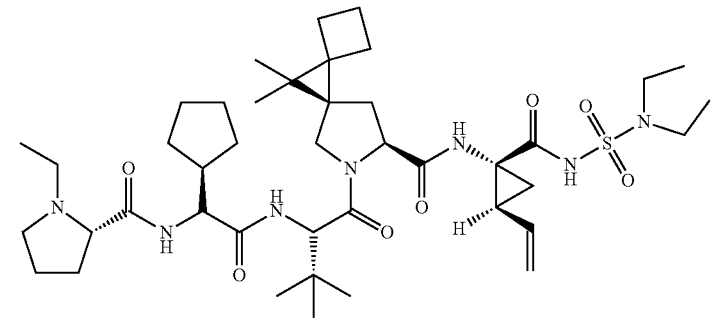 | (5R,8S)-7-[(2S)-2-{[(2S)-2-cyclopentyl-2-({[(2S)-1-ethylpyrrolidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 98 | 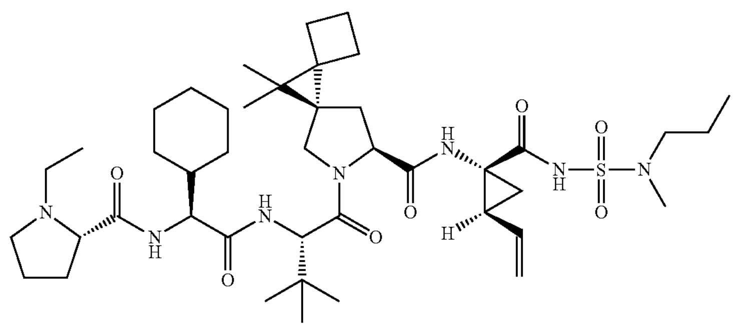 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(C)CCC] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-10,10-dimethyl-N-[(1R,2S)-1-({[methyl(propyl)amino]sulfonyl}carbamoyl)-2-vinylcyclopropyl]-7-azadispiro[3.0.4.1]decane-8-carboxamide |
| 99 | 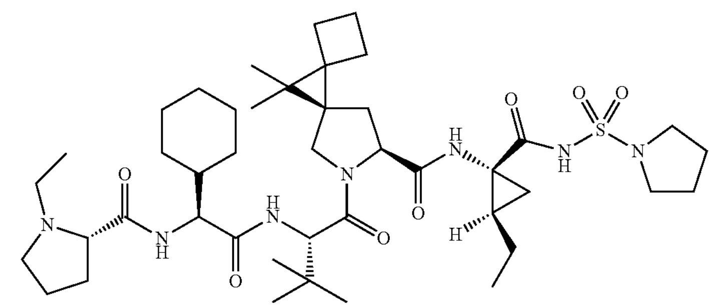 [SMILES: CC[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide |
| 100 | 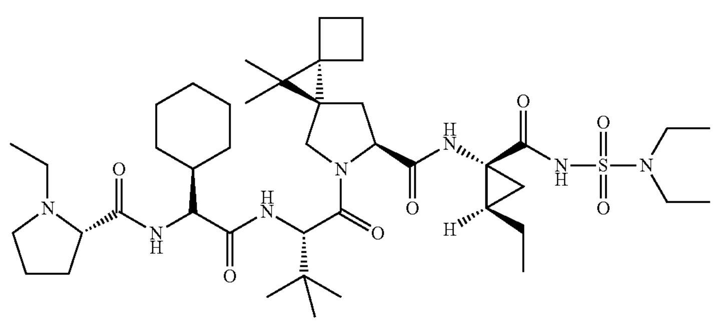 | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide |
| 101 | 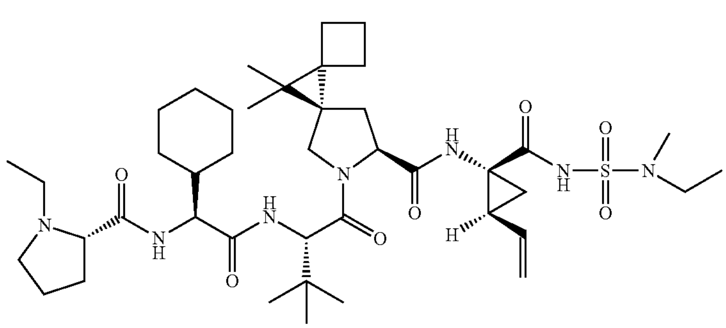 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(C)CC] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 102 | 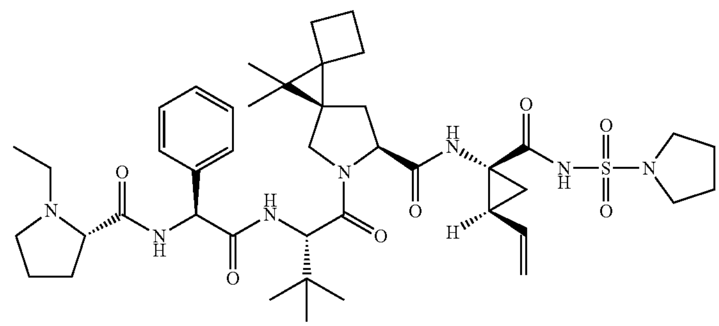 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)c1ccccc1)C(C)(C)C)C(C)(C)C21CCC1)C(=O)NS(=O)(=O)N1CCCC1] | (5R,8S)-7-[(2S)-2-{[(2S)-2-({[(2S)-1-ethylpyrrolidin-2-yl]carbonyl}amino)-2-phenylacetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 103 | 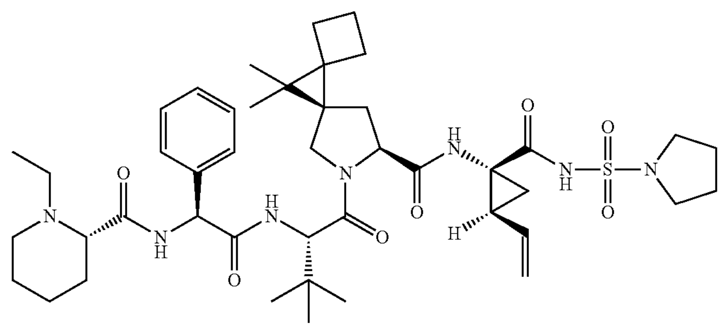 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1CC)c1ccccc1)C(C)(C)C)C(C)(C)C21CCC1)C(=O)NS(=O)(=O)N1CCCC1] | (5R,8S)-7-[(2S)-2-{[(2S)-2-({[(2S)-1-ethylpiperidin-2-yl]carbonyl}amino)-2-phenylacetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 104 | 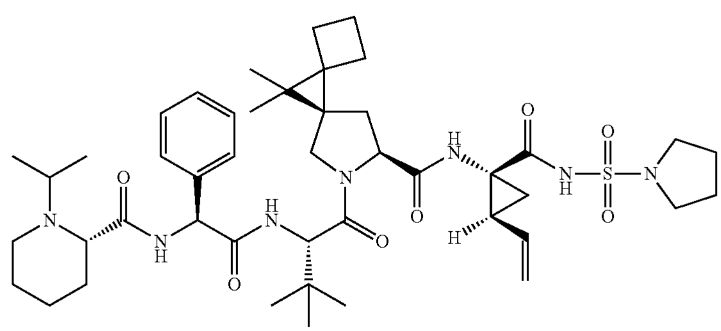 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)c1ccccc1)C(C)(C)C)C(C)(C)C21CCC1)C(=O)NS(=O)(=O)N1CCCC1] | (5R,8S)-7-[(2S)-2-{[(2S)-2-({[(2S)-1-isopropylpiperidin-2-yl]carbonyl}amino)-2-phenylacetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 105 | 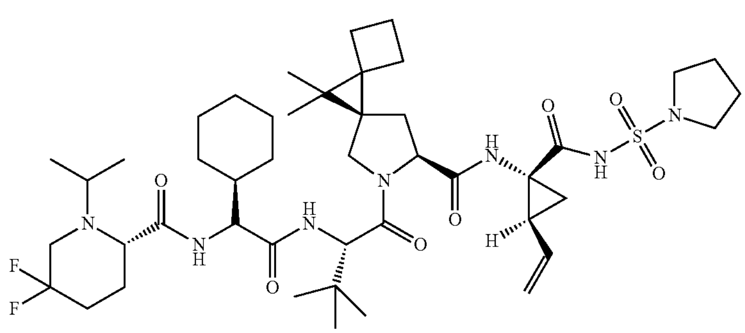 | (5R,8S)-7-[(2S)-2-cyclohexyl-2-({[(2S)-5,5-difluoro-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 106 | 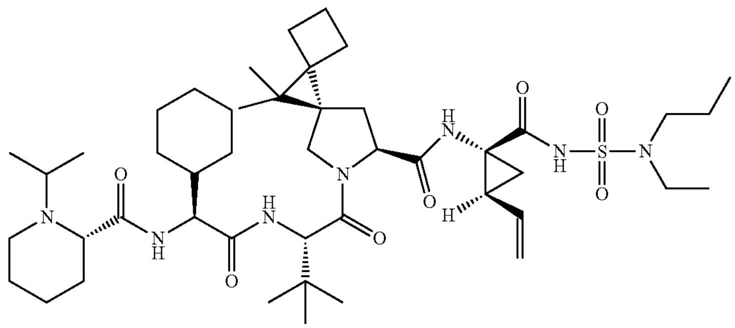 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(CC)CCC] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[ethyl(propyl)amino]sulfonyl}carbamoyl)-2-vinylcyclopropyl]-10,10-dimethyl-7-azadispiro[3.0.4.1]decane-8-carboxamide |
| 107 | 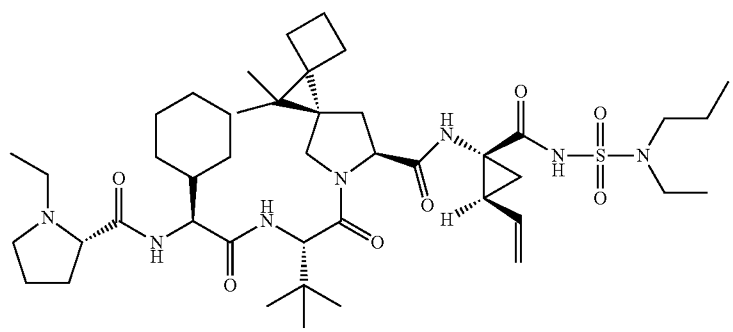 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(CC)CCC] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-({[ethyl(propyl)amino]sulfonyl}carbamoyl)-2-vinylcyclopropyl]-10,10-dimethyl-7-azadispiro[3.0.4.1]decane-8-carboxamide |
| 108 | 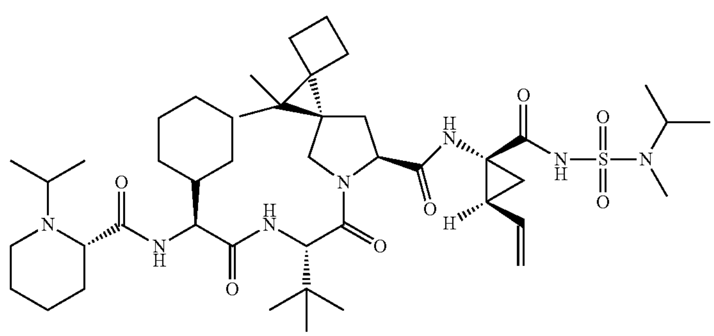 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)C(C)C] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[isopropyl(methyl)amino]sulfonyl}carbamoyl)-2-vinylcyclopropyl]-10,10-dimethyl-7-azadispiro[3.0.4.1]decane-8-carboxamide |
| 109 | 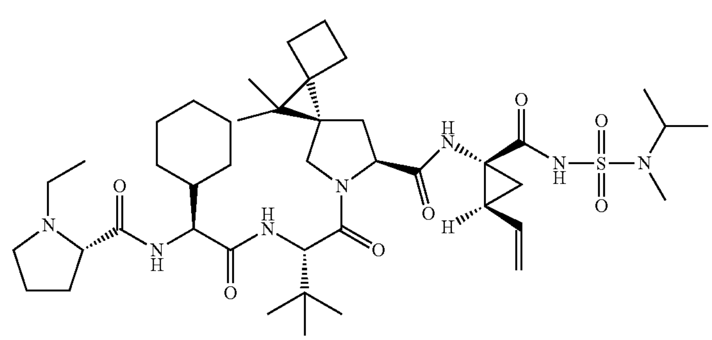 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(C)C(C)C] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-({[isopropyl(methyl)amino]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 110 | 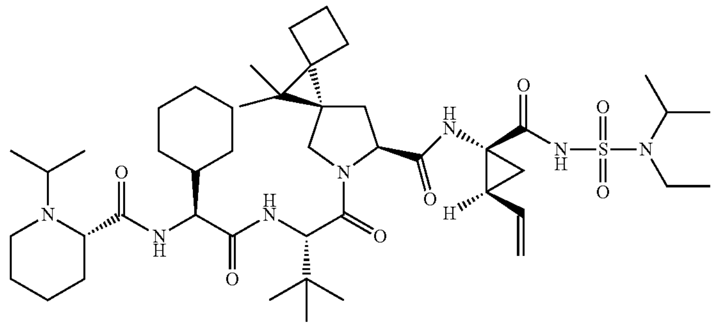 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(CC)C(C)C] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[ethyl(isopropyl)amino]sulfonyl}carbamoyl)-2-vinylcyclopropyl]-10,10-dimethyl-7-azadispiro[3.0.4.1]decane-8-carboxamide |
| 111 | 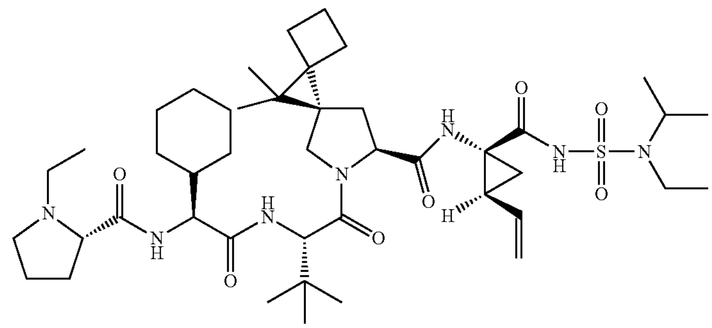 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(CC)C(C)C] | (5R,8S)-7-[(2S)-2-{[(2S)-2-cyclohexyl-2-({[(2S)-1-ethylpyrrolidin-2-yl]carbonyl}amino)acetyl]amino}-3,3-dimethylbutanoyl]-N-[(1R,2S)-1-({[ethyl(isopropyl)amino]sulfonyl}carbamoyl)-2-vinylcyclopropyl]-10,10-dimethyl-7-azadispiro[3.0.4.1]decane-8-carboxamide |
| 112 | 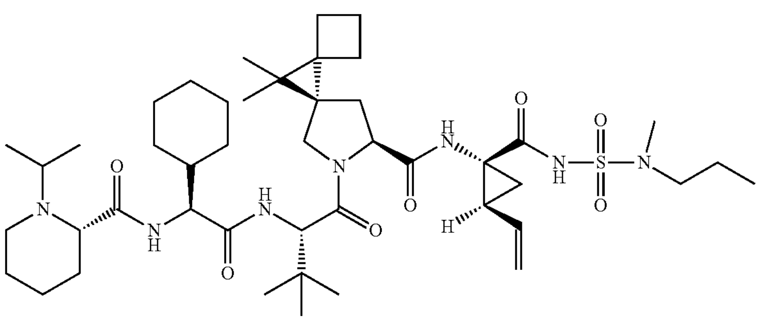 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)CCC] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-[(1R,2S)-1-({[methyl(propyl)amino]sulfonyl}carbamoyl)-2-vinylcyclopropyl]-7-azadispiro[3.0.4.1]decane-8-carboxamide |
| 113 | 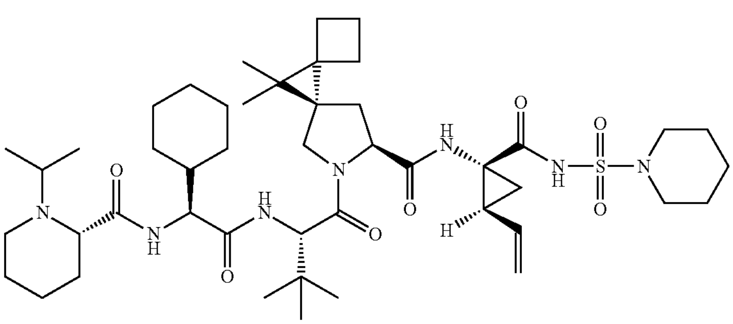 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N1CCCCC1] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-{(1R,2S)-1-[(piperidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 114 | 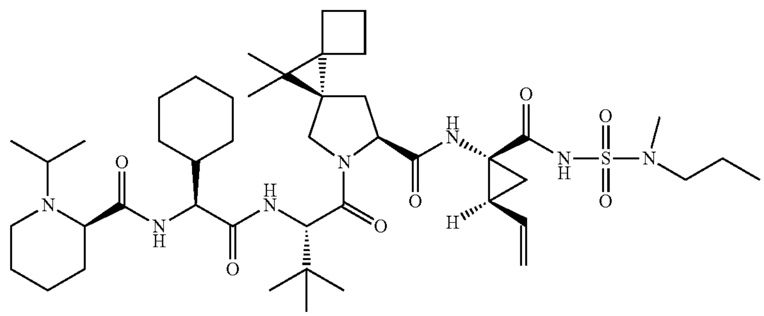 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(C)CCC] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-10,10-dimethyl-N-[(1R,2S)-1-({[methyl(propyl)amino]sulfonyl}carbamoyl)-2-vinylcyclopropyl]-7-azadispiro[3.0.4.1]decane-8-carboxamide |
| 115 | 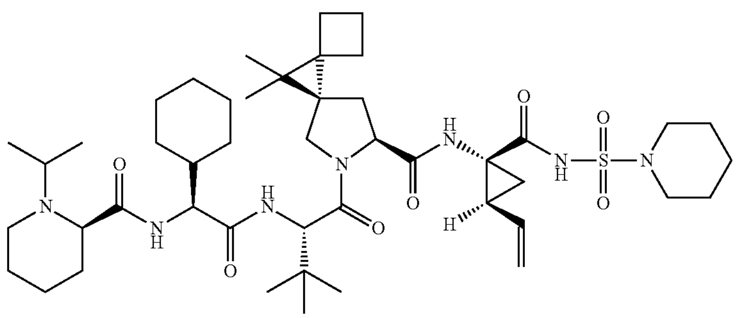 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N1CCCCC1] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-10,10-dimethyl-N-{(1R,2S)-1-[(piperidin-1-ylsulfonyl)carbamoyl]-2-vinylcyclopropyl}-7-azadispiro[3.0.4.1]decane-8-carboxamide |
| 116 | 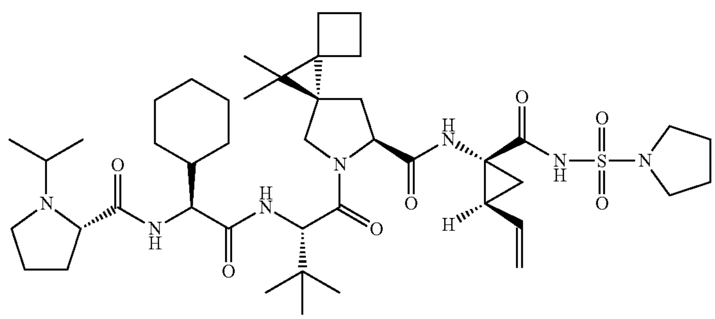 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide |
| 117 | 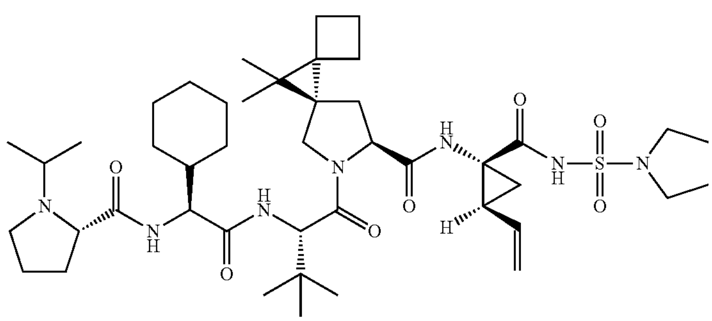 [SMILES: C=C[C@@H]1C[C@]1(NC(=O)[C@@H]1C[C@@]2(CN1C(=O)[C@@H](NC(=O)[C@@H](NC(=O)[C@@H]1CCCN1C(C)C)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2S)-1-isopropylpyrrolidin-2-yl]carbonyl}amino)acetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide |
| 118 | 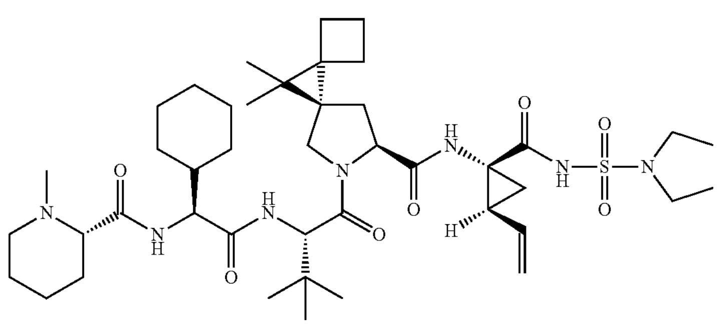 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C)C1CCCCC1)C(C)(C)C)C(C)(C)C21CCC1)C(=O)NS(=O)(=O)N(CC)CC] | (5R,8S)-7-[(2S)-2-{[(2S)-2-cylcohexyl-2-({[(2S)-1-methylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 119 | 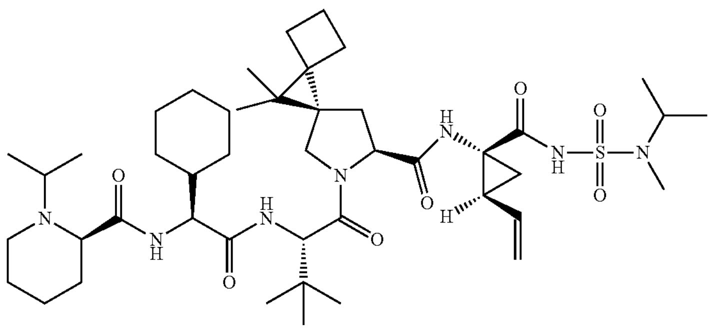 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(C)C(C)C] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2S)-1-({[isopropyl(methyl)amino]sulfonyl}carbamoyl)-2-vinylcyclopropyl]-10,10-dimethyl-7-azadispiro[3.0.4.1]decane-8-carboxamide |
| 120 | 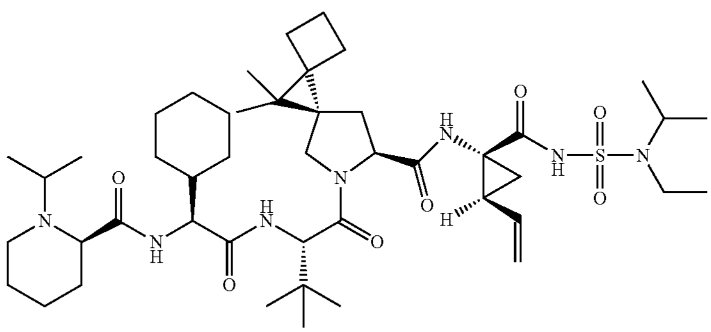 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(CC)C(C)C] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2S)-1-({[ethyl(isopropyl)amino]sulfonyl}carbamoyl)-2-vinylcyclopropyl]-10,10-dimethyl-7-azadispiro[3.0.4.1]decane-8-carboxamide |
| 121 | 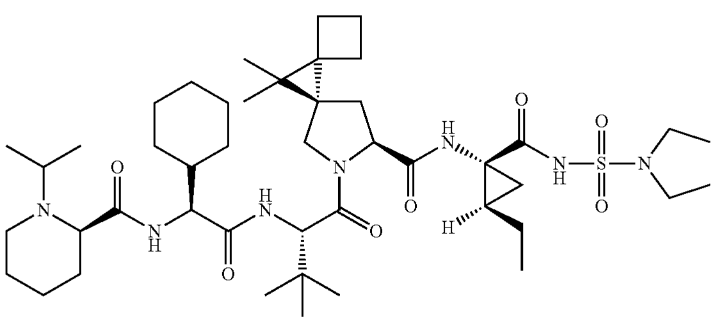 | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2R)-1-{[(diethylamino)sulfonyl]carbamoyl}-2-ethylcyclopropyl]-10,10-dimethyl-7-azadispiro[3.0.4.1]decane-8-carboxamide |
| 122 | 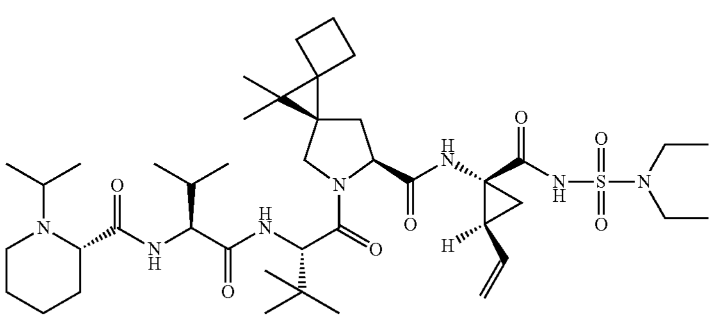 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C(C)C)C(C)(C)C)C(C)(C)C21CCC1)C(=O)NS(=O)(=O)N(CC)CC] | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-3-methylbutanoyl]amino}-3,3-dimethylbutanoyl]-10,10-dimethyl-7-azadispiro[3.0.4.1]decane-8-carboxamide |

TABLE A-continued

| Cmpd. # | Structure | Name |
|---|---|---|
| 123 | 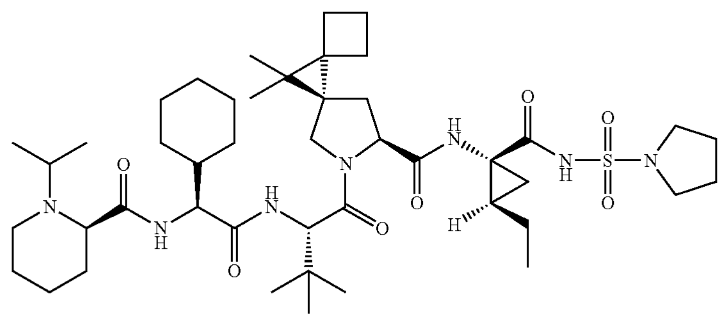 [SMILES: CC[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N1CCCC1] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-{(1R,2R)-2-ethyl-1-[(pyrrolidin-1-ylsulfonyl)carbamoyl]cyclopropyl}-10,10-dimethyl-7-azadispiro[3.0.4.1]decane-8-carboxamide |
| 124 | 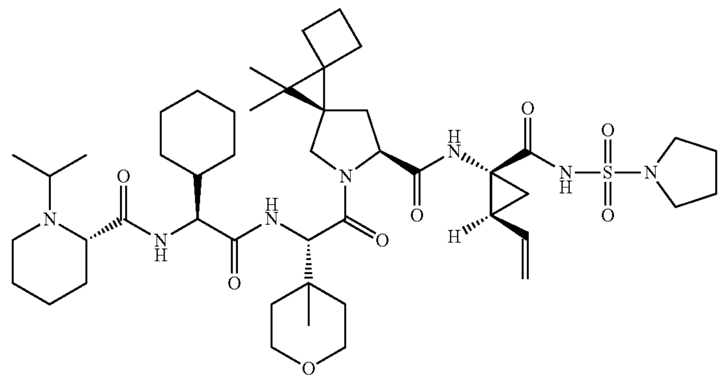 | (5R,8S)-7-[(2S)-2-{[(2S)-2-cyclohexyl-2-({[(2S)-1-isopropylpiperidin-2-yl]carbonyl}amino)acetyl]amino}-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 125 | 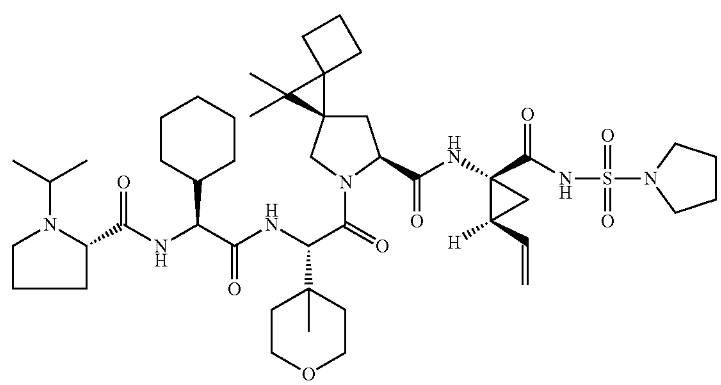 | (5R,8S)-7-[(2S)-2-{[(2S)-2-cyclohexyl-2-({[(2S)-1-ethylpyrrolidin-2-yl]carbonyl}amino)acetyl]amino}-2-(4-methyltetrahydro-2H-pyrazn-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 126 | 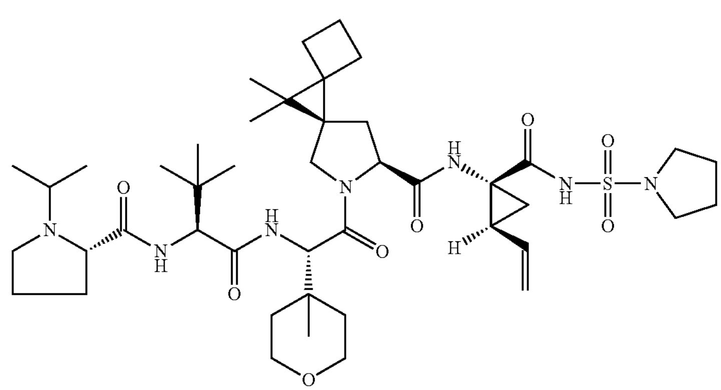 | 1-ethyl-L-prolyl-N-[(1S)-2-[(5R,8S)-10,10-dimethyl-8-({(1R,2S)-1-[(pyrrolidin-1-ylsulfonyl)carbamoyl]-2-vinylcyclopropyl}carbamoyl)-7-azadispiro[3.0.4.1]dec-7-yl]-1-(4-methyltetrahydro-2H-pyran-4-yl)-2-oxoethyl]-3-methyl-L-valinamide |

TABLE A-continued

| Cmpd. # | Structure | Name |
|---|---|---|
| 127 | 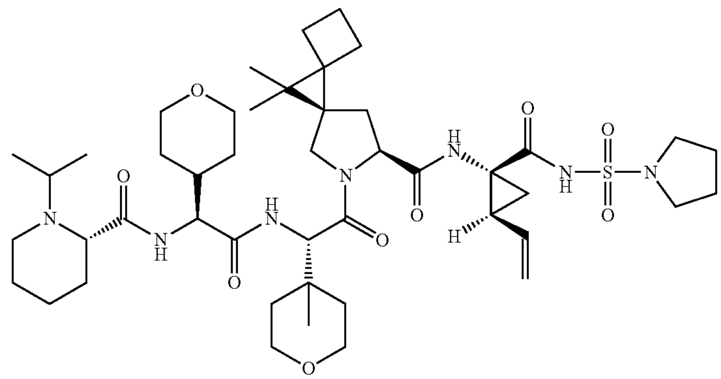 | (5R,8S)-7-[(2S)-2-{[(2S)-2-({[(2S)-1-isopropylpiperidin-2-yl]carbonyl}amino)-2-(tetrahydro-2H-pyran-4-yl)acetyl]amino}-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 128 | 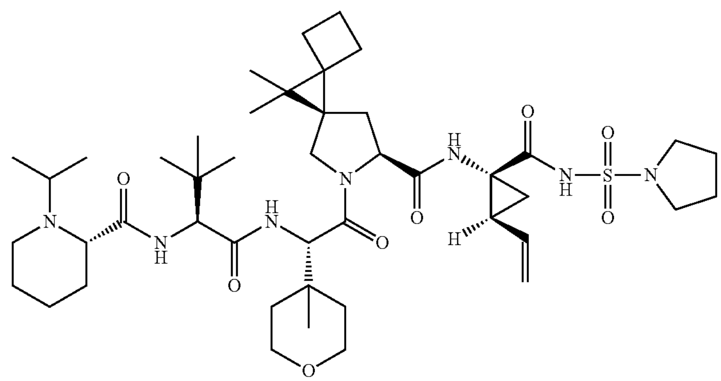 | (5R,8S)-7-[(2S)-2-[(N-{[(2S)-1-isopropylpiperidin-2-yl]carbonyl}-3-methyl-L-valyl)amino]-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 129 | 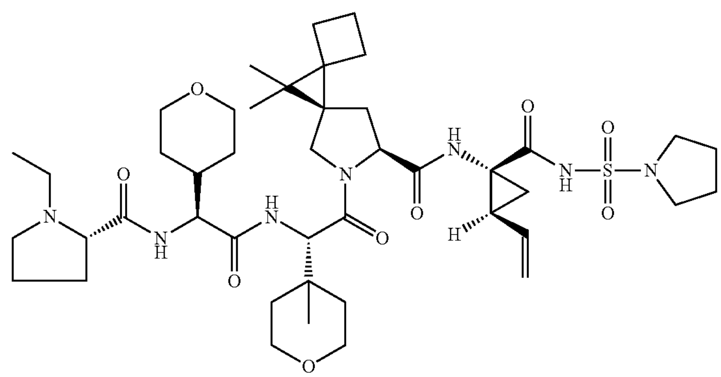 | (5R,8S)-7-[(2S)-2-{[(2S)-2-({[(2S)-1-ethylpyrrolidin-2-yl]carbonyl}amino)-2-(tetrahydro-2H-pyran-4-yl)acetyl]amino}-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 130 | 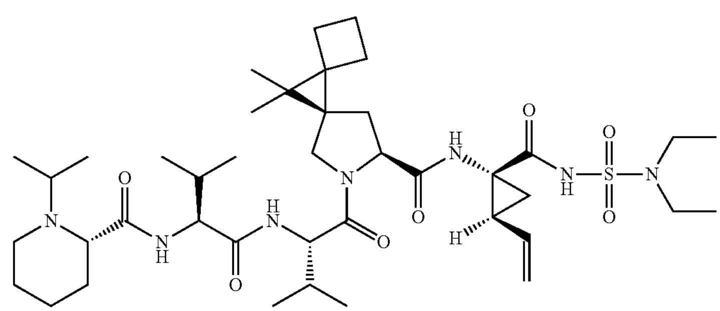 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C(C)C)C(C)C)C(C)(C)C21CCC1)C(=O)NS(=O)(=O)N(CC)CC] | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-3-methylbutanoyl]amino}-3-methylbutanoyl]-10,10-dimethyl-7-azadispiro[3.0.4.1]decane-8-carboxamide |

TABLE A-continued

| Cmpd. # | Structure | Name |
|---|---|---|
| 131 | 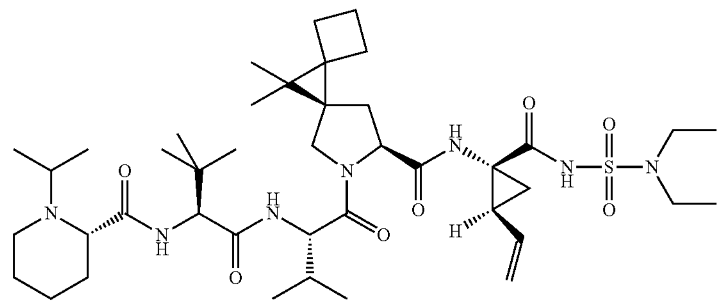 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C(C)(C)C)C(C)C)C(C)(C)C21CCC1)C(=O)NS(=O)(=O)N(CC)CC] | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-3,3-dimethylbutanoyl]amino}-3-methylbutanoyl]-10,10-dimethyl-7-azadispiro[3.0.4.1]decane-8-carboxamide |
| 132 | 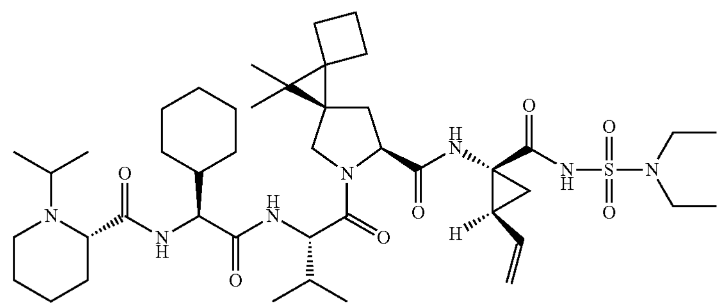 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)C)C(C)(C)C21CCC1)C(=O)NS(=O)(=O)N(CC)CC] | (5R,8S)-7-[(2S)-2-{[(2S)-2-cyclohexyl-2-({[(2S)-1-isopropylpiperidin-2-yl]carbonyl}amino)acetyl]amino}-3-methylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 133 | 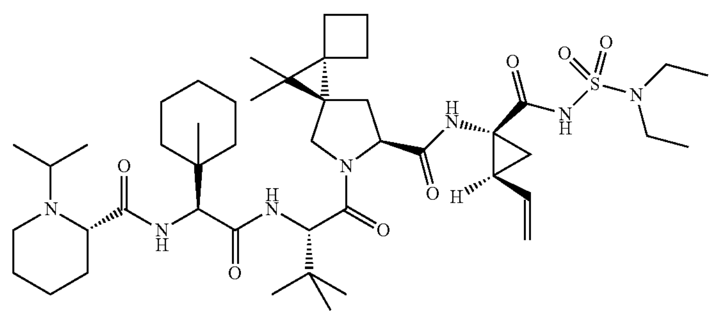 | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-2-(1-methylcyclohexyl)acetyl]amino}-3,3-dimethylbutanol]-10,10-dimethyl-7-azadispiro[3.0.4.1]decane-8-carboxamide |
| 134 | 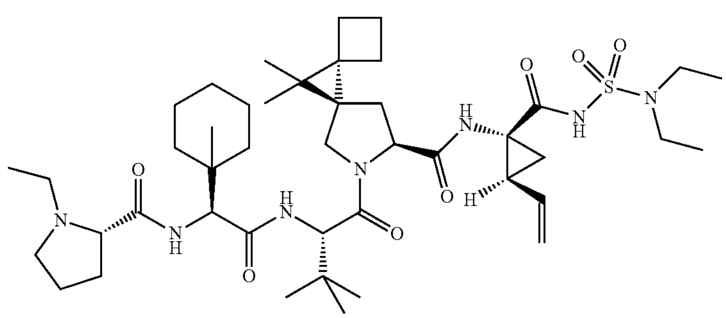 | (5R,8S)-N-[(1R,2S)-1-{[(diethylamino)sulfonyl]carbamoyl}-2-vinylcyclopropyl]-7-[(2S)-2-{[(2S)-2-({[(2S)-1-ethylpyrrolidin-2-yl]carbonyl}amino)-2-(1-methylcyclohexyl)acetyl]amino}-3,3-dimethylbutanoyl]-10,10-dimethyl-7-azadispiro[3.0.4.1]decane-8-carboxamide |
| 135 | 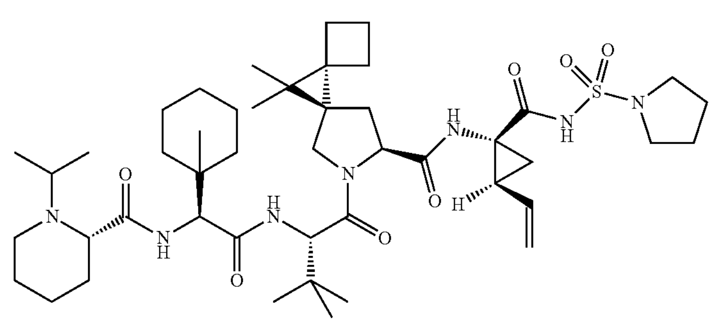 | (5R,8S)-7-[(2S)-2-{[(2S)-2-({[(2S)-1-isopropylpiperidin-2-yl]carbonyl}amino)-2-(1-methylcyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

| Cmpd. # | Structure | Name |
|---|---|---|
| 136 | 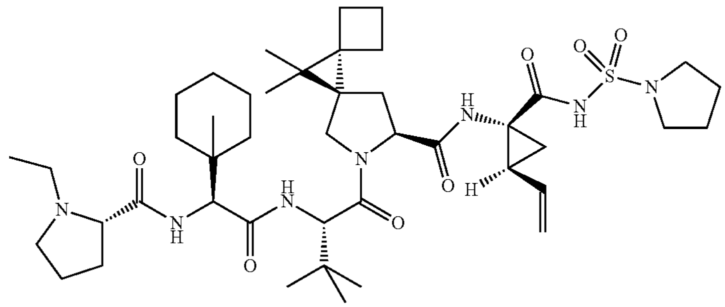 | (5R,8S)-7-[(2S)-2-{[(2S)-2-({[(2S)-1-ethylpyrrolidin-2-yl]carbonyl}amino)-2-(1-methylcyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 137 | 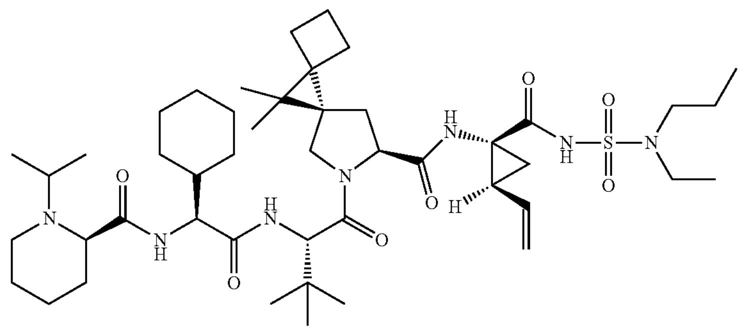 [SMILES: C=C[C@@H]1C[C@]1(NC(=O)[C@@H]1C[C@@]2(CN1C(=O)[C@@H](NC(=O)[C@@H](NC(=O)[C@H]1CCCCN1C(C)C)C1CCCCC1)C(C)(C)C)C(C)(C)C21CCC1)C(=O)NS(=O)(=O)N(CC)CCC] | (5R,8S)-7-[(2S)-2-{[(2S)-2-cyclohexyl-2-({[(2R)-1-isopropylpiperidin-2-yl]carbonyl}amino)acetyl]amino}-3,3-dimethylbutanoyl]-N-[(1R,2S)-1-({[ethyl(propyl)amino]sulfonyl}carbamoyl)-2-vinylcyclopropyl]-10,10-dimethyl-7-azadispiro[3.0.4.1]decane-8-carboxamide |
| 138 | 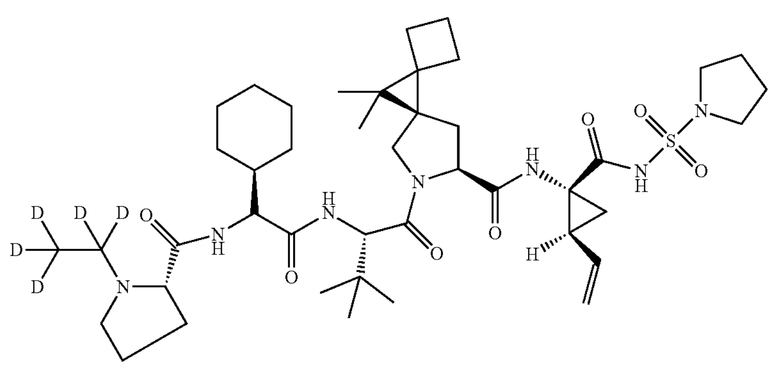 | (5R,8S)-7-[(2S)-2-{[(2S)-2-cyclohexyl-2-({[(2S)-1-d5-ethylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide-d5 |
| 139 | 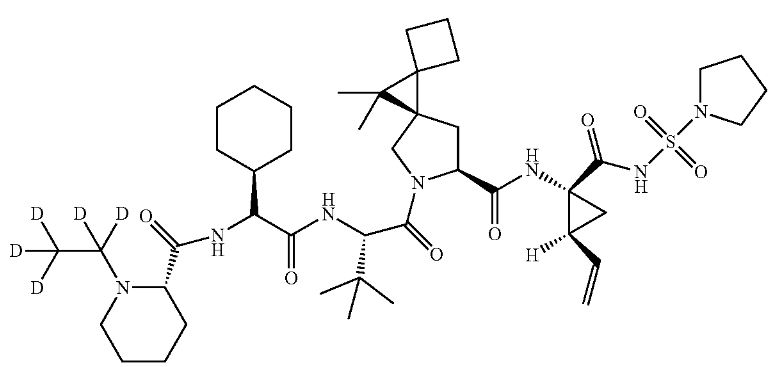 | (5R,8S)-7-[(2S)-2-{[(2S)-2-cyclohexyl-2-({[(2S)-1-d5-ethylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide-d5 |

TABLE A-continued

| Cmpd. # | Structure | Name |
|---|---|---|
| 140 | 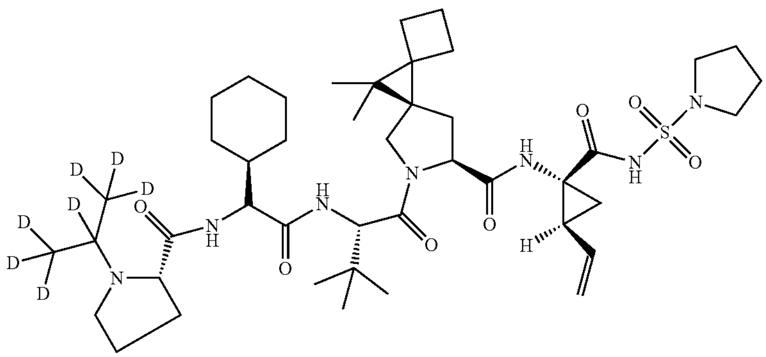 | (5R,8S)-7-[(2S)-2-{[(2S)-2-cyclohexyl-2-({[(2S)-1-d7-isopropylpyrrolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide-d7 |
| 141 | 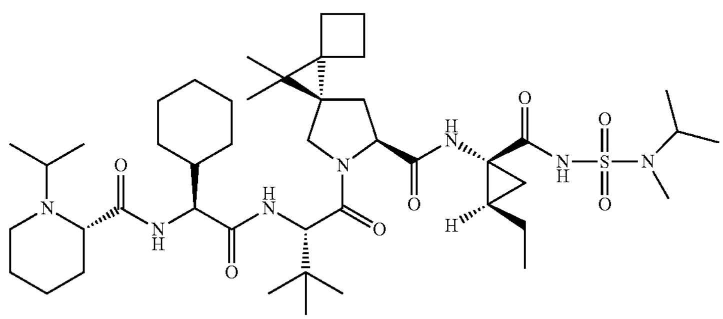 [SMILES: CC[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)C(C)C] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2R)-2-ethyl-1-({[isopropyl(methyl)amino]sulfonyl}carbamoyl)cyclopropyl]-10,10-dimethyl-7-azadispiro[3.0.4.1]decane-8-carboxamide |
| 142 | 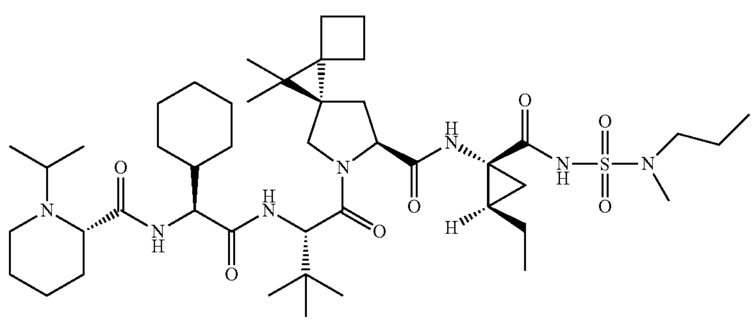 [SMILES: CCCN(C)S(=O)(=O)NC(=O)[C@@]1(NC(=O)[C@@H]2C[C@@]3(CN2C(=O)[C@@H](NC(=O)[C@@H](NC(=O)[C@@H]2CCCCN2C(C)C)C2CCCCC2)C(C)(C)C)C(C)(C)C32CCC2)C[C@H]1CC] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2R)-2-ethyl-1-({[methyl(propyl)amino]sulfonyl}carbamoyl)cyclopropyl]-10,10-dimethyl-7-azadispiro[3.0.4.1]decane-8-carboxamide |
| 143 | 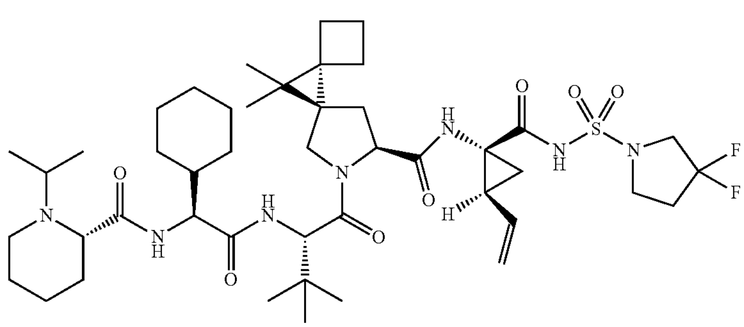 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-{[(3,3-difluoropyrrolidin-1-yl)sulfonyl]carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 144 | 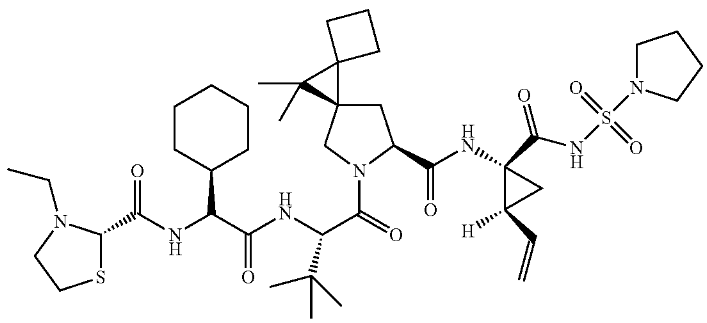 | (5R,8S)-7-[(2S)-2-{[(2S)-2-cyclohexyl-2-({[(2S)-3-ethyl-1,3-thiazolidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 145 | 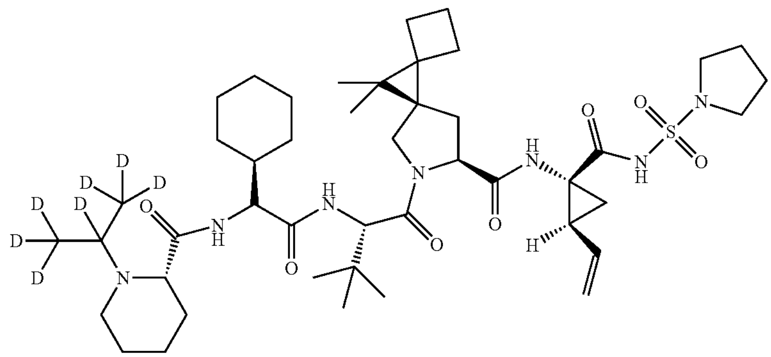 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide-d7 |
| 146 | 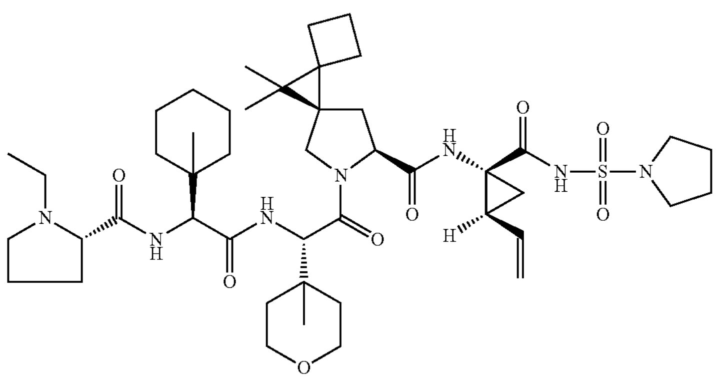 | (5R,8S)-7-[(2S)-2-{[(2S)-2-({[(2S)-1-ethylpyrrolidin-2-yl]carbonyl}amino)-2-(1-methylcyclohexyl)acetyl]amino}-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 147 | 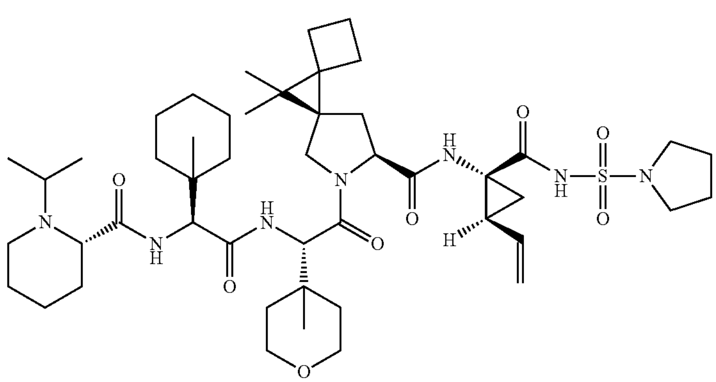 | (5R,8S)-7-[(2S)-2-{[(2S)-2-({[(2S)-1-isopropylpiperidin-2-yl]carbonyl}amino)-2-(1-methylcyclohexyl)acetyl]amino}-2-(4-methyltetrahydro-2H-pyran-4-yl)acetyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 148 | 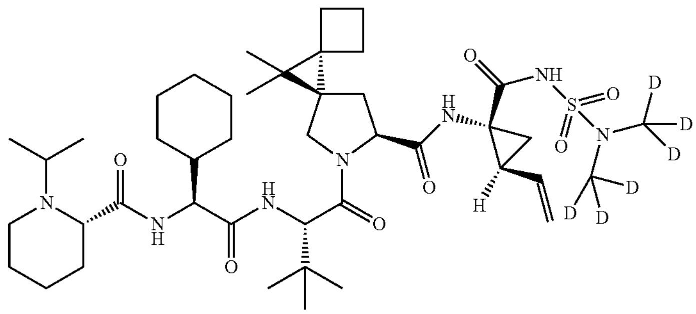 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-{[(d6-dimethylamino)sulfonyl]carbamoyl}-2-vinylcyclopropyl]-10,10-dimethyl-7-azadispiro[3.0.4.1]decane-8-carboxamide-d6 |
| 149 | 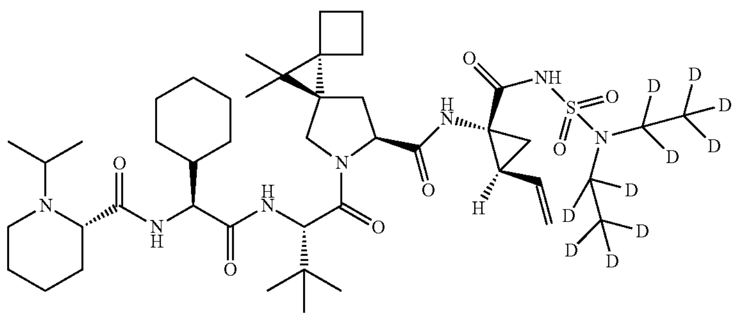 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-{[(d10-diethylamino)sulfonyl]carbamoyl}-2-vinylcyclopropyl]-10,10-dimethyl-7-azadispiro[3.0.4.1]decane-8-carboxamide-d10 |
| 150 | 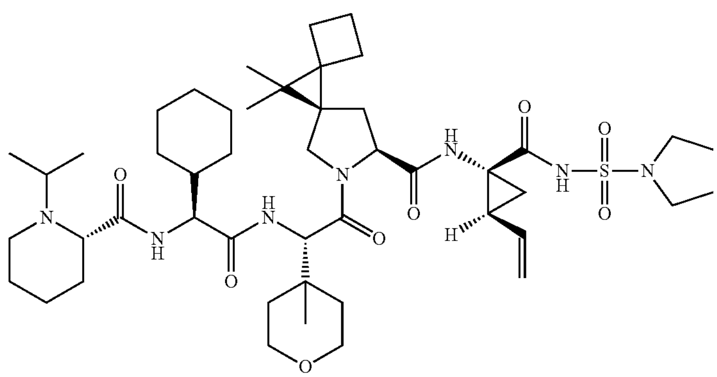 | (5R,8S)-7-[(2S)-2-{[(2S)-2-cyclohexyl-2-({[(2S)-1-isopropylpiperidin-2-yl]carbonyl}amino)acetyl]amino}-2-(4-methyltetrahydro-2H-pyran-4-yl)acetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 151 | 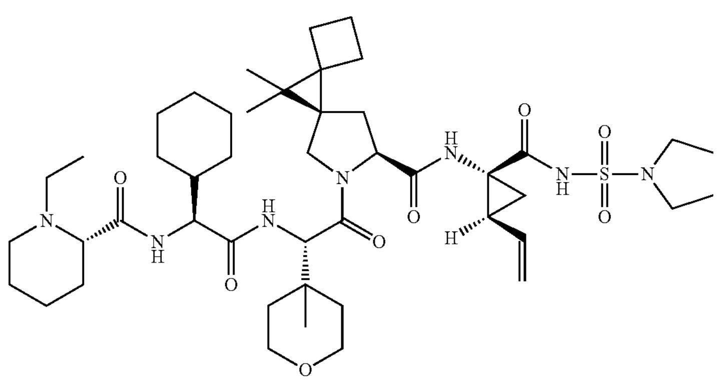 | (5R,8S)-7-[(2S)-2-{[(2S)-2-cyclohexyl-2-({[(2S)-1-ethylpiperidin-2-yl]carbonyl}amino)acetyl]amino}-2-(4-methyltetrahydro-2H-pyran-4-yl)acetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 152 | 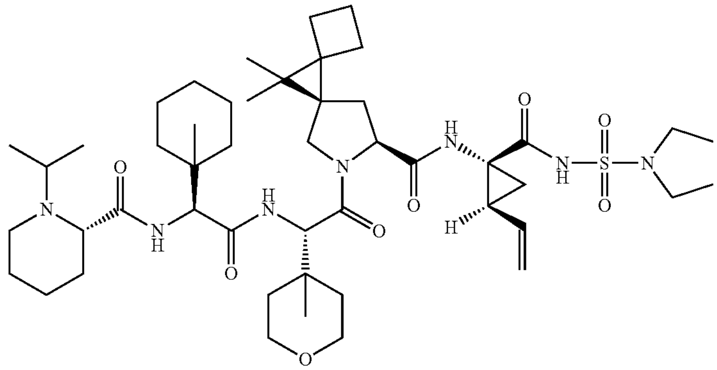 | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-2-(1-methylcyclohexyl)acetyl]amino}-2-(4-methyltetrahydro-2H-pyrazn-4-yl)acetyl]-10,10-dimethyl-7-azadispiro[3.0.4.1]decane-8-carboxamide |
| 153 | 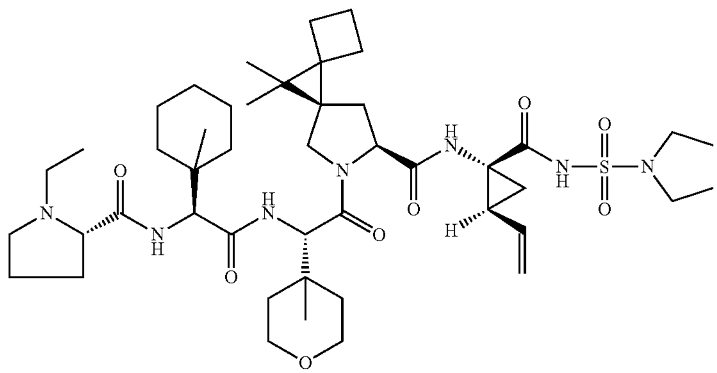 | (5R,8S)-N-[(1R,2S)-1-{[(diethylamino)sulfonyl]carbamoyl}-2-vinylcyclopropyl]-7-[(2S)-2-{[(2S)-2-({[(2S)-1-ethylpyrrolidin-2-yl]carbonyl}amino)-2-(1-methylcyclohexyl)acetyl]amino}-2-(4-methyltetrahydro-2H-pyrazn-4-yl)acetyl]-10,10-dimethyl-7-azadispiro[3.0.4.1]decane-8-carboxamide |
| 154 | 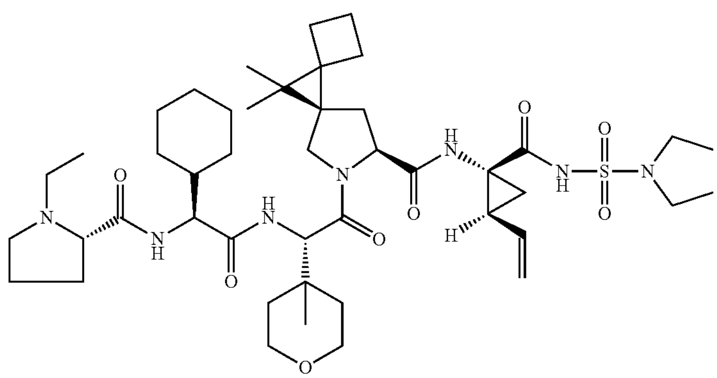 | (5R,8S)-7-[(2S)-2-{[(2S)-2-cyclohexyl-2-({[(2S)-1-ethylpyrrolidin-2-yl]carbonyl}amino)acetyl]amino}-2-(4-methyltetrahydro-2H-pyran-4-yl)acetyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 155 | 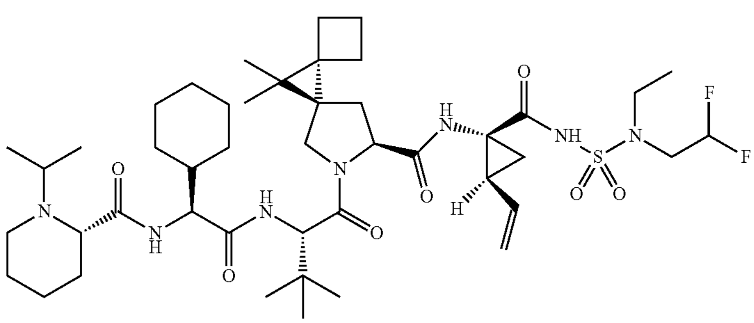 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[(2,2-difluoroethyl)(ethyl)amino]sulfonyl}carbamoyl)-2-vinylcyclopropyl]-10,10-dimethyl-7-azadispiro[3.0.4.1]decane-8-carboxamide |

TABLE A-continued

| Cmpd. # | Structure | Name |
|---|---|---|
| 156 | 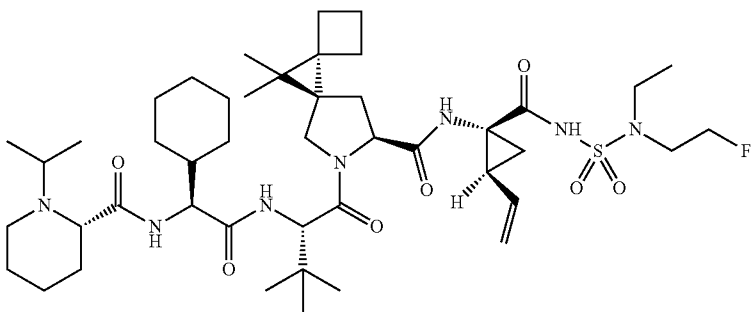 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanol]-N-[(1R,2S)-1-({[ethyl(2-fluoroethyl)amino]sulfonyl}carbamoyl)-2-vinylcyclopropyl]-10,10-dimethyl-7-azadispiro[3.0.4.1]decane-8-carboxamide |
| 157 | 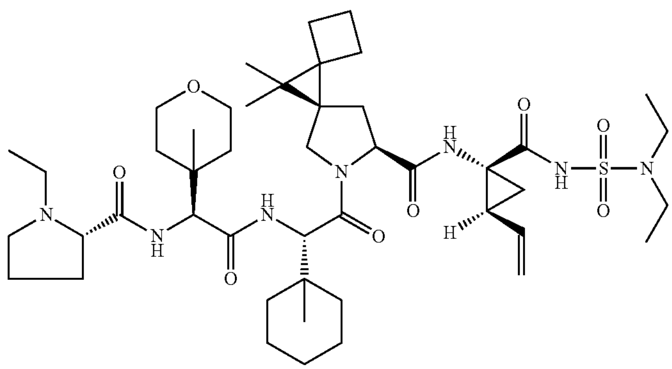 | (5R,8S)-N-[(1R,2S)-1-{[(diethylamino)sulfonyl]carbamoyl}-2-vinylcyclopropyl]-7-[(2S)-2-{[(2S)-2-({[(2S)-1-ethylpyrrolidin-2-yl]carbonyl}amino)-2-(4-methyltetrahydro-2H-pyran-4-yl)acetyl]amino}-2-(1-methylcyclohexyl)acetyl]-10,10-dimethyl-7-azadispiro[3.0.4.1]decane-8-carboxamide |
| 158 | 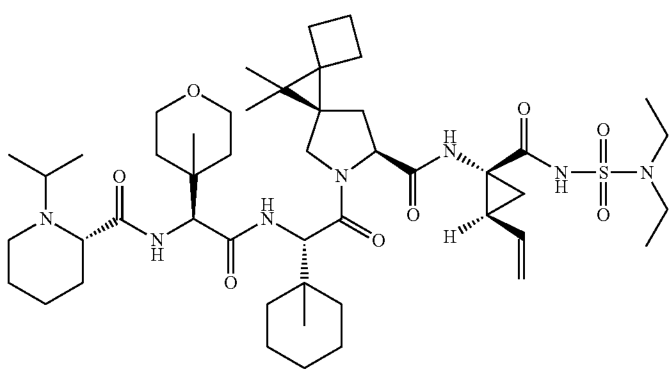 | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-2-(4-methyltetrahydro-2H-pyran-4-yl)acetyl]amino}-2-(1-methylcyclohexyl)acetyl]-10,10-dimethyl-7-azadispiro[3.0.4.1]decane-8-carboxamide |
| 159 | 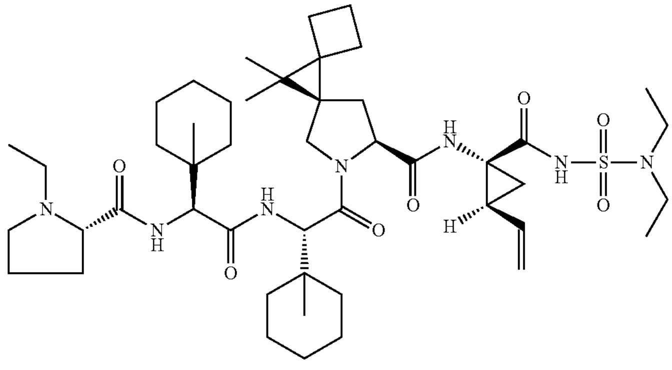 | (5R,8S)-N-[(1R,2S)-1-{[(diethylamino)sulfonyl]carbamoyl}-2-vinylcyclopropyl]-7-[(2S)-2-{[(2S)-2-({[(2S)-1-ethylpyrrolidin-2-yl]carbonyl}amino)-2-(1-methylcyclohexyl)acetyl]amino}-2-(1-methylcyclohexyl)acetyl]-10,10-dimethyl-7-azadispiro[3.0.4.1]decane-8-carboxamide |

TABLE A-continued

| Cmpd. # | Structure | Name |
|---|---|---|
| 160 | 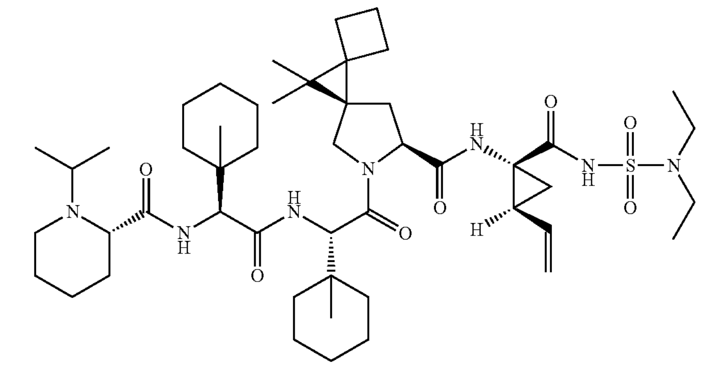 | (5R,8S)-N-[(1R,2S)-1-{[(diethylamino)sulfonyl]carbamoyl}-2-vinylcyclopropyl]-7-[(2S)-2-{[(2S)-2-({[(2S)-1-isopropylpiperidin-2-yl]carbonyl}amino)-2-(1-methylcyclohexyl)acetyl]amino}-2-(1-methylcyclohexyl)acetyl]-10,10-dimethyl-7-azadispiro[3.0.4.1]decane-8-carboxamide |
| 161 | 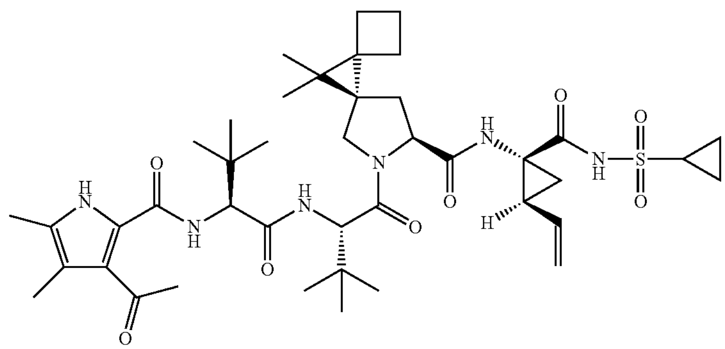 [SMILES: C=C[C@@H]1C[C@]1(NC(=O)[C@@H]1C[C@@]2(CN1C(=O)[C@@H](NC(=O)[C@@H](NC(=O)c1[nH]c(C)c(C)c1C(C)=O)C(C)(C)C)C(C)(C)C)C(C)(C)C21CCC1)C(=O)NS(=O)(=O)C1CC1] | (5R,8S)-7-[(2S)-2-{[(2S)-2-{[3-acetyl-4,5-dimethyl-1H-pyrrol-2-yl]carbonyl]amino}-3,3-dimethylbutanoyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 162 | 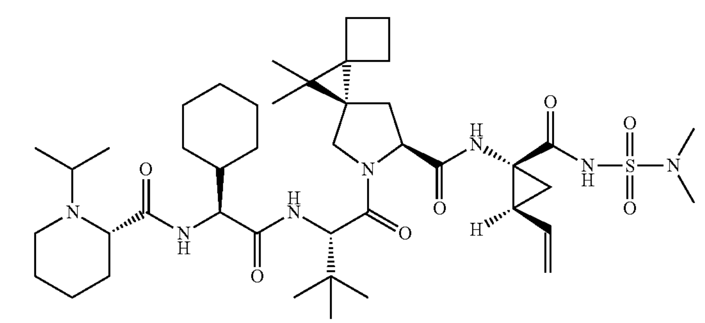 [SMILES: C=C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(C)C] | (5R,8S)-7-[(2S)-2-{[(2S)-2-cyclohexyl-2-{[(1-isopropylpiperidin-2-yl)carbonyl]amino}acetyl]amino}-3,3-dimethylbutanoyl]-N-[(1R,2S)-1-{[(dimethylamino)sulfonyl]carbamoyl}-2-vinylcyclopropyl]-10,10-dimethyl-7-azadispiro[3.0.4.1]decane-8-carboxamide |
| 163 | 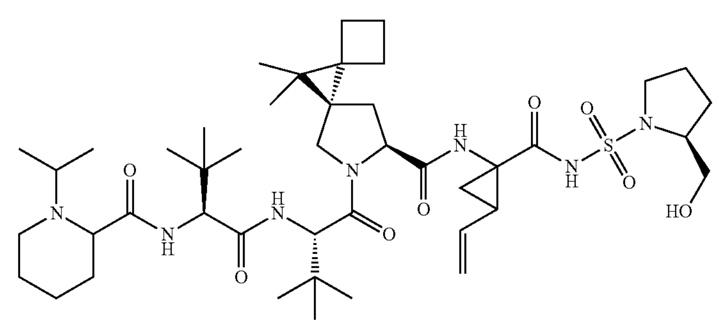 [SMILES: C=CC1CC1(NC(=O)[C@@H]1C[C@@]2(CN1C(=O)[C@@H](NC(=O)[C@@H](NC(=O)C1CCCCN1C(C)C)C(C)(C)C)C(C)(C)C)C(C)(C)C21CCC1)C(=O)NS(=O)(=O)N1CCC[C@H]1CO] | (5R,8S)-N-[1-({[(2S)-2-(hydroxymethyl)pyrrolidin-1-yl]sulfonyl}carbamoyl)-2-vinylcyclopropyl]-7-[(2S)-2-{[(2S)-2-{[(1-isopropylpiperidin-2-yl)carbonyl]amino}-3,3-dimethylbutanoyl]amino}-3,3-dimethylbutanoyl]-10,10-dimethyl-7-azadispiro[3.0.4.1]decane-8-carboxamide |

TABLE A-continued

| Cmpd. # | Structure | Name |
|---|---|---|
| 164 | 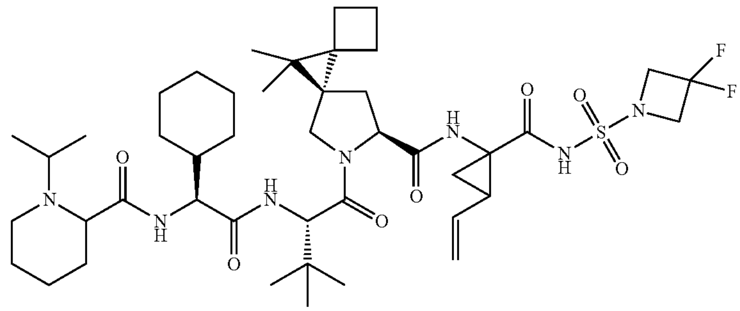 [SMILES: C=CC1CC1(NC(=O)[C@@H]1C[C@@]2(CN1C(=O)[C@@H](NC(=O)[C@@H](NC(=O)C1CCCCN1C(C)C)C1CCCCC1)C(C)(C)C)C(C)(C)C21CCC1)C(=O)NS(=O)(=O)N1CC(F)(F)C1] | (5R,8S)-7-[(2S)-2-{[(2S)-2-cyclohexyl-2-{[(1-isopropylpiperidin-2-yl)carbonyl]amino}acetyl]amino}-3,3-dimethylbutanoyl]-N-(1-{[(3,3-difluoroazetidin-1-yl)sulfonyl]carbamoyl}-2-vinylcyclopropyl)-10,10-dimethyl-7-azadispiro[3.0.4.1]decane-8-carboxamide |
| 165 | 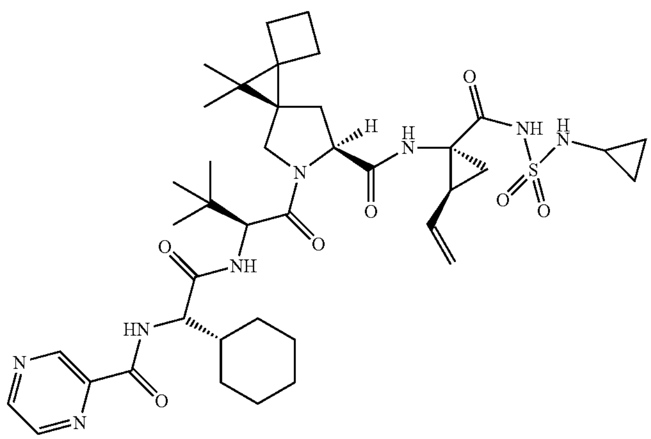 | (5R,8S)-7-[(2S)-2-({(2S)-2-cyclohexyl-2-[(pyrazin-2-ylcarbonyl)amino]acetyl}amino)-3,3-dimethylbutanoyl]-N-[(1R,2S)-1-{[(cyclopropylamino)sulfonyl]carbamoyl}-2-vinylcyclopropyl]-10,10-dimethyl-7-azadispiro[3.0.4.1]decane-8-carboxamide |
| 166 | 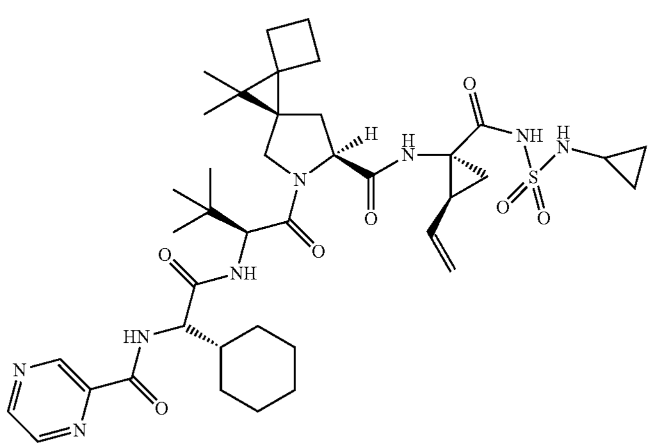 | (5R,8S)-N-[(1R,2S)-1-{[(tert-butylamino)sulfonyl]carbamoyl}-2-vinylcyclopropyl]-7-[(2S)-2-({(2S)-2-cyclohexyl-2-[(pyrazin-2-ylcarbonyl)amino]acetyl}amino)-3,3-dimethylbutanoyl]-10,10-dimethyl-7-azadispiro[3.0.4.1]decane-8-carboxamide |

| Cmpd. # | Structure | Name |
|---|---|---|
| 167 | 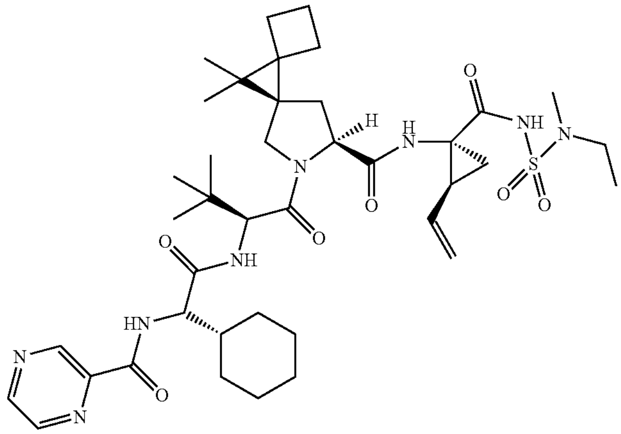 | (5R,8S)-7-[(2S)-2-({(2S)-2-cyclohexyl-2-[(pyrazin-2-ylcarbonyl)amino]acetyl}amino)-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |
| 168 | 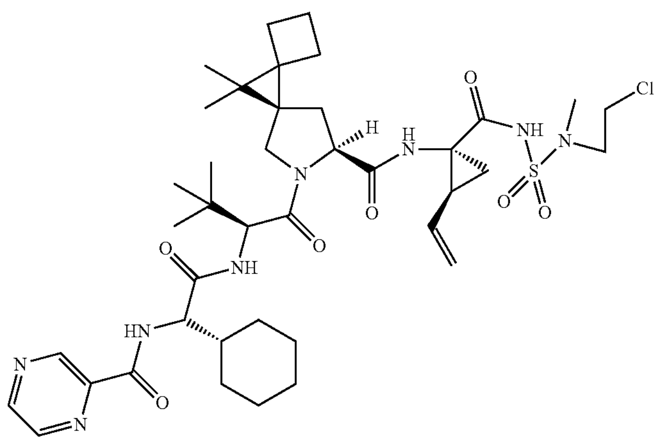 | (5R,8S)-N-[(1R,2S)-1-({[(2-chloroethyl)(methyl)amino]sulfonyl}carbamoyl)-2-vinylcyclopropyl]-7-[(2S)-2-({(2S)-2-cyclohexyl-2-[(pyrazin-2-ylcarbonyl)amino]acetyl}amino)-3,3-dimethylbutanoyl]-10,10-dimethyl-7-azadispiro[3.0.4.1]decane-8-carboxamide |
| 169 | 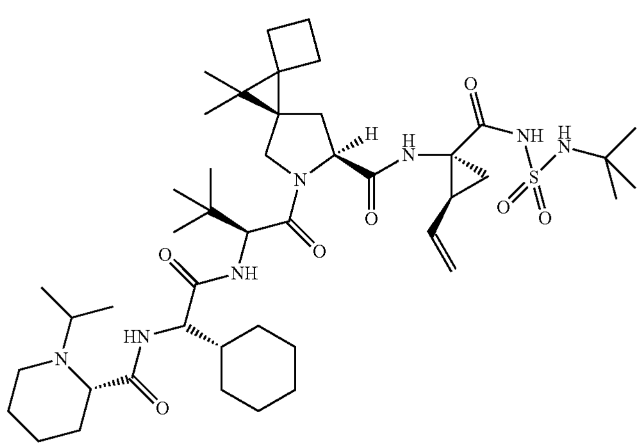 | (5R,8S)-N-[(1R,2S)-1-{[(tert-butylamino)sulfonyl]carbamoyl}-2-vinylcyclopropyl]-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-7-azadispiro[3.0.4.1]decane-8-carboxamide |

TABLE A-continued

| Cmpd. # | Structure | Name |
|---|---|---|
| 170 | 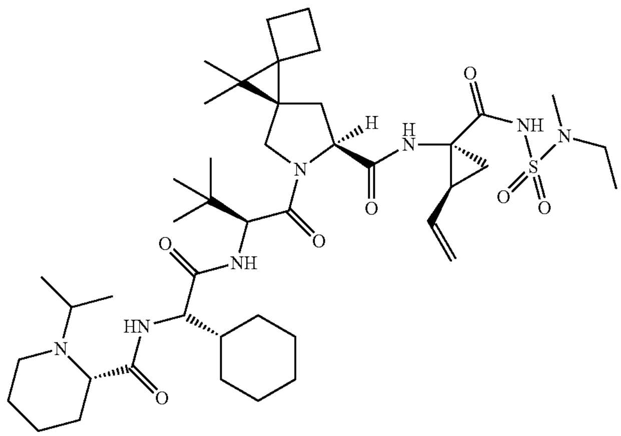 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-({[ethyl(methyl)amino]sulfonyl}carbamoyl)-2-vinylcyclopropyl]-10,10-dimethyl-7-azadispiro[3.0.4.1]decane-8-carboxamide |
| 171 | 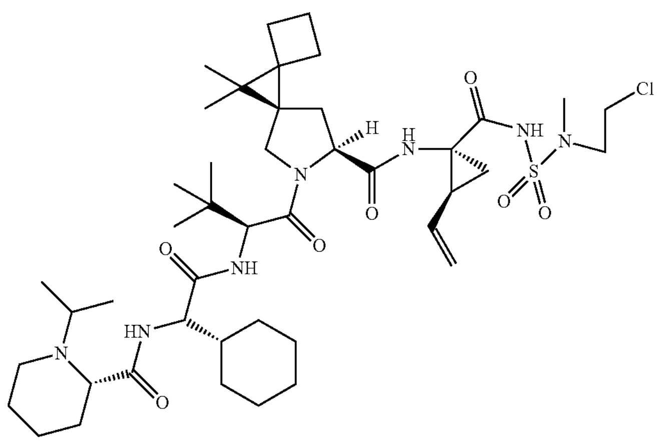 | (5R,8S)-N-[(1R,2S)-1-({[(2-chloroethyl)(methyl)amino]sulfonyl}carbamoyl)-2-vinylcyclopropyl]-7-[(2S)-2-{[(2S)-2-cyclohexyl-2-({[(2S)-1-isopropylpiperidin-2-yl]carbonyl}amino)acetyl]amino}-3,3-dimethylbutanoyl]-10,10-dimethyl-7-azadispiro[3.0.4.1]decane-8-carboxamide |
| 172 | 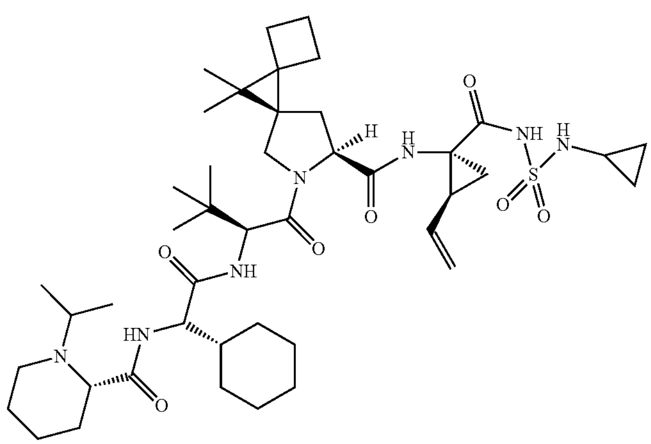 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-{[(cyclopropylamino)sulfonyl]carbamoyl}-2-vinylcyclopropyl]-10,10-dimethyl-7-azadispiro[3.0.4.1]decane-8-carboxamide |

TABLE A-continued

| Cmpd. # | Structure | Name |
|---|---|---|
| 173 | 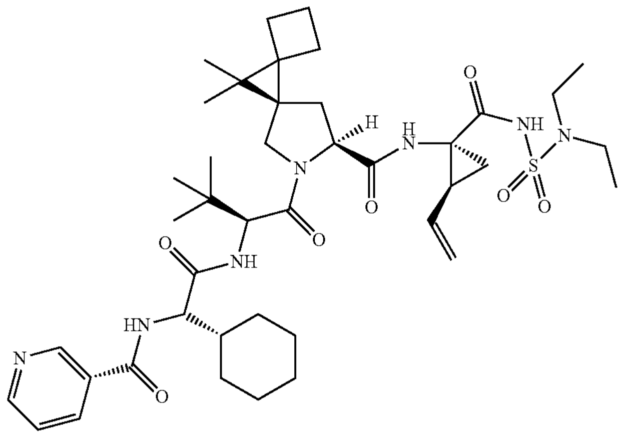 | (5R,8S)-7-[(2S)-2-({(2S)-2-cyclohexyl-2-[(pyrazin-2-ylcarbonyl)amino]acetyl}amino)-3,3-dimethylbutanoyl]-N-[(1R,2S)-2-{[(diethylamino)sulfonyl]carbamoyl}-2-vinylcyclopropyl]-10,10-dimethyl-7-azadispiro[3.0.4.1]decane-8-carboxamide |
| 174 | 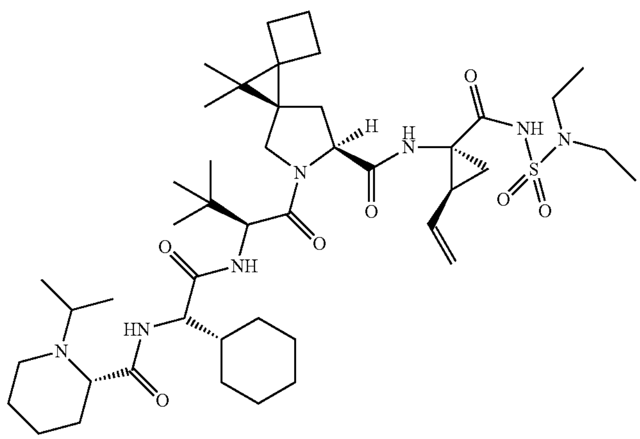 | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-[(1R,2S)-1-{[(diethylamino)sulfonyl]carbamoyl}-2-vinylcyclopropyl]-10,10-dimethyl-7-azadispiro[3.0.4.1]decane-8-carboxamide |
| 175 | 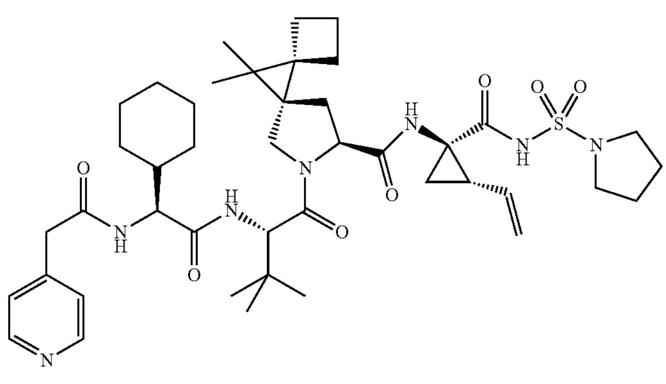 | (5R,8S)-7-[(2S)-2-({cyclohexyl[(pyridin-4-ylacetyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 176 | 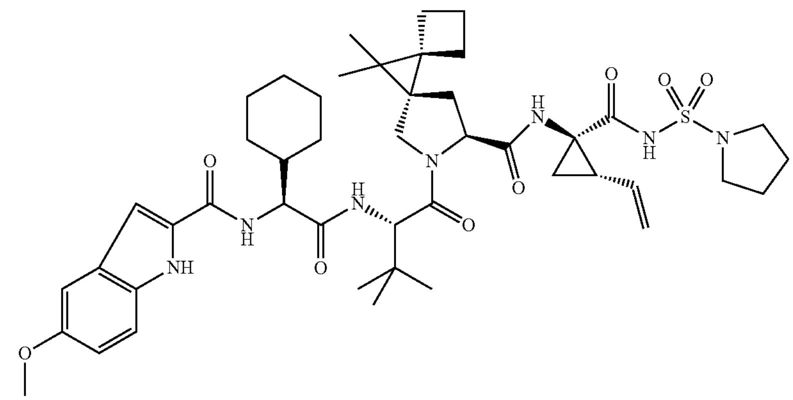 | (5R,8S)-7-{(2S)-2-[(cyclohexyl{[(5-methoxy-1H-indol-2-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 177 | 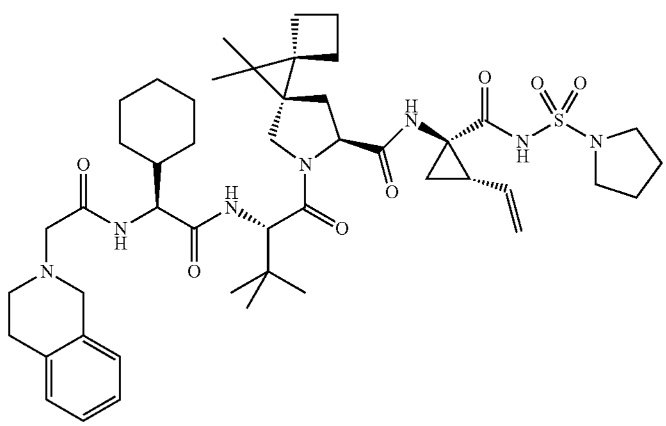 | (5R,8S)-7-[(2S)-2-({cyclohexyl[(3,4-dihydroisoquinolin-2(1H)-ylacetyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 178 | 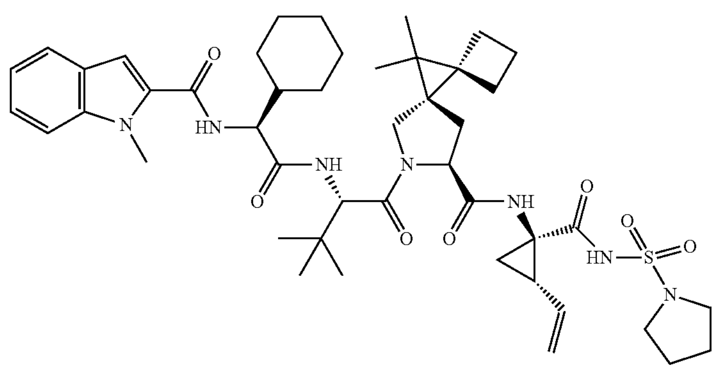 | (5R,8S)-7-{(2S)-2-[(cyclohexyl{[(1-methyl-1H-indol-2-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 179 | 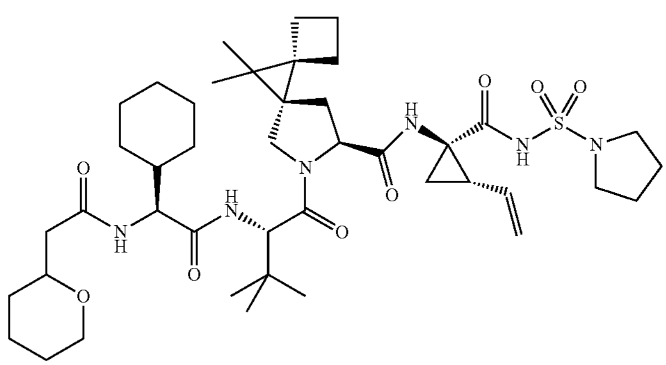 | (5R,8S)-7-[(2S)-2-({cyclohexyl[(tetrahydro-2H-pyran-2-ylacetyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 180 | 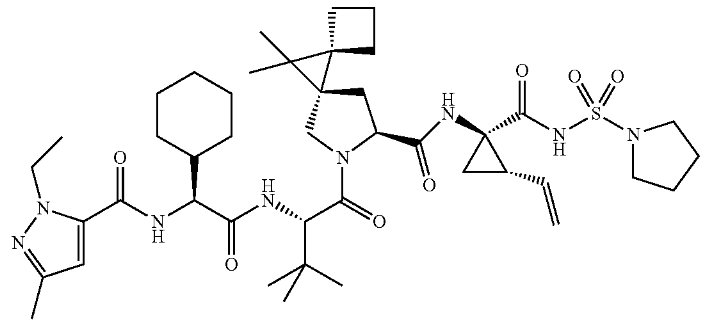 | (5R,8S)-7-{(2S)-2-[(cyclohexyl{[(1-ethyl-3-methyl-1H-pyrazol-5-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 181 | 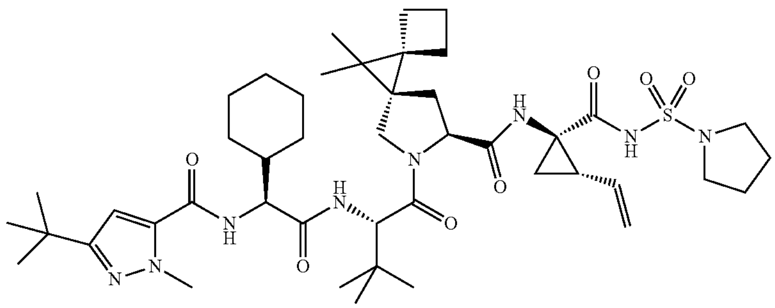 | (5R,8S)-7-[(2S)-2-{[{[(3-tert-butyl-1-methyl-1H-pyrazol-5-yl)carbonyl]amino}(cyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 182 | 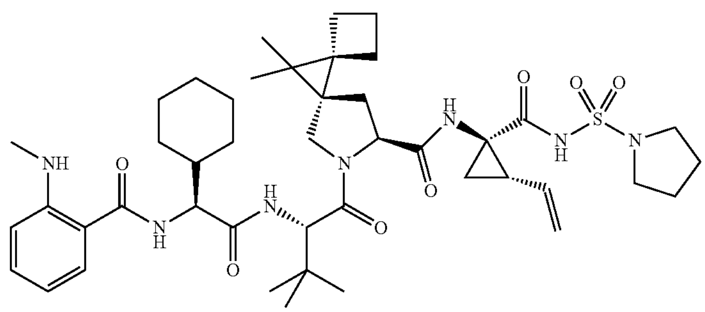 | (5R,8S)-7-{(2)-2-[(cyclohexyl{[2-(methylamino)benzoyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 183 | 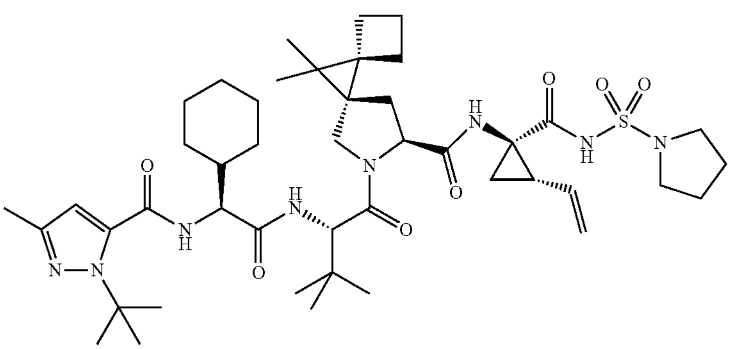 | (5R,8S)-7-[(2S)-2-{[{[(1-tert-butyl-3-methyl-1H-pyrazol-5-yl)carbonyl]amino}(cyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 184 | 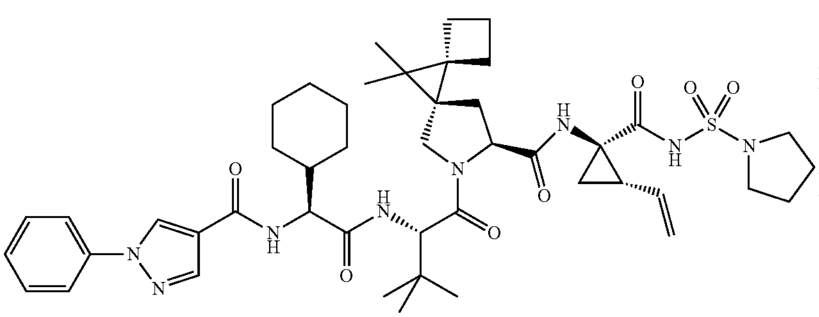 | (5R,8S)-7-{(2S)-2-[(cyclohexyl{[(1-phenyl-1H-pyrazol-4-yl)carbonyl]amino}acetyl)amino]-3,3-dimethylbutanoyl}-10,10-dimethyl-N-[(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 185 | 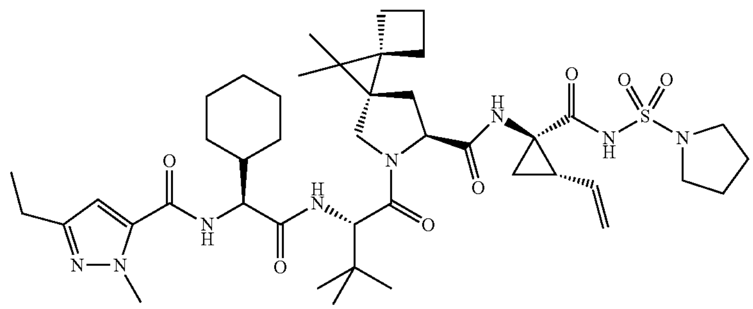 | (5R,8S)-7-{(2S)-2-[(cyclohexyl{[(3-ethyl-1-methyl-1H-pyrazol-5-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 186 | 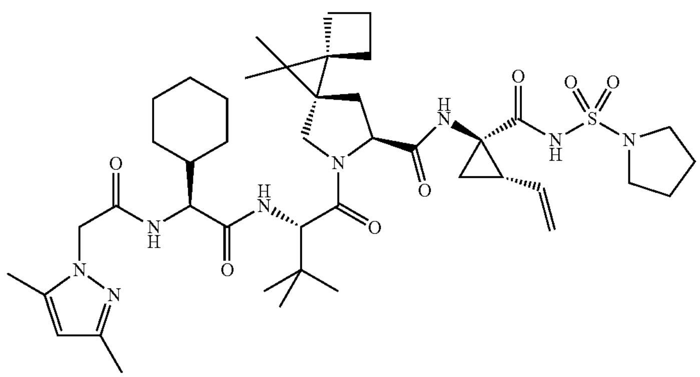 | (5R,8S)-7-{(2S)-2-[(cyclohexyl{[(3,5-dimethyl-1H-pyrazol-1-yl)acetyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 187 | 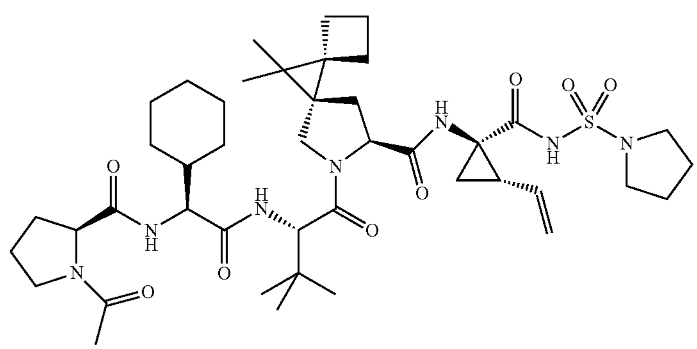 | (5R,8S)-7-[(2S)-2-{[({[(2S)-1-acetylpyrrolidin-2-yl]carbonyl}amino)(cyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 188 | 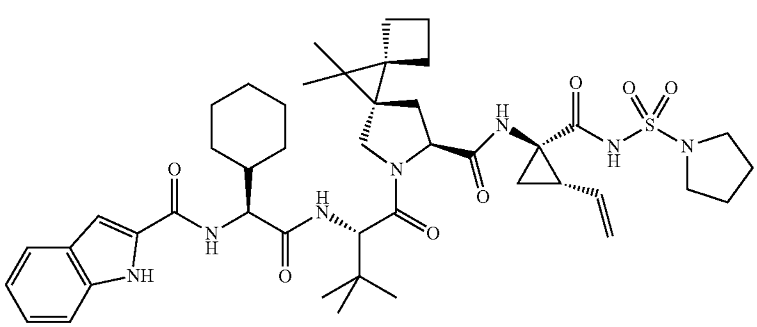 | (5R,8S)-7-[(2S)-2-({cyclohexyl[(1H-indol-2-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 189 | 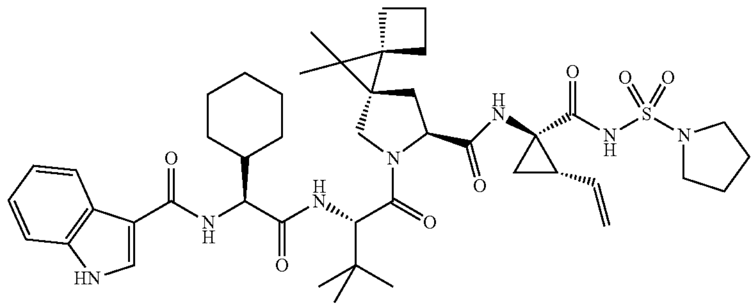 | (5R,8S)-7-[(2S)-2-({cyclohexyl[(1H-indol-3-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 190 | 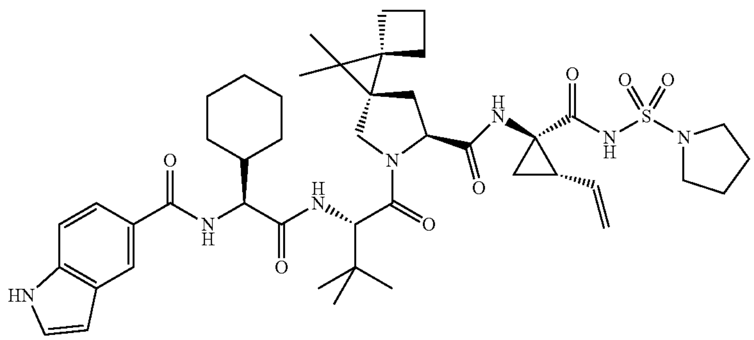 | (5R,8S)-7-[(2S)-2-({cyclohexyl[(1H-indol-5-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 191 | 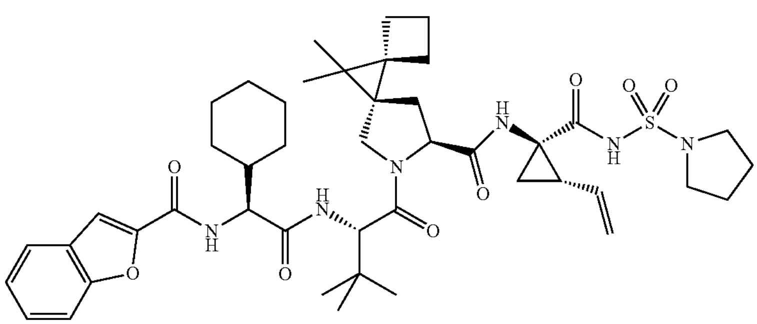 | (5R,8S)-7-[(2S)-2-({[(1-benzofuran-2-ylcarbonyl)amino](cyclohexyl)acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 192 | 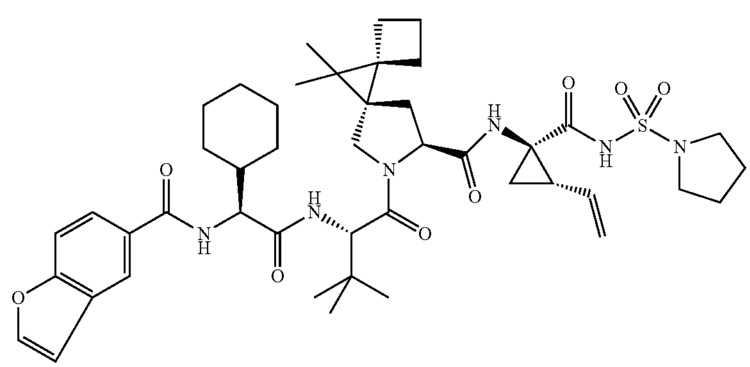 | (5R,8S)-7-[(2S)-2-({[(1-benzofuran-5-ylcarbonyl)amino](cyclohexyl)acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 193 | 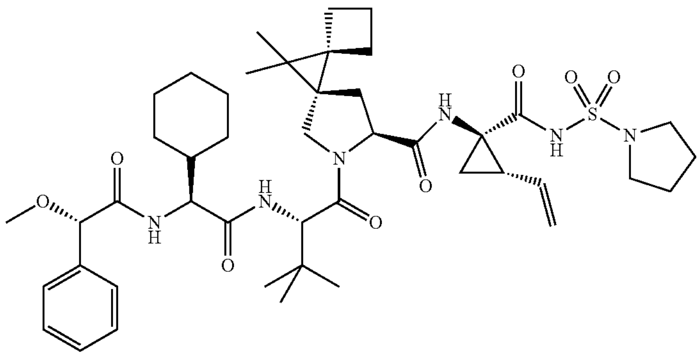 | (5R,8S)-7-{(2S)-2-[(cyclohexyl{[(2S)-2-methoxy-2-phenylacetyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 194 | 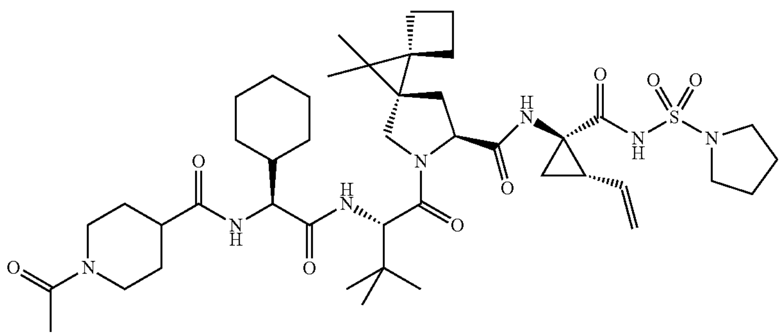 | (5R,8S)-7-[(2S)-2-{[{[(1-acetylpiperidin-4-yl)carbonyl]amino}(cyclohexyl)acetyl]amino}-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 195 | 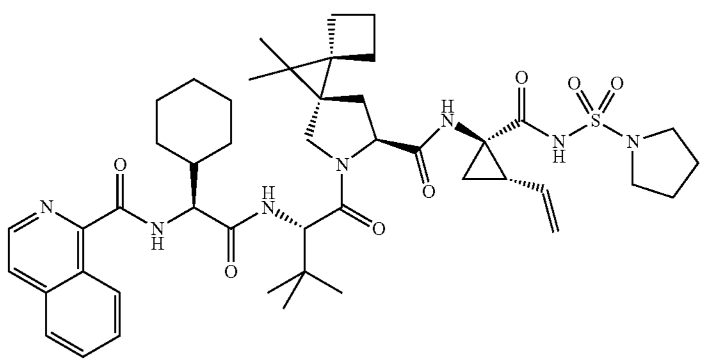 | (5R,8S)-7-[(2S)-2-({cyclohexyl[(isoquinolin-1-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 196 | 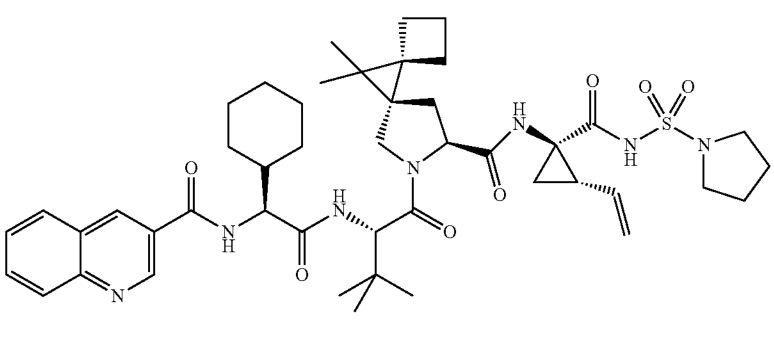 | (5R,8S)-7-[(2S)-2-({cyclohexyl[(quinolin-3-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 197 | 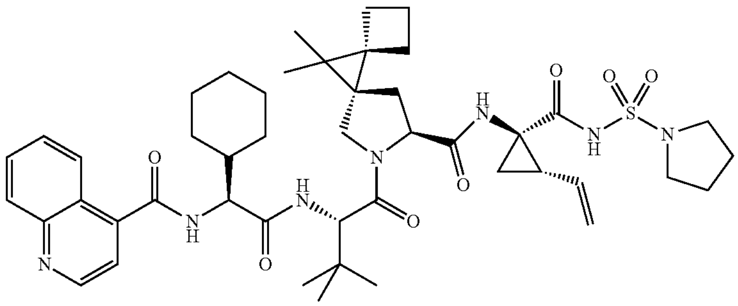 | (5R,8S)-7-[(2S)-2-({cyclohexyl[(quinolin-4-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 198 | 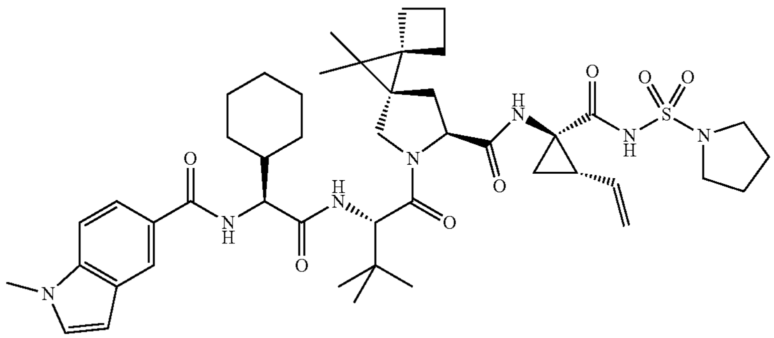 | (5R,8S)-7-{(2S)-2-[(cyclohexyl{[(1-methyl-1H-indol-5-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 199 | 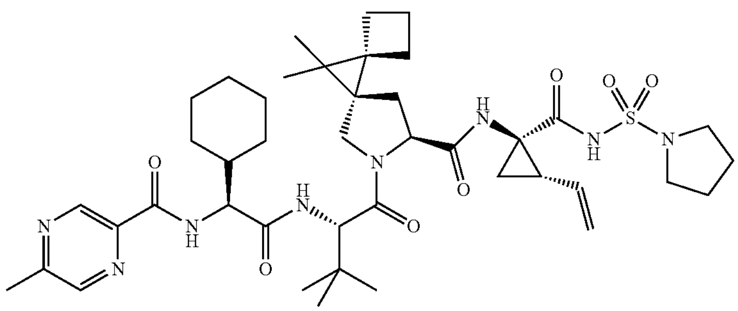 | (5R,8S)-7-{(2S)-2-[(cyclohexyl{[(5-methylpyrazin-2-yl)carbonyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 200 | 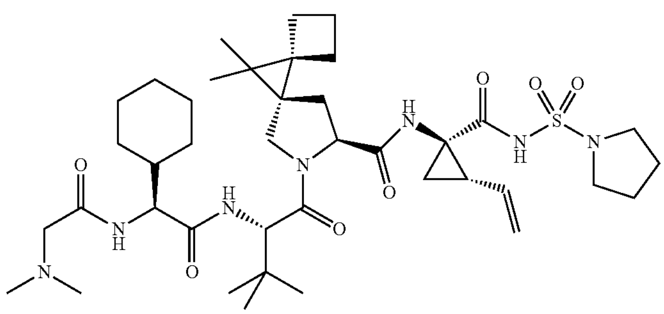 | (5R,8S)-7-{(2S)-2-[(cyclohexyl{[(dimethylamino)acetyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 201 | 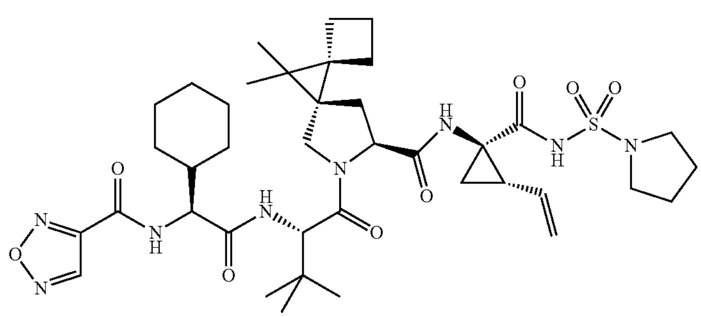 | (5R,8S)-7-[(2S)-2-({cyclohexyl[(1,2,5-oxadiazol-3-ylcarbonyl)amino]acetyl}amino)-3,3-dimethylbutanoyl]-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |

TABLE A-continued

| Cmpd. # | Structure | Name |
|---|---|---|
| 202 | 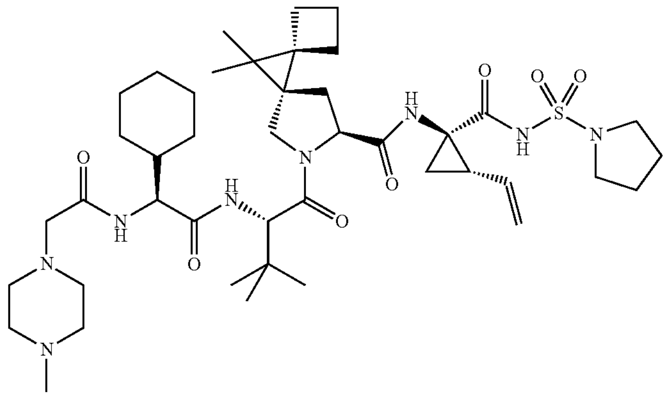 | (5R,8S)-7-{(2S)-2-[(cyclohexyl{[(4-methylpiperazin-1-yl)acetyl]amino}acetyl)amino]-3,3-dimethylbutanoyl}-10,10-dimethyl-N-{(1R,2S)-1-[(pyrrolidin-1-ylsulfonyl)carbamoyl]-2-vinylcyclopropyl}-7-azadispiro[3.0.4.1]decane-8-carboxamide |
| 203 | 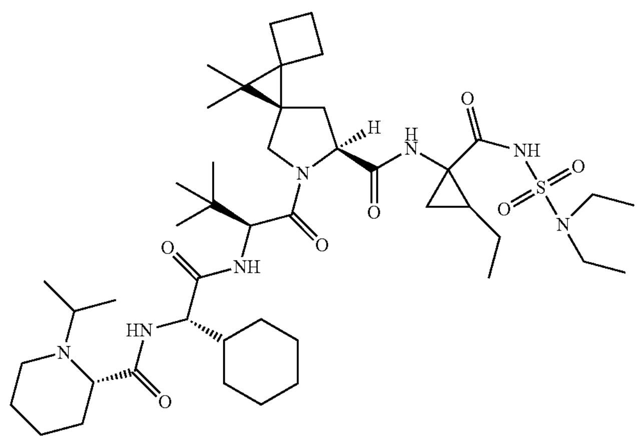 [SMILES: CCC1CC1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N(CC)CC] | (5R,8S)-7-[(2S)-2-{[(2S)-2-cyclohexyl-2-({[(2S)-1-isopropylpiperidin-2-yl]carbonyl}amino)acetyl]amino}-3,3-dimethylbutanoyl]-N-(1-{[(diethylamino)sulfonyl]carbamoyl}-2-ethylcyclopropyl)-10,10-dimethyl-7-azadispiro[3.0.4.1]decane-8-carboxamide |

The compounds listed in Table B are also embodiments of the invention.

TABLE B

| Structure | Compound No. |
|---|---|
| 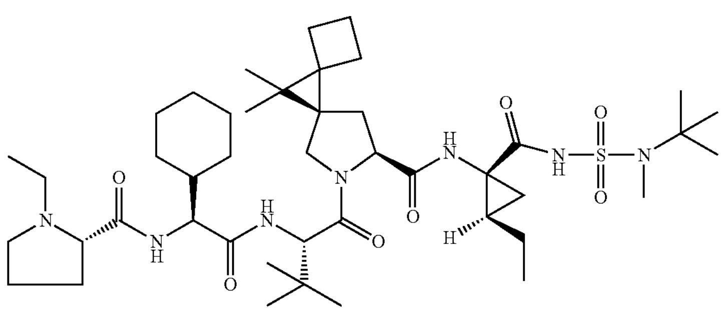 [SMILES: CC[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(C)C(C)(C)C] | 204 |

TABLE B-continued

| Structure | Compound No. |
|---|---|
| 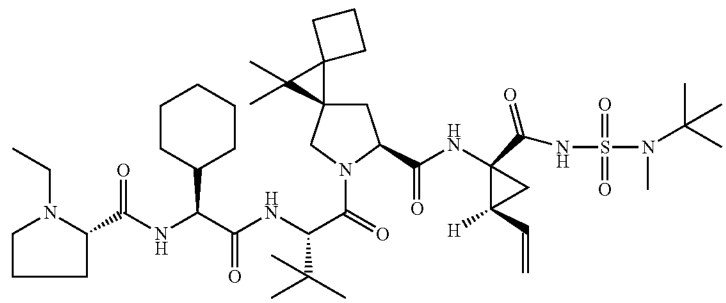 [SMILES: C=C[C@@H]1C[C@]1(NC(=O)[C@@H]1C[C@@]2(CN1C(=O)[C@@H](NC(=O)[C@@H](NC(=O)[C@@H]1CCCN1CC)C1CCCCC1)C(C)(C)C)C(C)(C)C21CCC1)C(=O)NS(=O)(=O)N(C)C(C)(C)C] | 205 |
| 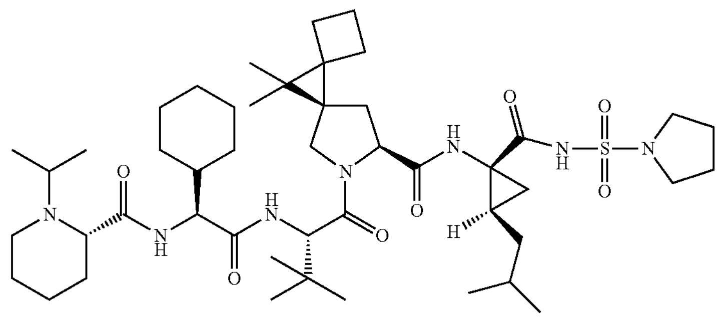 [SMILES: CC(C)C[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N1CCCC1] | 206 |
| 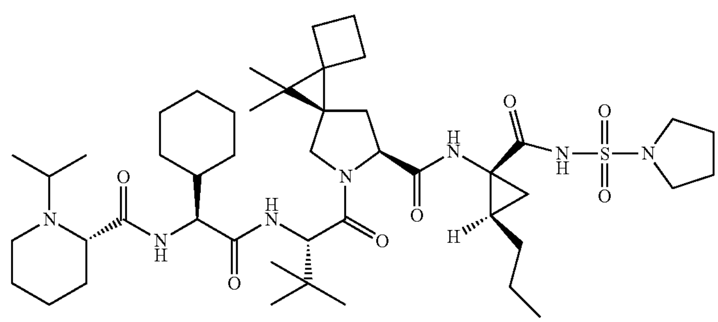 [SMILES: CCC[C@@H]1C[C@]1(NC(=O)[C@@H]1C[C@@]2(CN1C(=O)[C@@H](NC(=O)[C@@H](NC(=O)[C@@H]1CCCCN1C(C)C)C1CCCCC1)C(C)(C)C)C(C)(C)C21CCC1)C(=O)NS(=O)(=O)N1CCCC1] | 207 |
| 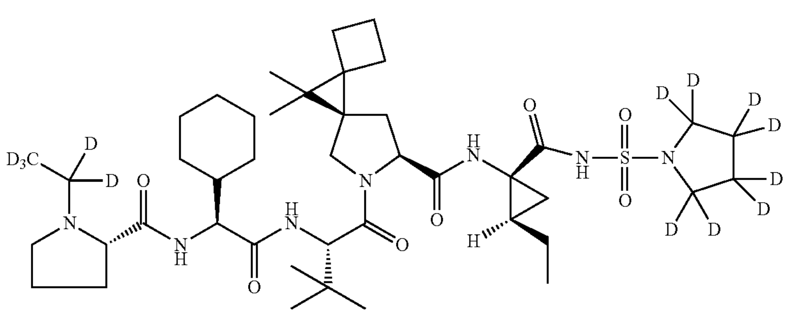 [SMILES: [2H]C([2H])([2H])C([2H])([2H])N1CCC[C@H]1C(=O)N[C@H](C(=O)N[C@H](C(=O)N1C[C@]2(C[C@H]1C(=O)N[C@]1(C(=O)NS(=O)(=O)N3C([2H])([2H])C([2H])([2H])C([2H])([2H])C3([2H])[2H])C[C@H]1CC)C(C)(C)C21CCC1)C(C)(C)C)C1CCCCC1] | 208 |
| 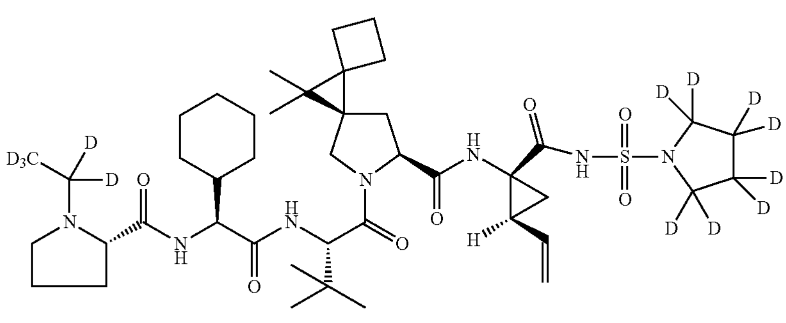 [SMILES: [2H]C([2H])([2H])C([2H])([2H])N1CCC[C@H]1C(=O)N[C@H](C(=O)N[C@H](C(=O)N1C[C@]2(C[C@H]1C(=O)N[C@]1(C(=O)NS(=O)(=O)N3C([2H])([2H])C([2H])([2H])C([2H])([2H])C3([2H])[2H])C[C@H]1C=C)C(C)(C)C21CCC1)C(C)(C)C)C1CCCCC1] | 209 |

TABLE B-continued

| Structure | Compound No. |
|---|---|
| 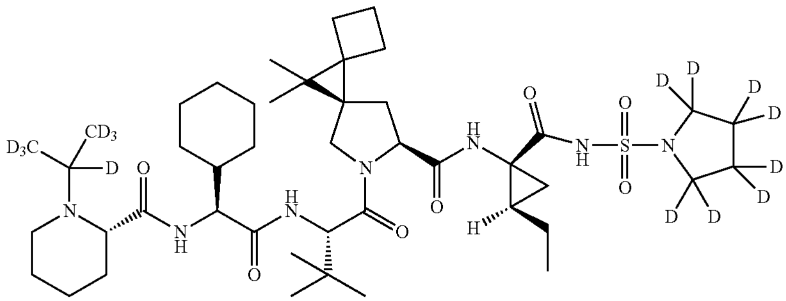 [SMILES: [2H]C([2H])([2H])C([2H])(N1CCCC[C@H]1C(=O)N[C@H](C(=O)N[C@H](C(=O)N1C[C@]2(C[C@H]1C(=O)N[C@]1(C(=O)NS(=O)(=O)N3C([2H])([2H])C([2H])([2H])C([2H])([2H])C3([2H])[2H])C[C@H]1CC)C(C)(C)C21CCC1)C(C)(C)C)C1CCCCC1)C([2H])([2H])[2H]] | 210 |
| 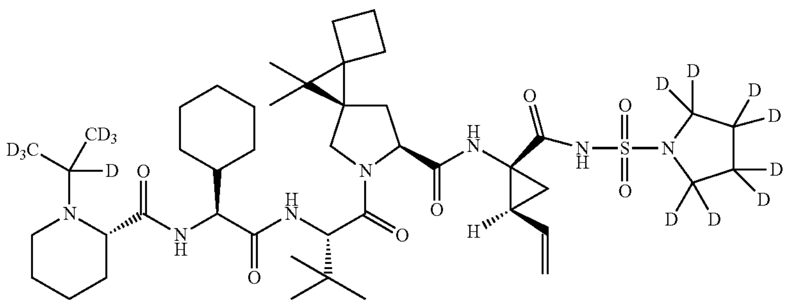 [SMILES: [2H]C([2H])([2H])C([2H])(N1CCCC[C@H]1C(=O)N[C@H](C(=O)N[C@H](C(=O)N1C[C@]2(C[C@H]1C(=O)N[C@]1(C(=O)NS(=O)(=O)N3C([2H])([2H])C([2H])([2H])C([2H])([2H])C3([2H])[2H])C[C@H]1C=C)C(C)(C)C21CCC1)C(C)(C)C)C1CCCCC1)C([2H])([2H])[2H]] | 211 |
| 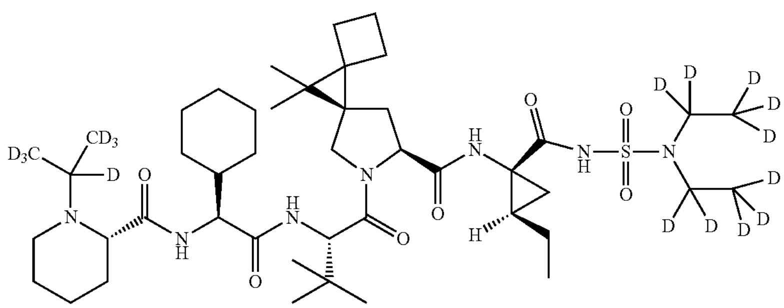 [SMILES: [2H]C([2H])([2H])C([2H])([2H])N(C([2H])([2H])C([2H])([2H])[2H])S(=O)(=O)NC(=O)[C@@]1(NC(=O)[C@@H]2C[C@@]3(CN2C(=O)[C@@H](NC(=O)[C@@H](NC(=O)[C@@H]2CCCCN2C([2H])(C([2H])([2H])[2H])C([2H])([2H])[2H])C2CCCCC2)C(C)(C)C)C(C)(C)C32CCC2)C[C@H]1CC] | 212 |
| 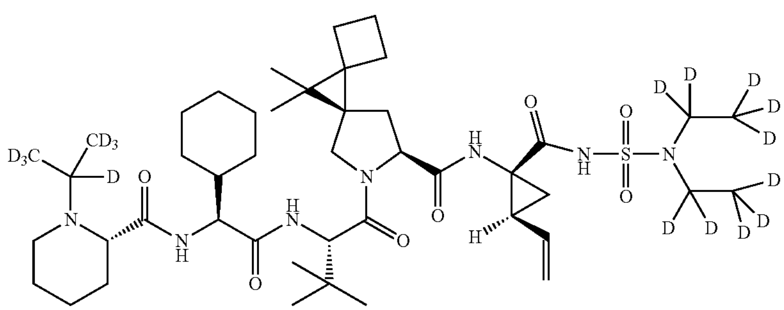 [SMILES: [2H]C([2H])([2H])C([2H])([2H])N(C([2H])([2H])C([2H])([2H])[2H])S(=O)(=O)NC(=O)[C@@]1(NC(=O)[C@@H]2C[C@@]3(CN2C(=O)[C@@H](NC(=O)[C@@H](NC(=O)[C@@H]2CCCCN2C([2H])(C([2H])([2H])[2H])C([2H])([2H])[2H])C2CCCCC2)C(C)(C)C)C(C)(C)C32CCC2)C[C@H]1C=C] | 213 |
| 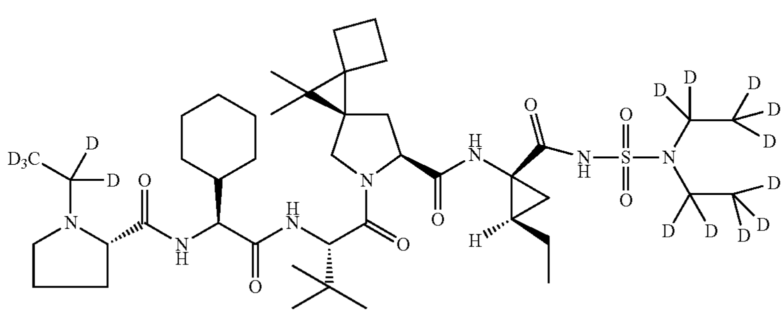 [SMILES: [2H]C([2H])([2H])C([2H])([2H])N1CCC[C@H]1C(=O)N[C@H](C(=O)N[C@H](C(=O)N1C[C@]2(C[C@H]1C(=O)N[C@]1(C(=O)NS(=O)(=O)N(C([2H])([2H])C([2H])([2H])[2H])C([2H])([2H])C([2H])([2H])[2H])C[C@H]1CC)C(C)(C)C21CCC1)C(C)(C)C)C1CCCCC1] | 214 |

TABLE B-continued

| Structure | Compound No. |
|---|---|
| (structure) | 215 |

Biological Activity

Example 20

HCV NS3-4A Protease Assay

The inhibitory activity of certain compounds of Table A against HCV NS3-4A serine protease is determined in a homogenous assay using the full-length NS3-4A protein (genotype 1a, strain HCV-1) and a commercially available internally-quenched fluorogenic peptide substrate as described by Taliani, M., et al. 1996 Anal. Biochem. 240:60-67, which is incorporated by reference in its entirety.

Example 21

Luciferase-Based HCV Replicon Assay

The antiviral activity and cytotoxicity of certain compounds of Table A is determined using a subgenomic genotype 1b HCV replicon cell line (Huh-Luc/neo-ET) containing a luciferase reporter gene, the expression of which is under the control of HCV RNA replication and translation. Briefly, 5,000 replicon cells are seeded in each well of 96-well tissue culture plates and are allowed to attach in complete culture media without G418 overnight. On the next day, the culture media are replaced with media containing a serially diluted compound of Table A in the presence of 10% FBS and 0.5% DMSO. After a 48-h treatment with the compound of Table A, the remaining luciferase activities in the cells are determined using BriteLite reagent (Perkin Elmer, Wellesley, Mass.) with a LMaxII plate reader (Molecular Probe, Invitrogen). Each data point represents the average of four replicates in cell culture. $IC_{50}$ is the concentration of the at which the luciferase activity in the replicon cells is reduced by 50%. The cytotoxicity of the compound of Table A is evaluated using an MTS-based cell viability assay.

Compounds in Table A supra have been tested in the protease assay of Example 20. The $IC_{50}$ values for each compound are provided in Table C. Compounds of Table A supra may have also been tested in the replicon assay of Example 21 and exhibit an $IC_{50}$ of less than about 100 nM or less.

TABLE C

| Compound Number | Protease assay Ex. 12 IC50 (μM) | LC-Method | Retention time | MS-method | Mass observed | Ion |
|---|---|---|---|---|---|---|
| 1 | 0.4 | I3 | 3.73 | I3 | 664.3 | M + H |
| 2 | 0.75 | I3 | 3.75 | I3 | 777.4 | M + H |
| 3 | 0.006 | B | 3.57 | J | 830.5 | M + H |
| 4 | 0.035 | I3 | 2.92 | I3 | 816.5 | M + H |
| 5 | 6.65 | I3 | 3.65 | I3 | 791.3 | M − H |
| 6 | 0.045 | I | 2.86 | I | 846.4 | M + H |
| 7 | 0.45 | I | 2.76 | I | 832.5 | M + H |
| 8 | 0.3 | I | 2.84 | I | 850.5 | M + H |
| 9 | 0.1 | I | 3.61 | I | 745.5 | M + H |
| 10 | 0.065 | B | 3.59 | J | 816.4 | M + H |
| 11 | 0.02 | B | 3.59 | J | 817.5 | M + H |
| 12 | 0.04 | B | 3.54 | J | 802.5 | M + H |
| 13 | 0.003 | D | 2.13 | E | 856.5 | M + H |
| 14 | 0.003 | B | 3.65 | J | 842.5 | M + H |
| 15 | 0.002 | B | 3.65 | J | 842.5 | M + H |
| 16 | 0.0023 | B | 3.62 | J | 842.5 | M + H |
| 17 | 0.0025 | B | 3.63 | J | 828.4 | M + H |
| 18 | 0.01 | B | 3.63 | J | 828.4 | M + H |
| 19 | 0.055 | B | 3.6 | J | 828.5 | M + H |
| 20 | 0.07 | B | 3.52 | J | 834.5 | M + H |
| 21 | 0.035 | B | 3.52 | J | 816.4 | M + H |
| 22 | 0.095 | B | 3.46 | J | 802.4 | M + H |
| 23 | 0.4 | B | 3.49 | J | 802.4 | M + H |
| 24 | 0.065 | B | 3.56 | J | 830.5 | M + H |
| 25 | 0.008 | B | 3.64 | J | 856.5 | M + H |
| 26 | 0.015 | B | 3.62 | J | 860.5 | M + H |
| 27 | 0.01 | B | 3.62 | J | 842.3 | M + H |
| 28 | 0.002 | B | 3.7 | J | 868.5 | M + H |
| 29 | 0.04 | B | 3.11 | J | 826.3 | M + H |
| 30 | 0.062 | B | 3.61 | J | 832.5 | M + H |
| 31 | 0.008 | B | 3.65 | J | 856.6 | M + H |
| 32 | 0.001 | B | 3.74 | J | 880.5 | M + H |
| 33 | 0.0035 | B | 3.65 | J | 872.5 | M + H |
| 34 | 0.0045 | B | 3.7 | J | 858.5 | M + H |
| 35 | 0.003 | B | 3.83 | G | 882.4 | M + H |
| 36 | 0.0035 | A3 | 5.11 | E | 842.3 | M + H |
| 37 | 0.0033 | A3 | 5.15 | E | 842.3 | M + H |
| 38 | 0.0035 | A3 | 5.07 | E | 828.3 | M + H |
| 39 | 0.0025 | A3 | 5.07 | E | 828.3 | M + H |
| 40 | 0.006 | A3 | 5.16 | E | 842.3 | M + H |
| 41 | 0.0009 | A3 | 4.82 | E | 884.18 | M+ |
| 42 | 0.04 | A3 | 5.854 | E | 837.04 | M+ |
| 43 | 0.06 | A3 | 5.549 | E | 811 | M+ |
| 44 | 0.015 | A3 | 4.6 | E | 858.14 | M− |
| 45 | 0.001 | A3 | 5.113 | J | 874.16 | M + H |
| 46 | 0.002 | A3 | 5.086 | J | 874.16 | M + H |
| 47 | 0.0048 | B | 3.65 | J | 856.5 | M + H |
| 48 | 0.0009 | B | 3.54 | J | 828.5 | M + H |
| 49 | 0.0033 | A3 | 5.536 | E | 870.2 | M+ |
| 50 | 0.0038 | A3 | 5.402 | E | 870.2 | M+ |
| 51 | 1.15 | B | 3.61; 3.67 | J | 754.5 | M + H |
| 52 | 0.0025 | A3 | 5.501 | E | 892.2 | M+ |
| 53 | 0.0017 | A3 | 5.257 | E | 856.17 | M+ |

TABLE C-continued

| Compound Number | Protease assay Ex. 12 IC50 (μM) | LC-Method | Retention time | MS-method | Mass observed | Ion |
|---|---|---|---|---|---|---|
| 54 | 0.0025 | A3 | 5.258 | E | 900.22 | M+ |
| 55 | 0.0014 | B | 3.61 | E | 846.4 | M + H |
| 56 | 0.008 | A3 | 5.078 | E | 874.18 | M+ |
| 57 | 0.0065 | A3 | 5.247 | E | 856.17 | M+ |
| 58 | 0.0035 | D | 2.104 | E | 842.5 | M + H |
| 59 | 0.0035 | D | 2.088 | E | 828.4 | M + H |
| 60 | 1.25 | D | 2.535 | E | 756.5 | M + H |
| 61 | 0.75 | D | 2.734 | E | 727.5 | M + H |
| 62 | 0.001 | B | 3.7 | E | 844.5 | M + H |
| 63 | 0.0012 | B | 3.66 | E | 830.5 | M + H |
| 64 | 0.002 | B | 3.83 | E | 884.5 | M + H |
| 65 | 0.0045 | B | 3.7 | E | 858.5 | M + H |
| 66 | 0.0055 | B | 3.8 | E | 868.3 | M + H |
| 67 | 0.02 | A3 | 4.817 | E | 858.14 | M+ |
| 68 | 0.95 | A3 | 5.987 | E | 752.96 | M+ |
| 69 | 0.05 | A3 | 4.73 | J | 851.5 | M + H |
| 70 | 0.035 | B | 3.56 | J | 851.5 | M + H |
| 71 | 0.04 | A3 | 6.279 | M | 910.1 | M + H |
| 72 | 0.07 | A3 | 4.937 | M | 892.11 | M + H |
| 73 | 0.015 | A3 | 4.692 | M | 874.12 | M + H |
| 74 | 0.065 | A3 | 4.84 | E | 906.13 | M + H |
| 75 | 0.03 | A3 | 4.731 | E | 888.14 | M + H |
| 76 | 0.08 | A3 | 5.972 | E | 918.13 | M + H |
| 77 | 0.0009 | B | 3.72 | E | 844.3 | M + H |
| 78 | 0.65 | A3 | 5.11/5.26 | E | 688.88 | M+ |
| 79 | 0.0025 | B | 4.422 | H | 842.5 | M − H |
| 80 | 0.002 | B | 4.503 | H | 868.5 | M − H |
| 81 | 0.004 | B | 4.378 | H | 828.4 | M − H |
| 82 | 0.0025 | B | 3.91 | J | 828.5 | M + H |
| 83 | 0.002 | A3 | 5.25 | E | 880.14 | M + H |
| 84 | 0.006 | B | 4.017 | H | 884.5 | M − H |
| 85 | 0.0045 | B | 4.013 | H | 870.4 | M − H |
| 86 | 0.0045 | B | 4.252 | H | 844.5 | M − H |
| 87 | 0.007 | D | 2.267 | E | 844.5 | M + H |
| 88 | 0.5 | A3 | 5.545 | E | 724.91 | M+ |
| 89 | 0.03 | A3 | 5.747 | E | 878.12 | M+ |
| 90 | 0.0065 | A3 | 5.319 | E | 858.18 | M+ |
| 91 | 0.005 | B | 3.61 | J | 830.5 | M + H |
| 92 | 0.003 | B | 3.61 | J | 844.5 | M + H |
| 93 | 0.002 | B | 3.57 | J | 816.4 | M + H |
| 94 | 0.0015 | B | 3.61 | J | 830.5 | M + H |
| 95 | 0.005 | D | 2.41 | E | 842.5 | M + H |
| 96 | 0.007 | B | 3.664 | H | 856.5 | M − H |
| 97 | 0.01 | B | 3.484 | H | 814.3 | M − H |
| 98 | 0.007 | D | 2.26 | E | 830.5 | M + H |
| 99 | 0.02 | D | 2.093 | E | 830.5 | M + H |
| 100 | 0.01 | B | 3.813 | H | 830.5 | M − H |
| 101 | 0.0025 | B | 3.72 | J | 816.4 | M + H |
| 102 | 0.008 | B | 3.651 | H | 820.3 | M − H |
| 103 | 0.02 | B | 3.81 | H | 834.4 | M − H |
| 104 | 0.015 | B | 3.738 | H | 848.3 | M − H |
| 105 | 0.045 | A3 | 5.385 | E | 892.15 | M+ |
| 106 | 0.01 | B | 3.84 | B | 872.5 | M + H |
| 107 | 0.009 | B | 3.76 | E | 844.5 | M + H |
| 108 | 0.006 | B | 3.69 | E | 858.4 | M + H |
| 109 | 0.0025 | B | 3.66 | E | 830.3 | M + H |
| 110 | 0.008 | B | 3.8 | E | 872.5 | M + H |
| 111 | 0.008 | B | 3.74 | E | 844.5 | M + H |
| 112 | 0.0014 | B | 3.72 | J | 858.5 | M + H |
| 113 | 0.0035 | B | 3.77 | J | 870.5 | M + H |
| 114 | 0.0045 | B | 3.7 | J | 858.5 | M + H |
| 115 | 0.0045 | B | 3.7 | J | 870.5 | M + H |
| 116 | 0.0045 | B | 3.67 | J | 844.5 | M + H |
| 117 | 0.0055 | B | 3.76 | J | 846.5 | M + H |
| 118 | 0.0045 | B | 3.66 | J | 830.5 | M + H |
| 119 | 0.0065 | B | 3.68 | J | 858.5 | M + H |
| 120 | 0.01 | B | 3.75 | E | 872.5 | M + H |
| 121 | 0.007 | B | 3.72 | J | 860.5 | M + H |
| 122 | 0.0014 | D | 2.07 | E | 818.5 | M + H |
| 123 | 0.008 | B | 3.69 | E | 858.5 | M + H |
| 124 | 0.0015 | A3 | 4.892 | E | 898.21 | M − H |
| 125 | <0.0003 | A3 | 4.761 | E | 870.15 | M+ |
| 126 | 0.006 | A3 | 4.58 | E | 844.12 | M − H |
| 127 | 0.004 | A3 | 4.327 | E | 900.18 | M − H |
| 128 | 0.0014 | A3 | 4.742 | E | 872.17 | M − H |
| 129 | 0.006 | A3 | 4.161 | E | 872.13 | M − H |
| 130 | 0.008 | D | 2.002 | E | 804.4 | M + H |
| 131 | 0.0055 | D | 2.053 | E | 818.5 | M + H |
| 132 | 0.0028 | | | E | 844.5 | M + H |
| 133 | 0.003 | A3 | 5.574 | E | 872.21 | M+ |
| 134 | 0.005 | A3 | 5.427 | E | 844.16 | M+ |
| 135 | 0.0045 | A3 | 5.401 | E | 870.2 | M+ |
| 136 | 0.007 | A3 | 5.27 | E | 842.14 | M+ |
| 137 | 0.0035 | B | 3.83 | E | 872.5 | M + H |
| 138 | 0.003 | A3 | 5.552 | E | 833.15 | M+ |
| 139 | 0.0035 | A3 | 5.589 | E | 847.17 | M + H |
| 140 | 0.0025 | A3 | 5.592 | E | 849.19 | M + H |
| 141 | 0.008 | B | 3.62 | E | 860.7 | M + H |
| 142 | 0.01 | B | 3.64 | E | 860.7 | M + H |
| 143 | 0.003 | A3 | 5.33 | E | 892.15 | M+ |
| 144 | 0.009 | A3 | 5.24/5.33 | E | 846.15 | M+ |
| 145 | 0.0059 | A3 | 5.688 | E | 863.21 | M + H |
| 146 | 0.003 | A3 | 4.944 | E | 884.18 | M+ |
| 147 | 0.0015 | A3 | 5.115 | E | 912.23 | M+ |
| 148 | 0.0008 | A3 | 5.447 | E | 836.17 | M + H |
| 149 | 0.0015 | A3 | 5.783 | E | 868.25 | M + H |
| 150 | 0.0024 | A3 | 5.541 | E | 900.22 | M + H |
| 151 | 0.002 | A3 | 5.446 | E | 886.19 | M + H |
| 152 | 0.0011 | A3 | 5.624 | E | 914.25 | M + H |
| 153 | 0.0018 | A3 | 5.496 | E | 886.19 | M + H |
| 154 | 0.0028 | A3 | 5.365 | E | 872.17 | M + H |
| 155 | 0.0044 | A3 | 5.394 | E | 894.17 | M − H |
| 156 | 0.0013 | A3 | 5.246 | E | 876.18 | M − H |
| 157 | 0.001 | A3 | 5.217 | E | 886.19 | M − H |
| 158 | 0.022 | A3 | 5.331 | E | 914.25 | M+ |
| 159 | 0.011 | A3 | 5.839 | E | 884.22 | M − H |
| 160 | 0.003 | A3 | 5.923 | E | 912.28 | M − H |
| 161 | 0.065 | A5 | 1.63 | A5 | 840.5 | M + H |
| 162 | 0.0009 | A4 | 1.48 | A4 | 830.8 | M + H |
| 163 | 1.5 | A4 | 1.27 | A4 | 861.6 | M + H |
| 164 | 0.008 | A6 | 14.96 | A6 | 879.6 | M + H |
| 165 | 0.0062 | A5 | 1.49 | A5 | 795.4 | M + H |
| 166 | 0.01 | A5 | 1.55 | A5 | 812.8 | M + H |
| 167 | 0.0006 | A5 | 1.51 | A5 | 798.7 | M + H |
| 168 | 0.03 | A5 | 1.51 | A5 | 832.8 | M + H |
| 169 | 0.0015 | A5 | 1.67 | A5 | 860 | M + H |
| 170 | 0.0005 | A5 | 1.66 | A5 | 845 | M + H |
| 171 | 0.001 | A5 | 1.48 | A5 | 879 | M + H |
| 172 | 0.0025 | A5 | 1.42 | A5 | 842.9 | M + H |
| 173 | 0.003 | A5 | 1.55 | A5 | 812.7 | M + H |
| 174 | 0.0006 | A4 | 1.61 | A4 | 858.6 | M + H |
| 175 | 0.01 | A6 | 6.76 | A6 | 822.46 | M + H |
| 176 | 0.025 | A6 | 7.68 | A6 | 876.47 | M + H |
| 177 | 0.025 | A6 | 8.22 | A6 | 876.5 | M + H |
| 178 | 0.08 | A6 | 8.14 | A6 | 860.48 | M + H |
| 179 | 0.025 | A6 | 7.62 | A6 | 829.49 | M + H |
| 180 | 0.03 | A6 | 7.56 | A6 | 839.48 | M + H |
| 181 | 0.09 | A6 | 8.13 | A6 | 867.52 | M + H |
| 182 | 0.07 | A6 | 8.09 | A6 | 836.47 | M + H |
| 183 | 0.095 | A6 | 7.93 | A6 | 867.52 | M + H |
| 184 | 0.035 | A6 | 7.68 | A6 | 873.47 | M + H |
| 185 | 0.04 | A6 | 7.63 | A6 | 839.49 | M + H |
| 186 | 0.065 | A6 | 7.36 | A6 | 839.49 | M + H |
| 187 | 0.025 | A6 | 6.68 | A6 | 842.48 | M + H |
| 188 | 0.02 | A6 | 7.79 | A6 | 846.46 | M + H |
| 189 | 0.025 | A6 | 7.35 | A6 | 846.46 | M + H |
| 190 | 0.02 | A6 | 7.31 | A6 | 846.46 | M + H |
| 191 | 0.055 | A6 | 8.08 | A6 | 847.44 | M + H |
| 192 | 0.025 | A6 | 7.75 | A6 | 847.44 | M + H |
| 193 | 0.025 | A6 | 7.91 | A6 | 851.47 | M + H |
| 194 | 0.01 | A6 | 6.66 | A6 | 856.5 | M + H |
| 195 | 0.075 | A6 | 8.29 | A6 | 858.46 | M + H |
| 196 | 0.02 | A6 | 7.51 | A6 | 858.46 | M + H |
| 197 | 0.04 | A6 | 7.35 | A6 | 858.46 | M + H |
| 198 | 0.04 | A6 | 7.65 | A6 | 860.47 | M + H |
| 199 | 0.014 | A6 | 7.62 | A6 | 823.45 | M + H |
| 200 | 0.008 | A6 | 7.02 | A6 | 788.48 | M + H |
| 201 | 0.035 | A6 | 6.78 | A6 | 799.42 | M + H |

TABLE C-continued

| Compound Number | Protease assay Ex. 12 IC50 (μM) | LC-Method | Retention time | MS-method | Mass observed | Ion |
|---|---|---|---|---|---|---|
| 202 | 0.02 | A6 | 5.89 | A6 | 843.52 | M + H |
| 203 | 0.008 | A6 | 13.62 | A6 | 860.2 | M + H |

Those skilled in the art will recognize, or be able to ascertain using no more than routine experimentation, many equivalents to the specific embodiments and methods described herein. Such equivalents are intended to be encompassed by the scope of the following claims.

What is claimed is:
1. A compound of Formula (III):

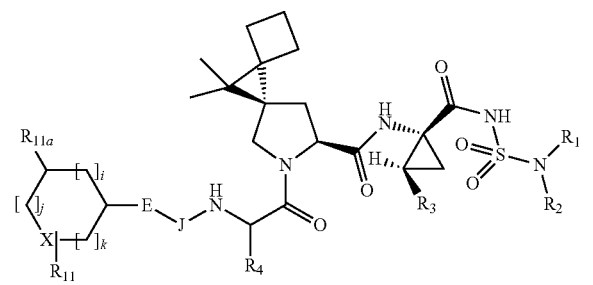

(III)

or a pharmaceutically acceptable salt thereof;
wherein
$R_1$ and $R_2$, taken in combination with the N to which they are attached, form a saturated, unsaturated or aromatic heterocyclic ring having 0, 1, or 2 additional ring heteroatoms independently selected from N, O, and S and which heterocyclic ring has from 4 to 7 total ring atoms, said heterocycle having 0, 1, 2, or 3 substituents which are independently selected from $C_1$-$C_4$alkyl, halo$C_1$-$C_4$alkyl, $C_2$-$C_4$alkenyl, $C_2$-$C_4$alkynyl, hydroxyl, $C_1$-$C_4$alkoxy, halo$C_1$-$C_4$alkoxy, amino, mono- and di-$C_{1-4}$alkylamino, amino$C_1$-$C_4$alkyl, $C_1$-$C_4$alkanoylamino$C_1$-$C_4$alkyl;
$R_3$ is $C_1$-$C_6$alkyl or $C_2$-$C_6$alkenyl;
$R_4$ is $C_1$-$C_8$alkyl, $C_3$-$C_8$cycloalkyl, or saturated 5 or 6 membered heterocyclic ring having 1 or 2 ring heteroatoms independently selected from N, O and S, each of which is substituted with 0-2 $C_1$-$C_4$ alkyl groups;
J is a bond or a divalent residue of the formula:

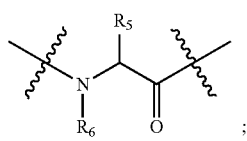

$R_5$ is $C_1$-$C_8$alkyl, $C_3$-$C_8$cycloalkyl, or saturated 5 or 6 membered heterocyclic ring having 1 or 2 ring heteroatoms independently selected from N, O and S, each of which is substituted with 0-2 $C_1$-$C_4$ alkyl groups;
$R_6$ is hydrogen or $C_1$-$C_4$alkyl;
E is a bond, $CH_2$, $C(O)$, $S(O)_2$, $C(R_9)_2C(O)$, or $C(O)C(R_9)_2$, $R_9$ is independently selected at each occurrence from hydrogen and $C_1$-$C_4$alkyl;
X is absent or selected from $NR^{11a}$ or oxygen;
i and k are independently selected integers selected from the group consisting of 0, 1, 2, 3 and 4;
j is an integer selected from the group consisting of 1, 2, 3 and 4, wherein the sum of i+j+k is less than or equal to 5 and greater than or equal to 2 when X is absent and the sum of i+j+k is less than or equal to 4 and greater than or equal to 1 when X is oxygen;
$R^{11}$ represents zero to three residues each independently selected at each occurrence from the group consisting of halogen, hydroxy, amino, $C_{1-4}$alkyl, $C_{3-6}$cycloalkyl, $C_{1-4}$alkoxy, mono- and di-$C_{1-4}$alkylamino, hydroxy$C_{1-4}$alkyl, and $C_{1-4}$alkoxy$C_{1-4}$alkyl; and
$R^{11a}$ is independently selected at each occurrence from the group consisting of hydrogen, $C_{1-4}$alkyl, halo$C_{1-4}$alkyl, $C_{3-6}$cycloalkyl, hydroxy$C_{1-4}$alkyl, and $C_{1-4}$alkoxy$C_{1-4}$alkyl.

2. The compound of Formula (IV):

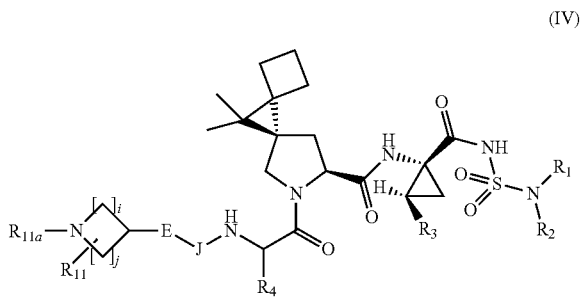

(IV)

or a pharmaceutically acceptable salt thereof;
wherein
$R_1$ and $R_2$, taken in combination with the N to which they are attached, form a saturated, unsaturated or aromatic heterocyclic ring having 0, 1, or 2 additional ring heteroatoms independently selected from N, O, and S and which heterocyclic ring has from 4 to 7 total ring atoms, said heterocycle having 0, 1, 2, or 3 substituents which are independently selected from $C_1$-$C_4$alkyl, halo $C_1$-$C_4$alkyl, $C_2$-$C_4$alkenyl, $C_2$-$C_4$alkynyl, hydroxyl, $C_1$-$C_4$alkoxy, halo$C_1$-$C_4$alkoxy, amino, mono- and di-$C_{1-4}$alkylamino, amino$C_1$-$C_4$alkyl, $C_1$-$C_4$alkanoylamino$C_1$-$C_4$alkyl;
$R_3$ is $C_1$-$C_6$alkyl or $C_2$-$C_6$alkenyl;
$R_4$ is $C_1$-$C_8$alkyl, $C_3$-$C_8$cycloalkyl, or saturated 5 or 6 membered heterocyclic ring having 1 or 2 ring heteroatoms independently selected from N, O or S, each of which is substituted with 0-2 $C_1$-$C_4$ alkyl groups;
J is a bond or a divalent residue of the formula:

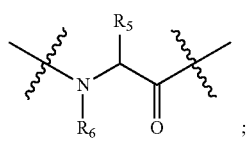

$R_5$ is $C_1$-$C_8$alkyl, $C_3$-$C_8$cycloalkyl, or saturated 5 or 6 membered heterocyclic ring having 1 or 2 ring heteroatoms independently selected from N, O or S, each of which is substituted with 0-2 $C_1$-$C_4$ alkyl groups;

$R_6$ is hydrogen or $C_1$-$C_4$alkyl;

E is a bond, $CH_2$, $C(O)$, $S(O)_2$, $C(R_9)_2C(O)$, or $C(O)C(R_9)_2$, $R_9$ is independently selected at each occurrence from hydrogen and $C_1$-$C_4$alkyl;

i is an integer selected from the group consisting of 0, 1, 2, 3 and 4;

j is an integer selected from the group consisting of 1, 2, 3 and 4, wherein the sum of i+j is less than or equal to 5 and greater than or equal to 2;

$R^{11}$ represents zero to three residues each independently selected at each occurrence from the group consisting of halogen, hydroxy, amino, $C_{1-4}$alkyl, $C_{3-6}$cycloalkyl, $C_{1-4}$alkoxy, mono- and di-$C_{1-4}$alkylamino, hydroxy$C_{1-4}$alkyl, and $C_{1-4}$alkoxy$C_{1-4}$alkyl; and $R^{11a}$ is independently selected at each occurrence from the group consisting of hydrogen, $C_{1-4}$alkyl, halo$C_{1-4}$alkyl, $C_{3-6}$cycloalkyl, hydroxy$C_{1-4}$alkyl, and $C_{1-4}$alkoxy$C_{1-4}$alkyl.

3. The compound of claim 1 of the Formula (V):

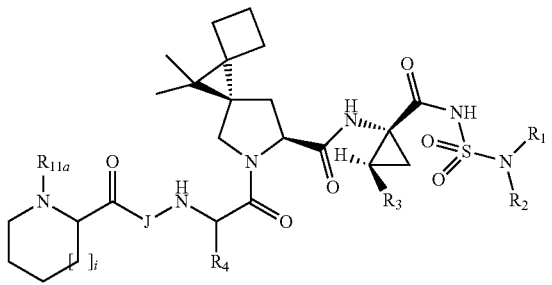

(V)

or a pharmaceutically acceptable salt thereof;
wherein
i is 0 or 1; and
$R^{11a}$ is hydrogen or $C_{1-4}$alkyl.

4. The compound of claim 3, wherein
J is a divalent residue of the formula:

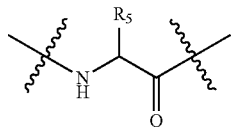

wherein
$R_5$ is $C_1$-$C_6$alkyl, $C_4$-$C_7$cycloalkyl, or saturated 5 or 6 membered heterocyclic ring having 1 or 2 ring heteroatoms independently selected from N, O and S, each of which is substituted with 0-2$C_1$-$C_4$ alkyl groups.

5. The compound claim 3, wherein $R_4$ and $R_5$ are independently selected from the group consisting of tert-butyl, cyclohexyl, 1-methyl-cyclohexyl, tetrahydropyran-4-yl and 1-methyl-tetrahydropyran-4-yl.

6. The compound of claim 3, wherein $R_1$ and $R_2$ taken in combination with the N to which they are attached, form a saturated, unsaturated or aromatic heterocyclic ring having 0, 1, or 2 additional ring heteroatorms independently selected from N, O, and S and which heterocyclic ring has from 4 to 7 total ring atoms, said heterocycle having 0, 1, 2, or 3 substituents which are independently selected from $C_1$-$C_4$alkyl, halo $C_1$-$C_4$alkyl, $C_2$-$C_4$alkenyl, $C_2$-$C_4$alkynyl, hydroxyl, $C_1$-$C_4$alkoxy, halo$C_1$-$C_4$alkoxy, amino, mono- and di-$C_{1-4}$alkylamino, amino$C_1$-$C_4$alkyl, $C_1$-$C_4$alkanoylamino$C_1$-$C_4$alkyl.

7. The compound of claim 6, wherein $R_1$, $R_2$ and the nitrogen atom to which they are attached form a pyrrolidinyl ring, a piperidinyl ring or a morpholinyl ring.

8. The compound of claim 3, in which $R_{11a}$ is $C_1$-$C_4$alkyl.

9. The compound of claim 8, in which $R_{11a}$ is selected from the group consisting of ethyl, and isopropyl.

10. A pharmaceutically acceptable formulation for the treatment of an HCV-associated disorder, comprising:
the compound according to claim 1, and
a pharmaceutically acceptable excipient.

11. A pharmaceutically acceptable formulation for the treatment of an HCV-associated disorder, comprising:
the compound according to claim 2, and
a pharmaceutically acceptable excipient.

12. A pharmaceutically acceptable formulation for the treatment of an HCV-associated disorder, comprising:
the compound according to claim 4, and
a pharmaceutically acceptable excipient.

* * * * *